(12) United States Patent
Calderwood et al.

(10) Patent No.: US 7,709,468 B2
(45) Date of Patent: May 4, 2010

(54) IMIDAZO BASED HETEROCYCLES

(75) Inventors: David J. Calderwood, Framingham, MA (US); Kristine E. Frank, Worcester, MA (US); Patrick Betschmann, Shrewsbury, MA (US); Gavin C. Hirst, Princeton, MA (US); Eric C. Brieinlinger, Charlton, MA (US); Michael J. Morytko, Framingham, MA (US); Richard W. Dixon, Jefferson, MA (US)

(73) Assignee: Abbott Laboratories, Abbott Park, IL (US)

( * ) Notice: Subject to any disclaimer, the term of this patent is extended or adjusted under 35 U.S.C. 154(b) by 787 days.

(21) Appl. No.: 11/514,626

(22) Filed: Sep. 1, 2006

(65) Prior Publication Data

US 2007/0099925 A1     May 3, 2007

Related U.S. Application Data

(60) Provisional application No. 60/714,016, filed on Sep. 2, 2005, provisional application No. 60/837,560, filed on Aug. 14, 2006.

(51) Int. Cl.
  *C07D 487/04* (2006.01)
  *A61K 31/498* (2006.01)
(52) U.S. Cl. ............... 514/217.05; 514/235.8; 514/249; 540/599; 544/122; 544/315; 544/331; 544/350
(58) Field of Classification Search ............ 544/122, 544/315, 331, 350; 540/599; 514/217.05, 514/235.08, 249, 235.8
See application file for complete search history.

(56) References Cited

U.S. PATENT DOCUMENTS

| | | | |
|---|---|---|---|
| 4,242,344 A | 12/1980 | Lumma | |
| 4,636,502 A | 1/1987 | Spitzer | |
| 5,498,774 A | 3/1996 | Mitsudera et al. | |
| 6,995,144 B2 | 2/2006 | Ozaki et al. | |
| 2003/0119864 A1 | 6/2003 | Gordon et al. | |
| 2003/0191307 A1 | 10/2003 | Blumenkoph et al. | |
| 2003/0207885 A1 | 11/2003 | Hutrchinson et al. | |
| 2004/0023972 A1 | 2/2004 | Sundermann et al. | |
| 2004/0028716 A1 | 2/2004 | Marks et al. | |
| 2004/0063715 A1 | 4/2004 | Paruch et al. | |
| 2004/0067948 A1 | 4/2004 | Hallett | |
| 2004/0072831 A1 | 4/2004 | Moon et al. | |
| 2004/0176390 A1 | 9/2004 | Blumberg et al. | |
| 2004/0186148 A1 | 9/2004 | Shankar et al. | |
| 2004/0220189 A1 | 11/2004 | Sun et al. | |
| 2005/0009832 A1 | 1/2005 | Sun et al. | |
| 2005/0130980 A1 | 6/2005 | Paruch et al. | |
| 2005/0282826 A1 | 12/2005 | Malamas et al. | |
| 2006/0079530 A1 | 4/2006 | Gordon et al. | |
| 2006/0106023 A1 | 5/2006 | Guzi et al. | |
| 2006/0135761 A1 | 6/2006 | Datta et al. | |
| 2006/0135767 A1 | 6/2006 | Feng et al. | |
| 2006/0183746 A1 | 8/2006 | Currie et al. | |
| 2006/0241104 A1 | 10/2006 | Borzilleri et al. | |
| 2006/0252760 A1 | 11/2006 | Gordon et al. | |

FOREIGN PATENT DOCUMENTS

| | | |
|---|---|---|
| EP | 0154494 | 9/1985 |
| EP | 0 185 346 | 12/1985 |
| EP | 0204285 | 12/1986 |
| EP | 0404190 | 12/1990 |
| WO | WO 97/30053 | 8/1987 |
| WO | WO 89/03833 | 5/1989 |
| WO | WO 91/00092 | 1/1991 |
| WO | WO 91/19497 | 12/1991 |
| WO | WO 92/20350 | 11/1992 |
| WO | WO 92/20642 | 11/1992 |
| WO | WO 95/12584 | 5/1995 |
| WO | WO 95/12594 | 5/1995 |
| WO | WO 92/10498 | 6/1995 |
| WO | WO 95/21843 | 8/1995 |
| WO | WO 96/28160 | 9/1996 |
| WO | WO 96/34866 | 11/1996 |
| WO | WO 99/28322 | 6/1999 |
| WO | WO 01/49322 | 1/2001 |
| WO | WO 01/27110 | 4/2001 |

(Continued)

OTHER PUBLICATIONS

Bundgaard, Design of Prodrugs: Introduction, p. 1, 1985.*
Silverman, Prodrugs and Drug Delivery Systems, The Organic Chemistry of Drug Design and Drug Action, pp. 352-400, 1992.*

*Primary Examiner*—Deepak Rao
(74) *Attorney, Agent, or Firm*—Gale B. O'Brien; Kenneth Zwicker

(57) ABSTRACT

The present invention is directed to novel imidazopyrazine and imidazopyrimidine compounds of formula (I)

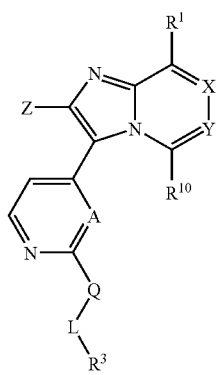

wherein the variables are as defined herein. The compounds of formula (I) are useful as kinase inhibitors and as such would be useful in treating certain conditions and diseases, especially inflammatory conditions and diseases and proliferative disorders and conditions, for example, cancers.

27 Claims, No Drawings

FOREIGN PATENT DOCUMENTS

| | | |
|---|---|---|
| WO | WO 01/27111 | 4/2001 |
| WO | WO 01/27119 | 4/2001 |
| WO | WO 01/34203 | 5/2001 |
| WO | WO 01/34605 | 5/2001 |
| WO | WO 01/74331 | 10/2001 |
| WO | WO 01/81344 | 11/2001 |
| WO | WO 02/10140 | 2/2002 |
| WO | WO 02/10170 | 2/2002 |
| WO | WO 02/26665 | 4/2002 |
| WO | WO 02/053558 | 7/2002 |
| WO | WO 02/060492 | 8/2002 |
| WO | WO 02/085903 | 10/2002 |
| WO | WO 02/096318 | 12/2002 |
| WO | WO 02/096363 | 12/2002 |
| WO | WO 03/000682 | 1/2003 |
| WO | WO 03/004498 | 1/2003 |
| WO | WO 03/006471 | 1/2003 |
| WO | WO 03/030841 | 4/2003 |
| WO | WO 03/040100 | 5/2003 |
| WO | WO 03/051886 | 6/2003 |
| WO | WO 03/062392 | 7/2003 |
| WO | WO 03/070732 | 8/2003 |
| WO | WO 03/082817 | 10/2003 |
| WO | WO 03/084948 | 10/2003 |
| WO | WO 03/089434 | 10/2003 |
| WO | WO 2004/000820 | 12/2003 |
| WO | WO 2004/020189 | 3/2004 |
| WO | WO 2004/021989 | 3/2004 |
| WO | WO 2004/022054 | 3/2004 |
| WO | WO 2004/022562 | 3/2004 |
| WO | WO 2004/024074 | 3/2004 |
| WO | WO 2004/026310 | 4/2004 |
| WO | WO 2004/028541 | 4/2004 |
| WO | WO 2004/035588 | 4/2004 |
| WO | WO 2004/037817 | 5/2004 |
| WO | WO 2004/041826 | 5/2004 |
| WO | WO 2004/108722 | 6/2004 |
| WO | WO 2004/058266 | 7/2004 |
| WO | WO 2004/072080 | 8/2004 |
| WO | WO 2004/072081 | 8/2004 |
| WO | WO 2004/074289 | 9/2004 |
| WO | WO 2004/074290 | 9/2004 |
| WO | WO 2004/082638 | 9/2004 |
| WO | WO 2004/103276 | 12/2004 |
| WO | WO 2004/107863 | 12/2004 |
| WO | WO 2005/000309 | 1/2005 |
| WO | WO 2005/012306 | 2/2005 |
| WO | WO 2005/014599 | 2/2005 |
| WO | WO 2005/014633 | 2/2005 |
| WO | WO 2005/019220 | 3/2005 |
| WO | WO 2005/023771 | 3/2005 |
| WO | WO 2005/034837 | 4/2005 |
| WO | WO 2005/113553 | 4/2005 |
| WO | WO 2005/047290 | 5/2005 |
| WO | WO 2005/061506 | 7/2005 |
| WO | WO 2005/103022 | 11/2005 |
| WO | WO 2005/103052 | 11/2005 |
| WO | WO 2005/120513 | 12/2005 |
| WO | WO 2006/013095 | 2/2006 |
| WO | WO 2006/025567 | 3/2006 |
| WO | WO 2006/029980 | 3/2006 |
| WO | WO 2006/034312 | 3/2006 |
| WO | WO 2006/038001 | 4/2006 |
| WO | WO 2006/044509 | 4/2006 |
| WO | WO 2006/045096 | 4/2006 |
| WO | WO 2006/049339 | 5/2006 |
| WO | WO 2006/053121 | 5/2006 |
| WO | WO 2004/052286 | 6/2006 |
| WO | WO 2006/065755 | 6/2006 |
| WO | WO 2006/065788 | 6/2006 |
| WO | WO 2006/070943 | 7/2006 |
| WO | WO 2006/078891 | 7/2006 |
| WO | WO 2006/125101 | 11/2006 |
| WO | WO 2006/131003 | 12/2006 |
| WO | WO 2006/133559 | 12/2006 |
| WO | WO 2007/002540 | 1/2007 |

\* cited by examiner

IMIDAZO BASED HETEROCYCLES

CROSS REFERENCE TO RELATED APPLICATION

This application is a continuation-in-part and claims priority to U.S. Provisional Application Ser. No. 60/714,016 filed on Sep. 2, 2005 and U.S. Provisional Application Ser. No. 60/837,560 filed on Aug. 14, 2006.

BACKGROUND OF THE INVENTION

Protein phosphorylation, at specific amino acid residues, is important for the regulation of many cellular processes including cell cycle progression and division, signal transduction, and apoptosis. The phosphorylation is usually a transfer reaction of the terminal phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine (S/T) kinases. The phosphorylation reactions, and counteracting phosphatase reactions, on the tyrosine, serine and threonine residues are involved in countless cellular processes that underlie responses to diverse intracellular signals, regulation of cellular functions, and activation or deactivation of cellular processes. A cascade of protein kinases often participate in intracellular signal transduction and are necessary for the realization of cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell. Given the importance and diversity of protein kinase function, it is not surprising that alterations in phosphorylation are associated with many diseases such as cancer, diabetes, inflammation, and hypertension.

The identification of effective small molecules that specifically inhibit protein kinases involved in abnormal or inappropriate cell proliferation, signaling, differentiation, protein production, or metabolism is therefore desirable. In particular, the identification of methods and compounds that specifically inhibit the function of kinases that are involved in immune modulation or proliferative disorders.

The present invention provides novel compounds that inhibit one or more S/T kinase or receptor or non-receptor tyrosine kinase. The compounds of the present invention affect cytokine inhibitory activity.

Cytokine mediated diseases and cytokine inhibition, suppression and antagonism are used in the context of diseases or conditions in which excessive or unregulated production or activity of one or more cytokine occurs. Examples of such cytokines are tumour necrosis factor alpha (TNFα), interleukin-1 (IL-1), interleukin-6 (IL-6) and interleukin-8 (IL-8). There remains a need for compounds which are useful in treating cytokine mediated diseases, and as such, inhibit, suppress or antagonize the production or activity of cytokines such as TNF, IL-1, IL-6 and IL-8.

The p38 MAP kinase (p38, also known as CSBP or SAPK) signaling pathway has been reported to be responsible for the expression of pro-inflammatory cytokines (such as TNF, IL-1, IL-6, IL-8) that are elevated in many inflammatory and auto-immune diseases (see J. C. Lee, *Nature Reviews Drug Discovery* 2003, 2, 717-726 and references cited therein). This pathway has been shown to be activated by cellular stressors, such as osmotic shock, UV light, free radicals, bacterial toxins, viruses, cytokines, chemokines and in response, mediates the expression of several cytokines including, but not limited to, TNF, IL-1, IL-6 and IL-8. In cells of myeloid lineage, such as macrophages and monocytes, both IL-1 and TNFα are transcribed in response to p38 activation. Subsequent translation and secretion of these and other cytokines initiates a local or systemic inflammatory response in adjacent tissue and through infiltration of leukocytes. While this response is a normal part of the physiological response to cellular stress, acute or chronic cellular stress leads to the excess or unregulated expression of pro-inflammatory cytokines. This, in turn, leads to tissue damage, often resulting in pain and debilitation. (see G. Panayi, *N Engl J Med* 2001, 344(12), 907; J. Smolen *Nature Reviews Drug Discovery* 2003, 2, 473 and references cited therein). The four known isoforms of p38 MAP kinase (p38 α, β, γ, δ) each showing different expression levels, tissue distributions and regulation, support the concept that they are involved in the etiology of many diseases.

Many solid tumours increase in mass through proliferation of malignant cells and stromal cells, including endothelial cells. In order for a tumor to grow lager than 2-3 mm in diameter, it must form a vasculature, a process known as angiogenesis. A selective p38 inhibitor has been shown to inhibit angiogenesis (see J. R. Jackson, *J. Pharmacol Exp. Therpaeutics*, 1998, 284, 687). Because angiogenesis is a critical component of the mass expansion of solid tumours, the development of new p38 kinase inhibitors for the inhibition of this process represents a promising approach for anti-tumour therapy. The compounds of the present invention are also useful in inhibiting growth of susceptible neoplasms (see R. M. Schultz, *Potential of p38 MAP kinase inhibitors in the treatment of cancer*. In: E. Jucker (editor), *Progress in Drug Research* 2003, 60, 59-92. The term "susceptible neoplasm" used in present application includes human cancers such as malignant melanoma, colorectal carcinoma, gastric carcinoma, breast carcinoma and non-small cell lung carcinoma.

Furthermore, inhibition of p38 kinase may be effective in treatment of certain viral conditions such as influenza (*J. Immunology*, 2000, 164, 3222), rhinovirus (*J. Immunology*, 2000, 165, 5211) and HIV (*Proc. Nat. Acad. Sci.*, 1998, 95, 7422).

In summary, a number of inhibitors of p38 kinase are under active investigation for the treatment of a variety of disorders (Boehm, Adams *Exp. Opin. Ther. Patents* 2000, 10(1), 25-37. There remains a need for treatment in this field for compounds that are cytokine suppressive, i.e compounds that are capable of inhibiting p38 kinase.

SUMMARY OF THE INVENTION

The present invention is directed to a compound of formula (I), referred to as embodiment IA,

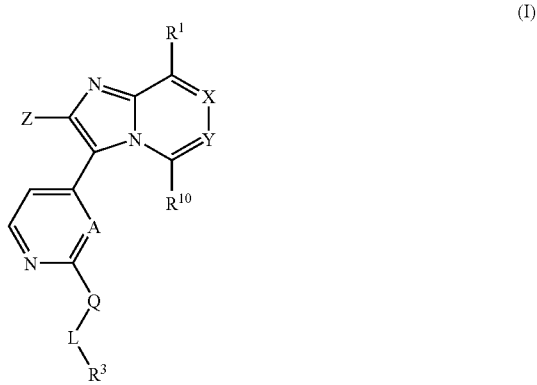

pharmaceutically acceptable salts thereof, metabolites thereof, isomers thereof, or pro-drugs thereof, wherein Z is an optionally substituted aryl or heteroaryl;

X and Y are each independently N, $CR^4$ or N-oxide, provided that X and Y cannot both be $CR^4$ or X and Y cannot both be N-oxide;

A is N, $CR^4$ or N-oxide;

$R^1$ and $R^{10}$ is each independently H, OH, F, Cl, Br, I, $CF_3$, CN, $OCF_3$, nitro or amino; or $R^1$ and $R^{10}$ is each independently selected from the optionally substituted group consisting of aryloxy, ($C_1$-$C_6$)alkyl, ($C_1$-$C_6$)alkoxy, ($C_1$-$C_6$)alkyl-O—($C_1$-$C_6$)alkyl, ($C_2$-$C_8$)alkenyl, ($C_2$-$C_8$)alkynyl, ($C_3$-$C_8$)cycloalkyl, ($C_3$-$C_8$)cycloalkyl($C_1$-$C_6$)alkyl, heterocyclyl, aryl, —$CO_2$($C_1$-$C_6$)alkyl, —$CONR^5R^6$, —$SO_2NR^5R^6$, $SO_{(n)}$alkyl, —$NHCOR^5$, —$NHSO_2R^5$, —N(($C_1$-$C_4$)alkyl)$COR^5$, —N(($C_1$-$C_4$)alkyl)$SO_2R^5$, $NR^5R^6$, O($C_1$-$C_6$)alkyl-$R^7$ and ($C_1$-$C_6$)alkyl$R^7$;

Q is $N(R^2)$, O, S or is a bond;

L is a bond, ($C_1$-$C_6$)alkyl, C(O), —C(O)—O—, —C(O)—N(H)—, SO or $SO_2$;

$R^3$ is selected from the group consisting of H, —C(O)$NR^5R^6$, —$NR^2C(O)R^5$, —$NR^2C(O)_2R^5$, C(O)$OR^2$,

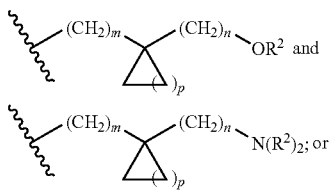

$R^3$ is selected from the optionally substituted group consisting of aryl, heterocyclyl, heterocyclylalkylaryl, 1,4-dioxaspiro[4.5]decane, azabicyclo[3.2.1]octane and azabicyclo[2.2.2]octane; or $R^3$ is selected from the optionally substituted group consisting of ($C_1$-$C_9$)alkyl and ($C_3$-$C_8$)cycloalkyl;
wherein the ($C_1$-$C_9$)alkyl and ($C_3$-$C_8$)cycloalkyl are optionally substituted with one or more ($C_1$-$C_6$)alkyl, ($C_1$-$C_6$)alkyl-$OR^2$, $OR^2$ or $N(R^2)_2$;

$R^2$ for each occurrence is independently H or ($C_1$-$C_4$)alkyl;

$R^4$ is H, OH, F, Cl, Br, I, $CF_3$, CN, $OCF_3$, nitro or amino; or $R^4$ is selected from optionally substituted group consisting of ($C_1$-$C_6$)alkyl, ($C_1$-$C_6$)alkoxy, aryloxy, ($C_2$-$C_8$)alkenyl, ($C_2$-$C_8$)alkynyl, heterocyclyl, aryl, —$CONR^5R^6$, —$SO_2NR^5R^6$, —$SO_{(n)}$alkyl, —$NR^2COR^5$, —$NR^2SO_2R^5$, —$NR^5R^6$, —$CO_2$($C_1$-$C_6$)alkyl, —N(($C_1$-$C_4$)alkyl)CO—$R^5$, or —N(($C_1$-$C_4$)alkyl)$SO_2$—$R^5$;

$R^5$ and $R^6$ are each independently H, or are independently selected from the optionally substituted group consisting of ($C_1$-$C_6$)alkyl, ($C_1$-$C_6$)alkoxy, ($C_2$-$C_6$)hydroxyalkyl, ($C_2$-$C_6$)aminoalkyl, ($C_3$-$C_8$)cycloalkyl, aryl and heterocyclyl; or $R^5$ and $R^6$ are taken together with the N atom to which they are attached to form an optionally substituted heteroaryl or heterocyclyl ring;

$R^7$ is $CF_3$, $NR^5R^6$, OH, ($C_1$-$C_6$)alkoxy or optionally substituted ($C_3$-$C_8$)cycloalkyl;

m is 0, 1 or 2;

n is 0, 1, 2; and p is 1, 2, 3 or 4.

A preferred embodiment of a compound of formula (I), referred to as embodiment IB, pharmaceutically acceptable salts thereof, metabolites thereof, isomers thereof, or pro-drugs thereof, wherein Z is optionally substituted aryl.

A preferred embodiment of any of the foregoing embodiments, referred to as embodiment IC, pharmaceutically acceptable salts thereof, metabolites thereof, isomers thereof, or pro-drugs thereof, $R^1$ is H, Cl, methoxy, methyl, ethyl, isopropyl, $OCH(CH_3)_2$, $OCH_2CF_3$, $OCF_3$, $OCH_2$-cyclopropyl, $CH_2$-cyclopropyl, $NHCH_3$, $N(CH_3)_2$, $NH_2$, $OCH_2CH_2OCH_3$, $OCH_2CH(CH_3)_2$ or cyclopropyl;

$R^{10}$ is H;

X is N or N-oxide;

Y is $CR^4$;

Z is optionally substituted naphthyl or optionally substituted phenyl wherein one or more substituents are selected from the group consisting of F, Cl, $CF_3$ and $CH_3$;

A is N;

Q is $N(R^2)$;

L is a bond, $CH(CH_3)$, ($C_1$-$C_4$)alkyl or C(O);

$R^3$ is selected from the optionally substituted group consisting of ($C_2$-$C_5$)alkyl, cyclopropyl, cyclopentyl and cyclohexyl wherein the alkyl, cyclopropyl, cyclopentyl and cyclohexyl are optionally substituted with one or more alkyl, $OR^2$ or $N(R^2)_2$; or $R^3$ is selected from $NHC(O)R^5$ or the optionally substituted group consisting of azepanyl, phenyl, piperidinyl, pyrimidinyl, pyrrolidinyl, tetrahydrofuranyl, tetrahydrothiopyranyl, thienyl, C(O)$OR^2$, tetrahydropyranyl, 1,4-dioxaspiro[4.5]decane, azabicyclo[2.2.2]octane, azabicyclo[3.2.1]octane,

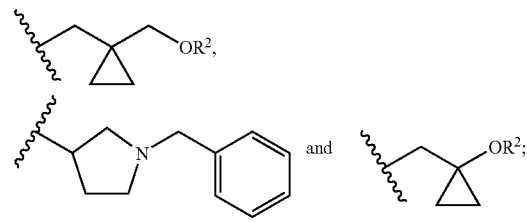

wherein one or more substituents are selected from the group consisting of alkyl, alkyl-$OR^2$, $OR^2$, $NR^2$, $S(O)_2$—$CH_3$, C(O)$CH_3$, C(O)OC($CH_3$)$_3$, C(O)$CH_2$OH, methyl, oxo and COOH;

$R^2$ is H, methyl or t-butyl;

$R^4$ is H, methyl, ethyl, $OCH_3$ or Cl; and $R^5$ is methyl or OC($CH_3$)$_3$.

A preferred embodiment of any of the foregoing embodiments, referred to as embodiment ID, pharmaceutically acceptable salts thereof, metabolites thereof, isomers thereof, or pro-drugs thereof, wherein $R^1$ is H, methoxy, methyl, ethyl, isopropyl, $OCH(CH_3)_2$, $OCH_2CF_3$, $OCH_2$-cyclopropyl, $CH_2$-cyclopropyl, $NHCH_3$, $N(CH_3)_2$, $NH_2$, $OCH_2CH_2OCH_3$ or $OCH_2CH(CH_3)_2$;

X is N;

Z is unsubstituted naphthyl or phenyl optionally substituted with one or more F, Cl, $CF_3$ or methyl;

L is a bond, $CH(CH_3)$, or $CH_2$;

$R^3$ is selected from the optionally substituted group consisting of cyclopropyl, cyclopentyl, cyclohexyl and $(C_3-C_5)$alkyl wherein one or more substituents are selected from the group consisting of alkyl, alkyl-$OR^2$, $OR^2$ and $N(R^2)_2$; or $R^3$ is selected from the optionally substituted group consisting of phenyl, piperidinyl, tetrahydropyranyl, tetrahydrothiopyranyl, thienyl, 1,4-dioxaspiro[4.5]decane, azabicyclo [3.2.1]octane,

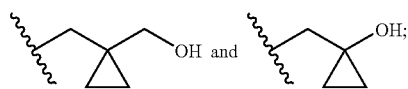

wherein one or more substituents are selected from the group consisting of alkyl, alkyl$OR^2$, $OR^2$, $S(O)_2$—$CH_3$, $C(O)CH_3$, $C(O)OC(CH_3)_3$, $C(O)CH_2OH$, methyl and COOH;

$R^2$ is H or t-butyl; and $R^4$ is H, methyl, or ethyl.

A preferred embodiment of any of the foregoing embodiments, referred to as embodiment IE, pharmaceutically acceptable salts thereof, metabolites thereof, isomers thereof, or pro-drugs thereof, wherein $R^1$ is H, methoxy, methyl, ethyl, $OCH(CH_3)_2$ or $CH_2$-cyclopropyl;

Y is CH;

Z is phenyl optionally substituted with one or more F, Cl, $CF_3$ or methyl;
wherein the substituents can be meta, para or disubstituted ortho, para;

$R^3$ is selected from the group consisting of unsubstituted cyclopropyl, unsubstituted phenyl, unsubstituted cyclopentyl, unsubstituted cyclohexyl, unsubstituted thienyl,

$(C_3-C_5)$alkyl substituted with one or more alkyl, alkyl-$OR^2$ or $OR^2$, and piperidinyl substituted with $S(O)_2$—$CH_3$, $C(O)CH_3$, $C(O)OC(CH_3)_3$, $C(O)CH_2OH$ or COOH; and $R^2$ is H or t-butyl.

A preferred embodiment of any of the foregoing embodiments, referred to as embodiment IF, pharmaceutically acceptable salts thereof, metabolites thereof, isomers thereof, or pro-drugs thereof, wherein $R^1$ is H, methoxy, methyl, $OCH(CH_3)_2$ or —$CH_2$-cyclopropyl;

Q is N(H);

L is a bond or $CH(CH_3)$; and $R^3$ is selected from the group consisting of unsubstituted cyclopropyl, unsubstituted cyclopentyl, unsubstituted cyclohexyl, unsubstituted phenyl,

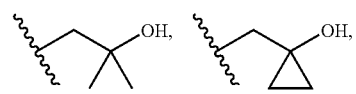

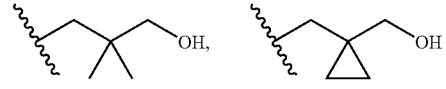

and piperidinyl wherein the piperidinyl is substituted with $S(O)_2$—$CH_3$ or $C(O)CH_3$.

A preferred embodiment of any of the foregoing embodiments, referred to as embodiment IG, pharmaceutically acceptable salts thereof, metabolites thereof, isomers thereof, or pro-drugs thereof, wherein the compound is

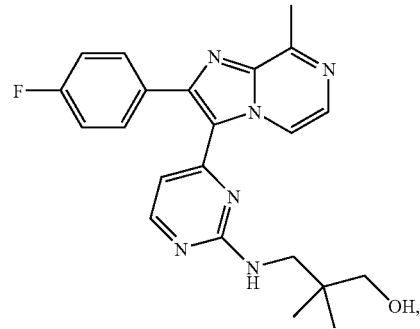

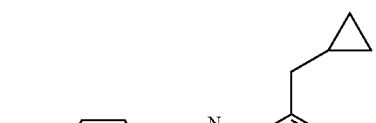

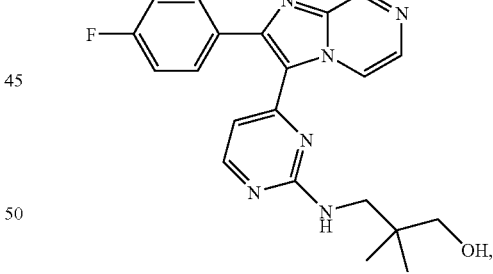

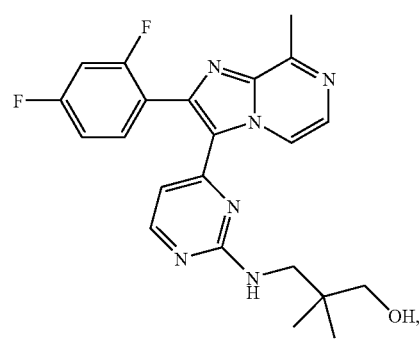

-continued

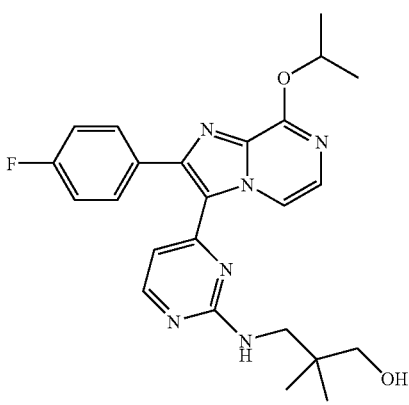

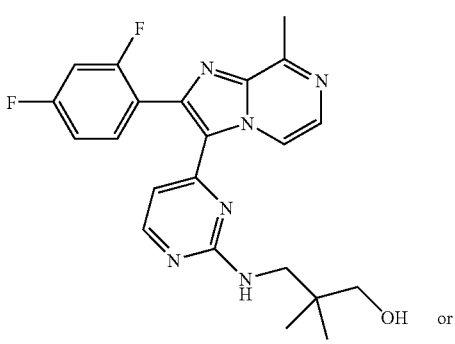

or

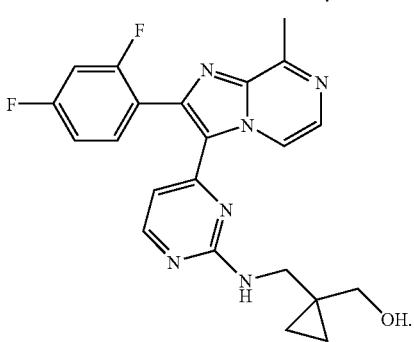

The present invention is further directed to a compound of formula (I),

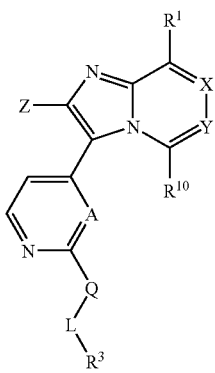

pharmaceutically acceptable salts thereof, metabolites thereof, isomers thereof, or pro-drugs thereof, wherein Z is an optionally substituted aryl or heteroaryl;

X and Y are each independently N, $CR^4$ or N-oxide, provided that X and Y cannot both be $CR^4$ or X and Y cannot both be N-oxide;

A is N, $CR^4$ or N-oxide;

$R^1$ and $R^{10}$ is each independently H, OH, F, Cl, Br, I, $CF_3$, CN, $OCF_3$, nitro or amino; or $R^1$ and $R^{10}$ is each independently selected from the optionally substituted group consisting of aryloxy, $(C_1-C_6)$alkyl, $(C_1-C_6)$alkoxy, $(C_1-C_6)$alkyl-O—$(C_1-C_6)$alkyl, $(C_2-C_8)$alkenyl, $(C_2-C_8)$alkynyl, $(C_3-C_8)$cycloalkyl, $(C_3-C_8)$cycloalkyl$(C_1-C_6)$alkyl, heterocyclyl, aryl, —$CO_2(C_1-C_6)$alkyl, —$CONR^5R^6$, —$SO_2NR^5R^6$, $SO_{(n)}$alkyl, —$NHCOR^5$, —$NHSO_2R^5$, —$N((C_1-C_4)$alkyl$)COR^5$, —$N((C_1-C_4)$alkyl$)SO_2R^5$, $NR^5R^6$, $O(C_1-C_6)$alkyl-$R^7$ and $(C_1-C_6)$alkyl$R^7$;

Q is $N(R^2)$, O, S or is a bond;

L is a bond, $(C_1-C_6)$alkyl, C(O), —C(O)—O—, —C(O)—N(H)—, SO or $SO_2$;

$R^3$ is selected from the group consisting of H, —C(O)$NR^5R^6$, —$NR^2C(O)R^5$, —$NR^2C(O)_2R^5$,

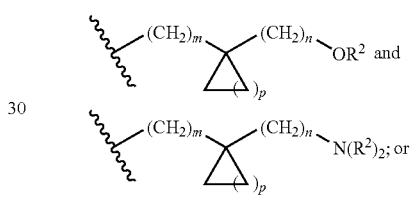

$R^3$ is selected from the optionally substituted group consisting of aryl, heterocyclyl, heterocyclylalkylaryl, 1,4-dioxaspiro[4.5]decane, azabicyclo[3.2.1]octane, azabicyclo[2.2.2]octane, $(C_1-C_9)$alkyl and $(C_3-C_8)$cycloalkyl;

wherein the $(C_1-C_9)$alkyl and $(C_3-C_8)$cycloalkyl are optionally substituted with one or more $(C_1-C_6)$alkyl, $(C_1-C_6)$alkyl-$OR^2$, $OR^2$ or $N(R^2)_2$;

$R^2$ for each occurrence is independently H or $(C_1-C_4)$alkyl;

$R^4$ is H, OH, F, Cl, Br, I, $CF_3$, CN, $OCF_3$, nitro or amino; or $R^4$ is selected from optionally substituted group consisting of $(C_1-C_6)$alkyl, $(C_1-C_6)$alkoxy, aryloxy, $(C_2-C_8)$alkenyl, $(C_2-C_8)$alkynyl, heterocyclyl, aryl, —$CONR^5R^6$, —$SO_2NR^5R^6$, —$SO(f)$alkyl, —$NR^2COR^5$, —$NR^2SO_2R^5$, —$NR^5R^6$, —$CO_2(C_1-C_6)$alkyl, —$N((C_1-C_4)$alkyl$)CO—R^5$, or —$N((C_1-C_4)$alkyl$)SO_2—R^5$;

$R^5$ and $R^6$ are each independently H, or are independently selected from the optionally substituted group consisting of $(C_1-C_6)$alkyl, $(C_1-C_6)$alkoxy, $(C_2-C_6)$hydroxyalkyl, $(C_2-C_6)$aminoalkyl, $(C_3-C_8)$cycloalkyl, aryl and heterocyclyl; or $R^5$ and $R^6$ are taken together with the N atom to which they are attached to form an optionally substituted heteroaryl or heterocyclyl ring;

$R^7$ is $CF_3$, $NR^5R^6$, OH, $(C_1-C_6)$alkoxy or optionally substituted $(C_3-C_8)$cycloalkyl;

m is 0, 1 or 2;

n is 0, 1, 2; and p is 1, 2, 3 or 4.

A preferred embodiment of a compound of formula (I), referred to as embodiment 1, pharmaceutically acceptable salts thereof, metabolites thereof, isomers thereof, or prodrugs thereof, wherein Z is optionally substituted aryl.

A preferred embodiment of a compound of formula (I), referred to as embodiment 2, pharmaceutically acceptable salts thereof, metabolites thereof, isomers thereof, or prodrugs thereof, wherein $R^1$ is H, methoxy, methyl, ethyl, isopropyl, $OCH(CH_3)_2$, $OCH_2CF_3$, $OCH_2$-cyclopropyl, $CH_2$-cyclopropyl, $NHCH_3$, $N(CH_3)_2$, $NH_2$, $OCH_2CH_2OCH_3$, $OCH_2CH(CH_3)_2$ or cyclopropyl, $R^{10}$ is H, X is N or N-oxide, Y is $CR^4$, Z is optionally substituted naphthyl or optionally substituted phenyl wherein one or more substituents are selected from the group consisting of F, Cl, $CF_3$ and $CH_3$, A is N, Q is $N(R^2)$, L is a bond, $CH(CH_3)$, $(C_1-C_4)$alkyl or $C(O)$, $R^3$ is selected from the optionally substituted group consisting of $(C_2-C_5)$alkyl, cyclopropyl, cyclopentyl and cyclohexyl wherein the alkyl, cyclopropyl, cyclopentyl and cyclohexyl are optionally substituted with one or more alkyl, $OR^2$ or $N(R^2)_2$; or $R^3$ is selected from $NHC(O)R^5$ or the optionally substituted group consisting of azepanyl, phenyl, piperidinyl, pyrimidinyl, pyrrolidinyl, tetrahydrofuranyl, tetrahydrothiopyranyl, thienyl, tetrahydropyranyl, 1,4-dioxaspiro[4.5]decane, azabicyclo[2.2.2]octane, azabicyclo[3.2.1]octane,

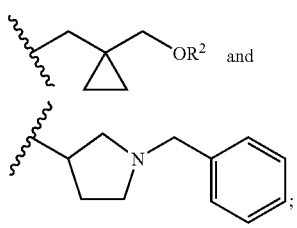

and wherein one or more substituents are selected from the group consisting of alkyl, alkyl-$OR^2$, $OR^2$, $NR^2$, $S(O)_2$—$CH_3$, $C(O)CH_3$, $C(O)OC(CH_3)_3$, $C(O)CH_2OH$, methyl, oxo and COOH, $R^2$ is H, methyl or t-butyl, $R^4$ is H, ethyl, $OCH_3$ or Cl; and $R^5$ is methyl or $OC(CH_3)_3$.

A preferred embodiment of a compound of formula (I), referred to as embodiment 3, pharmaceutically acceptable salts thereof, metabolites thereof, isomers thereof, or prodrugs thereof, wherein $R^1$ is H, methoxy, methyl, ethyl, isopropyl, $OCH(CH_3)_2$, $OCH_2CF_3$, $OCH_2$-cyclopropyl, $CH_2$-cyclopropyl, $NHCH_3$, $N(CH_3)_2$, $NH_2$, $OCH_2CH_2OCH_3$ or $OCH_2CH(CH_3)_2$, X is N, Z is unsubstituted naphthyl or phenyl optionally substituted with one or more F, Cl, $CF_3$ or methyl, L is a bond, $CH(CH_3)$, or $CH_2$, $R^3$ is selected from the optionally substituted group consisting of cyclopropyl, cyclopentyl, cyclohexyl and $(C_3-C_5)$alkyl wherein one or more substituents are selected from the group consisting of alkyl, alkyl-$OR^2$, $OR^2$ and $N(R^2)_2$; or $R^3$ is selected from the optionally substituted group consisting of phenyl, piperidinyl, tetrahydropyranyl, tetrahydrothiopyranyl, thienyl, 1,4-dioxaspiro[4.5]decane and azabicyclo[3.2.1]octane or

wherein one or more substituents are selected from the group consisting of alkyl, alkylOR$^2$, $OR^2$, $S(O)_2$—$CH_3$, $C(O)CH_3$, $C(O)OC(CH_3)_3$, $C(O)CH_2OH$, COOH and methyl; $R^2$ is H or t-butyl and $R^4$ is H or ethyl.

A preferred embodiment of a compound of formula (I), referred to as embodiment 4, pharmaceutically acceptable salts thereof, metabolites thereof, isomers thereof, or prodrugs thereof, $R^1$ is H, methoxy, methyl, ethyl, $OCH(CH_3)_2$ or $CH_2$-cyclopropyl, Y is CH, Z is phenyl optionally substituted with one or more F, Cl, $CF_3$ or methyl; wherein the substituents can be meta, para or disubstituted ortho, para; $R^3$ is selected from the group consisting of unsubstituted cyclopropyl, $(C_3-C_5)$alkyl substituted with one or more alkyl, alkyl-$OR^2$ or $OR^2$, unsubstituted phenyl, unsubstituted cyclopentyl, unsubstituted cyclohexyl, unsubstituted thienyl and piperidinyl substituted with $S(O)_2$—$CH_3$, $C(O)CH_3$, $C(O)OC(CH_3)_3$, $C(O)CH_2OH$ or COOH, and $R^2$ is H or t-butyl.

A preferred embodiment of a compound of formula (I), referred to as embodiment 5, pharmaceutically acceptable salts thereof, metabolites thereof, isomers thereof, or prodrugs thereof, $R^1$ is H, methoxy, methyl, $OCH(CH_3)_2$ or —$CH_2$-cyclopropyl, Q is N(H);

L is a bond or $CH(CH_3)$, and $R^3$ is selected from the group consisting of unsubstituted cyclopropyl, unsubstituted cyclopentyl, unsubstituted cyclohexyl, unsubstituted phenyl,

and piperidinyl wherein the piperidinyl is substituted with $S(O)_2$—$CH_3$ or $C(O)CH_3$.

A preferred embodiment of a compound of formula (I), referred to as embodiment 6, pharmaceutically acceptable salts thereof, metabolites thereof, isomers thereof, or prodrugs thereof, wherein the compound is

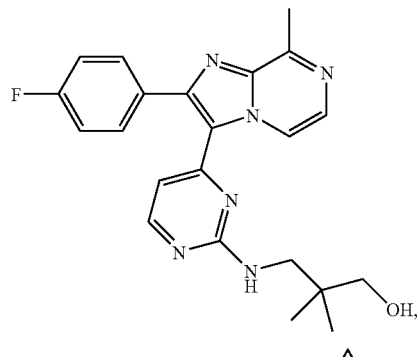

-continued

The present invention is further directed to a compound of formula (I), referred to as embodiment A (I)

pharmaceutically acceptable salts thereof, metabolites thereof, isomers thereof, or pro-drugs thereof, wherein Z is an optionally substituted aryl or heteroaryl;

X and Y are each independently N, $CR^4$ or N-oxide, provided that X and Y cannot both be $CR^4$ or X and Y cannot both be N-oxide;

A is N or $CR^4$;
  $R^4$ is H, F, Cl, Br, I, $CF_3$, CN, $OCF_3$, $(C_1$-$C_6)$alkyl, $(C_1$-$C_6)$alkoxy, nitro, amino, aryloxy, $(C_2$-$C_8)$alkenyl, $(C_2$-$C_8)$alkynyl, heterocyclyl, aryl, —$CONR^5R^6$, —$SO_2NR^5R^6$, —$SO_{(n)}$alkyl, —$NR^2COR^5$, —$NR^2SO_2R^5$, or —$NR^5R^6$;

$R^1$ and $R^{10}$ is each independently H, F, Cl, Br, I, $CF_3$, CN, $OCF_3$, nitro, amino, aryloxy, $(C_1$-$C_6)$alkyl, $(C_1$-$C_6)$alkoxy, $(C_2$-$C_8)$alkenyl, $(C_2$-$C_8)$alkynyl, heterocyclyl, aryl, —$CO_2(C_1$-$C_6)$alkyl, —$CONR^5R^6$, —$SO_2NR^5R^6$, $SO_{(n)}$alkyl, —$NHCOR^5$, —$NHSO_2R^5$, —$N((C_1$-$C_4)$alkyl$)COR^5$, —$N((C_1$-$C_4)$alkyl$)SO_2R^5$, or $NR^5R^6$;

$R^5$ and $R^6$ are each independently H, $(C_1$-$C_6)$alkyl, $(C_2$-$C_6)$hydroxyalkyl, $(C_2$-$C_6)$aminoalkyl, $(C_3$-$C_8)$cycloalkyl, aryl or heterocyclyl;
  or $R^5$ and $R^6$ are taken together with the N atom to which they are attached to form a heteroaryl or heterocyclyl ring;

Q is $N(R^2)$, O, S or is a bond;
  $R^2$ is H or $(C_1$-$C_4)$alkyl;

L is a bond, $(C_1$-$C_4)$alkyl, C(O), —C(O)—O—, —C(O)—N(H)— or $SO_2$;

$R^3$ is H, $(C_1$-$C_6)$alkyl optionally substituted with one or more $OR^2$ or $N(R^2)_2$, $(C_3$-$C_8)$cycloalkyl optionally substituted with one or more $OR^2$ or $N(R^2)_2$, optionally substituted aryl, or optionally substituted heterocyclyl; and n is 0, 1, 2.

A preferred embodiment of embodiment A referred to as embodiment B, pharmaceutically acceptable salts thereof, metabolites thereof, isomers thereof, or pro-drugs thereof, wherein Z is selected from the optionally substituted group consisting of phenyl, naphthyl, azaindolyl, benzo(b)thienyl, benzimidazolyl, benzofuranyl, benzoxazolyl, benzothiazolyl, benzothiadiazolyl, benzothiophenyl, benzoxadiazolyl, furanyl, imidazolyl, imidazopyridinyl, indolyl, indolinyl, indazolyl, isoindolinyl, isoxazolyl, isothiazolyl, oxadiazolyl, oxazolyl, purinyl, pyranyl pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, tetrahydroindolyl, tetrazolyl, thiadiazolyl, thienyl, thiomorpholinyl, thiophenyl, triazolyl and tropanyl.

A preferred embodiment of embodiment C, referred to as embodiment D, is where Z is optionally substituted phenyl, naphthyl, furanyl or thiophenyl.

A preferred embodiment of embodiment D, referred to as embodiment E, is where Z is phenyl or naphthyl optionally substituted with one or more substituents each independently selected from the group consisting of F, Cl, methyl, $CF_3$, and $OCF_3$.

A preferred embodiment of embodiment E, referred to as embodiment F, is where Z is optionally substituted phenyl, substituted at either the meta- or para-position by F, Cl, methyl, $CF_3$, and $OCF_3$.

A preferred embodiment of any of the foregoing embodiments is where $R^1$ is H or halo.

A preferred embodiment of any of the foregoing embodiments is where $R^{10}$ is H, halo or —$NR^5R^6$.

A preferred embodiment of any of the foregoing embodiments is where $R^{10}$ is H.

A preferred embodiment of any of the foregoing embodiments is where A is N.

A preferred embodiment of any of the foregoing embodiments is where $R^2$ is H.

A preferred embodiment of any of the foregoing embodiments is where L is a bond or CO.

A preferred embodiment of any of the foregoing embodiments is where $R^3$ is methyl, ethyl, propyl, isopropyl, butyl, iso-butyl, sec-butyl, tert-butyl, pentyl, isopentyl, hexyl, iso-hexyl, cyclopropyl, cyclobutyl, cyclopentyl, cyclohexyl, —C(H)($CH_3$)phenyl, —C(H)($CH_2CH_3$)phenyl, piperidinyl, or N-acylpiperidinyl.

Other embodiments of the present invention are disclosed in the present specification.

DETAILED DESCRIPTION OF THE INVENTION

Protein kinases are a broad and diverse class, of over 500 enzymes, that include oncogenes, growth factors receptors, signal transduction intermediates, apoptosis related kinases and cyclin dependent kinases. They are responsible for the transfer of a phosphate group to specific tyrosine, serine or threonine amino acid residues, and are broadly classified as tyrosine and Serine/Threonine kinases as a result of their substrate specificity. Serine/Threonine Kinases (S/T kinases) are a large sub-family of protein kinases that specifically transfer a phosphate group to a terminal hydroxyl moiety of specific serine or threonine residues (Hanks et al., (1988) Science, 241: 42-52). A number of S/T kinase family members are involved in inflammatory signaling, tumor growth or cellular transformation. For example, the mitogen-activated protein kinases (MAPKs) are S/T kinases that act as intermediates within the signaling cascades of Toll like receptors (TLRs), such as TLR4, growth/survival factors, such as EGF, and death receptors, such as the TNF receptor. Activation of MAPKs, such as extracellular signal-regulated kinases (ERK1-2), p38α, c-Jun N-terminal kinase (JNK) or MAP-KAP-K2 (MK2) have been shown to transduce signaling in cells, such as monocytes/macrophages, resulting in the extracellular production of pro-inflammatory cytokines, such as TNF.

The p38 MAP kinase (p38, also known as CSBP or SAPK) signaling pathway has been reported to be responsible for the expression of pro-inflammatory cytokines (such as TNF, IL-1, IL-6, IL-8) that are elevated in many inflammatory and auto-immune diseases (see J. C. Lee, Nature Reviews Drug Discovery 2003, 2, 717-726 and references cited therein). This pathway has been shown to be activated by cellular stressors, such as osmotic shock, UV light, free radicals, bacterial toxins, viruses, cytokines, chemokines and in response, mediates the expression of several cytokines including, but not limited to, TNF, IL-1, IL-6 and IL-8. In cells of myeloid lineage, such as macrophages and monocytes, both IL-1 and TNFα are transcribed in response to p38 activation. Subsequent translation and secretion of these and other cytokines initiates a local or systemic inflammatory response in adjacent tissue and through infiltration of leukocytes. While this response is a normal part of the physiological response to cellular stress, acute or chronic cellular stress leads to the excess or unregulated expression of pro-inflammatory cytokines. This, in turn, leads to tissue damage, often resulting in pain and debilitation. (see G. Panayi, N Engl J Med 2001, 344(12), 907; J. Smolen Nature Reviews Drug Discovery 2003, 2, 473 and references cited therein). The four known isoforms of p38 MAP kinase (p38 α, β, γ, δ) each showing different expression levels, tissue distributions and regulation, support the concept that they are involved in the etiology of inflammatory, auto-immune and other diseases.

In summary, a number of inhibitors of p38 kinase are under active investigation for the treatment of a variety of disorders (Boehm, Adams Exp. Opin. Ther. Patents 2000, 10(1), 25-37). There remains a need for treatment in this field for compounds that are cytokine suppressive, i.e compounds that are capable of inhibiting p38 kinase.

Protein tyrosine kinases (PTKs) are enzymes that catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, Neuron 9:383-391). Aberrant or excessive PTK activity has been observed in many disease states including benign and malignant proliferative disorders as well as diseases resulting from inappropriate activation of the immune system (e.g. autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

Tyrosine kinases can be of the receptor-type (having extracellular, transmembrane and intracellular domains) or the non-receptor type (being wholly intracellular).

Receptor Tyrosine Kinases (RTKs) comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, Ann. Rev. Biochem. 57:433-478, 1988; Ullrich and Schlessinger, Cell 61:243-254, 1990). The intrinsic function of RTKs is activated upon ligand binding, which results in phosphorylation of the receptor and multiple cellular substrates, and subsequently in a variety of cellular responses (Ullrich & Schlessinger, 1990, Cell 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response (e.g., cell division, differentiation, metabolic effects, and changes in the extracellular microenvironment; see Schlessinger and Ullrich, 1992, Neuron 9:1-20).

Non-receptor tyrosine kinases represent a collection of cellular enzymes which lack extracellular and transmembrane sequences. Over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. The Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bohlen, 1993, Oncogene 8:2025-2031, which is incorporated herein by reference.

Many of the kinases, whether a receptor or non-receptor tyrosine kinase or a S/T kinase have been found to be involved in cellular signaling pathways involved in numerous pathogenic conditions, including immunomodulation, inflammation, or proliferative disorders such as cancer.

In a related aspect the invention provides a method for inhibiting p38 in a human subject suffering from a disorder in which p38 activity is detrimental, comprising administering to the human subject a compound of Formula (I) such that p38 activity in the human subject is inhibited and treatment is achieved.

Many autoimmune diseases and disease associated with chronic inflammation, as well as acute responses, have been linked to activation of p38 MAP kinase and overexpression or dysregulation of inflammatory cytokines. The present compounds are useful in the treatment of inflammatory disorders including, but not limited to rheumatoid arthritis, osteoarthritis, asthma, chronic obstructive pulmonary disease (COPD), sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy and systemic lupus erythematosus.

The compounds of the invention are also useful in the treatment of cardiovascular disorders, such as acute myocardial infarction, acute coronary syndrome, chronic heart failure, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

The compounds of the invention are also useful in the treatment of an ocular condition, a cancer, a solid tumor, a sarcoma, fibrosarcoma, osteoma, melanoma, retinoblastoma, a rhabdomyosarcoma, glioblastoma, neuroblastoma, teratocarcinoma, an cancers such as lung, breast, stomach, bladder, colon, pancreas, ovarian, prostate and rectal cancer and hematopoietic malignancies (leukemia and lymphoma), Kaposi's sarcoma, Hodgkin's disease, lymphoma, myeloma, leukaemia, malignant ascites, hematopoietic cancers Crow-Fukase (POEMS) syndrome, a diabetic condition such as insulin-dependent diabetes mellitus glaucoma, diabetic retinopathy or microangiopathy, sickle cell anaemia, chronic inflammation, synovitis, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, vascular occlusion, carotid obstructive disease, ulcerative colitis, inflammatory bowel disease, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, *chlamydia, yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of formula (I) of the invention can be used alone or in combination with another therapeutic agent to treat such diseases. It should be understood that the compounds of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the p38 inhibitors of this invention. Non-limiting examples of therapeutic agents for rheumatoid arthritis with which a compound of formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. S/T kinase inhibitors of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD 154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (HUMIRA™), (PCT Publication No. WO 97/29131), CA2 (REMICADE™), CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of formula (I) of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and pS5TNFRIgG (Lenercept)), sIL-1RI, sIL-1RII, sIL-6R), antiinflammatory cytokines (e.g. IL-4, IL-10, IL-1, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO469, VX-702, AMG-548, VX-740, Roflumilast, IC-485, CDC-801, and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. IRAK, NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of formula (I) can be combined include the following: TNF antagonists, for example, anti-TNF antibodies, D2E7 (PCT Publication No. WO 97/29131; HUMIRA™), CA2 (REMICADE™), CDP 571, TNFR-Ig constructs, (p75TNFRIgG (ENBREL™) and p55TNFRIgG (LENERCEP™)) inhibitors and PDE4 inhibitors. A compound of formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors 6-mercaptopurines; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of formula (I) may also be combined with agents such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of formula (I) may also be combined with agents, such as alemtuzumab, dronabinol, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for angina with which a compound of formula (I) of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril and bisoprolol fumarate.

Non-limiting examples of therapeutic agents for ankylosing spondylitis with which a compound of formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, etanercept, and infliximab.

Non-limiting examples of therapeutic agents for asthma with which a compound of formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone and metaproterenol sulfate.

Non-limiting examples of therapeutic agents for COPD with which a compound of formula (I) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of formula (I) can be combined include the following: Interferon-alpha-2a, Interferon-alpha-2b, Interferon-alpha con 1, Interferon-alpha-n 1, pegylated interferon-alpha-2a, pegylated interferon-alpha-2b, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of formula (I) can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, and sulfasalazine.

Non-limiting examples of therapeutic agents for psoriatic arthritis with which a compound of formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept and efalizumab.

Non-limiting examples of therapeutic agents for restenosis with which a compound of formula (I) can be combined include the following: sirolimus, paclitaxel, everolimus, tacrolimus, ABT-578, and acetaminophen.

Non-limiting examples of therapeutic agents for sciatica with which a compound of formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of formula (I) can be combined with IL-11 or anti-cytokine antibodies, for example, fonotolizumab (anti-IFNg antibody), or antireceptor receptor antibodies, for example, anti-IL-6 receptor antibody and antibodies to B-cell surface molecules. A compound of formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (PCT Publication No. WO 97/29131; HUMIRA™), CA2 (REMICADE™), CDP 571, TNFR-Ig constructs, (p75TNFRIgG (ENBREL™) and p55TNFRIgG (LENERCEPT™)).

In this invention, the following definitions are applicable:

A "therapeutically effective amount" is an amount of a compound of Formula I or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Physiologically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of formula I which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of formula I and their salts may exist in more than one crystal form and the present invention includes each crystal form and mixtures thereof.

Certain compounds of formula I and their salts may also exist in the form of solvates, for example hydrates, and the present invention includes each solvate and mixtures thereof.

Certain compounds of formula I may contain one or more chiral centers, and exist in different optically active forms. When compounds of formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula I contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of formula I and mixtures thereof.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —$CH_2$)C(O)H or a moiety that contains a carboxylic acid) wherein the free hydrogen is replaced by ($C_1$-$C_4$)alkyl, ($C_2$-$C_{12}$)alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$alkyl.

Other exemplary pro-drugs release an alcohol of Formula I wherein the free hydrogen of the hydroxyl substituent (e.g., $R^1$ contains hydroxyl) is replaced by $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylamino-methyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, $P(O)(OH)_2$, $—P(O)(O(C_1-C_6)alkyl)_2$ or glycosyl (the radical resulting from detachment of the hydroxyl of the hemiacetal of a carbohydrate).

The term "heterocyclic" or "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinesyl, piperazinyl, piperidinyl, pyrrolidinyl, quinicludinyl, thiomorpholinyl, tetrahydropyranyl and tetrahydrofuranyl.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindole, benzo(b)thienyl, benzimidazolyl, benzofuranyl, benzoxazolyl, benzothiazolyl, benzothiadiazolyl, benzoxadiazolyl, furans, imidazoles, imidazopyridine, indole, indolinyl, indazoles, isoindolinyl, isoxazoles, isothiazoles, oxadiazoles, oxazoles, purine, pyrans, pyrazines, pyrazoles, pyridines, pyrimidines, pyrroles, pyrrolo[2,3-d]pyrimidine, pyrazolo[3,4-d]pyrimidine), quinolines, quinazolines, triazoles, thiazoles, thiophenyl, tetrahydroindole, tetrazoles, thiadiazoles, thienyls, thiomorpholines, triaozles or tropanyl.

When the term "substituted heterocyclic" (or heterocyclyl) or "substituted heteroaryl" is used, what is meant is that the heterocyclic group is substituted with one or more substituents that can be made by one of ordinary skill in the art and results in a molecule that is a kinase inhibitor. For purposes of exemplification, which should not be construed as limiting the scope of this invention, preferred substituents for the heterocycle of this invention are each independently selected from the optionally substituted group consisting of alkenyl, alkoxy, alkoxyalkoxy, alkoxyalkyl, alkoxycarbonyl, alkoxycarbonylheterocycloalkoxy, alkyl, alkylcarbonyl, alkylester, alkyl-O—C(O)—, alkyl-heterocyclyl, alkyl-cycloalkyl, alkyl-nitrile, alkynyl, amido groups, amino, aminoalkyl, aminocarbonyl, carbonitrile, carbonylalkoxy, carboxamido, $CF_3$, CN, —C(O)OH, —C(O)H, —C(O)—C(CH$_3$)$_3$, —OH, —C(O)O-alkyl, —C(O)O-cycloalkyl, —C(O)O-heterocyclyl, —C(O)-alkyl, —C(O)-cycloalkyl, —C(O)-heterocyclyl, cycloalkyl, dialkylaminoalkoxy, dialkylaminocarbonylalkoxy, dialkylaminocarbonyl, halogen, heterocyclyl, a heterocycloalkyl group, heterocyclyloxy, hydroxy, hydroxyalkyl, nitro, $OCF_3$, oxo, phenyl, —SO$_2$CH$_3$, —SO$_2$CR$_3$, tetrazolyl, thienylalkoxy, trifluoromethylcarbonylamino, trifluoromethylsulfonamido, heterocyclylalkoxy, heterocyclyl-S(O)$_p$, cycloalkyl-S(O)$_p$, alkyl-S—, heterocyclyl-S, heterocycloalkyl, cycloalkylalkyl, heterocolthio, cycloalkylthio, —$Z^{105}$—C(O)N(R)$_2$, —$Z^{105}$—N(R)—C(O)—$Z^{200}$, —$Z^{105}$—N(R)—S(O)$_2$—$Z^{200}$, —$Z^{105}$—N(R)—C(O)—N(R)—$Z^{200}$, —N(R)—C(O)R, —N(R)—C(O)OR, OR—C(O)-heterocyclyl-OR, R$_c$ and —CH$_2$OR$_c$;

wherein R$_3$ is $C_1-C_4$ alkyl, $C_3-C_6$ cycloalkyl or phenyl;

wherein p is 0, 1 or 2;

where R$_c$ for each occurrence is independently hydrogen, optionally substituted alkyl, optionally substituted aryl, —(C$_1$-C$_6$)—NR$_d$R$_e$, -E-(CH$_2$)$_t$—NR$_d$R$_e$, -E-(CH$_2$)$_t$—O-alkyl, -E-(CH$_2$)$_t$—S-alkyl, or -E-(CH$_2$)$_t$—OH;

wherein t is an integer from about 1 to about 6;

$Z^{105}$ for each occurrence is independently a covalent bond, alkyl, alkenyl or alkynyl; and $Z^{200}$ for each occurrence is independently selected from an optionally substituted group selected from the group consisting of alkyl, alkenyl, alkynyl, phenyl, alkyl-phenyl, alkenyl-phenyl or alkynyl-phenyl;

E is a direct bond, O, S, S(O), S(O)$_2$, or NR$_f$, wherein R$_f$ is H or alkyl and R$_d$ and R$_e$ are independently H, alkyl, alkanoyl or SO$_2$-alkyl; or R$_d$, R$_e$ and the nitrogen atom to which they are attached together to form a five- or six-membered heterocyclic ring.

An "heterocycloalkyl" group, as used herein, is a heterocyclic group that is linked to a compound by an aliphatic group having from one to about eight carbon atoms. For example, a preferred heterocycloalkyl group is a morpholinomethyl group.

As used herein, "aliphatic" or "an aliphatic group" or notations such as "(C$_0$-C$_8$)" include straight chained or branched hydrocarbons which are completely saturated or which contain one or more units of unsaturation, and, thus, includes alkyl, alkenyl, alkynyl and hydrocarbons comprising a mixture of single, double and triple bonds. When the group is a C$_0$ it means that the moiety is not present or in other words, it is a bond. As used herein, "alkyl" means C$_1$-C$_8$ and includes straight chained or branched hydrocarbons, which are completely saturated. Preferred alkyls are methyl, ethyl, propyl, butyl, pentyl, hexyl and isomers thereof. As used herein, "alkenyl" and "alkynyl" means C$_2$-C$_8$ and includes straight chained or branched hydrocarbons which contain one or more units of unsaturation, one or more double bonds for alkenyl and one or more triple bonds for alkynyl.

As used herein, aromatic groups (or aryl groups) include aromatic carbocyclic ring systems (e.g. phenyl and cyclopentyldienyl) and fused polycyclic aromatic ring systems (e.g. naphthyl, biphenylenyl and 1,2,3,4-tetrahydronaphthyl).

As used herein, cycloalkyl means $C_3-C_{12}$ monocyclic or multicyclic (e.g., bicyclic, tricyclic, etc.) hydrocarbons that is completely saturated or has one or more unsaturated bonds but does not amount to an aromatic group. Preferred examples of a cycloalkyl group are cyclopropyl, cyclobutyl, cyclopentyl, cyclopentenyl, cyclohexyl and cyclohexenyl.

As used herein, amido group means —NHC(=O)—.

As used herein, acyloxy groups are —OC(O)R.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkenyl groups, alkoxy group (which itself can be substituted, such as —O—$C_1$-$C_6$-alkyl-OR, —O—$C_1$-$C_6$-alkyl-N(R)$_2$, and OCF$_3$), alkoxyalkoxy, alkoxycarbonyl, alkoxycarbonylpiperidinyl-alkoxy, alkyl groups (which itself can also be substituted, such as —$C_1$-$C_6$-alkyl-OR, —$C_1$-$C_6$-alkyl-N(R)$_2$, and —CF$_3$), alkylamino, alkylcarbonyl, alkylester, alkylnitrile, alkylsulfonyl, amino, aminoalkoxy, CF$_3$, COH, COOH, CN, cycloalkyl, dialkylamino, dialkylaminoalkoxy, dialkylaminocarbonyl, dialkylaminocarbonylalkoxy, dialkylaminosulfonyl, esters (—C(O)—OR, where R is groups such as alkyl, heterocycloalkyl (which can be substituted), heterocyclyl, etc., which can be substituted), halogen or halo group (F, Cl, Br, I), hydroxy, morpholinoalkoxy, morpholinoalkyl, nitro, oxo, OCF$_3$, optionally substituted phenyl, S(O)$_2$CH$_3$, S(O)$_2$CF$_3$, and sulfonyl, N-alkylamino or N,N-dialkylamino (in which the alkyl groups can also be substituted).

As used herein, the term "N-oxide" means $N^+O^{31}$.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 µl). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

|  | Parts by weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of formula I as a medicament.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

Enzyme Assays

The in vitro potency of compounds of formula (I) in inhibiting one or more of the protein kinases discussed herein or described in the art may be determined by the procedures detailed below.

The potency of compounds of formula (I) can be determined by the amount of inhibition of the phosphorylation of an exogenous substrate (e.g., a synthetic peptide (Z. Songyang et al., *Nature*. 373:536-539) by a test compound relative to control.

p38 Kinase Assay

Materials: Active p38α enzyme can be purchased from Upstate Biotechnology Inc. (UBI). Anti-phospho-MBP specific antibody can be purchased from UBI and Europium (Eu)-cryptate labeled by Cis-Bio International. SAXL (streptavidine linked XL) can be obtained for Prozyme. Biotin-MBP-peptide (Biot-Ahx-VHFFKNIVTPRTP-PPSQGKGAEGQR-OH) can be made by New England Peptide. HTRF reader RUBYstar was can be acquired from BMG Labtech.

The kinase assay is performed using the homogenous time-resolved fluorescence (HTRF) method (Mabile, 1991; Mathis, 1993). The assay mixture contains 7.8 nM p38α, 0.5 μM biotin-MBP-peptide, 0.1 mM ATP and compound (to a final 5% DMSO) in a buffer containing 20 mM MOPS pH 7.2, 10 mM $MgCl_2$, 5 mM EGTA, 5 mM β-phosphoglycerol, 1 mM $Na_3VO_4$, 0.01% Triton-X-100, 1 mM DTT. The reaction is carried out at room temperature in 96 half-well black plates (Corning). At designated time point, EDTA (to a final 0.1 M) is added to quench the reaction. The products are detected by addition of the revelation reagents (to a final 11 ng anti-phospho-MBP-Eu antibody and 0.34 μg SAXL). The plates are incubated in dark at 4° C. overnight, and read in the HTRF reader RUBYstar. The ratio between the signal at 620 nm and 665 nm at various inhibitor concentrations is used to calculate the $IC_{50}$.

REFERENCE (1) M. Mabile, G. Mathis, E. J. P., Jolu, D. Pouyat, C. Dumont, Patent WO 92:13264, 1991
(2) G. Mathis, Clin. Chem. 39 (1993) 1953-1959

Methods

Kinase assays: The kinase assays were performed using the homogenous time-resolved fluorescence (HTRF) method (Mabile, et al.; Mathis, et al.). IKKα and IKKβ (made in house) assay contained either 6.7 nM IKKα or 1.7 nM IKKβ, 0.5 μM biotin-IκBα-peptide (Cell Signaling), 0.01 mM ATP and compound in IKK buffer (20 mM MOPS pH 7, 10 mM $MgCl_2$, 5 mM EGTA, 5 mM β-phosphoglycerol, 1 mM $Na_3VO_4$, 0.01% Triton-X-100, 1 mM DTT, 5% DMSO). p38α and CDK2 (UBI) assays contained either 7.8 nM p38α: or 2.7 nM CDK2/cyclin A, and 0.5 μM biotin-MBP-peptide, 0.1 mM ATP and compound in the IKK Buffer. p38 assay contained 0.3 nM p38β, and 0.1 μM biotin-MBP-protein (UBI), 0.1 mM ATP and compound in the IKK Buffer. JNK1, JNK2 and JNK3 assays contained either 11.1 nM JNK1, 7.6 nM JNK2, or 2.4 nM JNK3, 1 μM biotin-ATF2-peptide (Cell Signaling), 0.01 mM ATP and compound in the IKK Buffer. KDR (make in house) assay contained 4.0 nM KDR, 2 μM biotin-FGFR-peptide, 0.1 mM ATP and compound in a buffer containing 50 mM HEPES, pH 7.1, 10 mM $MgCl_2$, 2 mM $MnCl_2$, 2.5 mM DTT, 0.01% BSA, 0.1 mM $Na_3VO_4$ and 5% DMSO. JAK1 (make in house) assay contained 3.6 nM JAK1, 2 μM biotin-FGFR-peptide, 0.001 mM ATP and compound in a buffer containing 50 mM MOPSO, pH 6.5, 10 mM $MgCl_2$, 2 mM $MnCl_2$, 2.5 mM DTT, 0.01% BSA, 0.1 mM $Na_3VO_4$ and 5% DMSO. All assays were carried out at RT for 60 min and stopped by addition of EDTA. The products were detected by addition of revelation reagents containing Europium labeled phospho-specific antibodies and SAXL. The plates were incubated in dark at 4° C. overnight, and read in the HTRF reader RUBYstar (BMG)

REFERENCE (3) M. Mabile, G. Mathis, E. J. P., Jolu, D. Pouyat, C. Dumont, Patent WO 92/13264, 1991
(4) G. Mathis, Clin. Chem. 39 (1993) 1953-1959

Cellular Assays

THP-1 cells from ATCC (TIB-202) are serum-starved and seeded at a density of $2\times10^5$/well in 100 μL of low serum RPMI media (0.5% FBS). 50 μl samples of compounds in appropriate serial dilutions are added to the wells. Compound stocks and dilutions in 100% DMSO are prepared such that final concentration of DMSO in RPMI media is 0.5%. Cells and compounds or controls are pre-incubated for 1 hour in a 37° C. incubator.

Cytokine release and P-Hsp27 induction is stimulated by LPS treatment. LPS (Sigma, L-4516) is reconstituted to a concentration of 1 mg/ml in endotoxin free $dIH_2O$, diluted in RPMI media such that 50 μl/well is added to each well for a final concentration of 1 μg/ml (excepting negative control wells). Plates with cells, compound and LPS are incubated at 37° C. for 45 minutes. This time point needs recalibration when new THP-1 cells are thawed.

For analysis of P-Hsp27 (phosphorylated Hsp27 protein), plates are vacuum filtered to remove media and compounds. Cells are washed twice with buffer (UBI, Assay Buffer #1, 43-010) using vacuum filtration. Then, 100 μl of cell lysis buffer (Biorad, 171-304011) is added per well and the plate is covered and shaken for 20 mins at 4° C. to lyse cells. Lysates are directly transferred to a flat bottom 96 well plate for analysis or stored frozen at −20° C. until analysis. Lysates are diluted 1:2 with assay buffer #1 and analysed by the Luminex method on a Bio-Plex machine following manufacturers directions (UBI, Phospho-HSP27 Beadmates kit, 46-607).

For analysis of cytokine release, plates are spun after incubation with LPS for 5 min at 1000 rpm and 100 μl of supernatant media is directly transferred to a $2^{nd}$ 96 well plate. Test plate with cells is returned to incubator O/N to be assayed for toxicity the next day (see below). Supernatant is stored at −20° C. until analysis. Supernatant media sample plates are analyzed in a standard ELISA format following manufacturers instructions (R&D, huTNFα ELISA assay kit). Toxicity analysis is done after the overnight incubation with compound. 50 μl of a 2.5 mg/ml solution of MTT (Sigma, M 2128) is added to cells. Plate is incubated at 37° C. for 3 hrs. 50 μl of 20% SDS is then added to solubilize the formazen dye. Plates are incubated at 37° C. for an additional 3 hrs and OD570 is measured on a spectrophotometer.

Materials:

Blood donors are in-house volunteers. Tubes used for drawing blood are 3.2% Buffered Sodium Citrate from Monoject, Mansfield, Mass., Catalog Number 340486. Dilution Plates and Assay Plates were from Corning, COSTAR Catalogs Numbers 3365 and 3599, respectively. Dimethyl sulphoxide (DMSO) was from Sigma, St. Louis, Mo., Catalog Number D2650. RPMI Media 1640 and HEPES Buffer Solution (1M) are from Invitrogen GIBCO Cell Culture Systems, Carlsbad, Calif., Catalog Numbers 11875 and 15630. Lipopolysaccharides from *Escherichia coli* 0127:B8 (LPS) was from Sigma, Catalog Number L4516. Tumor Necrosis Factor Alpha (TNF-α/TNFSF1A) ELISA kits were from R&D Systems, Inc., Minneapolis, Minn., Catalog Number PDTA00C.

Methods:

Blood is drawn from healthy donors into sodium citrate tubes within 1 hour of assay. Drugs were prepared in Dimethyl sulphoxide (DMSO) and serial dilute (1:3) with DMSO in Dilution Plate(s) to give 8 dilution points for each compound tested. Further dilution (1:100) of drug was made into RPMI Media 1640, 20 mM HEPES. Into wells of 96-well Assay Plate(s), 100 μL/well of diluted drug or control (1% DMSO in RPMI Media 1640, 20 mM HEPES) and 80 μL of blood is applied and pre-incubated for 30 minutes in an incubator set at 37 degrees centigrade. Tumor Necrosis Factor Alpha (TNF-α) is then stimulated with the addition of Lipopolysaccharides from *Escherichia coli* 0127:B8 (LPS, 50 ng/ml) for 3.5 hours at 37 degrees centigrade. Plates are spun at 183 g (1000 rpm in Beckman/Coulter Allegra 6KR centrifuge) for 10 minutes. Cell-free supernatant (75 μL/well) was collected and TNF-α: is measured by commercial ELISA kit, following protocol of manufacturer. Potency of drug to inhibit TNF-α in vitro is determined the percent reduction of measured TNF-α in wells with drug compared to control wells without drug. Results are represented as $IC_{50}$ values.

REFERENCE

Current Protocols in Immunology (2005) 7.18B-7.18B12.

LPS-Induced TNF Production In Vivo

Materials:

Lipopolysaccharide (LPS) from *Escherichia coli*, serotype 0111:B4 (Sigma, cat #L-4130, lot #095K4056)

Phosphate Buffered Saline pH 7.2 (Gibco)

PEG 200 (Sigma, cat #P3015)

Methylcellulose (Sigma, cat #M7027)

Male Lewis rats, 200-300 g (Charles River Laboratories)

Rat Tumor Necrosis Factor α (TNFα) ELISA kit (R&D Systems cat #RTA00)

Methods:

The test compound is prepared into vehicle (5% PEG 200, in 0.5% Methylcellulose) at the desired concentrations for dosing (1, 3, 10, 30,100 mg/kg). Lewis rats are pre-dosed with the compound(s) either intraperitoneally (i.p.) or orally (p.o.) at 0.002 ml/gram body weight one-two hours prior to the LPS challenge. Negative control includes rats treated with vehicle (5% PEG 200, in 0.5% Methylcellulose) alone. LPS is dissolved in phosphate buffered saline, sonicated and the rats are injected with 1 mg/kg intravenously (i.v.) at 0.001 ml/gram body weight. One hour after the LPS challenge the rats are cardiac bled and the serum is analyzed for TNFα by ELISA. The compound concentration is also determined in the serum.

The average concentration of TNFα in the vehicle treated group is taken as a maximal (100 percent) response. The mean TNFα levels in the compound treated groups are expressed as a percent of the maximal response. The percent of maximal TNFα responses at various doses or serum concentrations of the compound(s) are further analyzed using a four parameter curve fit of logarithmically transformed data (Graphpad Prism 4 software) to generate $ED_{50}$ and $EC_{50}$.

RELEVANT REFERENCE(S)

Azab A, et al. (1998). *Life Sci.* 63: 323-327.
Martinez E F, et. al (2004) *Biochem. Pharma.* 68:1321-1329.

The teachings of all references, including journal articles, patents and published patent applications, are incorporated herein by reference in their entirety.

Compounds of the invention may be prepared using the synthetic scheme illustrated in Scheme 1. Starting materials are commercially available or may be prepared by the procedures described herein or by procedures that would be well known to one skilled in the art of organic chemistry. The variables used in the Scheme are as defined herein or as in the claims. General procedures are noted in parentheses.

A method for preparing imidazopyrazine (X=N,Y=CR⁴) or imidazopyrimidine (X=CR⁴, Y=N) compounds of the invention is illustrated in Scheme 1. In Scheme 1, step i, a suitably substituted α-bromoketone 1 is reacted with an optionally substituted 2-amino heterocycle 2. These types of cyclization reactions are well established in the literature (see, for example, Spitzer, et al., *J Med Chem* 1988, 31, 1590-1595). This reaction is typically conducted in an organic solvent (such as EtOH or DMF) at temperatures at or below reflux (such as 80° C.). The product 3 is typically isolated from the reaction mixture as a solid by concentrating the mixture and then is used crude after extractive work up with a suitable organic solvent (such as DCM or EtOAc) or is purified either by crystallizing or triturating in an organic solvent (such as DCM, EtOH or EtOAc) or by flash silica gel chromatography. Compounds 3 can be used as is or first undergo functional group manipulation using methods known to one skilled in the art (see, for example, Larock, R. C. *Comprehensive Organic Transformations: A Guide to Functional Group Preparations*, 2$^{nd}$ edition, 1999, Wiley-VCH Publishers, New York). For example, if $R^1$=CO$_2$Me, a one- or two-step decarboxylation (using, for example, 1M HCl or LiOH.H$_2$O followed by 1M HCl) may be done to get $R^1$=H. Coupling of compounds 3 with a substituted pyridine or pyrimidine such as heterocycles 4 to produce compounds 5 as shown in step ii (Scheme 1) is frequently conducted with palladium-mediated arylation using a catalyst/ligand system such as Pd(OAc)$_2$/PPh$_3$ or PdCl$_2$(PPh$_3$)$_2$ (see, for example, Pivsa-Art, et al., *Bull Chem Soc Japan,* 1998, 71, 467-473). This reaction is typically carried out with a base (such as Cs$_2$CO$_3$ or KOAc) at elevated temperatures (for example, 80-100° C.) in a solvent such as DMF or NMP. Oxidation as shown in step iii (Scheme 1) is typically accomplished by treating a solution of 5 in an organic solvent (such as DCM) with an oxidant (such as an aqueous solution of Oxone® or m-CBPA) at room temperature to produce 6 (see, for example, Kennedy, R. J. and Stock A. M. *J Org Chem,* 1960, 25, 1901-1906 or Zanatta, et al., *Synthesis* 2003, (6), 894-898). Displacement of the sulfone leaving group of 6 with a nucleophile to provide 7 as shown in step iv (Scheme I, General procedure A) can be accomplished by a variety of methods known to one skilled in the art. For example, in the case of amine nucleophiles, compounds 6 are reacted with ammonia or the desired primary or secondary amine in an organic solvent (such as dioxane, toluene, or DMSO), with or without a hindered organic base (such as TEA), at elevated temperatures (see, for example, Clark, et al., *J Med Chem,* 2004, 47, 2724-2727). The compounds 7 can then be isolated and purified using standard techniques (such as crystallization, flash column chromatography, or reverse-phase liquid chromatography). Further functionalization of compounds 7 can be performed, if desired, using reactions known to one skilled in the art (see for example Larock, R. C. above). For example, formation of amides, ureas, or sulfonamides can be achieved by reaction of compounds 7 containing a primary or secondary amine. Also, deprotection of compounds 7 to yield an unprotected compound can be performed using conditions such as those described in Greene, T. W. and Wuts, P. G. M. *Protective Groups in Organic Synthesis,* 3$^{rd}$ Edition, 1999, Wiley-Interscience, New York. For example, a protecting group such as a t-butoxycarbonyl group can be removed from a protected amine to yield the unprotected amine and these deprotected compounds 7 may then be reacted further as described above.

Scheme 1:

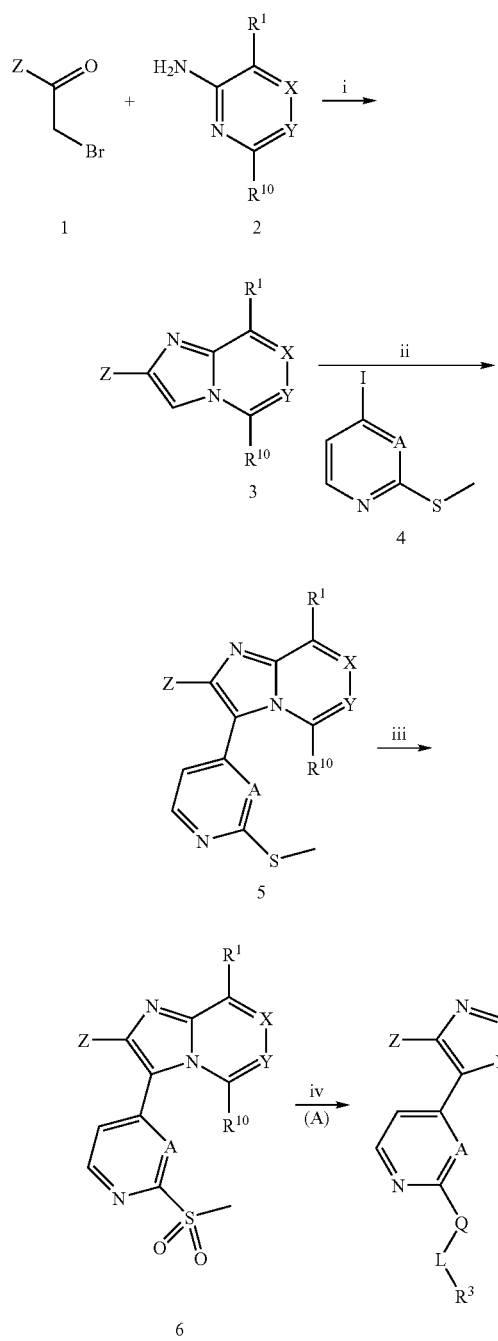

| Abbreviations | |
|---|---|
| ACN | Acetonitrile |
| Boc | tert-Butoxycarbonyl |
| bp | Boiling point |
| DCM | Dichloromethane (methylene chloride) |
| DIEA | N,N-Diisopropylethylamine |
| DME | 1,2-Dimethoxyethane |
| DMF | N,N-Dimethylformamide |
| DMSO | Dimethyl sulfoxide |

-continued

| Abbreviations | |
|---|---|
| EtOAc | Ethyl acetate |
| EtOH | Ethyl alcohol |
| $Et_2O$ | Diethyl ether |
| $Et_3N$ | Triethylamine |
| FCC | Flash column chromatography |
| HPLC | High-pressure liquid chromatography |
| IPA | Isopropyl alcohol |
| KOAc | Potassium acetate |
| LDA | Lithium diisopropylamide |
| LiHMDS | Lithium hexamethyldisilazide |
| m-CPBA | m-Chloroperbenzoic acid |
| MeMgBr | Methyl magnesium bromide |
| MeOH | Methyl alcohol |
| $Pd(OAc)_2$ | Palladium(II) acetate |
| RP-HPLC | Reverse-phase high-pressure liquid chromatography |
| TEA | Triethylamine |
| TFA | Trifluoroacetic acid |
| THF | Tetrahydrofuran |
| TLC | Thin layer chromatography |

GENERAL PROCEDURES AND EXAMPLES

The general synthetic schemes that were utilized to construct the majority of compounds disclosed in this application are described below in Schemes 2-17.

Scheme 2.
Displacement of a sulfone by a nucleophile (General Procedure A)

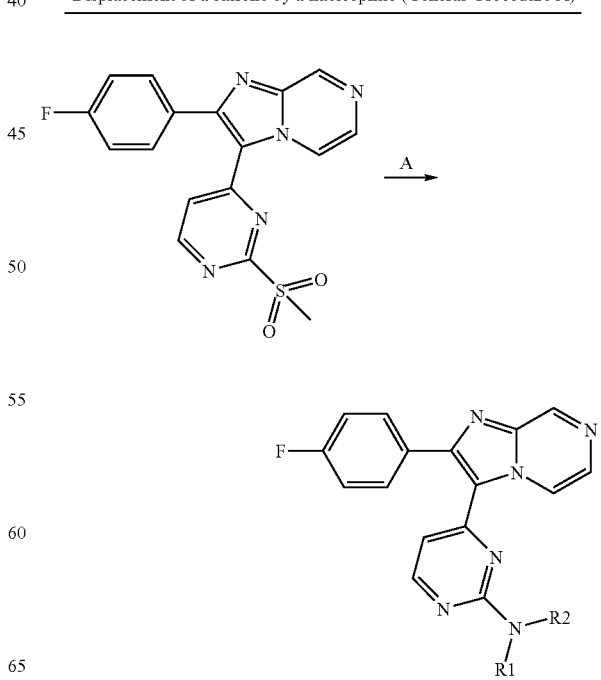

Scheme 3.
Displacement of a sulfone and/or a sulfoxide by a nucleophile
(General Procedure A.2)

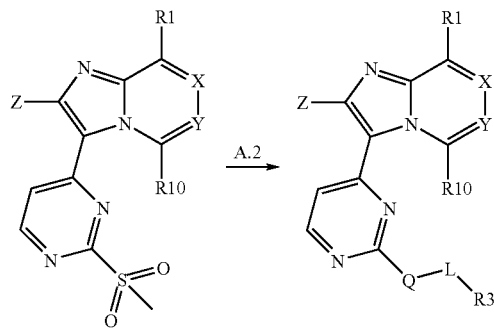

Scheme 4.
Cyclization to form a substituted imidazopyrazine
(General Procedure B)

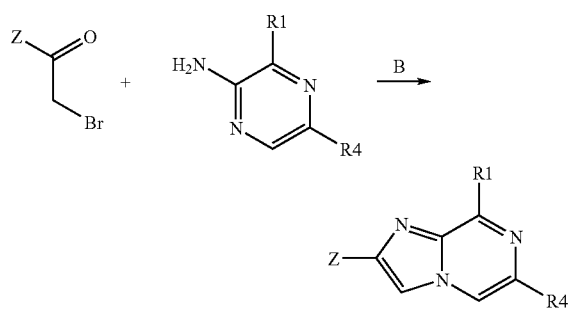

Scheme 5.
Hyrolysis of a substituted imidazol[1,2-α]pyrazine-8-carboxylic
acid methyl ester
(General Procedure C)

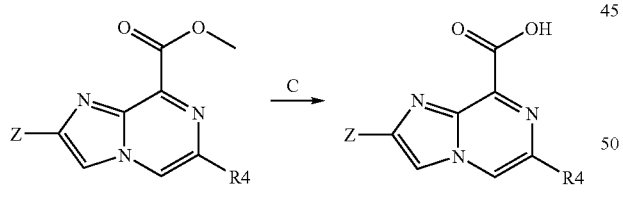

Scheme 6.
Decarboxylation of a substituted imidazol[1,2-α]pyrazine-8-carboxylic
acid (General Procedure D)

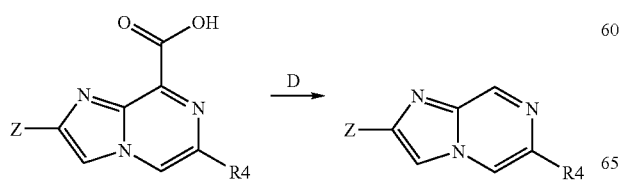

Scheme 7.
Direct decarboxylation of a substituted imidazol[1,2-a]pyrazine-8-
carboxylic acid methyl ester (General Procedure C)

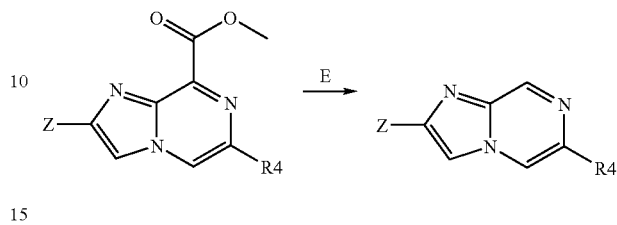

Scheme 8.
Palladium-mediated arylation (General Procedure F)

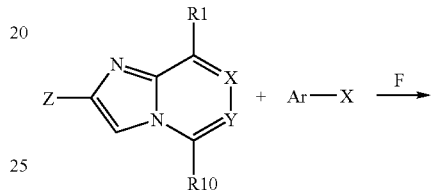

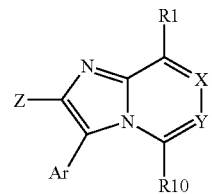

Scheme 9.
Oxidation of a sulfide to a sulfone and/or a sulfoxide
(General Procedure G)

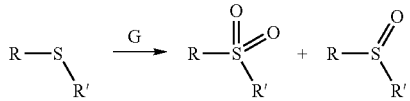

Scheme 10.
Acidic cleavage of a Boc-protected amine
(General Procedure I)

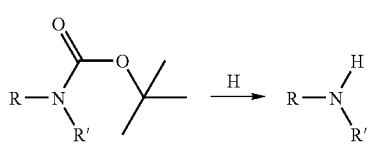

Scheme 11.
Formation of a sulfonamide from an
amine (General Procedure I)

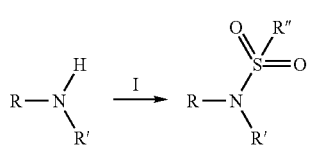

Scheme 12.
Formation of hydroxyl acetyl group from amine
(General Procedure J)

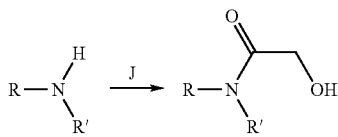

Scheme 13.
Conversion of an aryl or heteroaryl chloride to an aryl or
heteroaryl alkyl derivative (General Procedure K)

Ar—Cl + RMgBr $\xrightarrow{K}$ Ar—R

Scheme 14.
Displacement of an aryl or heteroaryl chloride with an alkoxide
(General Procedure L)

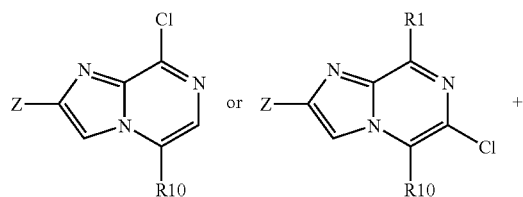

Scheme 15.
Bromination of a substituted acetophenone (General Procedure M)

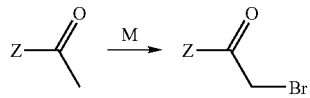

Scheme 16.
Deprotection of a methyl-protected alcohol using acid
(General Procedure N)

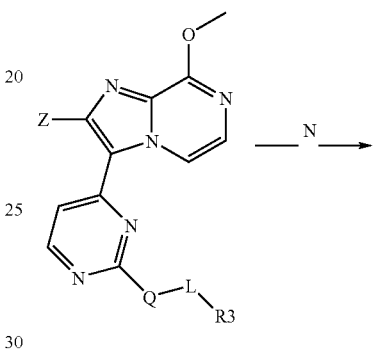

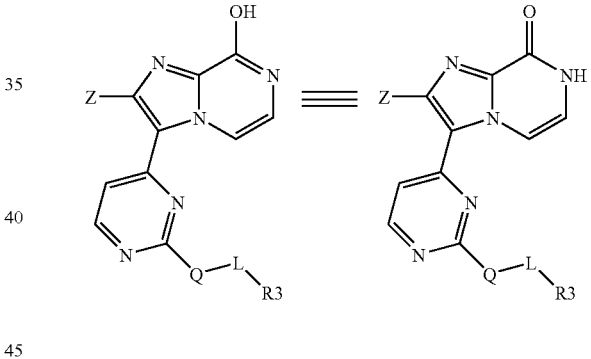

Scheme 17.
Displacement of an aryl or heteroarylchloride with an amine
(General Procedure O)

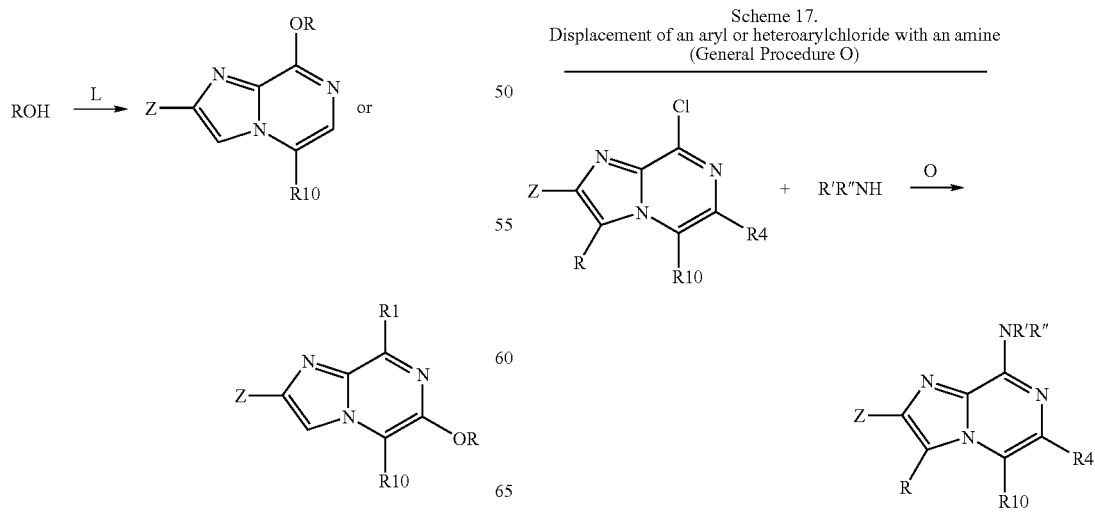

| LIST OF GENERAL PROCEDURES | |
|---|---|
| General Procedure A | Displacement of a sulfone by a nucleophile |
| General Procedure A.2 | Displacement of a sulfone and/or a sulfoxide by a nucleophile |
| General Procedure B | Cyclization to form a substituted imidazopyrazine |
| General Procedure C | Hydrolysis of a substituted imidazo [1,2-a] pyrazine-8-carboxylic acid methyl ester |
| General Procedure D | Decarboxylation of a substituted imidazo [1,2-a] pyrazine-8-carboxylic acid |
| General Procedure E | Direct decarboxylation of a substituted irnidazo [1,2-a] pyrazine-8-carboxylic acid methyl ester |
| General Procedure F | Palladium-mediated arylation |
| General Procedure G | Oxidation of a sulfide to a sulfone and/or a sulfoxide |
| General Procedure H | Acidic cleavage of a Boc-protected amine |
| General Procedure I | Formation of a sulfonamide from an amine |
| General Procedure J | Formation of hydroxyl acetyl group from an amine |
| General Procedure K | Conversion of an aryl or heteroaryl chloride to an aryl or heteroaryl alkyl derivative |
| General Procedure L | Displacement of an aryl or heteroaryl chloride with an alkoxide |
| General Procedure M | Bromination of a substituted acetophenone |
| General Procedure N | Deprotection of a methyl-protected alcohol using acid |
| General Procedure O | Displacement of an aryl or heteroaryl chloride with an amine |

The following examples are ordered according to the final general procedure used in their preparation. The synthetic routes to any novel intermediates are detailed by sequentially listing the general procedure (letter codes) in parentheses after their name. A worked example of this protocol is given below using Example #F.1.1 as a non-limiting illustration. Example #F.1.1 was prepared from 2-(2,4-difluorophenyl)-3-(2-methylsulfanylpyrimidin-4-yl)-imidazo[1,2-a]pyrazine using general procedure F as represented in the following synthetic scheme:

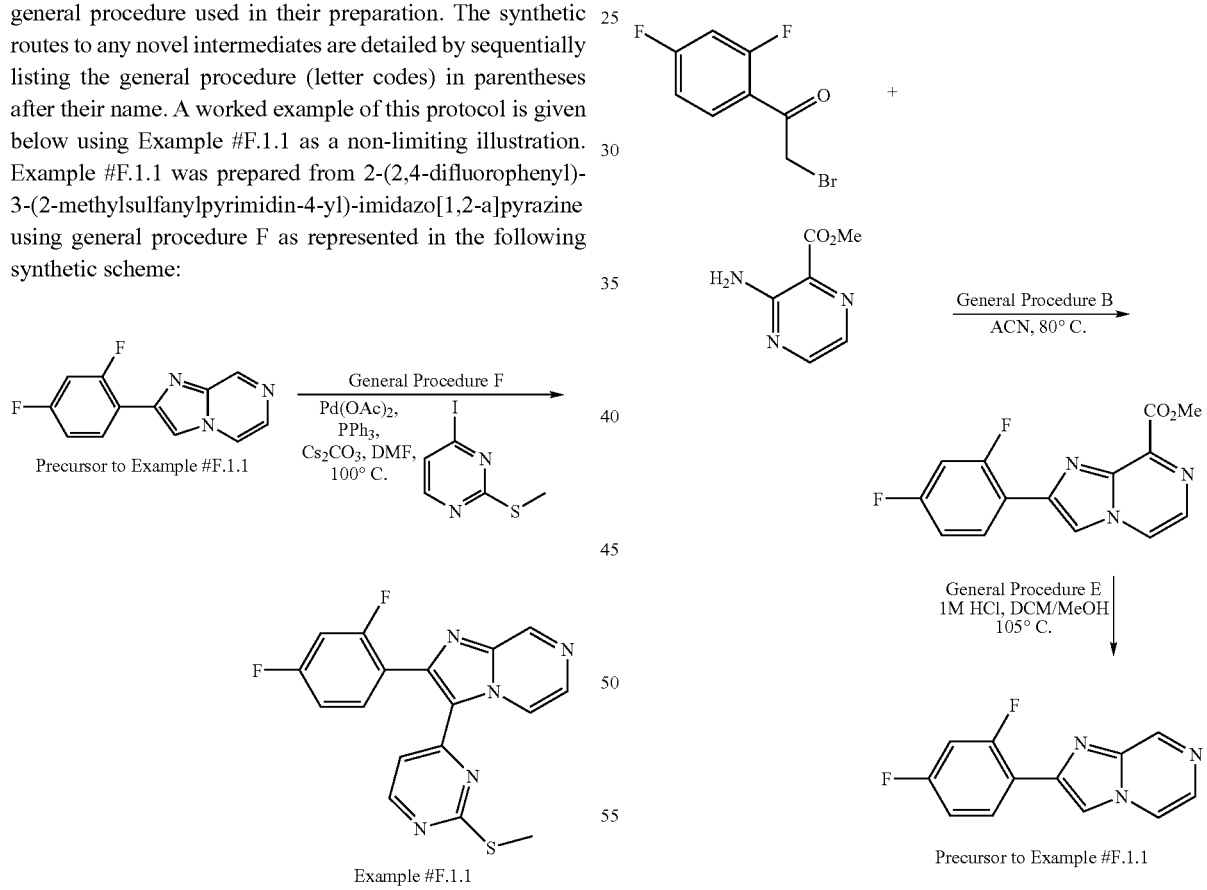

The precursor to Example #F.1.1, 2-(2,4-difluorophenyl)-3-(2-methylsulfanylpyrimidin-4-yl)-imidazo[1,2-a]pyrazine, was prepared by the noted reaction sequence: General Procedure B using 3-aminopyrazine-2-carboxylic acid methyl ester and 2-bromo-1-(2,4-difluorophenyl)-ethanone, General Procedure E using 1M HCl, which translates into the following synthetic scheme:

The general synthetic methods used in each general procedure follow and include an illustration of a compound that was synthesized using the designated general procedure. None of the specific conditions and reagents noted in the following are to be construed as limiting the scope of the invention and are provided for illustrative purposes only. All starting materials are commercially available from Sigma-Aldrich unless otherwise noted after the chemical name. Analytical data is included either in the illustrations of the general procedures or in the tables of examples. Unless otherwise stated, all ¹H NMR data were collected on a Varian Mercury Plus 400 MHz instrument; chemical shifts are quoted in parts per million (ppm). High-pressure liquid chromatography (HPLC) analytical data referenced to the table of HPLC conditions using the lower case method letter in parentheses provided in Table 1.

TABLE 1

LC/MS and HPLC methods

| Method | Conditions |
|---|---|
| a | LC/MS: 30% to 95% ACN/0.01M aqueous ammonium acetate over 2.0 min; 95% ACN/0.01M aqueous ammonium acetate for 1.5 min at 1.0 mL/min; UV λ = 210-360 nm; Genesis C8, 4 μm, 30 × 4.6 mm column; ESI +ve/−ve. |
| b | LC/MS: 5% to 95% ACN/0.01M aqueous ammonium acetate over 2.0 min; 95% ACN/0.01M aqueous ammonium acetate for 1.5 min at 1.4 mL/min; UV λ = 210-360 nm; Genesis C8, 4 μm, 30 × 4.6 mm column; ESI +ve/−ve. |
| c | RP-HPLC: 5% to 95% ACN/0.05M aqueous ammonium acetate, buffered to pH 4.5, over 25 min at 21 mL/min; UV λ = 254 nm; Hyperprep C18, 100 Å, 8 μm, 250 × 21.2 mm column. |
| d | RP-HPLC: 20% to 60% ACN/0.05M aqueous ammonium acetate, buffered to pH 4.5, over 40 min at 81 mL/min; UV λ = 254 nm; Hypersil HS-100, C18, 10 μm, 250 × 50 mm column. |
| e | RP-HPLC: 10% to 40% ACN/0.05M aqueous ammonium acetate, buffered to pH 4.5, over 40 min at 21 mL/min; UV λ = 254 nm; Hypersil HS-100, C18, 10 μm, 250 × 50 mm column. |
| f | LC/MS: 5% to 95% ACN/0.01M aqueous ammonium acetate over 3.7 min with a hold at 95% ACN/0.01M aqueous ammonium acetate for 1 min at 1.3 mL/min; Waters Atlantis dC18, 5 μm, 50 × 4.6 mm column. Detection methods are diode array (DAD) and evaporative light scattering (ELSD) detection as well as pos/neg electrospray ionization. |
| g | LC/MS: 5% to 95% ACN/0.01M aqueous ammonium acetate over 3.7 min with a hold at 95% ACN/0.01M aqueous ammonium acetate for 1 min at 1.3 mL/min; Zorbax XDB C18, 5 μm, 50 × 4.6 mm column. Detection methods are diode array (DAD) and evaporative light scattering (ELSD) detection as well as pos/neg electrospray ionization. |
| h | LC/MS: 5% to 95% ACN/5 mM aqueous ammonium acetate over 3.0 min; 95% to 100% ACN/5 mM aqueous ammonium acetate over 0.7 min; 95% to 5% ACN/5 mM aqueous ammonium acetate over 0.1 min; 5% ACN/5 mM aqueous ammonium acetate for 0.2 min at 2.0 ml/min; UV λ = 254 nm; Pecosphere C18, 3 μm, 80a, 33 × 4.6 mm column; ESI +ve/−ve. |
| i | RP-HPLC: 30% to 60% ACN/0.05M aqueous ammonium acetate, buffered to pH 4.5, over 30 min at 81 mL/min; UV λ = 254 nm; Hypersil HS-100, C18, 10 μm, 250 × 50 mm column. |

Preparation #1: 2-(4-Fluorophenyl)-imidazo[1,2-a]pyrazine-8-carboxylic acid methyl ester

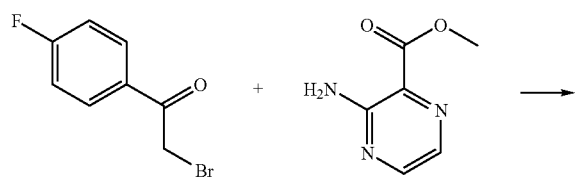

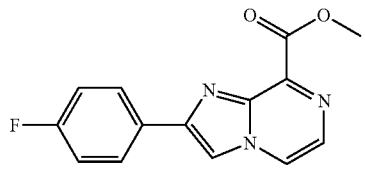

A mixture of 2-bromo-1-(4-fluorophenyl)ethanone (30.0 g, 138 mmol) and methyl 3-aminopyrazine-2-carboxylate (21.2 g, 138 mmol) in DMF (200 mL) was heated at about 80° C. for about 16 h. The mixture was allowed to cool to ambient temperature and was neutralized with saturated aqueous NaHCO₃. The mixture was diluted with DCM. The layers were separated and the aqueous layer was washed with DCM. The combined organic layers were washed with brine, dried over MgSO₄, and eluted through a silica gel plug with EtOAc as the eluent. The combined organic layers were concentrated under reduced pressure to yield 30 g black oil. The material was diluted with DCM and the insoluble materials were removed by filtration to yield 2.0 g of the title compound. A second crop was obtained similarly to yield 1.8 g. The remaining filtrate was purified by flash silica gel chromatography using EtOAc as an eluent to yield an additional 3.1 g of the title compound (6.9 g, 15%): LC/MS (Table 1, Method b) $R_t$=1.7 min; MS m/z: 272.3 (M+H)⁺.

Preparation #2: 2-(4-Fluorophenyl)imidazo[1,2-a]pyrazine

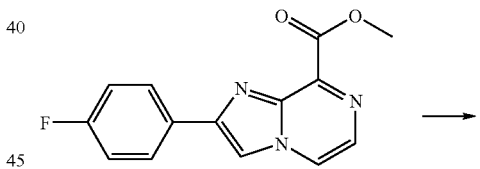

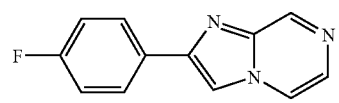

A mixture of 2-(4-fluorophenyl)imidazo[1,2-a]pyrazine-8-carboxylic acid methyl ester (Preparation #1, 6.30 g, 23.2 mmol) in DCM (66 mL) was treated with 1.0 M HCl in water (200 mL). The mixture was heated at about 105° C. open to the air for about 16 h. The solution was allowed to cool and was treated with saturated aqueous NaHCO₃ and DCM. The mixture was sonicated to dissolve all solids and the layers were separated. The aqueous layer was washed with EtOAc. The combined organic layers were dried over MgSO₄, filtered, and concentrated under reduced pressure to yield the title compound (4.60 g, 93%): LC/MS (Table 1, Method b) $R_t$=1.6 min; MS m/z: 214.3 (M+H)⁺.

Preparation #3: 2-(4-Fluorophenyl)-3-(2-methylsulfanylpyrimidin-4-yl)-imidazo[1,2-a]pyrazine

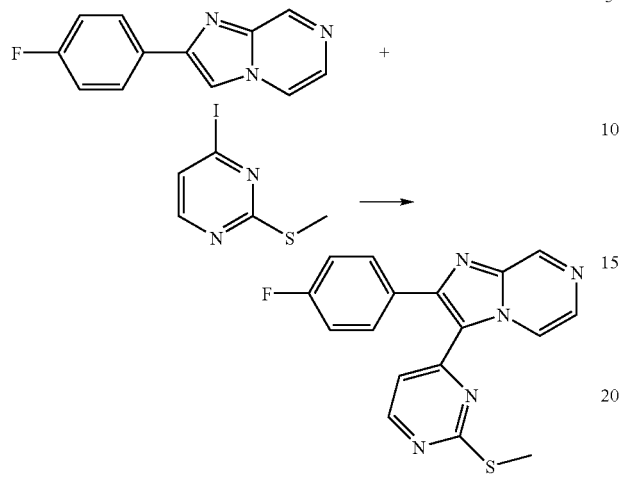

A mixture of 2-(4-fluorophenyl)imidazo[1,2-a]pyrazine (Preparation #2, 0.964 g, 4.52 mmol), 4-iodo-2-(methylthio)pyrimidine (Frontier, 2.28 g, 9.04 mmol), $Cs_2CO_3$ (2.21 g, 6.78 mmol), triphenylphosphine (0.474 g, 1.84 mmol), palladium acetate (0.203 g, 0.904 mmol), and DMF (10.5 mL) was heated at about 80° C. for about 13 h. The mixture was cooled to ambient temperature, diluted with water, and extracted with EtOAc. The combined organic layers were washed with brine, dried over $MgSO_4$, filtered, and concentrated under reduced pressure. The resulting material was triturated with EtOAc and filtered to yield the title compound (0.640 g, 41%): LC/MS (Table 1, Method b) $R_t$=2.0 min; MS m/z: 338.4 (M+H)$^+$.

Preparation #4: 2-(4-Fluorophenyl)-3-[2-(methanesulfonyl-pyrimidin-4-yl]imidazo[1,2-a]pyrazine

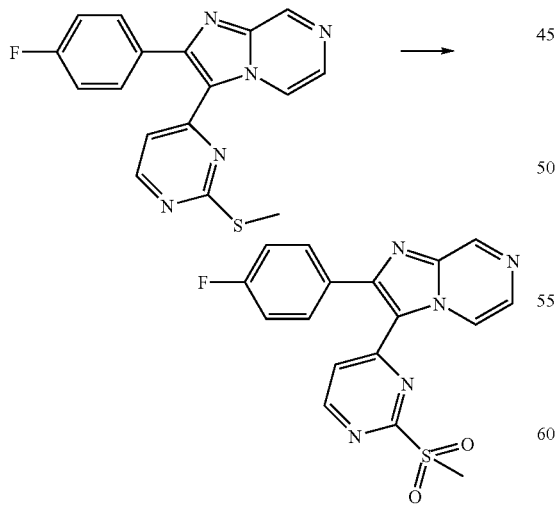

To a solution of 2-(4-fluorophenyl)-3-(2-methylsulfanylpyrimidin-4-yl)-imidazo[1,2-a]pyrazine (Preparation #3, 0.340 g, 1.01 mmol) in MeOH (15 mL) and DCM (15 mL) was added Oxone® (1.8 g, 3.0 mmol) in water (8 mL) to form a suspension. After about 18 h, the mixture was diluted with water and EtOAc. The layers were separated and the aqueous layer was washed with EtOAc. The combined organic layers were dried over $MgSO_4$, filtered, and concentrated under reduced pressure to yield 0.350 g yellow solid as a mixture of sulfone and sulfoxide. The majority of the solid (0.300 g) was carried on crude while a portion (0.050 g) was purified using RP-HPLC (Table 1, Method c) to yield the title compound after lyophilization (0.030 g): LC/MS (Table 1, Method b) $R_t$=1.6 min; MS m/z: 370.4 (M+H)$^+$.

Preparation #5: 3-Bromo-2-(4-fluorophenyl)imidazo[1,2-a]pyrazine

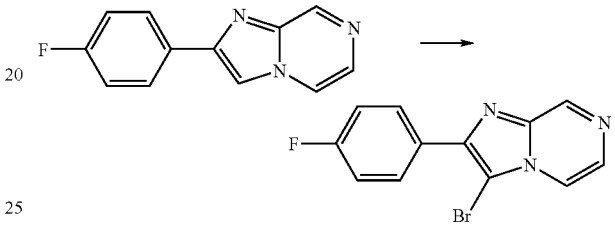

To a solution of 2-(4-fluorophenyl)imidazo[1,2-a]pyrazine (Preparation #2, 0.176 g, 0.783 mmol) in DCM (3 mL) was added N-bromosuccinimide (0.153 g, 0.862 mmol) dropwise. After about 20 minutes, the mixture was concentrated under reduced pressure and purified by flash silica gel chromatography using EtOAc as the eluent to yield the title compound (0.130 g, 54%>: LC/MS (Table 1, Method a) $R_t$=2.0 min; MS m/z: 294.2 (M+H)$^+$.

Preparation #6: 3-Methoxy-2,2-dimethylpropylamine HCl

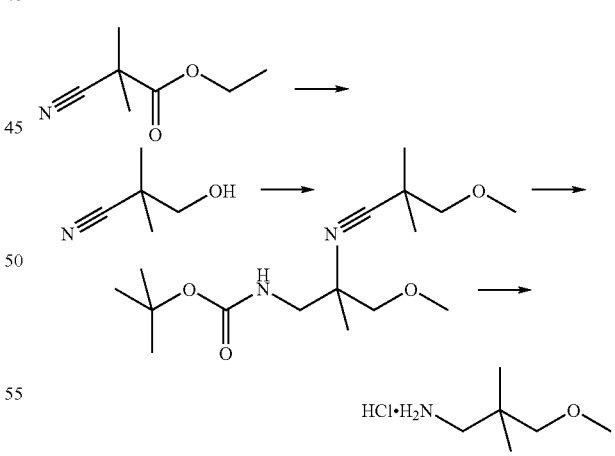

To a mixture of sodium tetrahydroborate (7.4 g, 200 mmol) in EtOH (100 mL) at about 0° C. was added cyanodimethylacetic acid ethyl ester (TCI, 10.0 g, 70.8 mmol) in EtOH (100 mL) over about 45 min. The mixture was allowed to warm to ambient temperature over about 30 min. After about 60 h, the solvents were removed in vacuo. The resulting material was treated with saturated aqueous $NH_4Cl$ (150 mL) and extracted using DCM (3×30 mL). The combined organic layers were dried over $Na_2SO_4$ and concentrated to yield the crude 3-hydroxy-2,2-dimethylpropionitrile (8.61 g). A mixture of crude 3-hydroxy-2,2-dimethyl-propionitrile (1.0 g, 10 mmol) in DCM (40 mL) was treated with tetrafluoroboric acid (1.4 g, 10 mmol) followed by 2 M trimethylsilyldiazomethane in heptane (5.0 mL, 10 mmol) at about 0° C. over about 10 min. The mixture was treated with additional 2 M trimethylsilyldiazomethane in heptane (2 mL, 4.0 mmol) after about 20 min, followed by additions of 2 M trimethylsilyldiazomethane in heptane (1.3 mL, 2.6 mmol) and 2 M trimethylsilyldiazomethane in heptane (1.3 mL, 2.6 mmol) after about 20 min intervals sequentially. The mixture was allowed to stir at about 0° C. for about 50 min before it was poured slowly over water. The layers were separated and the aqueous layer was extracted with DCM. The combined organic layers were washed with water, dried over $Na_2SO_4$, and concentrated to yield the crude 3-methoxy-2,2-dimethylpropionitrile as a yellow oil (1.2 g). Into a Parr shaker vessel was added crude 3-methoxy-2,2-dimethylpropionitrile (1.0 g, 8.8 mmol), 33% aqueous ammonium hydroxide (75 mL), MeOH (10 mL), and 8.0 M Raney® nickel in water (1 mL, 8.0 mmol). The materials were charged with hydrogen and shaken at ambient temperature. After about 16 h, the mixture was filtered over Celite® and treated with 5 M sodium hydroxide in water (2 mL), di-tert-butyldicarbonate (2.3 g, 11 mmol), and EtOAc (75 mL). After about 5 h, the layers were separated and the aqueous layer was washed with DCM. The combined organic layers were washed with water then dried over $Na_2SO_4$ and concentrated in vacuo. The residue was purified via FCC using EtOAc/heptane (1:4). The fractions containing product, as visualized on TLC with ninhydrin stain, were concentrated in vacuo to yield (3-methoxy-2,2-dimethylpropyl)-carbamic acid tert-butyl ester, which was treated with 1.25 M HCl in methanol (1 mL) at ambient temperature. After about 2 h, the mixture was concentrated in vacuo to give methoxy-2,2-dimethylpropylamine HCl: (0.090 g): $^1$H NMR (DMSO-$d_6$, 400 MHz) δ 3.85-3.75 (2H), 3.26 (3H), 3.13 (2H), 2.65-2.70 (2H), 0.91 (6H); TLC (acetone/MeOH 95:5) $R_f$=0.2.

Preparation #7:
2-(4-Fluorophenyl)-6-methoxyimidazo[1,2-a]pyrazine

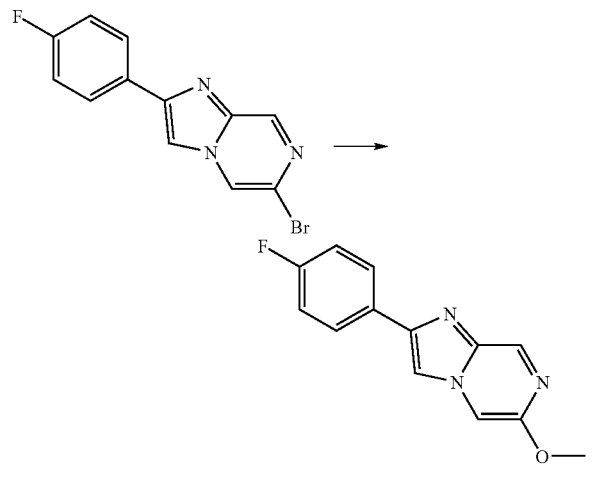

6-Bromo-2-(4-fluorophenyl)-imidazo[1,2-a]pyrazine (prepared from General Procedure B with 5-bromo-2-aminopyrazine and 2-bromo-4'-fluoroacetophenone, 1.05 g, 3.59 mmol), and 10% sodium hydroxide (6 mL) were combined in MeOH (12 mL). The reaction was heated in the microwave at 150 watts to about 100° C. for about 30 minutes. The reaction was cooled, diluted with water (50 mL), and filtered to provide 2-(4-fluorophenyl)-6-methoxyimidazo[1,2-a]pyrazine (0.513 g, 59%) on drying: LC/MS (Table 1, Method b) $R_t$=1.74 min; MS m/z: 244.2 (M+H)$^+$.

Preparation #8:
2-(4-Fluorophenyl)-8-vinylimidazo[1,2-a]pyrazine

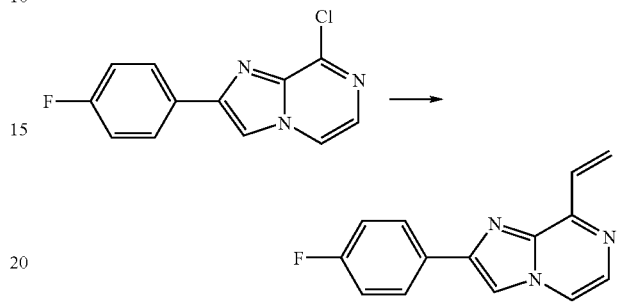

To a mixture of 8-chloro-2-(4-fluorophenyl)-imidazo[1,2-a]pyrazine (Example #6, Step A, 3.96 g, 16 mmol) in dioxane (80 mL) was added water (15.4 mL), sodium carbonate (EM Science, 5.08 g, 48 mmol), tri-t-butylphosphine tetrafluoroborate (Strem, 0.46 g, 1.6 mmol), and tris(dibenzylideneacetone)dipalladium(0) (0.73 g, 0.8 mmol). The reaction was degassed with nitrogen and then vinylboronic acid pinacolester (5.44 mL, 32 mmol) was added. The mixture was heated to about 95° C. for about 16 h. The reaction was cooled, EtOAc was added (250 mL), and the mixture was washed with water. The organic layer was dried over sodium sulfate, filtered, and evaporated. The residue was purified by FCC (33%-50% EtOAc/heptane). The residue was triturated with heptane and filtered to yield the title compound as a brown solid (2.46 g, 62%): LC/MS (Table 1, Method b) $R_t$=2.74 min; MS m/z: 240.3 (M+H)$^+$.

Preparation #9: {2-[2-(4-Fluorophenyl)-imidazo[1,2-a]pyrazin-8-yl]-ethyl}-carbamic acid tert-butyl ester

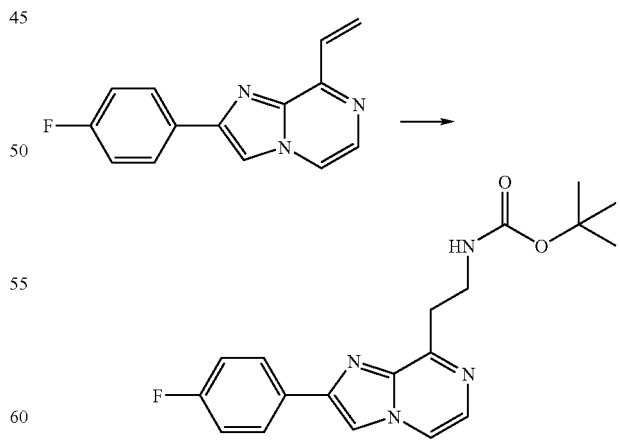

2-(4-Fluorophenyl)-8-vinylimidazo[1,2-a]pyrazine (Preparation #8, 1.8 g, 7.5 mmol) was dissolved in a mixture of dioxane (75 mL) and concentrated ammonium hydroxide (75 mL) and heated at about 90° C. for about 16 h. The solution was concentrated and extracted with EtOAc. The EtOAc layer was washed with brine, dried over sodium sulfate, filtered, and evaporated. The residue was dissolved in EtOH (10 mL) and di-tert-butyl dicarbonate (1.7 g, 7.8 mmol). The reaction was stirred for about 2 h. The reaction was concentrated and the residue was purified by FCC (50%-100% EtOAc/heptane) to provide the title compound as a tan solid (0.788 g, 29%): LC/MS (Table 1, Method b) $R_t$=2.52 min; MS m/z: 357.0 (M+H)$^+$.

Preparation #10: 8-Cyclopropylmethyl-2-(2,4-difluorophenyl)imidazo[1,2-a]pyrazine

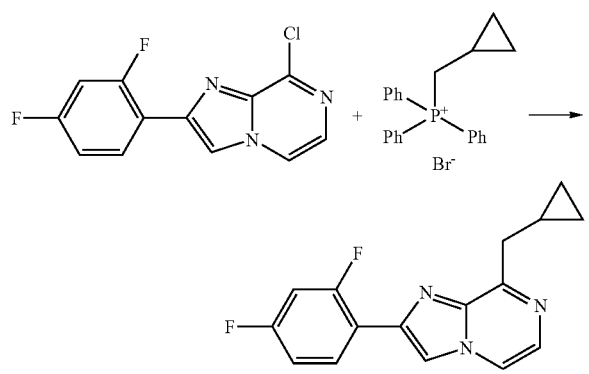

To a suspension of (cyclopropylmethyl)triphenylphosphonium bromide (Alfa Aesar, 10.2 g, 25.7 mmol) in dry DME (60 mL) kept between about −30° C. and 40° C. was added a 2.5M solution of n-butyllithium in hexanes (10.2 mL, 25.7 mmol) over about 5 min. After stirring between about −30° C. and −40° C. for about 45 min, 8-chloro-2-(2,4-difluorophenyl)imidazo[1,2-a]pyrazine (Example #13, Step A, 5.74 g, 23.2 mmol) was added. The mixture was warmed to ambient temperature, then stirred at about 85° C. for about 3.5 h, at which point a solution of Na$_2$CO$_3$ (1.364 g, 12.9 mmol) in water (50 mL) was added and heating was continued overnight. After cooling to ambient temperature, the mixture was partitioned between 1 N HCl and CHCl$_3$ and the organic phase extracted five more times with 1 N HCl. The combined aqueous phase was rendered alkaline with NaOH and extracted with Et$_2$O. After drying over Na$_2$SO$_4$ and concentration, the crude material was purified by silica gel chromatography with heptane/EtOAc (gradient 10-100% EtOAc). After concentration, the residue was three times re-dissolved in DCM and re-concentrated to give 0.728 g (22%) of the title compound as an orange solid: LC/MS (Table 1, Method g) $R_t$=3.08 min; MS m/z: 286.1 (M+H)$^+$.

General Procedure A: Displacement of a Sulfone by a Nucleophile

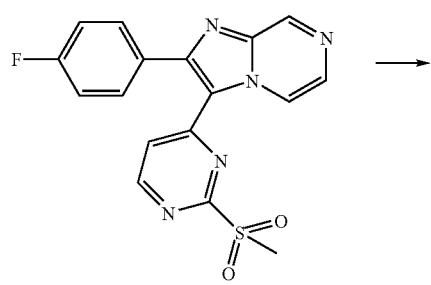

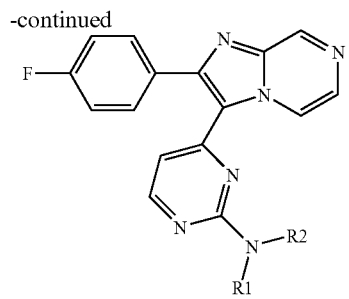

A mixture of 2-(4-fluorophenyl)-3-[2-(methanesulfonyl-pyrimidin-4-yl]imidazo[1,2-a]pyrazine (Preparation #4, 1 equiv), nucleophile (2 equiv), DIEA (2 equiv), and DMSO (0.7 M concentration) are heated at about 80° C. for about 15 h. The mixture is diluted with water and an organic solvent (for example, EtOAc or DCM). The layers are separated and the aqueous is extracted with organic solvent (such as EtOAc, DCM, or both sequentially). The combined organic layers are washed with brine, dried over MgSO$_4$, filtered, and concentrated under reduced pressure. The material is purified by crystallization or flash silica gel chromatography using an eluent such as EtOAc or DCM/MeOH/NH$_4$OH (for example, 990:9:1) to yield the target compound.

Illustration of General Procedure A

Example #A.1

4-4-[2-(4-Fluorophenyl)-imidazo[1,2-a]pyrazin-3-yl]-pyrimidin-2-ylaminopiperidine-1-carboxylic acid tert-butyl ester

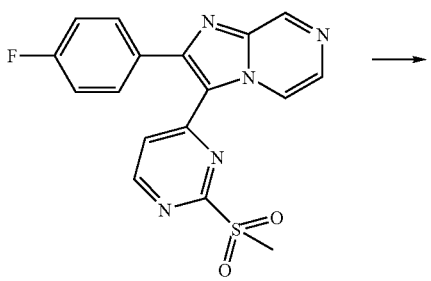

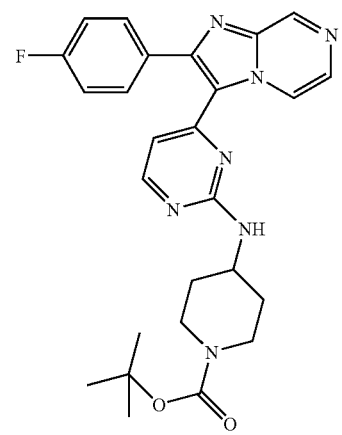

A mixture of 2-(4-fluorophenyl)-3-[2-(methanesulfonyl-pyrimidin-4-yl]imidazo[1,2-a]pyrazine (Preparation #4, 0.300 g, 0.73 mmol), tert-butyl 4-aminopiperidine-1-carboxylate (0.293 g, 1.46 mmol), DIEA (255 μL, 1.46 mmol), and DMSO (10 mL) was heated at about 80° C. for about 15 h. The mixture was diluted with water and EtOAc. The layers were separated and the aqueous layer was extracted with EtOAc followed by DCM. The combined organic layers were washed with brine, dried over MgSO$_4$, filtered, and concentrated under reduced pressure to yield 0.490 g of crude product. The material was purified by flash silica gel chromatography using EtOAc as an eluent to yield the title compound as a tan powder (0.168 g, 47%): LC/MS (Table 1, Method b) R$_t$=2.2 min; MS m/z: 488.3 (M−H)$^−$.

TABLE A.1

Examples prepared from 2-(4-fluorophenyl)-3-[2-(methanesulphonyl-pyrimidin-4-yl]imidazo[1,2-α]pyrazine (Preparation #4) using General Procedure A

| Nucleophile | Product | Example # | R$_t$ min (method) | m/z ESI+ (M + H)$^+$ |
|---|---|---|---|---|
| Cyclopropylamine | Cyclopropyl-{4-[2-(4-fluorophenyl)-imidazo[1,2-α]pyrazin-3-yl]-pyrimidin-2-yl}-amine | A.2 | 1.9 (b) | 347.5 |
| (S)-α-Methyl-benzylamine | {4-[2-(4-Fluorophenyl)-imidazo[1,2-α]pyrazin-3-yl]-pyrimidin-2-yl}-((S)-1-phenyl-ethyl)-amine | A.3 | 2.3 (b) | 411.6 |
| Cyclopentylamine | Cyclopentyl-{4-[2-(4-fluorophenyl)-imidazo[1,2-α]pyrazin-3-yl]-pyrimidin-2-yl}-amine | A.4 | 2.4 (b) | 375.2 |
| Cyclohexylamine | Cyclohexyl-{4-[2-(4-fluorophenyl)-imidazo[1,2-α]pyrazin-3-yl]-pyrimidin-2-yl}-amine | A.5 | 2.5 (b) | 389.2 |
| 1-Pyridin-2-ylmethylamine | {4-[2-(4-Fluorophenyl)-imidazo[1,2-α]pyrazin-3-yl]-pyrimidin-2-yl}-pyridin-2-ylmethylamine | A.6 | 1.8 (b) | 398.3 |
| (R)-α-Methyl-benzylamine | {4-[2-(4-Fluorophenyl)-imidazo[1,2-α]pyrazin-3-yl]-pyrimidin-2-yl}-((R)-1-phenyl-ethyl)-amine | A.7 | 2.5 (b) | 411.1 |
| Cyclohexyl-methylamine | Cyclohexyl-{4-[2-(4-fluorophenyl)-imidazo[1,2-α]pyrazin-3-yl]-pyrimidin-2-yl}-methylamine | A.8 | 2.9 (b) | 403.2 |
| Cyclopropylmethylamine | Cyclopropylmethyl-{4-[2-(4-fluorophenyl)-imidazo[1,2-α]pyrazin-3-yl]-pyrimidin-2-yl}-amine | A.9 | 2.2 (b) | 361.1 |
| Methylamine | {4-[2-(4-Fluorophenyl)-imidazo[1,2-α]pyrazin-3-yl]-pyrimidin-2-yl}-methylamine | A.10 | 2.9 (b) | 321.1 |
| Dimethylamine | {4-[2-(4-Fluorophenyl)-imidazo[1,2-α]pyrazin-3-yl]-pyrimidin-2-yl}-dimethylamine | A.11 | 3.5 (b) | 335.1 |
| Aminoquinuclidine dihydrochloride | (1-Aza-bicyclo[2.2.2]oct-3-yl)-{4-[2-(4-fluorophenyl)-imidazo[1,2-α]pyrazin-3-yl]-pyrimidin-2-yl}-amine | A.12 | 2.2 (b) | 416.7 |
| N,N,2,2-Tetramethylpropane-1,3-diamine | N'-{4-[2-(4-Fluorophenyl)-imidazo[1,2-α]pyrazin-3-yl]-pyrimidin-2-yl}-2,2,N,N-tetramethylpropane-1,3-diamine | A.13 | 2.3 (b) | 420.2 |
| (3R)-Quinuclidin-3-amine dihydrochloride | (S)-1-Aza-bicyclo[2.2.2]oct-3-yl-{4-[2-(4-fluorophenyl)-imidazo[1,2-α]pyrazin-3-yl]-pyrimidin-2-yl}-amine | A.14 | 2.2 (b) | 416.5 |
| 8-Methyl-8-aza-bicyclo[3.2.1]oct-3-ylamine dihydrochloride | {4-[2-(4-Fluorophenyl)-imidazo[1,2-α]pyrazin-3-yl]-pyrimidin-2-yl}-(8-methyl-8-aza-bicyclo[3.2.1]oct-3-yl)-amine | A.15 | 1.1 (b) | 430.7 |
| N-(2-Aminoethyl)morpholine | {4-[2-(4-Fluorophenyl)-imidazo[1,2-α]pyrazin-3-yl]-pyrimidin-2-yl}-(2-morpholin-4-yl-ethyl)-amine | A.16 | 2.0 (b) | 365.1 |
| 2-Methoxyethylamine | {4-[2-(4-Fluorophenyl)-imidazo[1,2-α]pyrazin-3-yl]-pyrimidin-2-yl}-(2-methoxyethyl)-amine | A.17 | 2.0 (b) | 393.2 |

TABLE A.1-continued

Examples prepared from 2-(4-fluorophenyl)-3-[2-(methanesulphonyl-pyrimidin-4- yl]imidazo[1,2-α]pyrazine (Preparation #4) using General Procedure A

| Nucleophile | Product | Example # | R$_t$ min (method) | m/z ESI+ (M + H)$^+$ |
|---|---|---|---|---|
| 3-Amino-2,2-dimethylpropan-1-ol [TCI-US] | 3-{4-[2-(4-Fluorophenyl)-imidazo[1,2-α]pyrazin-3-yl]-pyrimidin-2-ylamino}-2,2-dimethylpropan-1-ol | A.18 | 2.0 (b) | 393.2 |
| (S)-(−)-3-Aminoquinuclidine dihydrochloride | (R)-1-Aza-bicyclo[2.2.2]oct-3-yl-{4-[2-(4-fluoro-phenyl)-imidazo[1,2-α]pyrazin-3-yl]-pyrimidin-2-yl}-amine | A.19 | 1.9 (b) | 416.3 |
| Tetrahydrofurfurylamine | {4-[2-(4-Fluorophenyl)-imidazo[1,2-α]pyrazin-3-yl]-pyrimidin-2-yl}-(tetrahydro-furan-2-ylmethyl)-amine | A.20 | 2.6 (b) | 391.2 |
| 2-Amino-3-methyl-butan-1-ol | 2-{4-[2-(4-Fluorophenyl)-imidazo[1,2-α]pyrazin-3-yl]-pyrimidin-2-ylamino}-3-methyl-butan-1-ol | A.21 | 1.9 (b) | 393.3 |
| 1-Methylpiperidin-4-ylamine | {4-[2-(4-Fluorophenyl)-imidazo[1,2-α]pyrazin-3-yl]-pyrimidin-2-yl}-(1-methylpiperidin-4-yl)-amine | A.22 | 1.4 (b) | 404.7 |
| Thiophene-2-methanamine | {4-[2-(4-Fluorophenyl)-imidazo[1,2-α]pyrazin-3-yl]-pyrimidin-2-yl}-thiophen-2-ylmethylamine | A.23 | 2.3 (b) | 403.1 |
| 1,4-Dioxa-spiro[4.5]dec-8-ylamine | (1,4-Dioxa-spiro[4.5]dec-8-yl)-{4-[2-(4-fluorophenyl)-imidazo[1,2-α]pyrazin-3-yl]-pyrimidin-2-yl}-amine | A.24 | 2.1 (b) | 447.2 |
| 2,2,6,6-Tetramethylpiperidin-4-ylamine | {4-[2-(4-Fluorophenyl)-imidazo[1,2-α]pyrazin-3-yl]-pyrimidin-2-yl}-(2,2,6,6-tetramethylpiperidin-4-yl)-amine | A.25 | 1.6 (b) | 446.3 |
| 1,2,2,6,6-Pentamethylpiperidin-4-ylamine | {4-[2-(4-Fluorophenyl)-imidazo[1,2-α]pyrazin-3-yl]-pyrimidin-2-yl}-(1,2,2,6,6-pentamethylpiperidin-4-yl)-amine | A.26 | 1.6 (b) | 460.3 |
| Tetrahydro-thiopyran-4-yl amine | {4-[2-(4-Fluorophenyl)-imidazo[1,2-α]pyrazin-3-yl]-pyrimidin-2-yl}-(tetrahydro-thiopyran-4-yl)-amine | A.27 | 2.2 (b) | 407.2 |
| 4-Aminotetrahydropyran | {4-[2-(4-Fluorophenyl)-imidazo[1,2-α]pyrazin-3-yl]-pyrimidin-2-yl}-(tetrahydropyran-4-yl)-amine | A.28 | 1.8 (b) | 391.2 |
| N'1,N'1-Dimethyl-ethane-1,2-diamine | N'-{4-[2-(4-Fluorophenyl)-imidazo[1,2-α]pyrazin-3-yl]-pyrimidin-2-yl}-N,N-dimethyl-ethane-1,2-diamine | A.29 | 1.57 (g) | 378.26 |
| 2-Methylpropane-1,2-diamine | N'1-{4-[2-(4-Fluorophenyl)-imidazo[1,2-α]pyrazin-3-yl]-pyrimidin-2-yl}-2-methylpropane-1,2-diamine | A.30 | 1.59 (g) | 378.26 |
| 2-Pyrrolidin-1-yl-ethylamine | {4-[2-(4-Fluorophenyl)-imidazo[1,2-α]pyrazin-3-yl]-pyrimidin-2-yl}-(2-pyrrolidin-1-yl-ethyl)-amine hydrochloride | A.31 | 1.61 (g) | 404.28 |
| 3-Pyrrolidin-1-ylpropylamine (Ryan) | {4-[2-(4-Fluorophenyl)-imidazo[1,2-α]pyrazin-3-yl]-pyrimidin-2-yl}-(3-pyrrolidin-1-ylpropyl)-amine | A.32 | 1.64 (g) | 418.29 |
| (1-Ethylpyrrolidin-2-yl)-methylamine (Acros) | (1-Ethylpyrrolidin-2-ylmethyl)-{4-[2-(4-fluorophenyl)-imidazo[1,2-α]pyrazin-3-yl]-pyrimidin-2-yl}-amine | A.33 | 1.67 (g) | 418.29 |
| 1-Benzylpyrrolidin-3-ylamine [ASDI] | (1-Benzylpyrrolidin-3-yl)-{4-[2-(4-fluorophenyl)-imidazo[1,2-α]pyrazin-3-yl]-pyrimidin-2-yl}-amine | A.34 | 1.98 (g) | 466.34 |

TABLE A.1-continued

Examples prepared from 2-(4-fluorophenyl)-3-[2-(methanesulphonyl-pyrimidin-4-yl]imidazo[1,2-α]pyrazine (Preparation #4) using General Procedure A

| Nucleophile | Product | Example # | R, min (method) | m/z ESI+ (M + H)+ |
|---|---|---|---|---|
| N'1',N'1'-Dimethylpropane-1,3-diamine | N'-{4-[2-(4-Fluorophenyl)-imidazo[1,2-α]pyrazin-3-yl]-pyrimidin-2-yl}-N,N-dimethylpropane-1,3-diamine hydrochloride | A.35 | 1.59 (g) | 392.28 |
| 1-(3-Aminopropyl)-pyrrolidin-2-one | 1-(3-{4-[2-(4-Fluorophenyl)-imidazo[1,2-α]pyrazin-3-yl]-pyrimidin-2-ylamino}-propyl)-pyrrolidin-2-one | A.36 | 2.10 (g) | 432.32 |
| 3-Aminopyrrolidine-1-carboxylic acid tert-butyl ester (Astatech) | 3-{4-[2-(4-Fluorophenyl)-imidazo[1,2-α]pyrazin-3-yl]-pyrimidin-2-ylamino}-pyrrolidine-1-carboxylic acid tert-butyl ester | A.37 | 2.92 (g) | 476.34 |
| N-(2-Aminoethyl)-acetamide | N-(2-{4-[2-(4-Fluorophenyl)-imidazo[1,2-α]pyrazin-3-yl]-pyrimidin-2-ylamino}-ethyl)-acetamide | A.38 | 1.88 (g) | 392.26 |
| Pyridin-3-yl-methylamine | {4-[2-(4-Fluorophenyl)-imidazo[1,2-α]pyrazin-3-yl]-pyrimidin-2-yl}-pyridin-3-ylmethylamine | A.39 | 2.06 (g) | 398.24 |
| (3-Amino-2,2-dimethylpropyl)-carbamic acid tert-butyl ester [ASDI] | (3-{4-[2-(4-Fluorophenyl)-imidazo[1,2-α]pyrazin-3-yl]-pyrimidin-2-ylamino}-2,2-dimethylpropyl)-carbamicacid tert-butyl ester | A.40 | 2.41 (b) | 492.1 |

General Procedure A.2: Displacement of a Sulfone and/or a Sulfoxide by a Nucleophile

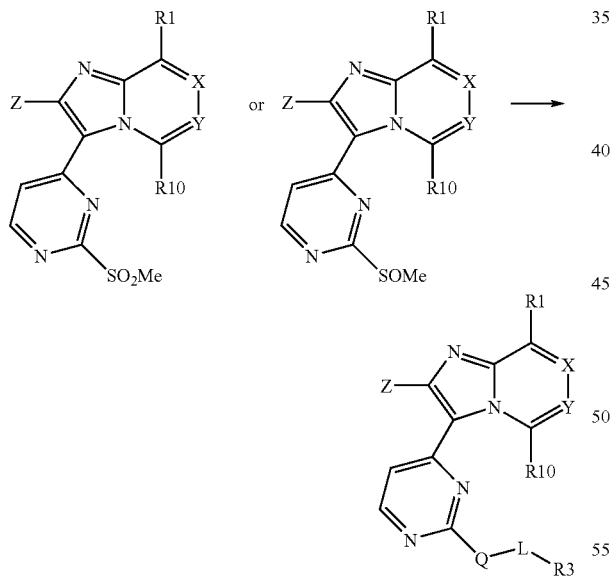

A mixture of a substituted 2-(aryl)-3-[2-(methanesulfonyl-pyrimidin-4-yl]imidazo[1,2-a]pyrazine or 2-(aryl)-3-[2-(methanesulfinyl-pyrimidin-4-yl]imidazo[1,2-a]pyrazine (1 equiv), a nucleophile (1-20 equiv, preferably 5 equiv), with or without an additional base, such as TEA or DIEA (1-3 equiv), and a suitable organic solvent (for example, ACN or DMSO) are heated at about 22-100° C. (preferably 60-80° C.) for about 148 h. Additional nucleophile is added if the reaction is not consuming all of the starting sulfone or sulfoxide (as monitored by LC/MS, HPLC or TLC). If the product precipitates during the reaction or upon cooling it is directly filtered and characterized or if necessary, is purified further as indicated below. Alternatively, the mixture is optionally concentrated under reduced pressure and is diluted with or partitioned between water and an organic solvent (for example, EtOAc or DCM). The layers are separated and the aqueous layer is extracted with additional organic solvent (such as EtOAc, DCM, or both sequentially). The combined organic layers may be optionally washed with brine, dried over Na$_2$SO$_4$ or MgSO$_4$, then decanted or filtered, prior to concentrating under reduced pressure. The crude material is purified by chromatography, trituration with an appropriate solvent, or crystallization from one or more solvents to yield the target compound.

Illustration of General Procedure A.2

Example #A.2.1

Cyclopropyl-4-[2-(4-fluorophenyl)-8-methylimidazo[1,2-a]pyrazin-3-yl]-pyrimidin-2-ylamine

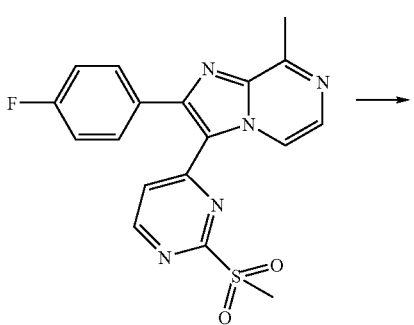

-continued

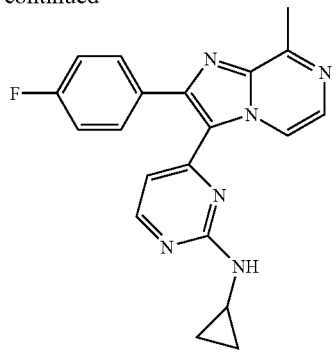

To a mixture of 2-(4-fluorophenyl)-3-(2-methanesulfonylpyrimidin-4-yl)-8-methylimidazo[1,2-a]pyrazine (Example #G.1; 3.66 g, 9.55 mmol) in ACN (70 mL) was added cyclopropylamine (3.31 mL, 47.7 mmol). The mixture was heated to about 80° C. After about 16 h, the mixture was treated with additional cyclopropylamine (3.0 mL, 43 mmol) and heated at about 80° C. for about another 4 h. The mixture was cooled to ambient temperature and filtered. The resulting solid was washed with ACN and dried to yield the title compound as a white solid (2.85 g, 83%): LC/MS (Table 1, Method b) $R_t$=2.0 min; MS m/z: 361.2 $(M+H)^+$.

TABLE A.2

Examples prepared from 3-(2-methanesulfonylpyrimidin-4-yl)-2-phenylimidazo[1,2-α]pyrazine (Example #G.1.34) using General Procedure A.2

| Nucleophile | Product | Example # | $R_t$ min (method) | m/z ESI+ $(M + H)^+$ |
|---|---|---|---|---|
| 4-Aminopiperidine-1-carboxylic acid tert-butyl ester | 4-[4-(2-Phenylimidazo[1,2-α]pyrazin-3-yl)-pyrimidin-2-ylamino]-piperidine-1-carboxylic acid tert-butyl ester | A.2.2 | 2.39 (f) | 472.2 |
| 1-Methanesulfonylpiperidin-4-ylamine | (1-Methanesulfonylpiperidin-4-yl)-[4-(2-phenylimidazo[1,2-α]pyrazin-3-yl)-pyrimidin-2-yl]-amine | A.2.3 | 1.87 (f) | 450.2 |
| 1-(4-Aminopiperidin-1-yl)-ethanone | 1-{4-[4-(2-Phenylimidazo[1,2-α]pyrazin-3-yl)-pyrimidin-2-ylamino]-piperidin-1-yl}-ethanone | A.2.4 | 1.73 (f) | 414.2 |
| Cyclopentylamine | Cyclopentyl-[4-(2-phenylimidazo[1,2-α]pyrazin-3-yl)-pyrimidin-2-yl]-amine | A.2.5 | 2.27 (b) | 357.2 |
| Cyclopropylamine | Cyclopropyl-[4-(2-phenylimidazo[1,2-α]pyrazin-3-yl)-pyrimidin-2-yl]-amine | A.2.6 | 1.83 (b) | 329.2 |
| (S)-1-Phenyl-ethylamine | ((S)-1-Phenyl-ethyl)-[4-(2-phenylimidazo[1,2-α]pyrazin-3-yl)-pyrimidin-2-yl]-amine | A.2.7 | 2.31 (b) | 393.2 |
| Cyclohexylamine | Cyclohexyl-[4-(2-phenylimidazo[1,2-α]pyrazin-3-yl)-pyrimidin-2-yl]-amine | A.2.8 | 2.58 (b) | 371.2 |

TABLE A.3

Examples prepared from 3-(2-methanesulfonylpyrimidin-4-yl)-2-naphthalen-2-ylimidazo[1,2-α]pyrazine (Example #G.1.35) using General Procedure A.2

| Nucleophile | Product | Example # | $R_t$ min (method) | m/z ESI+ $(M + H)^+$ |
|---|---|---|---|---|
| 1-Methanesulfonylpiperidin-4-ylamine | (1-Methanesulfonylpiperidin-4-yl)-[4-(2-naphthalen-2-ylimidazo[1,2-α]pyrazin-3-yl)-pyrimidin-2-yl]-amine | A.3.1 | 2.10 (f) | 500.2 |
| 4-Aminopiperidine-1-carboxylic acid tert-butyl ester | 4-[4-(2-Naphthalen-2-ylimidazo[1,2-α]pyrazin-3-yl)-pyrimidin-2-ylamino]-piperidine-1-carboxylic acid tert-butyl ester | A.3.2 | 2.65 (f) | 522.2 |
| 1-Methylpiperidin-4-ylamine | (1-Methylpiperidin-4-yl)-[4-(2-naphthalen-2-ylimidazo[1,2-α]pyrazin-3-yl)-pyrimidin-2-yl]-amine | A.3.3 | 1.67 (f) | 436.3 |
| 1-(4-Aminopiperidin-1-yl)-ethanone | 1-{4-[4-(2-Naphthalen-2-ylimidazo[1,2-α]pyrazin-3-yl)-pyrimidin-2-ylamino]-piperidin-1-yl}-ethanone | A.3.4 | 1.98 (f) | 464.3 |

TABLE A.3-continued

Examples prepared from 3-(2-methanesulfonylpyrimidin-4-yl)-2-naphthalen-2-ylimidazo[1,2-α]pyrazine (Example #G.1.35) using General Procedure A.2

| Nucleophile | Product | Example # | $R_t$ min (method) | m/z ESI+ $(M + H)^+$ |
|---|---|---|---|---|
| Cyclopentylamine | Cyclopentyl-[4-(2-naphthalen-2-ylimidazo[1,2-α]pyrazin-3-yl)-pyrimidin-2-yl]-amine | A.3.5 | 2.62 (b) | 407.2 |
| Cyclopropylamine | Cyclopropyl-[4-(2-naphthalen-2-ylimidazo[1,2-α]pyrazin-3-yl)-pyrimidin-2-yl]-amine | A.3.6 | 2.20 (b) | 379.3 |
| Cyclohexylamine | Cyclohexyl-[4-(2-naphthalen-2-ylimidazo[1,2-α]pyrazin-3-yl)-pyrimidin-2-yl]-amine | A.3.7 | 2.85 (b) | 421.3 |

TABLE A.4

Examples prepared from 3-(2-methanesulfonylpyrimidin-4-yl)-2-(3-trifluoromethylphenyl)-imidazo[1,2-α]pyrazine (Example #G.1.36) using General Procedure A.2

| Nucleophile | Product | Example # | $R_t$ min (method) | m/z ESI+ $(M + H)^+$ |
|---|---|---|---|---|
| Cyclopentylamine | Cyclopentyl-{4-[2-(3-trifluoromethylphenyl)-imidazo[1,2-α]pyrazin-3-yl]-pyrimidin-2-yl}-amine | A.4.1 | 2.57 (b) | 425.3 |
| Cyclopropylamine | Cyclopropyl-{4-[2-(3-trifluoromethylphenyl)-imidazo[1,2-α]pyrazin-3-yl]-pyrimidin-2-yl}-amine | A.4.2 | 2.12 (b) | 397.2 |
| Cyclohexylamine | Cyclohexyl-{4-[2-(3-trifluoromethylphenyl)-imidazo[1,2-α]pyrazin-3-yl]-pyrimidin-2-yl}-amine | A.4.3 | 2.67 (b) | 439.2 |
| (S)-1-Phenyl-ethylamine | ((S)-1-Phenyl-ethyl)-{4-[2-(3-trifluoromethylphenyl)-imidazo[1,2-α]pyrazin-3-yl]-pyrimidin-2-yl}-amine | A.4.4 | 2.52 (b) | 461.2 |
| 3-Amino-2,2-dimethylpropan-1-ol [Lancaster] | 2,2-Dimethyl-3-{4-[2-(3-trifluoromethylphenyl)-imidazo[1,2-α]pyrazin-3-yl]-pyrimidin-2-ylamino}-propan-1-ol | A.4.5 | 2.19 (f) | 443.17 |
| Tetrahydro-pyran-4-ylamine (Oakwood) | Tetrahydro-pyran-4-yl)-{4-[2-(3-trifluoromethylphenyl)-imidazo[1,2-α]pyrazin-3-yl]-pyrimidin-2-yl}-amine | A.4.6 | 2.82 (f) | 441.18 |
| 1-Methanesulfonylpiperidin-4-ylamine | (1-Methanesulfonylpiperidin-4-yl)-{4-[2-(3-trifluoromethylphenyl)-imidazo[1,2-α]pyrazin-3-yl]-pyrimidin-2-yl}-amine | A.4.7 | 2.78 (f) | 518.18 |

TABLE A.5

Examples prepared from 3-(2-methanesulfonylpyrimidin-4-yl)-2-m-tolylimidazo[1,2-α]pyrazine (Example #G.1.21) using General Procedure A.2

| Nucleophile | Product | Example # | $R_t$ min (method) | m/z ESI+ $(M + H)^+$ |
|---|---|---|---|---|
| Cyclopropylamine | Cyclopropyl-[4-(2-m-tolylimidazo[1,2-α]pyrazin-3-yl)-pyrimidin-2-yl]-amine | A.5.1 | 2.21 (f) | 343.2 |
| Cyclopentylamine | Cyclopentyl-[4-(2-m-tolylimidazo[1,2-α]pyrazin-3-yl)-pyrimidin-2-yl]-amine | A.5.2 | 2.60 (f) | 371.2 |
| Cyclohexylamine | Cyclohexyl-[4-(2-m-tolylimidazo[1,2-α]pyrazin-3-yl)-pyrimidin-2-yl]-amine | A.5.3 | 2.76 (f) | 385.2 |

TABLE A.5-continued

Examples prepared from 3-(2-methanesulfonylpyrimidin-4-yl)-2-m-tolylimidazo[1,2-α]pyrazine (Example #G.1.21) using General Procedure A.2

| Nucleophile | Product | Example # | $R_t$ min (method) | m/z ESI+ $(M + H)^+$ |
|---|---|---|---|---|
| (S)-1-Phenyl-ethyl amine | ((S)-1-Phenyl-ethyl)-[4-(2-m-tolylimidazo[1,2-α]pyrazin-3-yl)-pyrimidin-2-yl]-amine | A.5.4 | 2.64 (f) | 407.2 |
| 1-Methanesulfonylpiperidin-4-ylamine | (1-Methanesulfonylpiperidin-4-yl)-[4-(2-m-tolylimidazo[1,2-α]pyrazin-3-yl)-pyrimidin-2-yl]-amine | A.5.5 | 1.99 (f) | 464.2 |
| 3-Amino-2,2-dimethylpropan-1-ol [TCI-US] | 2,2-Dimethyl-3-[4-(2-m-tolylimidazo[1,2-α]pyrazin-3-yl)-pyrimidin-2-ylamino]-propan-1-ol | A.5.6 | 2.08 (f) | 389.2 |

TABLE A.6

Examples prepared from 2-(3,4-difluorophenyl)-3-(2-methanesulfonylpyrimidin-4-yl)-imidazo[1,2-α]pyrazine (Example #G.1.22) using General Procedure A.2

| Nucleophile | Product | Example # | $R_t$ min (method) | m/z ESI+ $(M + H)^+$ |
|---|---|---|---|---|
| Cyclopropylamine | Cyclopropyl-{4-[2-(3,4-difluorophenyl)-imidazo[1,2-α]pyrazin-3-yl]-pyrimidin-2-yl}-amine | A.6.1 | 2.15 (f) | 365.1 |
| 3-Amino-2,2-dimethylpropan-1-ol [TCI-US] | 3-{4-[2-(3,4-Difluorophenyl)-imidazo[1,2-α]pyrazin-3-yl]-pyrimidin-2-ylamino}-2,2-dimethylpropan-1-ol | A.6.2 | 2.04 (f) | 411.2 |
| 1-Methanesulfonylpiperidin-4-ylamine | {4-[2-(3,4-Difluorophenyl)-imidazo[1,2-α]pyrazin-3-yl]-pyrimidin-2-yl}-(1-methanesulfonylpiperidin-4-yl)-amine | A.6.3 | 1.97 (f) | 486.2 |

TABLE A.7

Examples prepared from 2-(4-chlorophenyl)-3-(2-methanesulfonylpyrimidin-4-yl)-imidazo[1,2-α]pyrazine (Example #G.1.1) using General Procedure A.2

| Nucleophile | Product | Example # | $R_t$ min (method) | m/z ESI+ $(M + H)^+$ |
|---|---|---|---|---|
| Cyclopropylamine | {4-[2-(4-Chlorophenyl)-imidazo[1,2-α]pyrazin-3-yl]-pyrimidin-2-yl}-cyclopropylamine | A.7.1 | 2.3 (b) | 363.1 |
| 3-Amino-2,2-dimethylpropan-1-ol [TCI-US] | 3-{4-[2-(4-Chlorophenyl)-imidazo[1,2-α]pyrazin-3-yl]-pyrimidin-2-ylamino}-2,2-dimethylpropan-1-ol | A.7.2 | 2.1 (b) | 409.2 |
| 1-Methanesulfonylpiperidin-4-ylamine hydrochloride (Atlantic SciTech) | {4-[2-(4-Chlorophenyl)-imidazo[1,2-α]pyrazin-3-yl]-pyrimidin-2-yl}-(1-methanesulfonylpiperidin-4-yl)-amine | A.7.3 | 2.1 (b) | 484.1 |

TABLE A.8

Examples prepared from 2-(2,4-difluorophenyl)-3-(2-methanesulfonylpyrimidin-4-yl)-imidazo[1,2-α]pyrazine (Example #G.1.4) using General Procedure A.2

| Nucleophile | Product | Example # | $R_t$ min (method) | m/z ESI+ $(M + H)^+$ |
|---|---|---|---|---|
| 3-Amino-2,2-dimethylpropan-1-ol [TCI-US] | 3-{4-[2-(2,4-Difluorophenyl)-imidazo[1,2-α]pyrazin-3-yl]-pyrimidin-2-ylamino}-2,2-dimethylpropan-1-ol | A.8.1 | 2.0 (b) | 411.1 |
| Cyclopropylamine | Cyclopropyl-{4-[2-(2,4-difluorophenyl)-imidazo[1,2-α]pyrazin-3-yl]-pyrimidin-2-yl}-amine | A.8.2 | 2.1 (b) | 365.1 |

TABLE A.9

Examples prepared from 2-(4-fluorophenyl)-3-(2-methanesulfonylpyrimidin-4-yl)-8-methylimidazo[1,2-α]pyrazine (Example #G.1) using General Procedure A.2

| Nucleophile | Product | Example # | $R_t$ min (method) | m/z ESI+ $(M + H)^+$ |
|---|---|---|---|---|
| 2-Amino-2-methyl-1-propanol | 2-{4-[2-(4-Fluorophenyl)-8-methylimidazo[1,2-α]pyrazin-3-yl]-pyrimidin-2-ylamino}-2-methylpropan-1-ol | A.9.1 | 1.9 (b) | 393.3 |
| tert-Butyl 4-aminopiperidine-1-carboxylate | 4-{4-[2-(4-Fluorophenyl)-8-methylimidazo[1,2-α]pyrazin-3-yl]-pyrimidin-2-ylamino}-piperidine-1-carboxylic acid tert-butyl ester | A.9.2 | 2.3 (b) | 504.4 |
| 1-Pyridin-2-ylmethanamine | {4-[2-(4-Fluorophenyl)-8-methylimidazo[1,2-α]pyrazin-3-yl]-pyrimidin-2-yl}-pyridin-2-ylmethyl-amine | A.9.3 | 1.9 (b) | 412.2 |
| 2,2,N'1',N'1'-Tetramethyl-propane-1,3-diamine | N'-{4-[2-(4-Fluorophenyl)-8-methylimidazo[1,2-α] pyrazin-3-yl]-pyrimidin-2-yl}-2,2,N,N-tetramethyl-propane-1,3-diamine | A.9.4 | 1.6 (b) | 434.3 |
| 8-Methyl-8-aza-bicyclo[3.2.1]oct-3-ylamine dihydrochloride (Oakwood) | {4-[2-(4-Fluorophenyl)-8-methylimidazo[1,2-α]pyrazin-3-yl]-pyrimidin-2-yl}-(8-methyl-8-aza-bicyclo[3.2.1]oct-3-yl)-amine | A.9.5 | 1.5 (b) | 444.3 |
| 2-Methoxyethylamine | {4-[2-(4-Fluorophenyl)-8-methylimidazo[1,2-α]pyrazin-3-yl]-pyrimidin-2-yl}-(2-methoxyethyl)-amine | A.9.6 | 2.1 (b) | 379.3 |
| 3-Methoxypropylamine | {4-[2-(4-Fluorophenyl)-8-methylimidazo[1,2-α]pyrazin-3-yl]-pyrimidin-2-yl}-(3-methoxypropyl)-amine | A.9.7 | 2.1 (b) | 393.3 |
| 3-Amino-1-propanol | 3-{4-[2-(4-Fluorophenyl)-8-methylimidazo[1,2-α]pyrazin-3-yl]-pyrimidin-2-ylamino}-propan-1-ol | A.9.8 | 1.8 (b) | 379.3 |
| 2,2-Dimethylpropylamine | (2,2-Dimethylpropyl)-{4-[2-(4-fluorophenyl)-8-methylimidazo[1,2-α]pyrazin-3-yl]-pyrimidin-2-yl}-amine | A.9.9 | 2.6 (b) | 391.4 |
| 1-Aminomethyl-cyclohexanol hydrochloride | 1-({4-[2-(4-Fluorophenyl)-8-methylimidazo[1,2-α] pyrazin-3-yl]-pyrimidin-2-ylamino}-methyl)-cyclohexanol | A.9.10 | 2.1 (b) | 433.4 |
| 2-Methoxy-1-methoxymethyl-ethylamine | {4-[2-(4-Fluorophenyl)-8-methylimidazo[1,2-α]pyrazin-3-yl]-pyrimidin-2-yl}-(2-methoxy-1-methoxymethyl-ethyl)-amine | A.9.11 | 2.0 (b) | 423.4 |
| 1-Amino-2-methylpropan-2-ol [Tyger] | 1-{4-[2-(4-Fluorophenyl)-8-methylimidazo[1,2-α]pyrazin-3-yl]-pyrimidin-2-ylamino}-2-methylpropan-2-ol | A.9.12 | 1.8 (b) | 393.3 |

TABLE A.9-continued

Examples prepared from 2-(4-fluorophenyl)-3-(2-methanesulfonylpyrimidin-4-yl)-8-methylimidazo[1,2-α]pyrazine (Example #G.1) using General Procedure A.2

| Nucleophile | Product | Example # | $R_t$ min (method) | m/z ESI+ (M + H)+ |
|---|---|---|---|---|
| 4-Aminoazepane-1-carboxylic acid tert-butyl ester [Magical] | 4-{4-[2-(4-Fluorophenyl)-8-methylimidazo[1,2-α]pyrazin-3-yl]-pyrimidin-2-ylamino}-azepane-1-carboxylic acid tert-butyl ester | A.9.13 | 2.5 (b) | 518.5 |
| 4-Aminotetra-hydropyran | {4-[2-(4-Fluorophenyl)-8-methylimidazo[1,2-α]pyrazin-3-yl]-pyrimidin-2-yl}-(tetrahydropyran-4-yl)-amine | A.9.14 | 1.9 (b) | 405.3 |
| (1-Aminomethyl-cyclopropyl)-methanol (J Med Chem 1972, 15(10), 1003-1006) | [1-({4-[2-(4-Fluorophenyl)-8-methylimidazo[1,2-α]pyrazin-3-yl]-pyrimidin-2-ylamino}-methyl)-cyclopropyl]-methanol | A.9.15 | 1.8 (b) | 405.3 |
| 3-Aminopropionamide | 3-{4-[2-(4-Fluorophenyl)-8-methylimidazo[1,2-α] pyrazin-3-yl]-pyrimidin-2-ylamino}-propionamide | A.9.16 | 1.50 (a) | 392.2 |
| 3-Methoxy-2,2-dimethylpropylamine (Preparation #6) | {4-[2-(4-Fluorophenyl)-8-methylimidazo[1,2-a]pyrazin-3-yl]pyrimidin-2-yl}-(3-methoxy-2,2-dimethylpropyl)amine | A.9.18 | 2.4 (b) | 421.2 |
| 3-Amino-2,2-dimethyl-propionic acid ethyl ester [Rarechem] | 3-{4-[2-(4-Fluorophenyl)-8-methylimidazo[1,2-a]pyrazin-3-yl]-pyrimidin-2-ylamino}-2,2-dimethylpropionic acid ethyl ester | A.9.19 | 2.3 (b) | 449.2 |
| (S)-3-Amino-propane-1,2-diol | (S)-3-{4-[2-(4-Fluorophenyl)-8-methylimidazo[1,2-a]pyrazin-3-yl]pyrimidin-2-ylamino}-propane-1,2-diol | A.9.20 | 1.76 (b) | 395.2 |

TABLE A.10

Examples prepared from 2-(4-fluorophenyl)-3-(2-methanesulfonylpyrimidin-4-yl)-8-methoxyimidazo[1,2-α]pyrazine (Example #G.1.6) using General Procedure A.2

| Nucleophile | Product | Example # | $R_t$ min (method) | m/z ESI+ (M + H)+ |
|---|---|---|---|---|
| Cyclopropylamine | Cyclopropyl-{4-[2-(4-fluorophenyl)-8-methoxyimidazo[1,2-α]pyrazin-3-yl]-pyrimidin-2-yl}-amine | A.10.1 | 2.1 (b) | 377.3 |
| (3-Amino-2,2-dimethylpropyl)-carbamic acid tert-butyl ester | (3-{4-[2-(4-Fluorophenyl)-8-methoxyimidazo[1,2-α]pyrazin-3-yl]-pyrimidin-2-ylamino}-2,2-dimethylpropyl)-carbamic acid tert-butyl ester | A.10.2 | 2.5 (b) | 522.4 |
| 3-Amino-2,2-dimethylpropan-1-ol [TCI-US] | 3-{4-[2-(4-Fluorophenyl)-8-methoxyimidazo[1,2-α] pyrazin-3-yl]-pyrimidin-2-ylamino}-2,2-dimethyl-propan-1-ol | A.10.3 | 2.02 (b) | 423.3 |
| (1-Aminomethyl-cyclopropyl)-methanol (J Med Chem 1972, 15(10), 1003-1006) | [1-({4-[2-(4-Fluorophenyl)-8-methoxyimidazo[1,2-a]pyrazin-3-yl]-pyrimidin-2-ylamino}-methyl)cyclopropyl]methanol | A.10.4 | 1.9 (b) | 421.2 |

TABLE A.11

Examples prepared from 2-(3-fluorophenyl)-3-(2-methanesulfonylpyrimidin-4-yl)-8-methylimidazo[1,2-α]pyrazine (Example #G.1.7) using General Procedure A.2

| Nucleophile | Product | Example # | $R_t$ min (method) | m/z ESI+ (M + H)$^+$ |
|---|---|---|---|---|
| Cyclopropylamine | Cyclopropyl-{4-[2-(3-fluorophenyl)-8-methylimidazo-[1,2-α]pyrazin-3-yl]-pyrimidin-2-yl}-amine | A.11.1 | 2.52 (g) | 361.3 |

TABLE A.12

Examples prepared from 2-(3,5-difluorophenyl)-3-(2-methanesulfonylpyrimidin-4-yl)-8-methylimidazo[1,2-α]pyrazine (Example #G.1.8) using General Procedure A.2

| Nucleophile | Product | Example # | $R_t$ min (method) | m/z ESI+ (M + H)$^+$ |
|---|---|---|---|---|
| Cyclopropylamine | Cyclopropyl-{4-[2-(3,5-difluorophenyl)-8-methylimidazo[1,2-α]pyrazin-3-yl-pyrimidin-2-yl}-amine | A.12.1 | 2.69 (g) | 379.3 |

TABLE A.13

Examples prepared from 2-(3-fluoro-5-trifluoromethylphenyl)-3-(2-methanesulfonylpyrimidin-4-yl)-8-methylimidazo[1,2-α]pyrazine (Example #G.1.9) using General Procedure A.2

| Nucleophile | Product | Example # | $R_t$ min (method) | m/z ESI+ (M + H)$^+$ |
|---|---|---|---|---|
| Cyclopropylamine | Cyclopropyl-{4-[2-(3-fluoro-5-trifluoromethylphenyl)-8-methylimidazo[1,2-α]pyrazin-3-yl]-pyrimidin-2-yl}-amine | A.13.1 | 3.04 (g) | 429.3 |

TABLE A.14

Examples prepared from 2-(4-fluorophenyl)-3-(2-methanesulfonylpyrimidin-4-yl)-8-(2,2,2-trifluoroethoxy)-imidazo[1,2-α]pyrazine (Example #G.1.10) using General Procedure A.2

| Nucleophile | Product | Example # | $R_t$ min (method) | m/z ESI+ (M + H)$^+$ |
|---|---|---|---|---|
| Cyclopropylamine | Cyclopropyl-{4-[2-(4-fluorophenyl)-8-(2,2,2-trifluoroethoxy)-imidazo[1,2-α]pyrazin-3-yl]-pyrimidin-2-yl}-amine | A.14.1 | 3.14 (g) | 445.3 |
| 3-Amino-2,2-dimethylpropan-1-ol [TCI-US] | 3-{4-[2-(4-Fluorophenyl)-8-(2,2,2-trifluoroethoxy)-imidazo[1,2-α]pyrazin-3-yl]-pyrimidin-2-ylamino}-2,2-dimethylpropan-1-ol | A.14.2 | 3.05 (g) | 491.3 |

TABLE A.15

Examples prepared from 2-(4-fluorophenyl)-8-isobutoxy-3-(2-methanesulfonylpyrimidin-4-yl)-imidazo[1,2-α]pyrazine (Example #G.1.11) using General Procedure A.2

| Nucleophile | Product | Example # | $R_t$ min (method) | m/z ESI+ $(M + H)^+$ |
|---|---|---|---|---|
| Cyclopropylamine | Cyclopropyl-{4-[2-(4-fluorophenyl)-8-isobutoxyimidazo[1,2-α]pyrazin-3-yl]-pyrimidin-2-yl}-amine | A.15.1 | 3.43 (g) | 419.3 |
| 3-Amino-2,2-dimethylpropan-1-ol [TCI-US] | 3-{4-[2-(4-Fluorophenyl)-8-isobutoxyimidazo[1,2-α]pyrazin-3-yl]-pyrimidin-2-ylamino}-2,2-dimethylpropan-1-ol | A.15.2 | 3.30 (g) | 465.4 |

TABLE A.16

Examples prepared from 8-cyclopropylmethoxy-2-(4-Fluorophenyl)-3-(2-methanesulfonylpyrimidin-4-yl)-imidazo[1,2-α]pyrazine (Example #G.1.12) using General Procedure A.2

| Nucleophile | Product | Example # | $R_t$ min (method) | m/z ESI+ $(M + H)^+$ |
|---|---|---|---|---|
| Cyclopropylamine | Cyclopropyl-{4-[8-cyclopropylmethoxy-2-(4-fluorophenyl)-imidazo[1,2-α]pyrazin-3-yl]-pyrimidin-2-yl}-amine | A.16.1 | 3.46 (g) | 417.3 |

TABLE A.17

Examples prepared from 2-(4-fluorophenyl)-3-(2-methanesulfonylpyrimidin-4-yl)-8-(2-methoxyethoxy)-imidazo[1,2-α]pyrazine (Example #G.1.13) using General Procedure A.2

| Nucleophile | Product | Example # | $R_t$ min (method) | m/z ESI+ $(M + H)^+$ |
|---|---|---|---|---|
| Cyclopropylamine | Cyclopropyl-{4-[2-(4-fluorophenyl)-8-(2-methoxyethoxy)-imidazo[1,2-α]pyrazin-3-yl]-pyrimidin-2-yl}-amine | A.17.1 | 2.64 (g) | 421.3 |

TABLE A.18

Examples prepared from 8-ethoxy-2-(4-fluorophenyl)-3-(2-methanesulfonylpyrimidin-4-yl)-imidazo[1,2-α]pyrazine (Example #G.1.14) using General Procedure A.2

| Nucleophile | Product | Example # | $R_t$ min (method) | m/z ESI+ $(M + H)^+$ |
|---|---|---|---|---|
| 3-Amino-2,2-dimethylpropan-1-ol [TCI-US] | 3-{4-[8-Ethoxy-2-(4-fluorophenyl)-imidazo[1,2-α]pyrazin-3-yl]-pyrimidin-2-ylamino}-2,2-dimethylpropan-1-ol | A.18.1 | 2.79 (g) | 437.2 |

TABLE A.19

Examples prepared from 2-(4-fluorophenyl)-8-isopropoxy-3-(2-methanesulfonylpyrimidin-4-yl)imidazo[1,2-α]pyrazine (Example #G.1.15) using General Procedure A.2

| Nucleophile | Product | Example # | $R_t$ min (method) | m/z ESI+ (M + H) |
|---|---|---|---|---|
| 3-Amino-2,2-dimethylpropan-1-ol [TCI-US] | 3-{4-[2-(4-Fluorophenyl)-8-isopropoxyimidazo[1,2-α]pyrazin-3-yl]pyrimidin-2-ylamino}-2,2-dimethylpropan-1-ol | A.19.1 | 3.01 (g) | 451.2 |

TABLE A.20

Examples prepared from 3-(2-methanesulfonylpyrimidin-4-yl)-8-methyl-2-(3-trifluoromethylphenyl)imidazo[1,2-α]pyrazine (Example #G.1.16) using General Procedure A.2

| Nucleophile | Product | Example # | $R_t$ min (method) | m/z ESI+ (M + H) |
|---|---|---|---|---|
| Cyclopropylamine | Cyclopropyl-{4-[8-methyl-2-(3-trifluoromethylphenyl)-imidazo[1,2-α]pyrazin-3-yl]pyrimidin-2-yl}amine | A.20.1 | 2.28 (a) | 411.2 |

TABLE A.21

Examples prepared from 3-(2-methanesulfonylpyrimidin-4-yl)-8-methyl-2-(4-trifluoromethylphenyl)imidazo[1,2-α]pyrazine (Example #G.1.17) using General Procedure A.2

| Nucleophile | Product | Example # | $R_t$ min (method) | m/z ESI+ (M + H) |
|---|---|---|---|---|
| Cyclopropylamine | Cyclopropyl-{4-[8-methyl-2-(4-trifluoromethylphenyl)-imidazo[1,2-α]pyrazin-3-yl]pyrimidin-2-yl}amine | A.21.1 | 2.33 (a) | 411.3 |

TABLE A.22

Examples prepared from 2-(2,4-difluorophenyl)-3-(2-methanesulfonylpyrimidin-4-yl)-8-methyl-2-imidazo[1,2-α]pyrazine (Example #G.1.19) using General Procedure A.2

| Nucleophile | Product | Example # | $R_t$ min (method) | m/z ESI+ (M + H) |
|---|---|---|---|---|
| Cyclopropylamine | Cyclopropyl-{4-[8-methyl-2-(2,4-difluorophenyl)-imidazo[1,2-α]pyrazin-3-yl]pyrimidin-2-yl}amine | A.22.1 | 2.11 (a) | 379.3 |

TABLE A.23

Examples prepared from 2-(3,4-difluorophenyl)-3-(2-Methanesulfonylpyrimidin-4-yl)-8-methyl-imidazo[1,2-α]pyrazine (Example #G.1.18) using General Procedure A.2

| Nucleophile | Product | Example # | $R_t$ min (method) | m/z ESI+ (M + H)+ |
|---|---|---|---|---|
| Cyclopropylamine | Cyclopropyl-{4-[8-methyl-2-(3,4-difluorophenyl)-imidazo[1,2-α]pyrazin-3-yl]pyrimidin-2-yl}amine | A.23.1 | 2.39 (a) | 379.3 |

TABLE A.23-continued

Examples prepared from 2-(3,4-difluorophenyl)-3-(2-Methanesulfonylpyrimidin-4-yl)-8-methyl-imidazo[1,2-α]pyrazine (Example #G.1.18) using General Procedure A.2

| Nucleophile | Product | Example # | $R_t$ min (method) | m/z ESI+ $(M + H)^+$ |
|---|---|---|---|---|
| 3-Amino-2,2-dimethyl-1-propanol [TCI-US] | 3-{4-[2-(3,4-Difluorophenyl)-8-methylimidazo[1,2-α] pyrazin-3-yl]-pyrimidin-2-ylamino}-2,2-dimethylpropan-1-ol | A.23.1 | 2.22 (a) | 425.3 |

TABLE A.24

Examples prepared from [2-(4-fluorophenyl)-3-(2-methanesulfonylpyrimidin-4-yl)-imidazo[1,2-α]pyrazin-8-yl]methylamine (Example #G.1.20) using General Procedure A.2

| Nucleophile | Product | Example # | $R_t$ min (method) | m/z ESI+ (M + H) |
|---|---|---|---|---|
| Cyclopropylamine | [3-(2-Cyclopropylamino pyrimidin-4-yl)-2-(4-fluoro-phenyl)imidazo[1,2,a]-pyrazin-8-yl]methylamine | A.24.1 | 2.18 (a) | 376.3 |
| 3-Amino-2,2-dimethyl-1-propanol [TCI-US] | 3-{4-[2-(4-Fluororophenyl)-8-methylaminoimidazo[1,2-a]pyrazin-3-yl]pyrimidin-2-ylamino}-2,2-dimethylpropan-1-ol | A.24.2 | 2.19 (a) | 422.3 |

TABLE A.25

Examples prepared from 2-(4-fluorophenyl)-8-isopropyl-3-(2-methanesulfonylpyrimidin-4-yl)-imidazo[1,2-α]pyrazine (Example #G.1.23) using General Procedure A.2

| Nucleophile | Product | Example # | $R_t$ min (method) | m/z ESI+ (M + H) |
|---|---|---|---|---|
| Cyclopropylamine | Cyclopropyl-{4-[2-(4-fluorophenyl)-8-isopropylimidazo[1,2-α]pyrazin-3-yl]-pyrimidin-2-yl}-amine | A.25.1 | 2.33 (f) | 389.2 |
| 3-Amino-2,2-dimethylpropan-1-ol [Lancaster] | 3-{4-[2-(4-Fluorophenyl)-8-isopropylimidazo[1,2-a]pyrazin-3-yl]pyrimidin-2-ylamino}-2,2-dimethylpropan-1-ol | A.25.2 | 3.09 (b) | 435.2 |
| (R)-3-Aminopropane-1,2-diol | (R)-3-{4-[2-(4-Fluorophenyl)-8-isopropylimidazo[1,2-a]pyrazin-3-yl]pyrimidin-2-ylamino}-propane-1,2-diol | A.25.3 | 2.17 (b) | 423.2 |
| (S)-3-Amino-propane-1,2-diol | (S)-3-{4-[2-(4-Fluorophenyl)-8-isopropylimidazo[1,2-a]pyrazin-3-yl]pyrimidin-2-ylamino}-propane-1,2-diol | A.25.4 | 2.17 (b) | 423.2 |
| 2,2-Dimethyl-propylamine | (2,2-Dimethylpropyl)-{4-[2-(4-fluorophenyl)-8-isopropylimidazo[1,2-a]pyrazin-3-yl]pyrimidin-2-yl}-amine | A.25.5 | 3.97 (b) | 419.3 |
| Tetrahydropyran-4-ylamine | {4-[2-(4-Fluorophenyl)-8-isopropylimidazo[1,2-a]pyrazin-3-yl]-pyrimidin-2-yl}-(tetrahydropyran-4-yl)-amine | A.25.6 | 3.05 (b) | 433.3 |

TABLE A.26

Examples prepared from 8-ethyl-2-(4-fluorophenyl)-3-(2-methanesulfonylpyrimidin-4-yl)-imidazo[1,2-α]pyrazine (Example #G.1.24) using General Procedure A.2

| Nucleophile | Product | Example # | $R_t$ min (method) | m/z ESI+ (M + H) |
|---|---|---|---|---|
| Cyclopropylamine | Cyclopropyl-{4-[8-ethyl-2-(4-fluorophenyl)-imidazo[1,2-α]pyrazin-3-yl]-pyrimidin-2-yl}-amine | A.26.1 | 2.17 (f) | 375.2 |
| 1-Amino-2-methylpropan-2-ol [Tyger] | 1-{4-[8-Ethyl-2-(4-fluorophenyl)imidazo[1,2-a]pyrazin-3-yl]pyrimidin-2-ylamino}-2-methylpropan-2-ol | A.26.2 | 2.16 (a) | 407.3 |
| 3-Amino-2,2-dimethyl-1-propanol [TCI-US] | 3-{4-[8-Ethyl-2-(4-fluorophenyl)imidazo[1,2-a]pyrazin-3-yl]pyrimidin-2-ylamino}2,2-dimethylpropan-1-ol | A.26.3 | 2.73 (g) | 421.2 |

TABLE A.27

Examples prepared from 2-(4-chloro-3-methylphenyl)-3-(2-methanesulfonylpyrimidin-4-yl)-imidazo[1,2-α]pyrazine (Example G.1.25) using General Procedure A.2

| Nucleophile | Product | Example # | $R_t$ min (method) | m/z ESI+ (M + H) |
|---|---|---|---|---|
| Cyclopropylamine | {4-[2-(4-Chloro-3-methylphenyl)-imidazo[1,2-α]pyrazin-3-yl]pyrimidin-2-yl}-cyclopropylamine | A.27.1 | 2.8 (b) | 377.8 |
| 3-Amino-2,2-dimethylpropan-1-ol [TCI-US] | 3-}4-[2-(4-Chloro-3-methylphenyl)-imidazo[1,2-α]pyrazin-3-yl]-pyrimidin-2-ylamino}-2,2-dimethylpropan-1-ol | A.27.2 | 2.7 (b) | 423.9 |
| Tetramethylpropane-1,3-diamine | N'-{4-[2-(4-Chloro-3-methylphenyl)-imidazo[1,2-α]pyrazin-3-yl]-pyrimidin-2-yl}-2,2,N,N-tetramethylpropane-1,3-diamine | A.27.3 | 1.9 (b) | 451.0 |

TABLE A.28

Examples prepared from 2-(2-fluoro-4-trifluoromethylphenyl)-3-(2-methanesulfonylpyrimidin-4-yl)-imidazo[1,2-α]pyrazine (Example G.1.26) using General Procedure A.2

| Nucleophile | Product | Example # | $R_t$ min (method) | m/z ESI+ (M + H) |
|---|---|---|---|---|
| Cyclopropylamine | Cyclopropyl-{4-[2-(2-fluoro-4-trifluoromethylphenyl)-imidazo[1,2-α]pyrazin-3-yl]-pyrimidin-2-yl}-amine | A.28.1 | 2.8 (b) | 415.2 |
| 3-Amino-2,2-dimethylpropan-1-ol [TCI-US] | 3-{4-[2-(2-Fluoro-4-trifluoromethylphenyl)-imidazo[1,2-α]pyrazin-3-yl]-pyrimidin-2-ylamino}-2,2-dimethylpropan-1-ol | A.28.2 | 2.7 (b) | 461.3 |
| Tetramethylpropane-1,3-diamine | N'-{4-[2-(2-Fluoro-4-trifluoromethylphenyl)-imidazo[1,2-α]pyrazin-3-yl]-pyrimidin-2-yl}-2,2,N,N-tetramethylpropane-1,3-diamine | A.28.3 | 2.0 (b) | 488.3 |

TABLE A.29

Examples prepared from 2-(4-chloro-2-fluorophenyl)-3-(2-methanesulfonylpyrimidin-4-yl)-imidazo[1,2-α]pyrazine (Example G.1.27) using General Procedure A.2

| Nucleophile | Product | Example # | $R_t$ min (method) | m/z ESI+ $(M + H)^+$ |
|---|---|---|---|---|
| Cyclopropylamine | {4-[2-(4-Chloro-2-fluorophenyl)-imidazo[1,2-α]pyrazin-3-yl]-pyrimidin-2-yl}-cyclopropylamine | A.29.1 | 2.3 (b) | 381.8 |
| 3-Amino-2,2-dimethylpropan-1-ol [TCI-US] | 3-{4-[2-(4-Chloro-2-fluorophenyl)-imidazo[1,2-α]pyrazin-3-yl]-pyrimidin-2-ylamino}-2,2-dimethylpropan-1-ol | A.29.2 | 2.5 (b) | 427.9 |

TABLE A.30

Examples prepared from 2-(3-chlorophenyl)-3-(2-methanesulfonylpyrimidin-4-yl)-imidazo[1,2-α]pyrazine (Example #G.1.37) using General Procedure A.2

| Nucleophile | Product | Example # | $R_t$ min (method) | m/z ESI+ $(M + H)^+$ |
|---|---|---|---|---|
| 3-Amino-2,2-dimethylpropan-1-ol [Lancaster] | 3-{4-[2-(3-Chlorophenyl)-imidazo[1,2-α]pyrazin-3-yl]-pyrimidin-2-ylamino}-2,2-dimethylpropan-1-ol | A.30.1 | 2.79 (f) | 409.17 |
| 1-Methanesulfonylpiperidin-4-ylamine | {4-[2-(3-Chlorophenyl)-imidazo[1,2-α]pyrazin-3-yl]-pyrimidin-2-yl}-(1-methanesulfonylpiperidin-4-yl)-amine | A.30.2 | 2.68 (f) | 484.15 |
| Tetrahydro-pyran-4-ylamine (Oakwood) | {4-[2-(3-Chlorophenyl)-imidazo[1,2-α]pyrazin-3-yl]-pyrimidin-2-yl}-(tetrahydro pyran-4-yl)-amine | A.30.3 | 2.44 (f) | 407.15 |

TABLE A.31

Examples prepared from 2-(3-chloro-4-fluorophenyl)-3-(2-methanesulfonylpyrimidin-4-yl)-imidazo[1,2-α]pyrazine (Example #G.1.42) using General Procedure A.2

| Nucleophile | Product | Example # | $R_t$ min (method) | m/z ESI+ $(M + H)^+$ |
|---|---|---|---|---|
| Cyclopropylamine | {4-[2-(3-Chloro-4-fluorophenyl)-imidazo[1,2-α]pyrazin-3-yl]-pyrimidin-2-yl}-cyclopropylamine | A.31.1 | 2.66 (f) | 381.10 |
| 3-Amino-2,2-dimethylpropan-1-ol [Lancaster] | 3-{4-[2-(3-Chloro-4-fluorophenyl)-imidazo[1,2-α]pyrazin-3-yl]-pyrimidin-2-ylamino}-2,2-dimethylpropan-1-ol | A.31.2 | 2.57 (g) | 427.11 |

TABLE A.32

Examples prepared from 6-chloro-2-(4-fluorophenyl)-3-(2-methanesulfonylpyrimidin-4-yl)-imidazo[1,2-α]pyrazine (Example #G.1.38) using General Procedure A.2

| Nucleophile | Product | Example # | $R_t$ min (method) | m/z ESI+ $(M + H)^+$ |
|---|---|---|---|---|
| Cyclopropylamine | {4-[6-Chloro-2-(4-fluorophenyl)-imidazo[1,2-α]pyrazin-3-yl]-pyrimidin-2-yl}-cyclopropylamine | A.32.1 | 3.18 (f) | 381.12 |

TABLE A.32-continued

Examples prepared from 6-chloro-2-(4-fluorophenyl)-3-(2-methanesulfonylpyrimidin-4-yl)-imidazo[1,2-α]pyrazine (Example #G.1.38) using General Procedure A.2

| Nucleophile | Product | Example # | $R_t$ min (method) | m/z ESI+ $(M + H)^+$ |
|---|---|---|---|---|
| 3-Amino-2,2-dimethylpropan-1-ol [Lancaster] | 3-{4-[6-Chloro-2-(4-fluorophenyl)-imidazo[1,2-α]pyrazin-3-yl]-pyrimidin-2-ylamino}-2,2-dimethylpropan-1-ol | A.32.2 | 2.77 (g) | 427.18 |

TABLE A.33

Examples prepared from 6-ethyl-2-(4-fluorophenyl)-3-(2-methanesulfonylpyrimidin-4-yl)-imidazo[1,2-α]pyrazine (Example #G.1.39) using General Procedure A.2

| Nucleophile | Product | Example # | $R_t$ min (method) | m/z ESI+ $(M + H)^+$ |
|---|---|---|---|---|
| Cyclopropylamine | {4-[6-Ethyl-2-(4-fluorophenyl)-imidazo[1,2-α]pyrazin-3-yl]-pyrimidin-2-yl}-cyclopropylamine | A.33.1 | 2.83 (g) | 375.29 |

TABLE A.34

Examples prepared from 2-(4-fluorophenyl)-3-(2-methanesulfonyl-pyrimidin-4-yl)-6-methoxy-imidazo[1,2-a]pyrazine (Example #G.1.40) using General Porcedure A.2

| Nucleophile | Product | Example # | $R_t$ min (method) | m/z ESI+ $(M + H)^+$ |
|---|---|---|---|---|
| Cyclopropylamine | Cyclopropyl-{4-[2-(4-fluorophenyl)-6-methoxyimidazo[1,2-α]pyrazin-3-yl]-pyrimidin-2-yl}-amine | A.34.1 | 2.68 (g) | 377.23 |
| 3-Amino-2,2-dimethylpropan-1-ol [Lancaster] | 3-{4-[2-(4-Fluorophenyl)-6-methoxyimidazo[1,2-α]pyrazin-3-yl]-pyrimidin-2-ylamino}-2,2-dimethylpropan-1-ol | A.34.2 | 2.58 (g) | 423.30 |

TABLE A.35

Examples prepared from 2-(2,4-difluorophenyl)-8-methyl-3-(2-methanesulfonylpyrimidin-4-yl)-imidazo[1,2-α]pyrazine (Example #G.1.43) using General Procedure A.2

| Nucleophile | Product | Example # | $R_t$ min (method) | m/z ESI+ $(M + H)^+$ |
|---|---|---|---|---|
| (1-Aminomethyl-cyclopropyl)-methanol (J Med Chem 1972, 15(10), 1003-1006) | [1-({4-[2-(2,4-Difluorophenyl)-8-methylimidazo[1,2-α]pyrazin-3-yl]-pyrimidin-2-ylamino}-methyl)-cyclopropyl]-methanol | A.35.1 | 2.17 (g) | 423.19 |
| 1-Aminomethyl-cyclopropanol | 1-({4-[2-(2,4-Difluorophenyl)-8-methylimidazo[1,2-a]pyrazin-3-yl]-pyrimidin-2-ylamino}methyl)cyclopropanol | A.35.2 | 1.73 (b) | 409.2 |
| 1-Amino-2-methylpropan-2-ol [Tyger] | 1-{4-[2-(2,4-Difluorophenyl)-8-methylimidazo[1,2-a]pyrazin-3-yl]-pyrimidin-2-ylamino}-2-methylpropan-2-ol | A.35.3 | 1.73 (b) | 411.2 |

TABLE A.36

Examples prepared from 2-(2,4-difluorophenyl)-3-(2-methanesulfonyl-pyrimidin-4-yl)-8-methoxyimidazo[1,2-a]pyrazine (Example #G.1.44) using General Procedure A.2

| Nucleophile | Product | Example # | $R_t$ min (method) | m/z ESI+ $(M + H)^+$ |
|---|---|---|---|---|
| 3-Amino-2,2-dimethylpropan-1-ol [TCI-US] | 3-{4-[2-(2,4-Difluorophenyl)-8-methoxy-imidazo[1,2-a]pyrazin-3-yl]-pyrimidin-2-ylamino}-2,2-dimethylpropan-1-ol | A.36.1 | 2.50 (g) | 441.1 |
| Cyclopropylamine | Cyclopropyl-{4-[2-(2,4-difluorophenyl)-8-methoxyimidazo[1,2-a]pyrazin-3-yl]-pyrimidin-2-yl}amine | A.36.2 | 2.60 (g) | 395.1 |

TABLE A.37

Examples prepared from 6-chloro-2-(4-fluorophenyl)-3-(2-methanesulfonyl-pyrimidin-4-yl)-8-methylimidazo[1,2-a]pyrazine (Example #G.1.45) using General Procedure A.2

| Nucleophile | Product | Example # | $R_t$ min (method) | m/z ESI+ $(M + H)^+$ |
|---|---|---|---|---|
| 3-Amino-2,2-dimethylpropan-1-ol [TCI-US] | 3-{4-[6-Chloro-2-(4-fluoro-phenyl)-8-methylimidazo[1,2-a]pyrazin-3-yl]-pyrimidin-2-ylamino}-2,2-dimethylpropan-1-ol | A.37.1 | 2.98 (g) | 441.1 |
| Cyclopropylamine | {4-[6-Chloro-2-(4-fluoro-phenyl)-8-methylimidazo[1,2-a]pyrazin-3-yl]-pyrimidin-2-yl}-cyclopropylamine | A.37.2 | 3.14 (g) | 395.1 |

TABLE A.38

Examples prepared from 2-(4-fluorophenyl)-3-(2-methanesulfonylpyrimidin-4-yl)-6,8-dimethyl-imidazo[1,2-a]pyrazine (Example #G.1.46) using General Procedure A.2

| Nucleophile | Product | Example # | $R_t$ min method | m/z ESI+ $(M + H)^+$ |
|---|---|---|---|---|
| 3-Amino-2,2-dimethylpropan-1-ol [TCI-US] | 3-{4-[2-(4-Fluorophenyl)-6,8-dimethylimidazo[1,2-a]pyrazin-3-yl]-pyrimidin-2-ylamino}-2,2-dimethylpropan-1-ol | A.38.1 | 2.55 (g) | 421.2 |
| (1-Aminomethyl-cyclopropyl)-methanol | [1-({4-[2-(4-Fluorophenyl)-6,8-dimethyl-imidazo[1,2-a]pyrazin-3-yl]-pyrimidin-2-lamino}-methyl)-cyclopropyl]-methanol | A.38.2 | 2.30 (g) | 419.2 |
| Cyclopropylamine | Cyclopropyl-{4-[2-(4-fluoro-phenyl)-6,8-dimethyl-imidazo[1,2-a]pyrazin-3-yl]-pyrimidin-2-yl}-amine | A.38.3 | 2.63 (g) | 375.2 |

TABLE A.39

Examples prepared from 2-(2,4-difluorophenyl)-3-(2-methanesulfonyl-pyrimidin-4-yl)-6,8-dimethylimidazo[1,2-a]pyrazine (Example #G.1.47) using General Procedure A.2

| Nucleophile | Product | Example # | $R_t$ min (method) | m/z ESI+ $(M + H)^+$ |
|---|---|---|---|---|
| 3-Amino-2,2-dimethylpropan-1-ol [TCI-US] | 3-{4-[2-(2,4-Difluorophenyl)-6,8-dimethyl-imidazo[1,2-a]pyrazin-3-yl]-pyrimidin-2-ylamino}-2,2-dimethyl-propan-1-ol | A.39.1 | 2.49 (g) | 439.2 |

TABLE A.39-continued

Examples prepared from 2-(2,4-difluorophenyl)-3-(2-methanesulfonyl-pyrimidin-4-yl)-6,8-dimethylimidazo[1,2-a]pyrazine (Example #G.1.47) using General Procedure A.2

| Nucleophile | Product | Example # | R$_t$ min (method) | m/z ESI+ (M + H)$^+$ |
|---|---|---|---|---|
| 1-Amino-2-methyl-propan-2-ol | 1-{4-[2-(2,4-Difluorophenyl)-6,8-dimethyl-imidazo[1,2-a]pyrazin-3-yl]-pyrimidin-2-ylamino}-2-methyl-propan-2-ol | A.39.2 | 2.22 (g) | 425.2 |

TABLE A.40

Examples prepared from 3-(2-methanesulfonylpyrimidin-4-yl)-8-methyl-2-(3-trifluoromethoxyphenyl)imidazo[1,2-a]pyrazine (Example #G.1.48) using General Procedure A.2

| Nucleophile | Product | Example # | R$_t$ min (method) | m/z ESI+ (M + H)$^+$ |
|---|---|---|---|---|
| 3-Amino-2,2-dimethylpropan-1-ol [TCI-US] | 2,2-Dimethyl-3-{4-[8-methyl-2-(3-trifluoromethoxyphenyl)-imidazo[1,2-a]pyrazin-3-yl]pyrimidin-2-ylamino}-propan-1-ol | A.40.1 | 2.3 (b) | 473.2 |

TABLE A.41

Examples prepared from 2-(2,4-difluorophenyl)-8-isopropoxy-3-(2-methanesulfonylpyrimidin-4-yl)imidazo[1,2-a]pyrazine (Example #G.1.51) using General Procedure A.2

| Nucleophile | Product | Example # | R$_t$ min (method) | m/z ESI+ (M + H)$^+$ |
|---|---|---|---|---|
| 1-Amino-2-methyl-propan-2-ol | 1-{4-[2-(2,4-Difluorophenyl)-8-isopropoxyimidazo[1,2-a]pyrazin-3-yl]pyrimidin-2-ylamino}-2-methylpropan-2-ol | A.41.1 | 2.0 (b) | 455.2 |
| 3-Amino-2,2-dimethylpropan-1-ol [TCI-US] | 3-{4-[2-(2,4-Difluorophenyl)-8-isopropoxyimidazo[1,2-a]pyrazin-3-yl]pyrimidin-2-ylamino}-2,2-dimethylpropan-1-ol | A.41.2 | 2.2 (b) | 469.3 |

TABLE A.42

Examples prepared from 2-(3-chlorophenyl)-3-(2-Methanesulfonyl-pyrimidin-4-yl)-8-methylimidazo[1,2-a]pyrazine (Example #G.1.53) using General Procedure A.2

| Nucleophile | Product | Example # | R$_t$ min (method) | m/z ESI+ (M + H)$^+$ |
|---|---|---|---|---|
| Cyclopropylamine | {4-[2-(3-Chlorophenyl)-8-methylimidazo[1,2-a]pyrazin-3-yl]pyrimidin-2-yl}cyclopropylamine | A.42.1 | 2.35 (a) | 377.3 |
| 3-Amino-2,2-dimethyl-1-propanol [TCI-US] | 3-{4-[2-(3-Chlorophenyl)-8-methyl-imidazo[1,2-a]pyrazin-3-yl]-pyrimidin-2-ylamino}-2,2-dimethyl-propan-1-ol | A.42.2 | 2.14 (a) | 423.3 |

TABLE A.43

Examples prepared from cyclopropyl-[2-(4-fluorophenyl)-3-(2-methanesulfonyl-pyrimidin-4-yl)imidazo[1,2-a]pyrazin-8-yl]amine (Example #G.1.54) using General Procedure A.2

| Nucleophile | Product | Example # | $R_t$ min (method) | m/z ESI+ $(M + H)^+$ |
|---|---|---|---|---|
| 3-Amino-2,2-dimethyl-1-propanol [TCI-US] | 3-{4-[8-Cyclopropylamino-2-(4-fluororophenyl)-imidazo[1,2-a] pyrazin-3-yl]pyrimidin-2-ylamino}-2,2-dimethyl-propan-1-ol | A.43.1 | 2.16 (a) | 448.4 |

TABLE A.44

Examples prepared from 2-(3-chlorophenyl)-3-(2-methanesulfonylpyrimidin-4-yl)-8-methoxyimidazo[1,2-a]pyrazine (Example #G.1.56) using General Procedure A.2

| Nucleophile | Product | Example # | $R_t$ min (method) | m/z ESI+ $(M + H)^+$ |
|---|---|---|---|---|
| Cyclopropylamine | {4-[2-(3-Chlorophenyl)-8-methoxyimidazo[1,2-a]pyrazin-3-yl]pyrimidin-2-yl}cyclopropylamine | A.44.1 | 2.86 (g) | 393.1 |
| 3-Amino-2,2-dimethyl-1-propanol [TCI-US] | 3-{4-[2-(3-Chlorophenyl)-8-methoxyimidazo[1,2-α] pyrazin-3-yl]-pyrimidin-2-ylamino}-2,2-dimethyl-propan-1-ol | A.44.2 | 2.76 (g) | 439.2 |

TABLE A.45

Examples prepared from 2-(4-fluorophenyl)-8-isobutyl-3-(2-methanesulfonyl-pyrimidin-4-yl)imidazo[1,2-a]pyrazine (Example #G.1.58) using General Procedure A.2

| Nucleophile | Product | Example # | $R_t$ min (method) | m/z ESI+ $(M + H)^+$ |
|---|---|---|---|---|
| 1-Amino-2-methylpropan-2-ol [Tyger] | 1-{4-[2-(4-Fluorophenyl)-8-isobutylimidazo[1,2-a]pyrazin-3-yl]pyrimidin-2-ylamino}-2-methylpropan-2-ol | A.45.1 | 2.47 (a) | 435.4 |
| 3-Amino-2,2-dimethyl-1-propanol [TCI-US] | 3-{4-[2-(4-Fluorophenyl)-8-isobutylimidazo[1,2-a]pyrazin-3-yl]pyrimidin-2-ylamino}-2,2-dimethylpropan-1-ol | A.45.2 | 3.20 (g) | 449.3 |

TABLE A.46

Examples prepared from 2-(2,4-difluorophenyl)-8-isopropyl-3-(2-methanesulfonyl-pyrimidin-4-yl)imidazo[1,2-a]pyrazine (Example #G.1.57) using General Procedure A.2

| Nucleophile | Product | Example # | $R_t$ min (method) | m/z ESI+ $(M + H)^+$ |
|---|---|---|---|---|
| 1-Amino-2-methylpropan-2-ol [Tyger] | 1-{4-[2-(2,4-Difluorophenyl)-8-isopropylimidazo[1,2-a]pyrazin-3-yl]pyrimidin-2-ylamino}-2-methylpropan-2-ol | A.46.1 | 2.53 (a) | 439.3 |
| 3-Amino-2,2-dimethyl-1-propanol [TCI-US] | 3-{4-[2-(2,4-Difluorophenyl)-8-isopropylimidazo[1,2-a]pyrazin-3-yl]pyrimidin-2-ylamino}-2,2-dimethylpropan-1-ol | A.46.2 | 3.01 (g) | 453.3 |

TABLE A.47

Examples prepared from {2-[2-(4-Fluorophenyl)-3-(2-methanesulfonyl-pyrimidin-4-yl)-imidazo[1,2-a]pyrazin-8-yl]-ethyl}-carbamic acid tert-butyl ester (Example #G.1.55) using General Procedure A.2

| Nucleophile | Product | Example # | $R_t$ min (method) | m/z ESI+ (M + H)+ |
|---|---|---|---|---|
| 3-Amino-2,2-dimethyl-1-propanol [TCI-US] | (2-{2-(4-Fluorophenyl)-3-[2-(3-hydroxy-2,2-dimethyl-propylamino)pyrimidin-4-yl]-imidazo[1,2-a]pyrazin-8-yl}-ethyl)-carbamic acid tert-butyl ester | A.47.1 | 2.77 (g) | 536.3 |

TABLE A.48

Example prepared from 8-chloro-2-(4-fluorophenyl)-3-(2-methanesulfonylpyrimidin-4-yl)imidazo[1,2-a]pyrazine (Example #18) using General Procedure A.2

| Nucleophile | Product | Example # | $R_t$ min (method) | m/z ESI+ (M + H)+ |
|---|---|---|---|---|
| 3-Amino-2,2-dimethyl-1-propanol [TCI-US] | 3-{4-[8-Chloro-2-(4-fluorophenyl)imidazo[1,2-a]pyrazin-3-yl]pyrimidin-2-ylamino}-2,2-dimethylpropan-1-ol | A.48.1 | 2.73 (g) | 427.1 |

TABLE A.49

Example prepared from 8-cyclopropylmethyl-2-(4-fluorophenyl)-3-(2-methanesulfonylpyrimidin-4-yl)imidazo[1,2-α]pyrazine (Example #8, step D) using General Procedure A.2

| Nucleophile | Product | Example # | $R_t$ min (method) | m/z ESI+ (M + H)+ |
|---|---|---|---|---|
| (1-Aminomethylcyclopropyl)methanol (J Med Chem 1972, 15(10), 1003-1006) | [1-({4-[8-Cyclopropylmethyl-2-(4-fluorophenyl)imidazo[1,2-a]pyrazin-3-yl]pyrimidin-2-ylamino}methyl)cyclopropyl]methanol | A.49.1 | 2.75 (g) | 445.2 |
| Cyclopropylamine | Cyclopropyl-{4-[8-cyclopropylmethyl-2-(4-fluorophenyl)imidazo[1,2-a]pyrazin-3-yl]pyrimidin-2-yl}amine | A.49.2 | 3.13 (g) | 401.3 |
| 3-Amino-2,2-dimethyl-1-propanol [TCI-US] | 3-{4-[8-Cyclopropylmethyl-2-(4-fluorophenyl)imidazo[1,2-a]pyrazin-3-yl]pyrimidin-2-ylamino}-2,2-dimethylpropan-1-ol | A.49.3 | 3.01 (g) | 447.2 |
| (1-Aminomethylcyclopropyl)methanol (J Med Chem 1972, 15(10), 1003-1006) | [1-({4-[8-Cyclopropylmethyl-2-(4-fluorophenyl)imidazo[1,2-a]pyrazin-3-yl]pyrimidin-2-ylamino}methyl)cyclopropyl]methanol | A.49.4 | 2.75 (g) | 445.2 |

TABLE A.50

Example prepared from 8-cyclopropylmethyl-2-(2,4-difluorophenyl)-3-(2-methanesulfonylpyrimidin-4-yl)imidazo[1,2-a]pyrazine (Example #G.1.59) using General Procedure A.2

| Nucleophile | Product | Example # | $R_t$ min (method) | m/z ESI+ (M + H)+ |
|---|---|---|---|---|
| 3-Amino-2,2-dimethyl-1-propanol [TCI-US] | 3-{4-[8-Cyclopropylmethyl-2-(2,4-difluorophenyl)imidazo[1,2-a]pyrazin-3-yl]pyrimidin-2-ylamino}-2,2-dimethylpropan-1-ol | A.50.1 | 2.93 (g) | 465.3 |

TABLE A.51

Examples prepared from [2-(4-fluorophenyl)-3-(2-methanesulfonylpyrimidin-4-yl)imidazo[1,2-a]pyrazin-8-yl]dimethylamine (Example #G.1.29) using General Procedure A.2

| Nucleophile | Product | Example # | R$_t$ min (method) | m/z ESI+ (M + H)$^+$ |
|---|---|---|---|---|
| Cyclopropylamine | [3-(2-Cyclopropylamino-pyrimidin-4-yl)-2-(4-fluorophenyl)imidazo[1,2-a]pyrazin-8-yl]dimethylamine | A.51.1 | 2.44 (b) | 390.3 |
| 3-Amino-2,2-dimethyl-1-propanol [TCI-US] | 3-{4-[8-Dimethylamino-2-(4-fluorophenyl)imidazo[1,2-a]pyrazin-3-yl]pyrimidin-2-ylamino}-2,2-dimethylpropan-1-ol | A.51.2 | 2.31 (b) | 436.4 |

TABLE A.52

Example prepared from 2-(4-fluorophenyl)-3-(2-methanesulfonylpyrimidin-4-yl)imidazo[1,2-a]pyrazin-8-ylamine (Example #G.1.28) using General Procedure A.2

| Nucleophile | Product | Example # | R$_t$ min (method) | m/z ESI+ (M + H)$^+$ |
|---|---|---|---|---|
| Cyclopropylamine | 3-(2-Cyclopropylamino-pyrimidin-4-yl)-2-(4-fluoro-phenyl)imidazo[1,2-a]pyrazin-8-ylamine | A.52.1 | 2.26 (g) | 362.2 |

TABLE A.53

Examples prepared from 8-cyclopropyl-2-(4-fluorophenyl)-3-(2-methanesulfonylpyrimidin-4-yl)imidazo[1,2-a]pyrazine and 8-cyclopropyl-2-(4-fluorophenyl)-3-(2-methanesulfinylpyrimidin-4-yl)imidazo[1,2-a]pyrazine (Examples #G.1.30 and G.1.31) using General Procedure A.2

| Nucleophile | Product | Example # | R$_t$ min (method) | m/z ESI+ (M + H)$^+$ |
|---|---|---|---|---|
| Cyclopropylamine | Cyclopropyl-{4-[8-cyclopropyl-2-(4-fluorophenyl)imidazo[1,2-a]pyrazin-3-yl]pyrimidin-2-yl}amine | A.53.1 | 3.12 (g) | 387.3 |
| 3-Amino-2,2-dimethyl-1-propanol [TCI-US] | 3-{4-[8-Cyclopropyl-2-(4-fluorophenyl)imidazo[1,2-a]pyrazin-3-yl]pyrimidin-2-ylamino}2,2-dimethylpropan-1-ol | A.53.2 | 3.01 (g) | 433.4 |

TABLE A.54

Examples prepared from 2-(3,4-difluorophenyl)-3-(2-methanesulfonylpyrimidin-4-yl)-8-methoxyimidazo[1,2-a]pyrazine and 2-(3,4-difluorophenyl)-3-(2-methanesulfinylpyrimidin-4-yl)-8-methoxyimidazo[1,2-a]pyrazine (Examples #G.1.32 and G.1.33) using General Procedure A.2

| Nucleophile | Product | Example # | R$_t$ min (method) | m/z ESI+ (M + H)$^+$ |
|---|---|---|---|---|
| Cyclopropylamine | Cyclopropyl-{4-[2-(3,4-difluorophenyl)-8-methoxyimidazo[1,2-a]pyrazin-3-yl]pyrimidin-2-yl}amine | A.54.1 | 2.72 (g) | 395.2 |
| 3-Amino-2,2-dimethyl-1-propanol [TCI-US] | 3-{4-[2-(3,4-Difluoro-phenyl)-8-methoxyimidazo[1,2-a]pyrazin-3-yl]pyrimidin-2-ylamino}-2,2-dimethylpropan-1-ol | A.54.2 | 2.63 (g) | 441.3 |

General Procedure B: Cyclization to Form a Substituted Imidazopyrazine

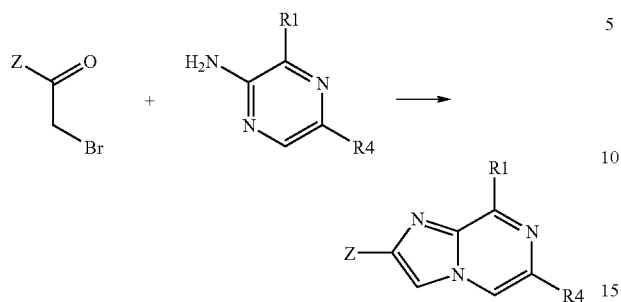

An appropriately substituted pyrazine (1-3 equiv) and a substituted 2-bromo-1-ethanone (1 equiv) are combined in a solvent such as ACN. The mixture is heated at about 60-100° C. for about 12-96 h. The reaction is cooled and the solvent is removed under vacuum. A suitable solvent, such as MeOH, is added and the solid is washed with a suitable solvent, such as MeOH, as it is collected by vacuum filtration. The mother liquor is concentrated to dryness to give the crude substituted imidazo[1,2-a]pyrazine derivative. Alternatively, the concentrated reaction mixture is partitioned between water and an appropriate solvent, such as DCM or EtOAc. The layers are separated and the aqueous layer is extracted with additional organic solvent (such as EtOAc, DCM, or both sequentially). The combined organic layers may be optionally washed with brine, dried over $Na_2SO_4$ or $MgSO_4$, then decanted or filtered, prior to concentrating under reduced pressure. The crude product is either used as is in the next step or is purified by chromatography, trituration with an appropriate solvent, or crystallization from one or more solvents to yield the target compound.

Illustration of General Procedure B

Preparation #B.1: 2-(4-Fluorophenyl)-imidazo[1,2-a]pyrazine-8-carboxylic acid methyl ester

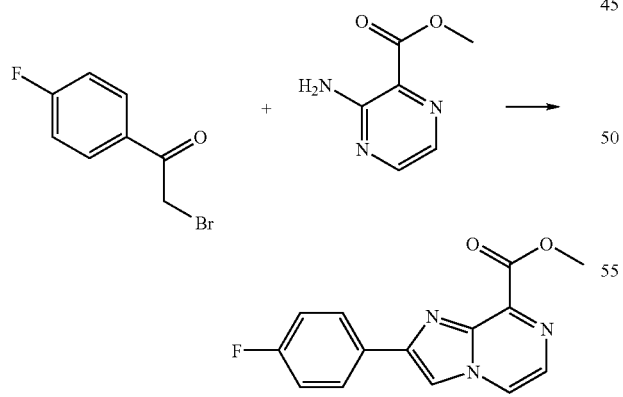

A mixture of 2-bromo-1-(4-fluorophenyl)ethanone (30.0 g, 138 mmol) and methyl 3-aminopyrazine-2-carboxylate (21.2 g, 138 mmol) in ACN (300 mL) was heated at about 80° C. The mixture was removed from heat after about 72 h and concentrated under reduced pressure. The crude material was partitioned between saturated aqueous $NaHCO_3$ (450 mL) and DCM (350 mL). The layers were separated and the aqueous layer was washed with additional DCM (2×250 mL). The combined organic layers were washed with water (3×350 mL) and brine (20 ml) then dried over $MgSO_4$, filtered, and concentrated under reduced pressure to give the crude title compound (38.7 g, 45.5%) that was carried on without further purification. LC/MS (Table 1, Method h) $R_f$=2.26 min; MS m/z: 272.2 $(M+H)^+$.

General Procedure C: Hydrolysis of a substituted imidazo[1,2-a]pyrazine-8-carboxylic acid methyl ester

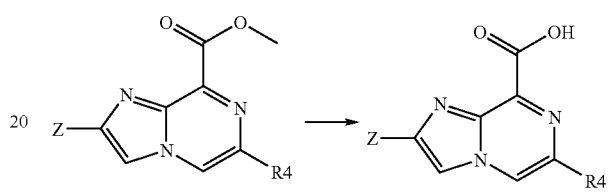

The substituted imidazo[1,2-a]pyrazine-8-carboxylic acid methyl ester is dissolved in a suitable solvent such as dioxane and then water is added. Lithium hydroxide hydrate (5-20 equiv, preferably 10 equiv) is added and the reaction is heated at about 40-60° C. for about 1-24 h. The reaction is filtered and washed with an appropriate solvent such as $Et_2O$ or EtOAc and then water. The solid is either used as is in the next step or is purified by chromatography, trituration with an appropriate solvent, or crystallization from one or more solvents to yield the target compound.

Illustration of General Procedure C

Preparation #C.1: 2-(4-Fluorophenyl)-imidazo[1,2-a]pyrazine-8-carboxylic acid

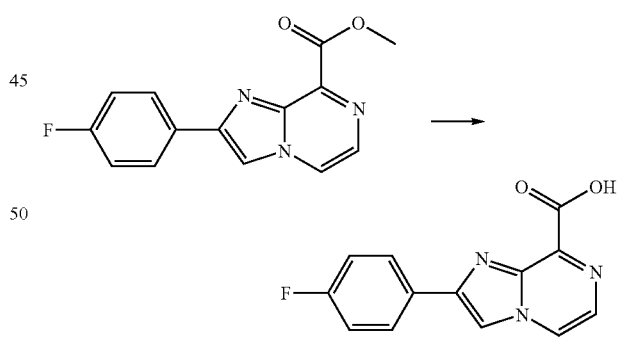

The crude methyl 2-(4-fluorophenyl)imidazo[1,2-a]pyrazine-8-carboxylate (35.7 g, 65.8 mmol) was dissolved in 1,4-dioxane (200 mL), then water (20.2 mL) and lithium hydroxide monohydrate (27.6 g, 658 mmol) were added. Heated to about 50° C. overnight. The reaction mixture was cooled to ambient temperature, filtered, and the collected solid was washed with $Et_2O$ (4×70 mL). The resulting brown solid was suspended in water (200 mL) and the pH was adjusted to ~5 with glacial HOAc (100 mL). The solid was collected, washed with water (4×75 mL) and $Et_2O$ (2×80 mL) to give the wet crude title compound (26.4 g, 156%) that was carried on without further purification. LC/MS (Table 1, Method b) R$_t$=1.21 min; MS m/z: 258.2 (M+H)$^+$.

General Procedure D: Decarboxylation of a Substituted imidazo[1,2-a]pyrazine-8-carboxylic acid

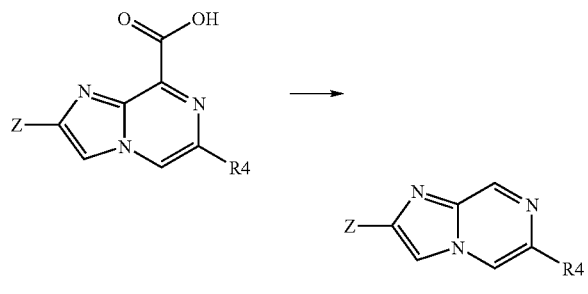

An imidazo[1,2-a]pyrazine-8-carboxylic acid is stirred in an acidic solution, such as 1M HCl, at about 50-110° C. After about 1-6 h, the solution is cooled to ambient temperature, neutralized with a base, such as solid NaHCO$_3$ or Na$_2$CO$_3$, and extracted into an organic solvent such as EtOAc or DCM. The combined organic layers may be optionally washed with brine, dried over Na$_2$SO$_4$ or MgSO$_4$, then decanted or filtered, prior to concentrating under reduced pressure. The crude material is purified by chromatography, trituration with an appropriate solvent, and/or crystallization from one or more solvents to yield the target compound.

Illustration of General Procedure D

Preparation #D.1:
2-(4-Fluorophenyl)-imidazo[1,2-a]pyrazine

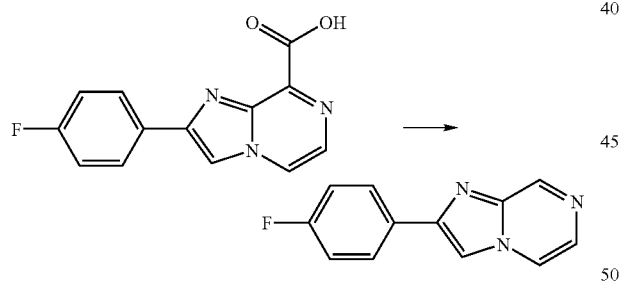

A mixture of 2-(4-fluorophenyl)imidazo[1,2-a]pyrazine-8-carboxylic acid (Preparation #C.1, 18.9 g, 66.1 mmol) and 1M of hydrogen chloride in water (500 mL) was heated to about 100° C. for about 2 h. The reaction mixture was cooled to ambient temperature and solid Na$_2$CO$_3$ (50.0 g) was added cautiously portion-wise to raise the pH to about 8-9. The resulting brown solid was collected washing with water (4×80 mL). The product in the filtrate was extracted with EtOAc (3×200 mL). In addition the solid was dissolved in EtOAc (1 L) and filtered from insoluble material. The combined organic extracts were washed with water (3×200 mL) and brine (150 mL), then dried over Na$_2$SO$_4$, filtered and concentrated under reduced pressure to yield a brown solid. The solid was stirred with Et$_2$O (8×150 mL); the insoluble solid was filtered each time until no product remained in the insoluble material. The Et$_2$O was evaporated to yield a brown solid, which was dissolved in EtOAc (25 mL) and purified by silica chromatography using the EtOAc as eluent to yield an orange/brown solid (5.12 g, 34.8%): LC/MS (Table 1, Method g) R$_t$=2.10 min; MS m/z: 214.1 (M+H)$^+$.

General Procedure E: Direct Decarboxylation of a Substituted imidazo[1,2-a]pyrazine-8-carboxylic acid methyl ester

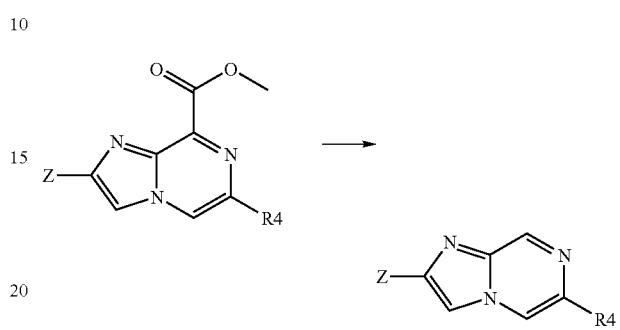

A substituted imidazo[1,2-a]pyrazine-8-carboxylic acid methyl ester is stirred in an acidic solution (for example, 1N HCl) with or without organic co-solvents (for example, DCM/MeOH) at about 50-110° C. After about 1-24 h, the solution is cooled to ambient temperature and neutralized with a base such as solid sodium bicarbonate. If the product precipitates during the neutralization it is directly filtered and characterized or if necessary, is purified further as indicated below. Alternatively, the mixture is optionally concentrated under reduced pressure and is diluted with or partitioned between water and an organic solvent (for example, EtOAc or DCM). The layers are separated and the aqueous layer is extracted with additional organic solvent (such as EtOAc, DCM, or both sequentially). The combined organic layers may be optionally washed with brine, dried over Na$_2$SO$_4$ or MgSO$_4$, then decanted or filtered, prior to concentrating under reduced pressure. The crude material is purified by chromatography, trituration with an appropriate solvent, or crystallization from one or more solvents to yield the target compound.

Illustration of General Procedure E

Preparation #E.1:
2-(2,4-Difluorophenyl)-imidazo[1,2-a]pyrazine

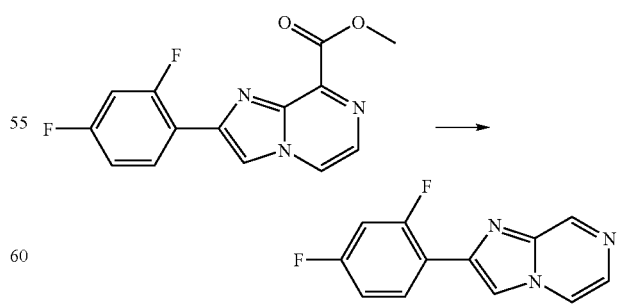

2-(2,4-Difluorophenyl)-imidazo[1,2-a]pyrazine-8-carboxylic acid methyl ester (prepared from general procedure B using 3-aminopyrazine-2-carboxylic acid methyl ester and 2-bromo-1-(2,4-difluorophenyl)-ethanone; 5.0 g, 17 mmol)

was dissolved in DCM (30 mL) and MeOH (30 mL) and was treated with 1.0 M aqueous HCl (160 mL). The mixture was heated at about 105° C. for about 13 h, allowed to cool to ambient temperature, and neutralized with NaHCO$_3$. The solid was filtered and dried overnight to yield the title compound (2.76 g, 70%): LC/MS (Table 1, Method b) $R_t$=1.9 min; MS m/z: 232.0 (M+H)$^+$.

General Procedure F: Palladium-Mediated Arylation

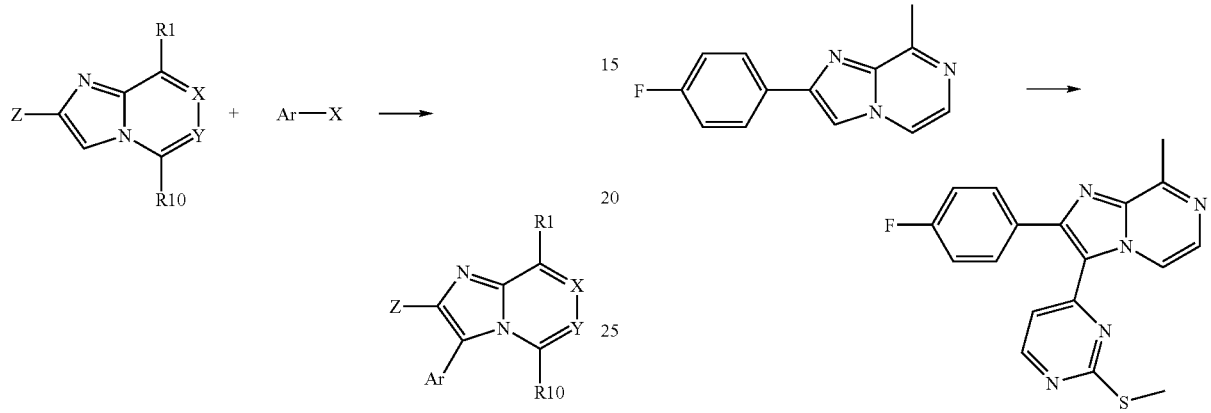

A mixture of an imidazo[1,2-a]pyrazine or an imidazo[1,2-c]pyrimidine (1 equiv) with an aryl halide (14 equiv), a base such as Cs$_2$CO$_3$, CsOAc or KOAc (1-3 equiv), a suitable catalyst/ligand combination such as palladium acetate (0.05-0.2 equiv) and triphenylphosphine (0.1-0.4 equiv), and a suitable solvent such as DMF is heated at about 70-110° C. Optionally the catalyst/ligand combination can be heated at about 70-110° C. in the solvent for about 20-60 min prior to the addition of the remaining reaction components. After about 2-96 h, the mixture is cooled to ambient temperature, diluted with water, and extracted with an organic solvent such as EtOAc. The combined organic layers may be optionally washed with brine, dried over Na$_2$SO$_4$ or MgSO$_4$, then decanted or filtered, prior to concentrating under reduced pressure. The crude material is purified by chromatography, trituration with an appropriate solvent, or crystallization from one or more solvents to yield the target compound.

Illustration of General Procedure F

Example #F.1A 2-(4-Fluorophenyl)-8-methyl-3-(2-methylsulfanylpyrimidin-4-yl)-imidazo[1,2-a]pyrazine Into a flask was added 2-(4-fluorophenyl)-8-methylimidazo[1,2-a]pyrazine (Preparation #K.1; 4.8 g, 21.0 mmol), 4-iodo-2-(methylthio)pyrimidine (Frontier, 9.4 g, 31.7 mmol), Cs$_2$CO$_3$ (10.3 g, 31.7 mmol), PPh$_3$ (2.2 g, 8.4 mmol), and DMF (50 mL). The mixture was degassed under vacuum and back-filled with N$_2$. The mixture was charged with Pd(OAc)$_2$ (0.95 g, 4.2 mmol) and heated at about 100° C. for about 16 h. The mixture was cooled to ambient temperature, diluted with water (200 mL), and extracted with DCM (3×200 mL). The combined organic layers were washed with brine (200 mL), dried over Na$_2$SO$_4$, filtered, and concentrated under reduced pressure. Purification by flash column chromatography (0-5% MeOH:DCM) followed by trituration in EtOAc yielded the title compound (4.30 g, 58% yield): LC/MS (Table 1, Method b) $R_t$=2.2 min; MS m/z: 352.3 (M+H)$^+$.

TABLE F.1

Examples prepared from 4-iodo-2-(methylthio)pyrimidine (Frontier) using General Procedure F

| Imidazo[1,2-α]pyrazine | Product | Example # | $R_t$ min (method) | m/z ESI+ (M + H)$^+$ |
|---|---|---|---|---|
| 2-(2,4-Difluorophenyl)-imidazo[1,2-α]pyrazine (prepared from B using 3-aminopyrazine-2-carboxylic acid methyl ester and 2-bromo-1-(2,4-difluorophenyl)-ethanone, E using 1M HCl) | 2-(2,4-Difluorophenyl)-3-(2-methylsulfanylpyrimidin-4-yl)-imidazo[1,2-α]pyrazine | F.1.1 | 2.2 (b) | 356.0 |
| 2-(4-Chlorophenyl)-imidazo[1,2-α]pyrazine (prepared from B using 3-aminopyrazine-2-carboxylic acid methyl ester and 2-bromo-1-(4-chlorophenyl)-ethanone, E using 1M HCl) | 2-(4-Chlorophenyl)-3-(2-methylsulfanylpyrimidin-4-yl)-imidazo[1,2-α]pyrazine | F.1.2 | 2.4 (b) | 354.1 |

TABLE F.1-continued

Examples prepared from 4-iodo-2-(methylthio)pyrimidine (Frontier) using General Procedure F

| Imidazo[1,2-α]pyrazine | Product | Example # | $R_t$ min (method) | m/z ESI+ $(M + H)^+$ |
|---|---|---|---|---|
| 2-(4-Fluorophenyl)-8-methoxyimidazo[1,2-α]pyrazine (Preparation #L.1) | 2-(4-Fluorophenyl)-8-methoxy-3-(2-methylsulfanylpyrimidin-4-yl)-imidazo[1,2-α]pyrazine | F.1.3 | 2.3 (b) | 368.2 |
| 2-(3-Fluorophenyl)-8-methylimidazo[1,2-α]pyrazine (prepared from B using 3-chloropyrazin-2-ylamine and 2-bromo-1-(3-fluorophenyl)-ethanone, K using 3M MeMgBr in Et$_2$O) | 2-(3-Fluorophenyl)-8-methyl-3-(2-methylsulfanylpyrimidin-4-yl)-imidazo[1,2-α]pyrazine | F.1.4 | 2.82 (g) | 352.2 |
| 2-(3,5-Difluorophenyl)-8-methylimidazo[1,2-α]pyrazine(prepared from B using 3-chloropyrazin-2-ylamine and 2-bromo-1-(3,5-difluorophenyl)-ethanone, K using 3M MeMgBr in Et$_2$O) | 2-(3,5-Difluorophenyl)-8-methyl-3-(2-methylsulfanylpyrimidin-4-yl)-imidazo[1,2-α]pyrazine | F.1.5 | 2.97 (g) | 370.2 |
| 2-(3-Fluoro-5-trifluoromethylphenyl)-8-methylimidazo[1,2-α]pyrazine (prepared from B using 3-chloropyrazin-2-ylamine and 2-bromo-1-(3-fluoro-5-trifluoromethylphenyl)-ethanone, K using 3 M MeMgBr in Et$_2$O) | 2-(3-Fluoro-5-trifluoromethylphenyl)-8-methyl-3-(2-methylsulfanylpyrimidin-4-yl)-imidazo[1,2-α]pyrazine | F.1.6 | 3.31 (g) | 420.2 |
| 2-(4-Fluorophenyl)-8-(2,2,2-trifluoroethoxy)-imidazo[1,2-α]pyrazine (prepared from B using 3-chloropyrazin-2-ylamine and 2-bromo-1-(4-fluorophenyl)-ethanone, L using 2,2,2-trifluoroethanol and sodium) | 2-(4-Fluorophenyl)-3-(2-methylsulfanylpyrimidin-4-yl)-8-(2,2,2-trifluoroethoxy)-imidazo[1,2-α]pyrazine | F.1.7 | 3.40 (g) | 436.1 |
| 2-(4-Fluorophenyl)-8-isobutoxyimidazo[1,2-α]pyrazine (prepared from B using 3-chloropyrazin-2-ylamine and 2-bromo-1-(4-fluorophenyl)-ethanone, L using isobutanol and sodium) | 2-(4-Fluorophenyl)-8-isobutoxy-3-(2-methylsulfanylpyrimidin-4-yl)-imidazo[1,2-α]pyrazine | F.1.8 | 3.72 (g) | 410.3 |
| 8-Cyclopropyl-methoxy-2-(4-fluorophenyl)-imidazo[1,2-α]pyrazine (prepared from B using 3-chloropyrazin-2-ylamine and 2-bromo-1-(4-fluorophenyl)-ethanone, L using cyclopropylmethanol and sodium) | 8-Cyclopropylmethoxy-2-(4-fluorophenyl)-3-(2-methylsulfanylpyrimidin-4-yl)-imidazo[1,2-α]pyrazine | F.1.9 | 3.53 (g) | 408.2 |
| 2-(4-Fluorophenyl)-8-(2-methoxyethoxy)-imidazo[1,2-α]pyrazine (prepared from B using 3-chloropyrazin-2-ylamine and 2-bromo-1-(4-fluorophenyl)-ethanone, L using 2-methoxyethanol and sodium) | 2-(4-Fluorophenyl)-8-(2-methoxyethoxy)-3-(2-methylsulfanylpyrimidin-4-yl)-imidazo[1,2-α]pyrazine | F.1.10 | 2.95 (g) | 412.2 |
| 8-Ethoxy-2-(4-fluorophenyl)-imidazo[1,2-α]pyrazine (prepared from B using 3-chloropyrazin-2-ylamine and 2-bromo-1-(4-fluorophenyl)-ethanone, L using ethanol and sodium) | 8-Ethoxy-2-(4-fluorophenyl)-3-(2-methylsulfanylpyrimidin-4-yl)-imidazo[1,2-α]pyrazine | F.1.11 | 3.22 (g) | 382.2 |
| 2-(4-Fluorophenyl)-8-isopropoxyimidazo-[1,2-α]pyrazine (prepared from B using 3-chloropyrazin-2-ylamine and 2-bromo-1-(4-fluorophenyl)-ethanone, L using isopropanol and sodium) | 2-(4-Fluorophenyl)-8-isopropoxy-3-(2-methylsulfanylpyrimidin-4-yl)-imidazo[1,2-α]pyrazine | F.1.12 | 3.45 (g) | 396.2 |

TABLE F.1-continued

Examples prepared from 4-iodo-2-(methylthio)pyrimidine (Frontier) using General Procedure F

| Imidazo[1,2-α]pyrazine | Product | Example # | $R_t$ min (method) | m/z ESI+ $(M + H)^+$ |
|---|---|---|---|---|
| 8-Methyl-2-(3-trifluoromethylphenyl)-imidazo[1,2-α]pyrazine (prepared from B using 3-chloropyrazin-2-ylamine and 2-bromo-1-(3-trifluoromethylphenyl)ethanone, K using 3M MeMgBr in Et$_2$O) | 8-Methyl-3-(2-methylsulfanylpyrimidin-4-yl)-2-(3-trifluoromethylphenyl)-imidazo[1,2-α]pyrazine | F.1.13 | 2.54 (a) | 402.3 |
| 8-Methyl-2-(4-trifluoromethylphenyl)-imidazo[1,2-α]pyrazine (prepared from B using 3-chloropyrazin-2-ylamine and 2-bromo-1-(4-trifluoromethylphenyl)-ethanone, K using 3M MeMgBr in Et$_2$O) | 8-Methyl-3-(2-methylsulfanylpyrimidin-4-yl)-2-(4-trifluoromethylphenyl)-imidazo[1,2-α]pyrazine | F.1.14 | 2.54 (a) | 402.3 |
| 2-(3,4-Difluorophenyl)-8-methyl-imidazo[1,2-α]pyrazine (prepared from B using 3-chloropyrazin-2-ylamine and 2-bromo-1-(3,4-difluorophenyl)-ethanone, K using 3M MeMgBr in Et$_2$O) | 2-(3,4-Difluorophenyl)-8-methyl-3-(2-methylsulfanylpyrimidin-4-yl)-imidazo[1,2-α]pyrazine | F.1.15 | 2.37 (a) | 370.2 |
| 2-(2,4-Diifluorophenyl)-8-methyl-imidazo[1,2-α]pyrazine (prepared from B using 3-chloropyrazin-2-ylamine and 2-bromo-1-(2,4-difluorophenyl)-ethanone, K using 3M MeMgBr in Et$_2$O) | 2-(2,4-Difluorophenyl)-8-methyl-3-(2-methylsulfanylpyrimidin-4-yl)imidazo[1,2-α]pyrazine | F.1.16 | 2.12 (a) | 370.2 |
| 2-(3-Chlorophenyl)-8-methyl-imidazo[1,2-α]pyrazine (prepared from B using 3-chloropyrazin-2-ylamine and Preparation #M.1, K using 3M MeMgBr in Et$_2$O) | 2-(3-Chlorophenyl)-8-methyl-3-(2-methylsulfanylpyrimidin-4-yl) imidazo[1,2-α]pyrazine | F.1.17 | 2.65 (a) | 368.3 |
| [2-(4-Fluorophenyl)-imidazo[1,2-α]pyrazin-8-yl]methylamine (Preparation #O.1) | [2-(4-Fluorophenyl)-3-(2-methylsulfanylpyrimidin-4-yl)-imidazo[1,2-α]pyrazin-8-yl]methylamine | F.1.18 | 2.48 (a) | 367.3 |
| 2-m-Tolylimidazo[1,2-α]pyrazine (prepared from M using 1-m-tolylethanone followed by B using 3-aminopyrazine-2-carboxylic acid methyl ester, C using LiOH, D using 1M HCl) | 3-(2-Methylsulfanylpyrimidin-4-yl)-2-m-tolylimidazo[1,2-α]pyrazine | F.1.19 | 2.19 (a) | 334.2 |
| 2-(3,4-Difluorophenyl)-imidazo[1,2-α]pyrazine (prepared from B using 2-bromo-1-(3,4-difluorophenyl)-ethanone and 3-aminopyrazine-2-carboxylic acid methyl ester, C using LiOH, D using 1M HCl) | 2-(3,4-Difluorophenyl)-3-(2-methylsulfanylpyrimidin-4-yl)-imidazo[1,2-α]pyrazine | F.1.20 | 2.18 (a) | 356.2 |
| 2-(4-Fluorophenyl)-8-isopropylimidazo[1,2-α]pyrazine (prepared from B using 3-chloropyrazin-2-ylamine and 2-bromo-1-(3-fluorophenyl)-ethanone, K using 2M isopropylmagnesuim chloride in THF) | 2-(4-Fluorophenyl)-8-isopropyl-3-(2-methylsulfanylpyrimidin-4-yl)-imidazo[1,2-α]pyrazine | F.1.21 | 2.46 (f) | 380.1 |
| 8-Ethyl-2-(4-fluorophenyl)-imidazo[1,2-α]pyrazine (prepared from B using 3-chloropyrazin-2-ylamine and 2-bromo-1-(3-fluorophenyl)-ethanone, K using 1M ethylmagnesuim chloride in THF) | 8-Ethyl-2-(4-fluorophenyl)-3-(2-methylsulfanylpyrimidin-4-yl)-imidazo[1,2-α]pyrazine | F.1.22 | 2.41 (a) | 366.3 |

TABLE F.1-continued

Examples prepared from 4-iodo-2-(methylthio)pyrimidine (Frontier) using General Procedure F

| Imidazo[1,2-α]pyrazine | Product | Example # | $R_t$ min (method) | m/z ESI+ $(M + H)^+$ |
|---|---|---|---|---|
| 2-(4-Chloro-3-methylphenyl)-imidazo[1,2-α]pyrazine (prepared from B using 3-aminopyrazine-2-carboxylic acid methyl ester and 2-bromo-1-(4-chloro-3-methylphenyl)-ethanone [Maybridge], E using 1M HCl) | 2-(4-Chloro-3-methylphenyl)-3-(2-methylsulfanylpyrimidin-4-yl)-imidazo[1,2-α]pyrazine | F.1.23 | 2.5 (b) | 368.8 |
| 2-(2-Fluoro-4-trifluoromethylphenyl)-imidazo[1,2-α]pyrazine (prepared from B using 3-aminopyrazine-2-carboxylic acid methyl ester and 2-bromo-1-(2-fluoro-4-trifluoromethylphenyl)-ethanone [Apollo Scientific], E using 1M HCl) | 2-(2-Fluoro-4-trifluoromethylphenyl)-3-(2-methylsulfanylpyrimidin-4-yl)-imidazo[1,2-α]pyrazine | F.1.24 | 2.3 (b) | 406.4 |
| 2-(4-Chloro-2-fluorophenyl)-imidazo[1,2-α]pyrazine (prepared from M using 1-(4-chloro-2-fluorophenyl)-ethanone[WO 2004073606 A2], followed by B using 3-aminopyrazine-2-carboxylic acid methyl ester and, E using 1M HCl) | 2-(4-Chloro-2-fluorophenyl)-3-(2-methylsulfanylpyrimidin-4-yl)-imidazo[1,2-α]pyrazine | F.1.25 | 2.4 (b) | 372.8 |
| [2-(4-Fluorophenyl)imidazo[1,2-α]pyrazin-8-yl]dimethylamine (prepared from B using 3-chloropyrazin-2-ylamine and 2-bromo-1-(4-fluorophenyl)ethanone, O using 2M dimethylamine in THF) | [2-(4-Fluorophenyl)-3-(2-methylsulfanylpyrimidin-4-yl)imidazo[1,2-α]pyrazin-8-yl]dimethylamine | F.1.26 | 2.61 (b) | 381.3 |
| 8-Cyclopropyl-2-(4-fluorophenyl)imidazo[1,2-α]pyrazine (prepared from B using 3-chloropyrazin-2-ylamine and 2-bromo-1-(4-fluorophenyl)ethanone, K using 0.5M cyclopropylmagnesium bromide in THF) | 8-Cyclopropyl-2-(4-fluorophenyl)-3-(2-methylsulfanylpyrimidin-4-yl)imidazo[1,2-α]pyrazine | F.1.27 | 3.47 (g) | 378.2 |
| 2-(3,4-Difluorophenyl)-8-methoxyimidazo[1,2-α]pyrazine (prepared from B using 3-chloropyrazin-2-ylamine and 2-bromo-1-(3,4-difluorophenyl)ethanone, L using sodium methoxide and methanol) | 2-(3,4-Difluorophenyl)-8-methoxy-3-(2-methylsulfanylpyrimidin-4-yl)imidazo[1,2-α]pyrazine | F.1.28 | 3.01 (g) | 386.2 |
| 2-(3-Chlorophenyl)-8-methoxyimidazo[1,2-α]pyrazine (prepared from B using 3-chloropyrazin-2-ylamine and Preparation #M.1, L using sodium methoxide and methanol) | 2-(3-Chlorophenyl)-8-methoxy-3-(2-methylsulfanylpyrimidin-4-yl)imidazo[1,2-α]pyrazine | F.1.29 | 3.20 (g) | 384.2 |
| 2-Phenylimidazo[1,2-α]pyrazine (prepared from B using 2-bromo-1-phenyl ethanone and 3-aminopyrazine-2-carboxylic acid methyl ester, C using LiOH, D using 1M HCl) | 3-(2-Methylsulfanylpyrimidin-4-yl)-2-phenylimidazo[1,2-α]pyrazine | F.1.30 | 1.93 (b) | 320.2 |
| 2-Naphthalen-2-ylimidazo[1,2-α]pyrazine (prepared from B using 2-bromo-1-naphthalen-2-yl-ethanone [Alfa Aesar] and 3-aminopyrazine-2-carboxylic acid methyl ester, C using LiOH, D using 1M HCl) | 3-(2-Methylsulfanylpyrimidin-4-yl)-2-naphthalen-2-ylimidazo[1,2-α]pyrazine | F.1.31 | 2.36 (b) | 370.2 |

TABLE F.1-continued

Examples prepared from 4-iodo-2-(methylthio)pyrimidine (Frontier) using General Procedure F

| Imidazo[1,2-α]pyrazine | Product | Example # | R$_t$ min (method) | m/z ESI+ (M + H)+ |
|---|---|---|---|---|
| 2-(3-Trifluoromethylphenyl)-imidazo[1,2-α]pyrazine (prepared from B using 2-bromo-1-(3-trifluoromethylphenyl)-ethanone (Maybridge) and 3-aminopyrazine-2-carboxylic acid methyl ester, C using LiOH, D using 1M HCl) | 3-(2-Methylsulfanylpyrimidin-4-yl)-2-(3-trifluoromethylphenyl)-imidazo[1,2-α]pyrazine | F.1.32 | 2.96 (g) | 388.06 |
| 2-(3-Chlorophenyl)-imidazo[1,2-α]pyrazine (prepared from M using 1-(3-chlorophenyl)-ethanone followed by B using 3-aminopyrazine-2-carboxylic acid methyl ester, C using LiOH, D using 1M HCl) | 2-(3-Chlorophenyl)-3-(2-methylsulfanylpyrimidin-4-yl)-imidazo[1,2-α]pyrazine | F.1.33 | 2.33 (b) | 354.2 |
| 6-Chloro-2-(4-fluorophenyl)-imidazo[1,2-α]pyrazine (prepared from B using 5-chloropyrazin-2-ylamine [WO04/056369] and 2-bromo-1-(4-fluorophenyl)-ethanone) | 6-Chloro-2-(4-fluorophenyl)-3-(2-methylsulfanylpyrimidin-4-yl)-imidazo[1,2-α]pyrazine | F.1.34 | 3.16 (g) | 372.18 |
| 2-(4-Fluorophenyl)-6-methoxyimidazo[1,2-α]pyrazine (Preparation #7) | 2-(4-Fluorophenyl)-6-methoxy-3-(2-methylsulfanylpyrimidin-4-yl)-imidazo[1,2-α]pyrazine | F.1.35 | 2.40 (b) | 368.2 |
| 2-(3-Chloro-4-fluorophenyl)-imidazo[1,2-α]pyrazine (prepared from M using 1-(3-chloro-4-fluorophenyl)-ethanone [Alfa Aesar] followed by B using 3-aminopyrazine-2-carboxylic acid methyl ester, C using LiOH, D using 1M HCl) | 2-(3-Chloro-4-fluorophenyl)-3-(2-methylsulfanylpyrimidin-4-yl)-imidazo[1,2-α]pyrazine | F.1.36 | 2.50 (b) | 372.2 |
| 2-(2,4-Difluorophenyl)-8-methylimidazo[1,2-α]pyrazine (prepared from B using 2-bromo-1-(2,4-difluorophenyl)-ethanone and 3-chloropyrazin-2-ylamine, K using 3M MeMgBr in Et$_2$O) | 2-(2,4-Difluorophenyl)-8-methyl-3-(2-methylsulfanylpyrimidin-4-yl)-imidazo[1,2-α]pyrazine | F.1.37 | 2.30 (b) | 370.3 |
| 2-(2,4-Difluorophenyl)-8-methoxy-imidazo[1,2-a]pyrazine (prepared from B using 3-chloro-pyrazin-2-ylamine and 2-bromo-1-(4-fluoro-phenyl)-ethanone, L using methanol and sodium) | 2-(2,4-Difluorophenyl)-8-methoxy-3-(2-methylsulfanylpyrimidin-4-yl)-imidazo[1,2-a]pyrazine | F.1.38 | 2.91 (g) | 386.1 |
| 6-Chloro-2-(4-fluoro-phenyl)-8-methyl-imidazo[1,2-a]pyrazine (prepared from B using 3,5-dichloropyrazin-2-ylamine [WO95/26957] and 2-bromo-1-(4-fluorophenyl)-ethanone, K using 3.0 M MeMgBr in Et$_2$O) | 6-Chloro-2-(4-fluorophenyl)-8-methyl-3-(2-methylsulfanylpyrimidin-4-yl)-imidazo[1,2-a]pyrazine | F.1.39 | 2.6 (g) | 402.0 |
| 2-(4-Fluorophenyl)-6,8-dimethyl-imidazo[1,2-a]pyrazine (prepared from B using 3,5-dimethyl-pyrazin-2-ylamine [Ryan Scientific Inc.] and 2-bromo-1-(4-fluorophenyl)-ethanone) | 2-(4-Fluorophenyl)-6,8-dimethyl-3-(2-methylsulfanylpyrimidin-4-yl)-imidazo[1,2-a]pyrazine | F.1.40 | 2.97 (g) | 366.1 |
| 2-(2,4-Difluoro-phenyl)-6,8-dimethyl-imidazo[1,2-a]pyrazine prepared from B using 3,5-dimethyl-pyrazin-2-ylamine [Ryan Scientific Inc.] and 2-bromo-1-(4-fluorophenyl)-ethanone) | 2-(2,4-Difluorophenyl)-6,8-dimethyl-3-(2-methylsulfanylpyrimidin-4-yl)-imidazo[1,2-a]pyrazine | F.1.41 | 2.92 (g) | 384.1 |

TABLE F.1-continued

Examples prepared from 4-iodo-2-(methylthio)pyrimidine (Frontier) using General Procedure F

| Imidazo[1,2-α]pyrazine | Product | Example # | R$_t$ min (method) | m/z ESI+ (M + H)$^+$ |
|---|---|---|---|---|
| 2-(2,4-Difluorophenyl)-8-isopropoxyimidazo[1,2-a]pyrazine (prepared from B using 2-bromo-2',4'-difluoroacetophenone and 3-chloropyrazin-2-ylamine, L using sodium isopropoxide in isopropyl alcohol) | 2-(2,4-Difluorophenyl)-8-isopropoxy-3-(2-methylsulfanylpyrimidin-4-yl)-imidazo[1,2-a]pyrazine | F.1.42 | 2.5 (b) | 414.2 |
| 8-Methyl-2-(3-trifluoromethoxy-phenyl)-imidazo[1,2-a]pyrazine (prepared from B using 3-(trifluoromethoxy)phenacyl bromide and 3-chloropyrazin-2-ylamine, K using 3M MeMgBr in Et$_2$O) | 8-Methyl-3-(2-methylsulfanylpyrimidin-4-yl)-2-(3-trifluoromethoxyphenyl)-imidazo[1,2-a]pyrazine | F.1.43 | 2.6 (b) | 418.1 |
| Cyclopropyl-[2-(4-fluorophenyl)imidazo[1,2-a]pyrazin-8-yl]amine (prepared from B using 3-chloropyrazin-2-ylamine and 2-bromo-1-(4-fluorophenyl)-ethanone, O using cyclopropylamine) | Cyclopropyl-[2-(4-fluorophenyl)-3-(2-methylsulfanylpyrimidin-4-yl)-imidazo[1,2-a]pyrazin-8-yl]amine | F.1.44 | 2.61 (a) | 393.3 |
| {2-[2-(4-Fluorophenyl)-imidazo[1,2-a]pyrazin-8-yl]-ethyl}-carbamic acid tert-butyl ester (Preparation #9) | {2-[2-(4-Fluorophenyl)-3-(2-methylsulfanylpyrimidin-4-yl)-imidazo[1,2-a]pyrazin-8-yl]-ethyl}-carbamic acid tert-butyl ester | F.1.45 | 3.11 (g) | 481.2 |
| 2-(2,4-Difluorophenyl)-8-isopropylimidazo[1,2-a]pyrazine (prepared from B using 3-chloropyrazin-2-ylamine and 2-bromo-1-(2,4-difluorophenyl)ethanone, K using 2 M isopropylmagnesium chloride in THF) | 2-(2,4-Difluorophenyl)-8-isopropyl-3-(2-methylsulfanylpyrimidin-4-yl)imidazo[1,2-a]pyrazine | F.1.46 | 3.45 (g) | 398.2 |
| 8-Cyclopropylmethyl-2-(2,4-difluorophenyl)imidazo[1,2-a]pyrazine (Preparation #10) | 8-Cyclopropylmethyl-2-(2,4-difluorophenyl)-3-(2-methylsulfanylpyrimidin-4-yl)imidazo[1,2-a]pyrazine | F.1.47 | 3.36 (g) | 410.2 |
| 2-(4-Fluorophenyl)-8-isobutylimidazo[1,2-a]pyrazine (prepared from B using 3-chloropyrazin-2-ylamine and 2-bromo-1-(4-fluorophenyl)ethanone, K using 2M isobutylmagnesium bromide in diethyl ether) | 2-(4-Fluorophenyl)-8-isobutyl-3-(2-methylsulfanylpyrimidin-4-yl)imidazo[1,2-a]pyrazine | F.1.48 | 3.65 (g) | 394.2 |

General Procedure G: Oxidation of a Sulfide to a Sulfone and/or a Sulfoxide

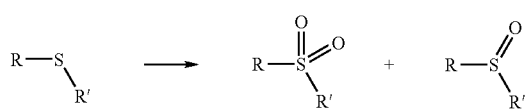

To a solution of a sulfide (1 equiv) in a suitable solvent such as MeOH:DCM (1:1) is added an oxidant (2-5 equiv) such as Oxone® (2-5 equiv) in water at ambient temperature or m-CPBA in DCM at about 0-25° C. After about 2-24 h, the mixture is diluted with water and an organic solvent such as DCM or EtOAc. The layers are separated and the aqueous layer is washed with additional organic solvent. The combined organic layers may be optionally washed with brine, dried over Na$_2$SO$_4$ or MgSO$_4$, then decanted or filtered, prior to concentrating under reduced pressure. The crude material is used as is in the next step or is preferably purified by trituration, crystallization, or flash silica gel chromatography to yield the target compound.

Illustration of General Procedure G

Example #G.1

2-(4-Fluorophenyl)-3-(2-methanesulfonylpyrimidin-4-yl)-8-methylimidazo[1,2-a]pyrazine

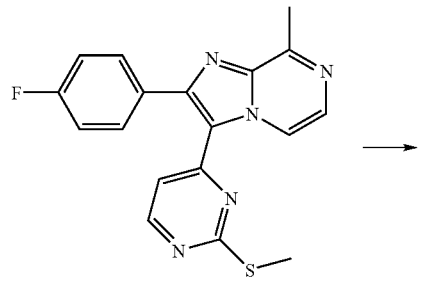 →

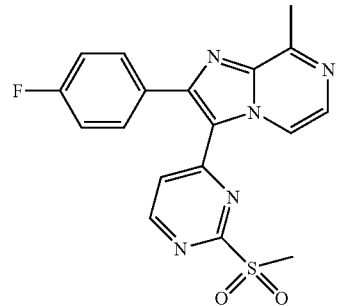

To a solution of 2-(4-fluorophenyl)-8-methyl-3-(2-methylsulfanylpyrimidin-4-yl)-imidazo[1,2-a]pyrazine (Example #F.1A; 8.58 g, 24.4 mmol) in MeOH (200 mL) and DCM (200 mL) at ambient temperature was added Oxone® (30.0 g, 48.8 mmol) in water (100 mL) to form a suspension. After about 20 h of stirring the layers were separated. The aqueous layer was washed with DCM (3×30 mL). Combined organic layers were washed with brine, dried over MgSO$_4$, and concentrated under reduced pressure to yield a yellow solid, which was purified via FCC using EtOAc as an eluent. The product-containing fractions were combined and concentrated under reduced pressure to give a white solid (6.5 g) that was recrystallized in IPA (700 mL) to yield the title compound (3.6 g) after filtration. Additional product was observed in the filtrate. (3.6 g, 38% yield): LC/MS (Table 1, Method b) R$_t$=1.7 min; MS m/z: 384.1 (M+H)$^+$.

TABLE G.1

Examples prepared from sulfides using General Procedure G

| Sulfide | Product | Example # | R$_t$ min (method) | m/z ESI+ (M + H)$^+$ |
|---|---|---|---|---|
| 2-(4-Chlorophenyl)-3-(2-methylsulfanylpyrimidin-4-yl)-imidazo[1,2-α]pyrazine (Example # F.1.2) | 2-(4-Chlorophenyl)-3-(2-methanesulfonylpyrimidin-4-yl)-imidazo[1,2-α]pyrazine | G.1.1 | 1.9 (b) | 386.1 |
| 2-(4-Chlorophenyl)-3-(2-methylsulfanylpyrimidin-4-yl)-imidazo[1,2-α]pyrazine (Example # F.1.2) | 2-(4-Chlorophenyl)-3-(2-methanesulfinylpyrimidin-4-yl)-imidazo[1,2-α]pyrazine | G.1.2 | 1.7 (b) | 370.1 |
| {4-[2-(4-Fluorophenyl)-imidazo[1,2-α]pyrazin-3-yl]-pyrimidin-2-yl}-(tetrahydrothiopyran-4-yl)-amine (Example #A.27) | 4-[2-(4-Fluorophenyl)-imidazo[1,2-α]pyrazin-3-yl]-pyrimidin-2-yl-(1-oxo-hexahydro-1λ'4'-thiopyran-4-yl)-amine | G.1.3 | 1.5 (b) | 423.1 |
| 2-(2,4-Difluorophenyl)-3-(2-methylsulfanylpyrimidin-4-yl)-imidazo[1,2-α]pyrazine (Example #F.1.1) | 2-(2,4-Difluorophenyl)-3-(2-methanesulfonylpyrimidin-4-yl)-imidazo[1,2-α]pyrazine | G.1.4 | 1.7 (b) | 388.1 |

TABLE G.1-continued

Examples prepared from sulfides using General Procedure G

| Sulfide | Product | Example # | R, min (method) | m/z ESI+ (M + H)+ |
|---|---|---|---|---|
| 2-(4-Fluorophenyl)-8-methoxy-3-(2-methylsulfanylpyrimidin-4-yl)-imidazo[1,2-α]pyrazine (Example #F.1.3) | 2-(4-Fluorophenyl)-3-(2-methanesulfinylpyrimidin-4-yl)-8-methoxyimidazo[1,2-α]pyrazine | G.1.5 | 1.6 (b) | 384.2 |
| 2-(4-Fluorophenyl)-8-methoxy-3-(2-methylsulfanylpyrimidin-4-yl)-imidazo[1,2-α]pyrazine (Example #F.1.3) | 2-(4-Fluorophenyl)-3-(2-methanesulfonylpyrimidin-4-yl)-8-methoxyimidazo[1,2-α]pyrazine | G.1.6 | 1.9 (b) | 400.2 |
| 2-(3-Fluorophenyl)-8-methyl-3-(2-methylsulfanylpyrimidin-4-yl)-imidazo[1,2-α]pyrazine (Example #F.1.4) | 2-(3-Fluorophenyl)-3-(2-methanesulfonylpyrimidin-4-yl)-8-methylimidazo[1,2-α]pyrazine | G.1.7 | 2.16 (g) | 384.2 |
| 2-(3,5-Difluorophenyl)-8-methyl-3-(2-methylsulfanylpyrimidin-4-yl)-imidazo[1,2-α]pyrazine (Example #F.1.5) | 2-(3,5-Difluorophenyl)-3-(2-methanesulfonylpyrimidin-4-yl)-8-methylimidazo[1,2-α]pyrazine | G.1.8 | 2.31 (g) | 402.2 |
| 2-(3-Fluoro-5-trifluoromethylphenyl)-8-methyl-3-(2-methylsulfanylpyrimidin-4-yl)-imidazo[1,2-α]pyrazine (Example #F.1.6) | 2-(3-Fluoro-5-trifluoromethylphenyl)-3-(2-methanesulfonylpyrimidin-4-yl)-8-methylimidazo[1,2-α]pyrazine | G.1.9 | 2.61 (g) | 452.2 |
| 2-(4-Fluorophenyl)-3-(2-methylsulfanylpyrimidin-4-yl)-8-(2,2,2-trifluoroethoxy)-imidazo[1,2a]pyrazine (Example #F.1.7) | 2-(4-Fluorophenyl)-3-(2-methanesulfonylpyrimidin-4-yl)-8-(2,2,2-trifluoroethoxy)-imidazo[1,2-α]pyrazine | G.1.10 | 2.75 (g) | 468.1 |
| 2-(4-Fluorophenyl)-8-isobutoxy-3-(2-methylsulfanylpyrimidin-4-yl)-imidazo[1,2-α]pyrazine (Example #F.1.8) | 2-(4-Fluorophenyl)-8-isobutoxy-3-(2-methanesulfonylpyrimidin-4-yl)-imidazo[1,2-α]pyrazine | G.1.11 | 2.96 (g) | 427.3 |
| 8-Cyclopropylmethoxy-2-(4-fluorophenyl)-3-(2-methylsulfanylpyrimidin-4-yl)-imidazo[1,2-α]pyrazine (Example #F.1.9) | 8-Cyclopropylmethoxy-2-(4-fluorophenyl)-3-(2-methanesulfonylpyrimidin-4-yl)-imidazo[1,2-α]pyrazine | G.1.12 | 2.69 (g) | 440.1 |
| 2-(4-Fluorophenyl)-8-(2-methoxyethoxy)-3-(2-methylsulfanylpyrimidin-4-yl)-imidazo[1,2-α]pyrazine (Example #F.1.10) | 2-(4-Fluorophenyl)-3-(2-methanesulfonylpyrimidin-4-yl)-8-(2-methoxyethoxy)-imidazo[1,2-α]pyrazine | G.1.13 | 2.32 (g) | 444.2 |

TABLE G.1-continued

Examples prepared from sulfides using General Procedure G

| Sulfide | Product | Example # | R$_t$ min (method) | m/z ESI+ (M + H)$^+$ |
|---|---|---|---|---|
| 8-Ethoxy-2-(4-fluorophenyl)-3-(2-methylsulfanylpyrimidin-4-yl)-imidazo[1,2-α]-pyrazine (Example #F.1.11) | 8-Ethoxy-2-(4-fluorophenyl)-3-(2-methane-sulfonylpyrimidin-4-yl)-imidazo[1,2-α]pyrazine | G.1.14 | 2.49 (g) | 414.2 |
| 2-(4-Fluorophenyl)-8-isopropoxy-3-(2-methylsulfanylpyrimidin-4-yl)-imidazo[1,2-α]pyrazine (Example #F.1.12) | 2-(4-Fluorophenyl)-8-isopropoxy-3-(2-methanesulfonylpyrimidin-4-yl)-imidazo[1,2-α]pyrazine | G.1.15 | 2.70 (g) | 428.2 |
| 8-Methyl-3-(2-methylsulfanylpyrimidin-4-yl)-2-(3-trifluoromethylphenyl)-imidazo[1,2-α]pyrazine (Example # F.1.13) | 3-(2-Methanesulfonylpyrimidin-4-yl)-8-methyl-2-(3-trifluoromethylphenyl)imidazo[1,2-α]pyrazine | G.1.16 | 1.87 (a) | 434.2 |
| 8-Methyl-3-(2-methylsulfanylpyrimidin-4-yl)-2-(4-trifluoromethylphenyl)-imidazo[1,2-α]pyrazine (Example # F.1.14) | 3-(2-Methanesulfonylpyrimidin-4-yl)-8-methyl-2-(4-trifluoromethylphenyl)imidazo[1,2-α]pyrazine | G.1.17 | 1.98 (a) | 434.2 |
| 2-(3,4-Difluorophenyl)-8-methyl-3-(2-methylsulfanylpyrimidin-4-yl)-imidazo[1,2-α]pyrazine (Example # F.1.15) | 2-(3,4-Difluorophenyl)3-(2-methanesulfonylpyrimidin-4-yl)-8-methyl-imidazo[1,2-α]pyrazine | G.1.18 | 1.73 (a) | 402.2 |
| 2-(2,4-Difluorophenyl)-8-methyl-3-(2-methylsulfanylpyrimidin-4-yl)imidazo[1,2-α]pyrazine (Example # F.1.16) | 2-(2,4-Difluorophenyl)-3-(2-Methanesulfonylpyrimidin-4-yl)-8-methyl-imidazo[1,2-α]pyrazine | G.1.19 | 1.73 (a) | 402.2 |
| 2-(4-Fluorophenyl)-3-(2-methylsulfanylpyrimidin-4-yl)-imidazo[1,2-α]pyrazin-8-yl]methylamine (Example # F.1.18) | [2-(4-Fluorophenyl)-3-(2-methanesulfonylpyrimidin-4-yl)-imidazo[1,2-α]pyrazin-8-yl]methylamine | G.1.20 | 1.82 (a) | 499.3 |
| 3-(2-Methylsulfanyl-pyrimidin-4-yl)-2-m-tolylimidazo[1,2-α]pyrazine (Example # F.1.19) | 3-(2-Methanesulfonyl-pyrimidin-4-yl)-2-m-tolylimidazo[1,2-α]pyrazine | G.1.21 | 1.57 (a) | 366.2 |
| 2-(3,4-Difluorophenyl)-3-(2-methylsulfanyl-pyrimidin-4-yl)-imidazo[1,2-α]pyrazine (Example # F.1.20) | 2-(3,4-Difluorophenyl)-3-(2-methanesulfonylpyrimidin-4-yl)-imidazo[1,2-α]pyrazine | G.1.22 | 1.60 (a) | 388.1 |
| 2-(4-Fluorophenyl)-8-isopropyl-3-(2-methylsulfanylpyrimidin-4-yl)-imidazo[1,2-α]pyrazine (Example # F.1.21) | 2-(4-Fluorophenyl)-8-isopropyl-3-(2-methanesulfonylpyrimidin-4-yl)-imidazo[1,2-α]pyrazine | G.1.23 | 2.05 (f) | 412.1 |

TABLE G.1-continued

Examples prepared from sulfides using General Procedure G

| Sulfide | Product | Example # | R$_t$ min (method) | m/z ESI+ (M + H)$^+$ |
|---|---|---|---|---|
| 8-Ethyl-2-(4-fluorophenyl)-3-(2-methylsulfanylpyrimidin-4-yl)-imidazo[1,2-α]pyrazine (Example # F.1.22) | 8-Ethyl-2-(4-fluorophenyl)-3-(2-methanesulfonylpyrimidin-4-yl)-imidazo[1,2-α]pyrazine | G.1.24 | 1.25 (a) | 398.2 |
| 2-(4-Chloro-3-methylphenyl)-3-(2-methylsulfanylpyrimidin-4-yl)-imidazo[1,2-α]pyrazine (Example # F.1.23) | 2-(4-Chloro-3-methylphenyl)-3-(2-methanesulfonylpyrimidin-4-yl)-imidazo[1,2-α]pyrazine | G.1.25 | 1.8 (b) | 400.8 |
| 2-(2-Fluoro-4-trifluoromethylphenyl)-3-(2-methylsulfanylpyrimidin-4-yl)-imidazo[1,2-α]pyrazine (Example # F.1.24) | 2-(2-Fluoro-4-trifluoromethylphenyl)-3-(2-methanesulfonylpyrimidin-4-yl)-imidazo[1,2-α]pyrazine | G.1.26 | 2.0 (b) | 438.4 |
| 2-(4-Chloro-2-fluorophenyl)-3-(2-methylsulfanylpyrimidin-4-yl)-imidazo[1,2-α]pyrazine (Example # F.1.25) | 2-(4-Chloro-2-fluorophenyl)-3-(2-methanesulfonylpyrimidin-4-yl)-imidazo[1,2-α]pyrazine | G.1.27 | 1.9 (b) | 404.8 |
| 2-(4-Fluorophenyl)-3-(2-methylsulfanylpyrimidin-4-yl)-imidazo[1,2-α]pyrazin-8-ylamine (Example # O.1.1) | 2-(4-Fluorophenyl)-3-(2-methanesulfonylpyrimidin-4-yl)imidazo[1,2-α]pyrazin-8-ylamine | G.1.28 | 1.55 (a) | 385.2 |
| [2-(4-Fluorophenyl)-3-(2-methylsulfanylpyrimidin-4-yl)-imidazo[1,2-α]pyrazin-8-yl]dimethylamine (Example # F.1.26) | [2-(4-Fluorophenyl)-3-(2-methanesulfonylpyrimidin-4-yl)imidazo[1,2-α]pyrazin-8-yl]dimethylamine | G.1.29 | 2.11 (b) | 413.3 |
| 8-Cyclopropyl-2-(4-fluorophenyl)-3-(2-methylsulfanylpyrimidin-4-yl)imidazo[1,2-α]pyrazine (Example #F.1.27) | 8-cyclopropyl-2-(4-fluorophenyl)-3-(2-methanesulfonylpyrimidin-4-yl)imidazo[1,2-α]pyrazine | G.1.30 | 2.67 (g) | 410.2 |
| 8-Cyclopropyl-2-(4-fluorophenyl)-3-(2-methylsulfanylpyrimidin-4-yl)imidazo[1,2-α]pyrazine (Example #F.1.27) | 8-cyclopropyl-2-(4-fluorophenyl)-3-(2-methanesulfinylpyrimidin-4-yl)imidazo[1,2-α]pyrazine | G.1.31 | 2.28 (g) | 394.2 |
| 2-(3,4-Difluorophenyl)-8-methoxy-3-(2-methylsulfanylpyrimidin-4-yl)imidazo[1,2-α]pyrazine (Example #F.1.28) | 2-(3,4-difluorophenyl)-3-(2-methanesulfonylpyrimidin-4-yl)-8-methoxyimidazo[1,2-α]pyrazine | G.1.32 | 2.37 (g) | 418.2 |
| 2-(3,4-Difluorophenyl)-8-methoxy-3-(2-methylsulfanylpyrimidin-4-yl)imidazo[1,2-α]pyrazine (Example #F.1.28) | 2-(3,4-difluorophenyl)-3-(2-methanesulfinylpyrimidin-4-yl)-8-methoxyimidazo[1,2-α]pyrazine | G.1.33 | 2.02 (g) | 402.2 |
| 3-(2-Methylsulfanylpyrimidin-4-yl)-2-phenylimidazo[1,2-α]pyrazine (Example #F.1.30) | 3-(2-Methanesulfonylpyrimidin-4-yl)-2-phenylimidazo[1,2-α]pyrazine | G.1.34 | 1.31 (b) | 352.1 |

TABLE G.1-continued

Examples prepared from sulfides using General Procedure G

| Sulfide | Product | Example # | R$_t$ min (method) | m/z ESI+ (M + H)$^+$ |
|---|---|---|---|---|
| 3-(2-Methylsulfanylpyrimidin-4-yl)-2-naphthalen-2-yl-imidazo[1,2-α]pyrazine (Example #F.1.31) | 3-(2-Methanesulfonyl-pyrimidin4-yl)-2-naphthalen-2-ylimidazo[1,2-α]pyrazine | G.1.35 | 1.71 (b) | 402.1 |
| 3-(2-Methylsulfanylpyrimidin-4-yl)-2-(3-trifluoromethylphenyl)-imidazo[1,2-α]pyrazine (Example #F.1.32) | 3-(2-Methanesulfonylpyrimidin-4-yl)-2-(3-trifluoromethylphenyl)-imidazo[1,2-α]pyrazine | G.1.36 | 2.38 (g) | 420.08 |
| 2-(3-Chlorophenyl)-3-(2-methylsulfanylpyrimidin-4-yl)-imidazo[1,2-α]pyrazine (Example #F.1.33) | 2-(3-Chlorophenyl)-3-(2-methanesulfonylpyrimidin-4-yl)-imidazo[1,2-α]pyrazine | G.1.37 | 1.68 (b) | 386.1 |
| 6-Chloro-2-(4-fluorophenyl)-3-(2-methylsulfanylpyrimidin-4-yl)-imidazo[1,2-α]pyrazine (Example #F.1.34) | 6-Chloro-2-(4-fluorophenyl)-3-(2-methanesulfonylpyrimidin-4-yl)-imidazo[1,2-α]pyrazine | G.1.38 | 2.47 (g) | 404.13 |
| 6-Ethyl-2-(4-fluorophenyl)-3-(2-methylsulfanylpyrimidin-4-yl)-imidazo[1,2-α]pyrazine (Example #12) | 6-Ethyl-2-(4-fluorophenyl)-3-(2-methanesulfonylpyrimidin-4-yl)-imidazo[1,2-α]pyrazine | G.1.39 | 1.82 (b) | 398.2 |
| 2-(4-Fluorophenyl)-6-methoxy-3-(2-methylsulfanylpyrimidin-4-yl)-imidazo[1,2-α]pyrazine (Example #F.1.35) | 2-(4-Fluorophenyl)-3-(2-methanesulfonyl-pyrimidin-4-yl)-6-methoxy-imidazo[1,2-a]pyrazine | G.1.40 | 2.32 (g) | 400.23 |
| 2-(4-Fluorophenyl)-6-methoxy-3-(2-methylsulfanylpyrimidin-4-yl)-imidazo[1,2-α]pyrazine (Example #F.1.35) | 2-(4-Fluorophenyl)-3-(2-methanesulfinylpyrimidin-4-yl)-6-methoxy-imidazo[1,2-α]pyrazine | G.1.41 | 1.99 (g) | 384.3 |
| 2-(3-Chloro-4-fluorophenyl)-3-(2-methylsulfanylpyrimidin-4-yl)-imidazo[1,2-α]pyrazine (Example #F.1.36) | 2-(3-Chloro-4-fluorophenyl)-3-(2-methanesulfonylpyrimidin-4-yl)-imidazo[1,2-α]pyrazine | G.1.42 | 1.75 (b) | 404.2 |
| 2-(2,4-Difluorophenyl)-8-methyl-3-(2-methylsulfanylpyrimidin-4-yl)-imidazo[1,2-α]pyrazine (Example #F.1.37) | 2-(2,4-Difluorophenyl)-8-methyl-3-(2-methanesulfonyl-pyrimidin-4-yl)-imidazo[1,2-α]pyrazine | G.1.43 | 1.86 (b) | 402.2 |
| 2-(2,4-Difluorophenyl)-8-methoxy-3-(2-methylsulfanylpyrimidin-4-yl)-imidazo[1,2-α]pyrazine (Example #F.1.38) | 2-(2,4-Difluorophenyl)-3-(2-methanesulfonylpyrimidin-4-yl)-8-methoxyimidazo[1,2-a]pyrazine | G.1.44 | 2.28 (g) | 418.0 |

TABLE G.1-continued

Examples prepared from sulfides using General Procedure G

| Sulfide | Product | Example # | R, min (method) | m/z ESI+ (M + H)+ |
|---|---|---|---|---|
| 6-Chloro-2-(4-fluorophenyl)-8-methyl-3-(2-methylsulfanylpyrimidin-4-yl)-imidazo[1,2-a]pyrazine (Example #F.1.39) | 6-Chloro-2-(4-fluorophenyl)-3-(2-methanesulfonylpyrimidin-4-yl)-8-methylimidazo[1,2-a]pyrazine | G.1.45 | 3.42 (g) | 386.1 |
| 2-(4-Fluorophenyl)-6,8-dimethyl-3-(2-methylsulfanylpyrimidin-4-yl)-imidazo[1,2-a]pyrazine (Example #F.1.40) | 2-(4-Fluorophenyl)-3-(2-methanesulfonylpyrimidin-4-yl)-6,8-dimethylimidazo[1,2-a]pyrazine | G.1.46 | 2.26 (g) | 398.1 |
| 2-(2,4-Difluorophenyl)-6,8-dimethyl-3-(2-methylsulfanylpyrimidin-4-yl)-imidazo[1,2-a]pyrazine (Example #F.1.41) | 2-(2,4-Difluorophenyl)-3-(2-methanesulfonylpyrimidin-4-yl)-6,8-dimethylimidazo[1,2-a]pyrazine | G.1.47 | 2.26 (g) | 416.1 |
| 8-Methyl-3-(2-methylsulfanylpyrimidin-4-yl)-2-(3-trifluoromethoxy-phenyl)-imidazo[1,2-a]pyrazine (Example # F.1.43) | 3-(2-Methanesulfonylpyrimidin-4-yl)-8-methyl-2-(3-trifluoromethoxyphenyl)-imidazo[1,2-a]pyrazine | G.1.48 | 2.0 (b) | 450.1 |
| 8-Methyl-3-(2-methylsulfanylpyrimidin-4-yl)-2-(3-trifluoromethoxyphenyl)-imidazo[1,2-a]pyrazine (Example # F.1.43) | 3-(2-Methanesulfinylpyrimidin-4-yl)-8-methyl-2-(3-trifluoromethoxy-phenyl)-imidazo[1,2-a]pyrazine | G.1.49 | 1.9 (b) | 434.1 |
| 2-(4-Fluorophenyl)-8-methyl-3-(2-methylsulfanylpyrimidin-4-yl)imidazo[1,2-a]pyrazine (Example #F.1A) | 2-(4-Fluorophenyl)-3-(2-methanesulfinylpyrimidin-4-yl)-8-methylimidazo[1,2-a]pyrazine | G.1.50 | 1.6 (b) | 368.2 |
| 2-(2,4-Difluorophenyl)-8-isopropoxy-3-(2-methylsufanylpyrimidin-4-yl)imidazo[1,2-a]pyrazine (Example #F.1.42) | 2-(2,4-Difluorophenyl)-8-isopropoxy-3-(2-methanesulfonylpyrimidin-4-yl)imidazo[1,2-a]pyrazine | G.1.51 | 2.0 (b) | 446.1 |
| 2-(2,4-Difluorophenyl)-8-isopropoxy-3-(2-methylsulfanylpyrimidin-4-yl)imidazo[1,2-a]pyrazine (Example #F.1.42) | 2-(2,4-Difluorophenyl)-8-isopropoxy-3-(2-methanesulfinylpyrimidin-4-yl)-imidazo[1,2-a]pyrazine | G.1.52 | 1.8 (b) | 430.2 |
| 2-(3-Chlorophenyl)-8-methyl-3-(2-methylsulfanylpyrimidin-4-yl) imidazo[1,2-α]pyrazine (Example # F.1.17) | 2-(3-Chlorophenyl)-3-(2-methanesulfonyl-pyrimidin-4-yl)-8-methyl imidazo[1,2-a]pyrazine | G.1.53 | 1.90 (a) | 400.2 |
| Cyclopropyl-[2-(4-fluorophenyl)-3-(2-methylsulfanylpyrimidin-4-yl)-imidazo[1,2-a]pyrazin-8-yl]amine (Example # F.1.44) | Cyclopropyl-[2-(4-fluorophenyl)-3-(2-methanesulfonyl-pyrimidin-4-yl)-imidazo[1,2-a]pyrazin-8-yl]amine | G.1.54 | 2.04 (a) | 425.2 |

TABLE G.1-continued

Examples prepared from sulfides using General Procedure G

| Sulfide | Product | Example # | R, min (method) | m/z ESI+ (M + H)+ |
|---|---|---|---|---|
| {2-[2-(4-Fluorophenyl)-3-(2-methylsulfanylpyrimidin-4-yl)-imidazo[1,2-a]pyrazin-8-yl]-ethyl}-carbamic acid tert-butyl ester (F.1.45) | {2-[2-(4-Fluorophenyl)-3-(2-methanesulfonylpyrimidin-4-yl)-imidazo[1,2-a]pyrazin-8-yl]-ethyl}-carbamic acid tert-butyl ester | G.1.55 | 2.52 (g) | 513.9 |
| 2-(3-Chlorophenyl)-8-methoxy-3-(2-methylsulfanylpyrimidin-4-yl)imidazo[1,2-a]pyrazine (Example #F.1.29) | 2-(3-Chlorophenyl)-3-(2-methanesulfonylpyrimidin-4-yl)-8-methoxyimidazo[1,2-a]pyrazine | G.1.56 | 2.45 (g) | 416.1 |
| 2-(2,4-Difluorophenyl)-8-isopropyl-3-(2-methylsulfanylpyrimidin-4-yl)imidazo[1,2-a]pyrazine (Example #F.1.46) | 2-(2,4-Difluorophenyl)-8-isopropyl-3-(2-methanesulfonylpyrimidin-4-yl)imidazo[1,2-a]pyrazine | G.1.57 | 2.73 (g) | 430.2 |
| 2-(4-Fluorophenyl)-8-isobutyl-3-(2-methylsulfanylpyrimidin-4-yl)imidazo[1,2-a]pyrazine (Example #F.1.48) | 2-(4-Fluorophenyl)-8-isobutyl-3-(2-methanesulfonylpyrimidin-4-yl)imidazo[1,2-a]pyrazine | G.1.58 | 2.85 (g) | 426.2 |
| 8-Cyclopropylmethyl-2-(2,4-difluorophenyl)-3-(2-methylsulfanyl-pyrimidin-4-yl)imidazo[1,2-a]pyrazine (Example #F.1.47) | 8-Cyclopropylmethyl-2-(2,4-difluorophenyl)-3-(2-methanesulfonylpyrimidin-4-yl)imidazo[1,2-a]pyrazine | G.1.59 | 2.67 (g) | 442.2 |

General Procedure H: Acidic Cleavage of a Boc-Protected Amine

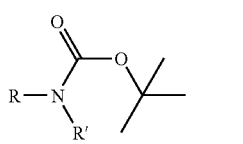

To a solution of a Boc-protected amine in a suitable solvent such as DCM or MeOH at about 0-25° C. is added a suitable acid such as TFA or 1.25M HCl in MeOH (5-100 equiv). After about 1-16 h, the mixture is concentrated under reduced pressure, diluted with water, neutralized with an aqueous base such as 1N NaOH and a suitable organic solvent such as EtOAc or DCM is added before or after neutralization. The layers are separated and the aqueous layer is washed with a suitable solvent (for example, EtOAc, DCM or both sequentially). The combined organic layers may be optionally washed with brine, dried over $Na_2SO_4$ or $MgSO_4$, then decanted or filtered, prior to concentrating under reduced pressure. The crude material is characterized as is or is purified by chromatography, trituration with an appropriate solvent, or crystallization from one or more solvents to yield the target compound.

Illustration of General Procedure H

Example #H.1

4-[2-(4-Fluorophenyl)-imidazo[1,2-a]pyrazin-3-yl]-pyrimidin-2-ylpiperidin-4-ylamine

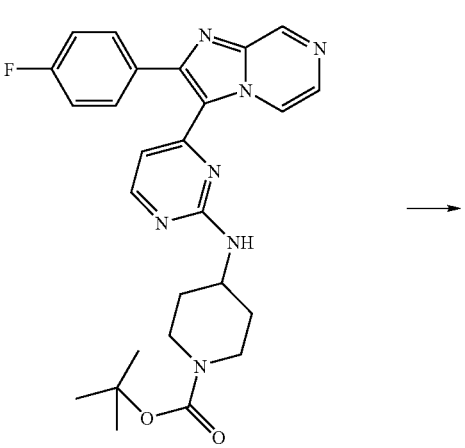

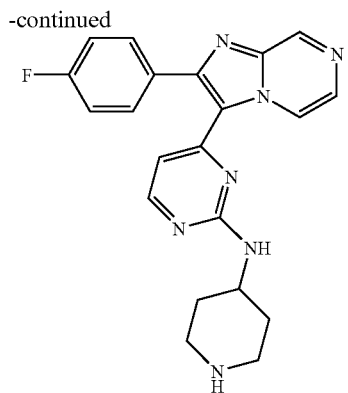

To a solution of 44-[2-(4-fluorophenyl)-imidazo[1,2-a]pyrazin-3-yl]-pyrimidin-2-ylaminopiperidine-1-carboxylic acid tert-butyl ester (Example #A.1, 0.148 g, 0.302 mmol) in DCM (5.0 mL) at about 0° C. was added TFA (0.75 mL). After about 3 h, the mixture was concentrated under reduced pressure and diluted with EtOAc, 1N NaOH, and water. The layers were separated and the aqueous layer was washed with EtOAc and DCM. The combined organic layers were dried over $MgSO_4$, filtered, and concentrated under reduced pressure to yield the title compound (0.070 g, 59%): LC/MS (Table 1, Method b) $R_t$=1.4 min; MS m/z: 390.5 $(M+H)^+$.

TABLE H.1

Examples from Boc-protected amines using General Procedure H

| Protected material | Product | Example # | $R_t$ min (method) | m/z ESI+ $(M + H)^+$ |
|---|---|---|---|---|
| 4-{4-[2-(4-Fluorophenyl)-8-methylimidazo[1,2-α]pyrazin-3-yl]-pyrimidin-2-ylamino}-piperidine-1-carboxylic acid tert-butyl ester using TFA (Example #A.9.2) | {4-[2-(4-Fluorophenyl)-8-methylimidazo[1,2-α]pyrazin-3-yl]-pyrimidin-2-yl}-piperidin-4-ylamine | H.1.1 | 1.4 (b) | 404.3 |
| (3-{4-[2-(4-Fluorophenyl)-8-methoxyimidazo[1,2-α]pyrazin-3-yl]-pyrimidin-2-ylamino}-2,2-dimethylpropyl)-carbamic acid tert-butyl ester using TFA (Example #A.10.2) | N'1'-{4-[2-(4-Fluorophenyl)-8-methoxyimidazo[1,2-α]pyrazine-3-yl]-pyrimidin-2-yl}-2,2-dimethylpropane-1,3-diamine | H.1.2 | 1.6 (b) | 422.4 |
| 4-[4-(2-Naphthalen-2-ylimidazo[1,2-α]pyrazin-3-yl)-pyrimidin-2-ylamino]-piperidine-1-carboxylic acid tert-butyl ester using HCl in methanol (Example #A.3.2) | [4-(2-Naphthalen-2-ylimidazo[1,2-α]pyrazin-3-yl)-pyrimidin-2-yl]-piperidin-4-ylamine | H.1.3 | 1.61 (f) | 422.3 |
| 4-[4-(2-Phenylimidazo[1,2-α]pyrazin-3-yl)-pyrimidin-2-ylamino]-piperidine-1-carboxylic acid tert-butyl ester using HCl in methanol (Example #A.2.2) | [4-(2-Phenylimidazo[1,2-α]pyrazin-3-yl)-pyrimidin-2-yl]-piperidin-4-ylamine | H.1.4 | 1.39 (f) | 372.2 |

TABLE H.1-continued

Examples from Boc-protected amines using General Procedure H

| Protected material | Product | Example # | $R_t$ min (method) | m/z ESI+ $(M + H)^+$ |
|---|---|---|---|---|
| (3-{4-[2-(4-Fluorophenyl)-imidazo[1,2-α]pyrazin-3-yl]-pyrimidin-2-ylamino}-2,2-dimethylpropyl)-carbamic acid tert-butyl ester using HCl in methanol (Example #A.40) | N'1'-{4-[2-(4-Fluorophenyl)-imidazo[1,2-α]pyrazin-3-yl]-pyrimidin-2-yl}-2,2-dimethylpropane-1,3-diamine | H.1.5 | 1.66 (g) | 392.3 |
| 3-{4-[2-(4-Fluorophenyl)-imidazo[1,2-α]pyrazin-3-yl]-pyrimidin-2-ylamino}-pyrrolidine-1-carboxylic acid tert-butyl ester using HCl in methanol (Example # A.37) | {4-[2-(4-Fluorophenyl)-imidazo[1,2-α]pyrazin-3-yl]-pyrimidin-2-yl}-pyrrolidin-3-ylamine | H.1.6 | 1.63 (g) | 376.3 |
| 4-{4-[2-(4-Fluorophenyl)-8-methylimidazo[1,2-a]pyrazin-3-yl]-pyrimidin-2-ylamino}-azepane-1-carboxylic acid tert-butyl ester using TFA (Example #A.9.13) | {4-[2-(4-Fluorophenyl)-8-methylimidazo[1,2-a]pyrazin-3-yl]-pyrimidin-2-yl}-perhydroazepin-4-ylamine | H.1.7 | 1.4 (b) | 418.3 |
| (2-{2-(4-Fluorophenyl)-3-[2-(3-hydroxy-2,2-dimethyl-propylamino)-pyrimidin-4-yl]-imidazo[1,2-a]pyrazin-8-yl}-ethyl)-carbamic acid tert-butyl ester using HCl in methanol (Example #A.47.1) | 3-{4-[8-(2-Aminoethyl)-2-(4-fluorophenyl)imidazo[1,2-a]pyrazin-3-yl]pyrimidin-2-ylamino}-2,2-dimethylpropan-1-ol hydrochloride | H.1.8 | 1.73 (g) | 436.27 |

General Procedure I: Formation of a Sulfonamide from an Amine

A sulfonyl chloride is added to a mixture of an amine and a suitable base (for example, DIEA) in a suitable solvent, such as DCM, at ambient temperature. After about 1-10 days, the mixture is treated with a basic solution, such as saturated aqueous $NaHCO_3$, and the layers are separated. The combined organic layers may be optionally washed with brine, dried over $Na_2SO_4$ or $MgSO_4$, then decanted or filtered, prior to concentrating under reduced pressure. The crude material is characterized as is or is purified by chromatography, trituration with an appropriate solvent, or crystallization from one or more solvents to yield the target compound.

Illustration of General Procedure I

Example #I.1

4-[2-(4-Fluorophenyl)-imidazo[1,2-a]pyrazin-3-yl]-pyrimidin-2-yl-(1-methanesulfonylpiperidin-4-yl)-amine

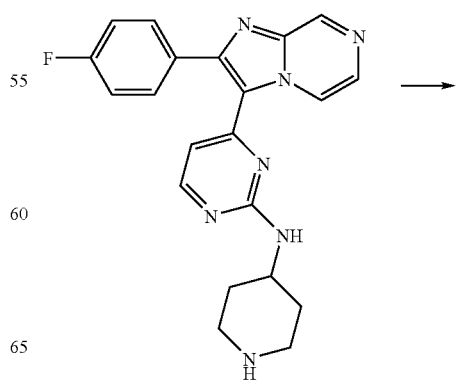

-continued

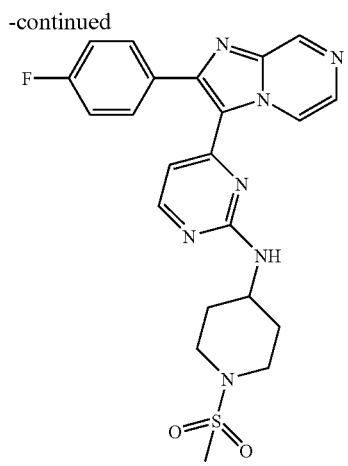

To a mixture of 4-[2-(4-fluorophenyl)-imidazo[1,2-a]pyrazin-3-yl]-pyrimidin-2-ylpiperidin-4-ylamine (Example # H.1; 0.200 g, 0.514 mmol) and DIEA (0.18 mL, 1.0 mmol) in DCM (3 mL) at ambient temperature was added methanesulfonyl chloride (0.062 g, 0.539 mmol). After about six days, the mixture was treated with saturated aqueous NaHCO$_3$ and the layers were separated. The combined organic layers were dried over MgSO$_4$ and concentrated under reduced pressure. The crude material was triturated with EtOAc and filtered to yield the title compound after drying (0.090 g, 37%): LC/MS (Table 1, Method b) R$_t$=1.7 min; MS m/z: 468.6 (M+H)$^+$.

TABLE I.1

Examples from phenysulfonyl chloride using General Procedure I

| Amine | Product | Example # | R$_t$ min (method) | m/z ESI+ (M + H)$^+$ |
|---|---|---|---|---|
| 4-[2-(4-Fluorophenyl)-imidazo[1,2-α]pyrazin-3-yl]-pyrimidin-2-ylamine (Example #D.1) | N-{4-[2-(4-Fluorophenyl)-imidazo[1,2-α]pyrazin-3-yl]-pyrimidin-2-yl}-benzenesulfonamide | I.1.1 | 1.8 (b) | 447.6 |

General Procedure J: Formation of Hydroxyl Acetyl Group from an Amine

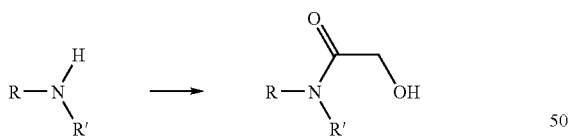

A solution of an amine in a suitable solvent, such as THF, is cooled to about 0° C. and then a suitable base, such as TEA, is added followed by addition of acetic acid chlorocarbonyl methyl ester (1-2 equiv, preferably 1.1 equiv). After about 2-36 h, the mixture is allowed to warm to ambient temperature and filtered, washing with a suitable solvent, such as MeOH. The filtrate is treated with suitable base (0.9-2.0 equiv) to hydrolyze the ester, such as aqueous sodium hydroxide, at ambient temperature. Additional base is added if the reaction is not consuming all of the intermediate ester (as monitored by LC/MS, HPLC or TLC). After about 2-36 h, the mixture is acidified to about pH 5 using a suitable acid, such as aqueous 1 N HCl. The mixture is treated with suitable organic solvent, such as DCM, and water, and the layers are separated. The aqueous layer is washed with appropriate solvent, such as DCM. The combined organic layers may be optionally washed with brine, dried over Na$_2$SO$_4$ or MgSO$_4$, then decanted or filtered, prior to concentrating under reduced pressure. The crude material is characterized as is or is purified by chromatography, trituration with an appropriate solvent, or crystallization from one or more solvents to yield the target compound.

Illustration of General Procedure J

Example #J.1

1-(4-{4-[2-(4-Fluorophenyl)-8-methylimidazo[1,2-a]pyrazin-3-yl]-pyrimidin-2-ylamino}-piperidin-1-yl)-2-hydroxyethanone

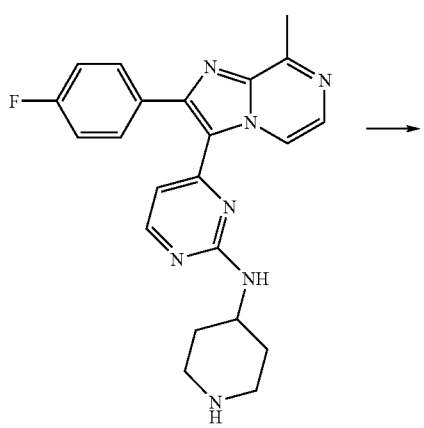

-continued

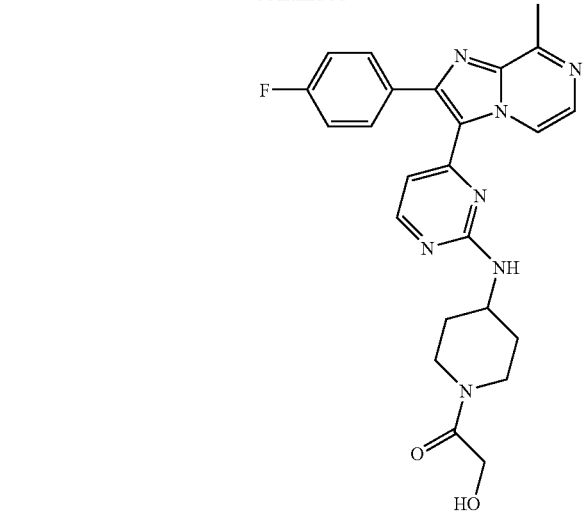

A solution of 4-[2-(4-Fluorophenyl)-8-methylimidazo[1,2-a]pyrazin-3-yl]-pyrimidin-2-ylpiperidin-4-ylamine (Example #H.1.1; 0.2 g, 0.5 mmol) in THF (1.1 mL, 1.4 mmol) was cooled to about 0° C. Then TEA (0.13 mL, 0.94 mmol) was added followed by acetic acid chlorocarbonylmethyl ester (0.077 g, 0.56 mmol). After about 16 h, the mixture was allowed to warm to ambient temperature and filtered, washing with MeOH. The filtrate was treated with 2.50 M aqueous sodium hydroxide (0.20 mL) at ambient temperature. After about 16 h, the mixture was treated with additional 2.50 M aqueous sodium hydroxide (0.16 mL). After about 6 h, the mixture was acidified to pH 5 using 1 N HCl. The mixture was treated with DCM and water, and the layers were separated. The aqueous layer was washed with DCM (3×20 mL). The combined organic layers were dried over MgSO$_4$ and concentrated. The crude material was taken up in DCM/MeOH and purified via FCC using DCM/2.5% NH$_4$OH in MeOH (95:5) to yield the title compound as a white solid after drying (0.115 g, 50%): LC/MS (Table 1, Method b) R$_t$=1.6 min; MS m/z: 462.3 (M+H)$^+$.

TABLE J.1

Examples from amines using General Procedure J

| Amine | Product | Example # | R$_t$ min (method) | m/z ESI- (M − H)$^-$ |
|---|---|---|---|---|
| [4-(2-Naphthalen-2-ylimidazo[1,2-α]pyrazin-3-yl)-pyrimidin-2-yl]-piperidin-4-ylamine (Example #H.1.3) | 2-Hydroxy-1-{4-[4-(2-naphthalen-2-ylimidazo[1,2-α]pyrazin-3-yl)-pyrimidin-2-ylamino]-piperidin-1-yl}-ethanone | J.1.1 | 1.8 (b) | 478.3 |

General Procedure K: Conversion of an Aryl or Heteroaryl Chloride to an Aryl or Heteroaryl Alkyl Derivative

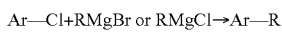

Ar—Cl+RMgBr or RMgCl→Ar—R

An alkyl Grignard reagent (for example, MeMgBr or isopropylmagnesium chloride) (1-5 equiv) in an appropriate solvent, such as Et$_2$O or THF, was added drop-wise to a mixture of a substituted aryl chloride (1 equiv), ferric acetylacetonate (0.03-0.10 equiv, preferably 0.05 equiv), in a suitable solvent (for example, THF and NMP [10:1]) at about −10 to 0° C. The mixture is warmed to ambient temperature over about 1 hour. Additional alkyl Grignard reagent (1-5 equiv) is added after cooling to about 0° C. if the reaction is not consuming all of the starting aryl chloride (as monitored by LC/MS, HPLC or TLC) and the mixture is again allowed to warm to ambient temperature over about 1 h. After about 0.5-24 h at ambient temperature, the mixture is quenched with water and extracted with EtOAc. The layers are separated and the aqueous layer is washed with additional organic solvent. The combined organic layers may be optionally washed with brine, dried over Na$_2$SO$_4$ or MgSO$_4$, then decanted or filtered, prior to concentrating under reduced pressure. The crude material is used as is or is purified by chromatography, trituration with an appropriate solvent, or crystallization from one or more solvents to yield the target compound.

Illustration of General Procedure K

Preparation #K.1:
2-(4-Fluorophenyl)-8-methylimidazo[1,2-a]pyrazine

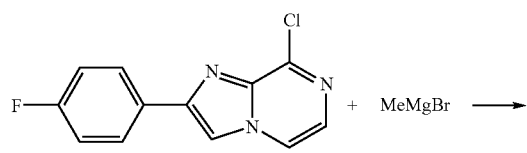

+ MeMgBr →

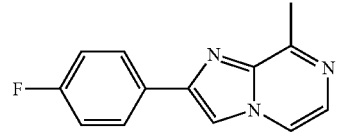

A solution of 3M MeMgBr in Et$_2$O (16.1 mL, 48.3 mmol) was added drop-wise to a mixture of 8-chloro-2-(4-fluorophenyl)-imidazo[1,2-a]pyrazine (prepared using general procedure B using 3-chloropyrazin-2-ylamine and 2-bromo-1-(4-fluorophenyl)-ethanone; 10.0 g, 40.6 mmol), ferric acetylacetonate (0.71 g, 2.0 mmol), THF (240 mL), and NMP (23 mL) at about 0° C. The mixture was warmed to ambient temperature over about 1 hour. After about 1 hour, the reaction was cooled to about 0° C. and treated with additional 3 M MeMgBr in Et$_2$O (4 mL, 12 mmol). The mixture was allowed to warm to ambient temperature over about 1 h. After about an additional 1 h, the mixture was quenched with water and extracted with EtOAc. The organic layers were combined and dried with Na$_2$SO$_4$. After concentration, the crude material was purified by FCC on silica gel using EtOAc as an eluent to afford the expected product as an off-white solid (9.6 g, 100%): LC/MS (Table 1, Method b) R$_t$=1.8 min; MS m/z: 228.2 (M+H)$^+$.

General Procedure L: Displacement of an Aryl or Heteroaryl Chloride with an Alkoxide

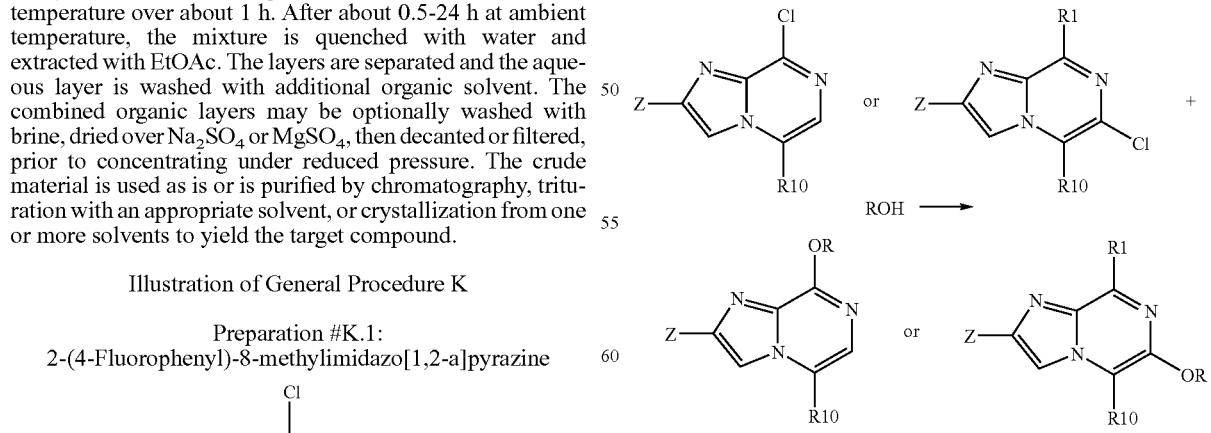

A solution of a sodium alkoxide (2-20 equiv) in alcohol is prepared by adding a commercially available sodium alkoxide to the corresponding alcohol or by slowly adding sodium metal to an alcohol at about 0-25° C. and optionally heating at about reflux until the sodium is consumed. To the resulting solution of sodium alkoxide in alcohol at ambient temperature is added an appropriately substituted aryl chloride (1 equiv). The mixture is heated at about 50-80° C. for about 1-6 h then cooled to ambient temperature. The reaction mixture may be filtered to isolate crude material, which is either used as is in a next step or is purified by chromatography, trituration with an appropriate solvent, or crystallization from one or more solvents to yield the target compound. Alternatively the reaction mixture is partitioned between water and an appropriate organic solvent (e.g. EtOAc). The layers are separated and the organic layer is optionally washed with brine, dried over $Na_2SO_4$ or $MgSO_4$, then decanted or filtered, prior to concentrating under reduced pressure. The crude material is purified by chromatography, trituration with an appropriate solvent, or crystallization from one or more solvents to yield the target compound.

Illustration of General Procedure L

Preparation #L.1:
2-(4-Fluorophenyl)-8-methoxyimidazo[1,2-a]pyrazine

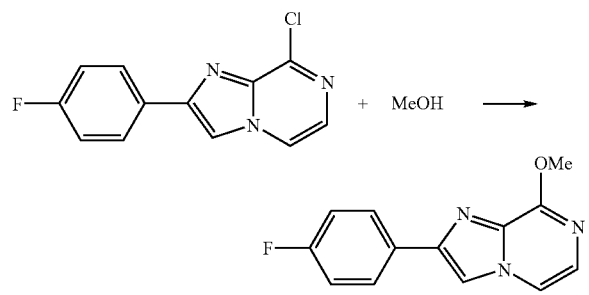

A mixture of MeOH (18 mL) and sodium (1.1 g, 48 mmol) was stirred at ambient temperature until the sodium was consumed then 8-chloro-2-(4-fluorophenyl)-imidazo[1,2-a]pyrazine (prepared from general procedure B using 3-chloropyrazin-2-ylamine and 2-bromo-1-(4-fluorophenyl)-ethanone; 1.0 g, 4 mmol) was added. The mixture was heated at about 50° C. for about 1 h. The mixture was cooled to ambient temperature and filtered. The beige solid isolated was carried on crude. (0.98 g, 100%): LC/MS (Table 1, Method b) $R_t$=1.8 min; MS m/z: 244.1 (M+H)$^+$.

General Procedure M: Bromination of a Substituted Acetophenone

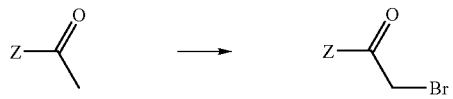

To a stirred solution of an acetophenone (1 equiv) in a suitable solvent (e.g. DCM) at about 20-25° C. is added drop-wise a solution of bromine (1 equiv) in a suitable solvent (e.g. DCM) over about 10-30 min. After the addition is complete, the solution is stirred at ambient temperature for about 15 min. Ice-cold water is added to the reaction solution and stirred for about 5-10 min. The organic layer is separated and washed with ice-cold water. The organic layer is dried over $MgSO_4$, filtered, and concentrated under reduced pressure. The oil residue is stirred in an appropriate solvent (e.g. petroleum ether [bp 30-60° C.]) at about 35-45° C. for about 5-10 min. A magnetic stirrer bar is added to the mixture, the reaction is stirred rapidly, and the internal temperature is reduced to about −10 to −5° C. for about 5-10 min. The resulting solid is washed with an appropriate solvent (e.g. petroleum ether [bp 30-60° C.]) at ca. 0-5° C. The crude material is used as is, purified by chromatography, trituration with an appropriate solvent, or crystallization from one or more solvents to yield the target compound.

Illustration of General Procedure M

Preparation #M.1:
2-Bromo-1-(3-chlorophenyl)-ethanone

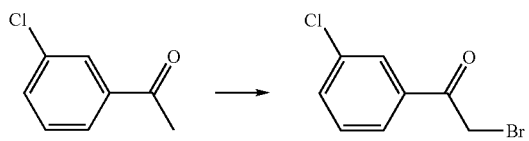

To a stirred solution of 3-chloroacetophenone (18.2 g, 0.118 mol) in DCM (150 mL, 2.3 mol), at about 20-25° C. was added drop-wise a solution of bromine (6.00 mL, 0.116 mol) in DCM (20 mL) over about 15 min. After the addition was complete the pale yellow solution was stirred at ambient temperature for about 15 min. Ice-cold water (100 mL) was added to the reaction solution and stirred for about 5 min. The organic layer was separated and washed with ice-cold water (2×150 mL). The organic layer was dried over $MgSO_4$, filtered, and the solvent removed in vacuo to yield a pale yellow oil (31.01 g). The oil residue was stirred with petroleum ether [bp 30-60° C.] (50 mL) at about 40° C. for about 5 min and almost all the oil had dissolved. A magnetic stirrer bar was added to the mixture and rapidly stirred whilst the internal temperature was reduced to about −10 to −5° C. Held at about −5° C. for about 5 min before the off-white solid was collected. The crystalline solid was washed with ice-cold petroleum ether [bp 30-60° C.] (2×40 mL) and dried under reduced pressure to yield an off-white powdery solid (23.8 g, 82.2%): $^1$H NMR (400 MHz, CDCl$_3$) δ 7.96 (1H), δ 7.86 (1H), δ 7.59 (1H), δ 7.45 (1H), δ 4.42 (2H); TLC (EtOAc/heptane 1:1) $R_f$ 0.59.

General Procedure N: Deprotection of a Methyl-Protected Alcohol Using Acid

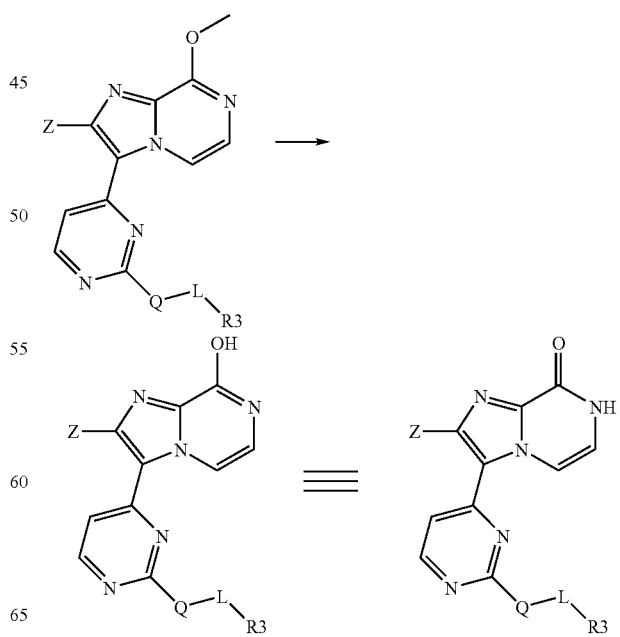

Substituted 8-methoxy imidazopyrazine (1 equiv) is treated with acid (for example 4M hydrogen bromide in acetic acid or 6 M HCl in water) (30-50 equiv) at about 22-50° C. for about 14 h. If the product precipitates during the reaction or upon cooling it is directly filtered and characterized or if necessary, is purified further as indicated below. Alternatively, the mixture is optionally concentrated under reduced pressure, neutralized with base (such as a saturated solution of NaHCO$_3$), and is diluted with or partitioned between water and an organic solvent (for example DCM/MeOH, preferably 95:5). The layers are separated and the aqueous layer is extracted with additional organic solvent (such as DCM/MeOH, preferably 95:5). The combined organic layers may be optionally washed with brine, dried over Na$_2$SO$_4$ or MgSO$_4$, then decanted or filtered, prior to concentrating under reduced pressure. The crude material is purified by trituration or crystallization using a suitable solvent (such as MeOH or Et$_2$O) to yield the target compound.

Illustration of General Procedure N

Example #N.1

3-(2-Cyclopropylaminopyrimidin-4-yl)-2-(4-fluorophenyl)-7H-imidazo[1,2-a]pyrazin-8-one

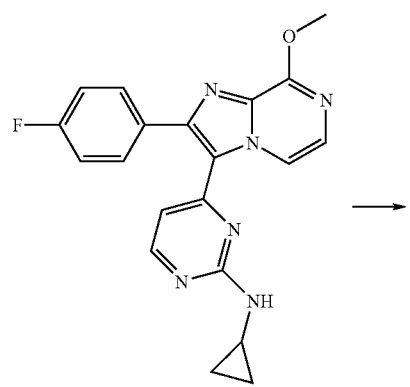

→

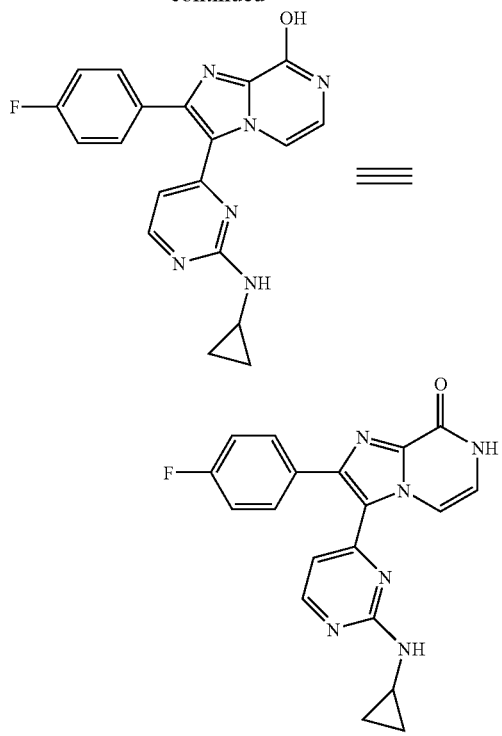

Cyclopropyl-{4-[2-(4-fluorophenyl)-8-methoxyimidazo[1,2-a]pyrazin-3-yl]-pyrimidin-2-yl}-amine (Example #A.10.1, 0.156 g, 0.414 mmol) was treated with a 4 M solution of hydrogen bromide in acetic acid (3 mL, 12 mmol) at ambient temperature. After about 45 min the mixture was treated with Et$_2$O and filtered, washing the solid successively with Et$_2$O, saturated aqueous NaHCO$_3$ and Et$_2$O. The solid was then dried in the oven for about 16 h to yield the product as white solid (0.115 g, 77%): LC/MS (Table 1, Method b) R$_t$=1.7 min; MS m/z: 361.4 (M–H)⁻.

TABLE N.1

Example prepared from 3-{4-[2-(4-fluorophenyl)-8-methoxyimidazo[1,2-a]pyrazin-3-yl]-pyrimidin-2-ylamino}-2,2-dimethyl-propan-1-ol (Example # A.10.3) using General Procedure N

| Acid | Product | Example # | R$_t$ min (method) | m/z ESI+ (M + H)⁺ |
|---|---|---|---|---|
| 4M Hydrogen bromide in acetic acid | Acetic acid 3-4-[2-(4-fluorophenyl)-8-oxo-7,8-dihydroimidazo[1,2-a]pyrazin-3-yl]-pyrimidin-2-ylamino-2,2-dimethylpropyl ester | N.1.1 | 2.28 (g) | 451.2 |
| 6M aqueous HCl [VWR] | 2-(4-Fluorophenyl)-3-[2-(3-hydroxy-2,2-dimethyl-propylamino)-pyrimidin-4-yl]-7H-imidazo[1,2-a]pyrazin-8-one | N.1.2 | 1.65 (b) | 409.2 |

General Procedure O: Displacement of an Aryl or Heteroaryl Chloride with an Amine

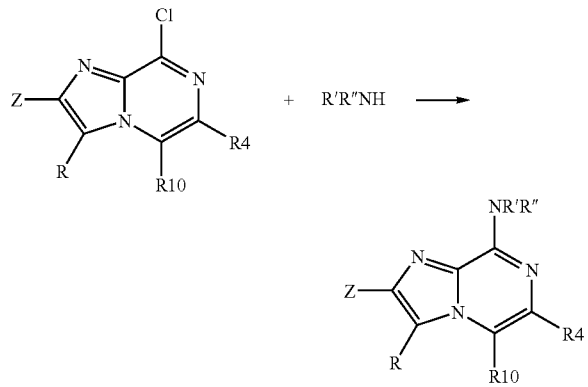

In a sealed tube vessel, an appropriately substituted aryl chloride (1 equiv) and an amine (1-170 equivalents) with or without an appropriate solvent or mixture of solvents (for example EtOH, ACN, tetrahydrofuran, 1,4-dioxane and/or water, preferably EtOH or 1,4 dioxane) is heated at about 60-120° C. for about 1-24 h then cooled to ambient temperature. The reaction mixture may be filtered to isolate crude material, which is either used as is in a next step or is purified by chromatography, trituration with an appropriate solvent, or crystallization from one or more solvents to yield the target compound. Alternatively the reaction mixture is partitioned between water and an appropriate organic solvent (e.g. EtOAc). The layers are separated and the organic layer is optionally washed with brine, dried over $Na_2SO_4$ or $MgSO_4$, then decanted or filtered, prior to concentrating under reduced pressure. The crude material is purified by chromatography, trituration with an appropriate solvent, or crystallization from one or more solvents to yield the target compound.

Illustration of General Procedure O

Preparation #O.1: [2-(4-Fluorophenyl)-imidazo[1,2-a]pyrazin-8-yl]methylamine

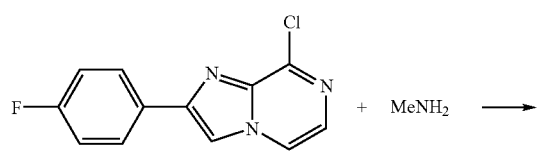

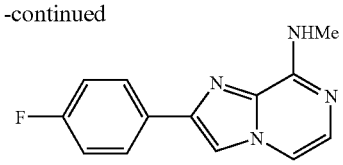

In a sealed tube vessel was added 8M methylamine in EtOH (10 mL, 80 mmol) and 8-chloro-2-(4-fluorophenyl)-imidazo[1,2-a]pyrazine (prepared from general procedure B using 3-chloropyrazin-2-ylamine and 2-bromo-1-(4-fluorophenyl)-ethanone; 2.30 g, 9.3 mmol). The mixture was heated at about 100° C. for about 1 h. The mixture was cooled to ambient temperature and the reaction mixture was partitioned between water and dichloromethane. The layers were separated. The organic layer was washed with brine, dried over $Na_2SO_4$, and filtered prior to concentrating under reduced pressure. The product was purified by silica gel chromatography using EtOAc/heptane (1:1) to give the title compound as a beige solid (2.05 g, 91%): LC/MS (Table 1, Method a) $R_t$=1.70 min; MS m/z: 243.3 (M+H)$^+$.

TABLE O.1

Example prepared from an aryl chloride using General Procedure O

| Aryl chloride | Product | Example # | $R_t$ min (method) | m/z ESI+ (M + H)$^+$ |
|---|---|---|---|---|
| 8-Chloro-2-(4-fluorophenyl)-3-(2-methylsulfanylpyrimidin-4-yl)imidazo[1,2-α]pyrazine (Example # 7) | 2-(4-Fluorophenyl)-3-(2-methylsulfanylpyrimidin-4-yl)imidazo[1,2-α]pyrazin-8-ylamine | O.1.1 | 2.54 (b) | 353.2 |

Example #B.1

2-(4-Fluorophenyl)-3-pyridin-4-ylimidazo[1,2-a]pyrazine

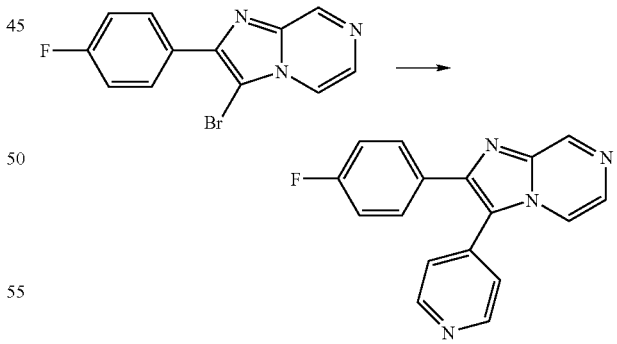

To a 25 mL round bottom flask charged with 3-bromo-2-(4-fluorophenyl)-imidazo[1,2-a]pyrazine (Preparation #5, 0.090 g, 0.31 mmol), 4-pyridineboronic acid (0.045 g, 0.37 mmol), Pd(PPh$_3$)$_4$ (0.018 g, 0.015 mmol) and Cs$_2$CO$_3$ (0.250 g, 0.77 mmol) was added DME (10 mL) followed by water (1 mL). The reaction was allowed to stir at ambient temperature for about 3 minutes followed by submersion into an oil bath which was at about 90° C. After about 16 h, the reaction was concentrated in-vacuo and then purified by RP-HPLC (Table 1, Method d). The pure fractions were combined, concentrated, and lyophilized for about 12 h to give the title compound as a white solid (0.025 g, 23%): LC/MS (Table 1, Method b) $R_t$=1.54 min; MS m/z: 291.2 (M+H)$^+$.

Example #C.1

2-(4-Fluorophenyl)-3-(2-methoxypyrimidin-4-yl)-imidazo[1,2-a]pyrazine

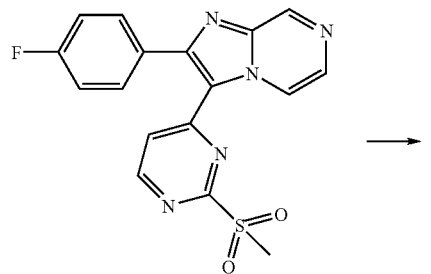

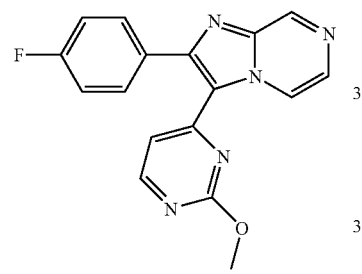

A mixture of 2-(4-fluorophenyl)-3-[2-(methanesulfonylpyrimidin-4-yl]imidazo[1,2-a]pyrazine (Preparation # 4, 0.020 g, 0.054 mmol) and 7 M ammonia in MeOH (0.20 mL) was stirred at ambient temperature for about 15 h. The mixture was diluted with DMF and purified by RP-HPLC (Table 1, Method c) to yield the title compound (0.005 g, 30%): LC/MS (Table 1, Method b) $R_t$=1.8 min; MS m/z: 322.4 (M+H)$^+$.

Example #D.1

4-[2-(4-Fluorophenyl)-imidazo[1,2-a]pyrazin-3-yl]-pyrimidin-2-ylamine

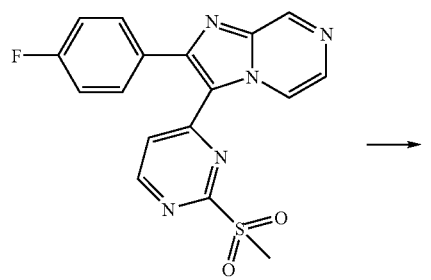

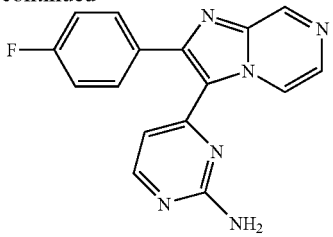

A mixture of 2-(4-fluorophenyl)-3-[2-(methanesulfonylpyrimidin-4-yl]imidazo[1,2-a]pyrazine (Preparation # 4, 0.050 g, 0.14 mmol) and 0.5 M ammonia in dioxane (2.0 mL) was stirred at about 80° C. for about 16 h. The mixture was diluted with DCM and water. Layers were separated and the aqueous layer was washed with DCM. The combined organic layers were dried over MgSO$_4$, filtered, and concentrated under reduced pressure. The resulting white solid was purified by RP-HPLC (Table 1, method c) to yield the title compound (0.005 g, 10%): LC/MS (Table 1, Method b) $R_t$=1.6 min; MS m/z: 307.5 (M+H)$^+$.

Example #E.1

4-[2-(4-Fluorophenyl)-imidazo[1,2-a]pyrazin-3-yl]-pyrimidin-2-ylpiperidin-4-ylamine

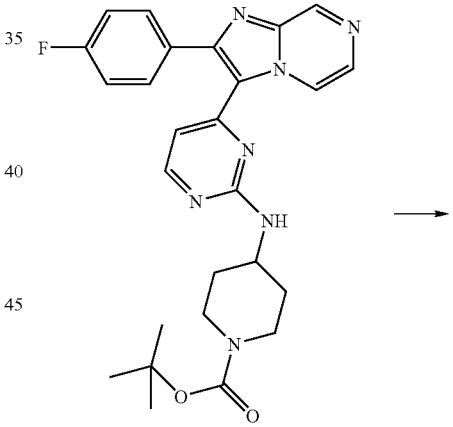

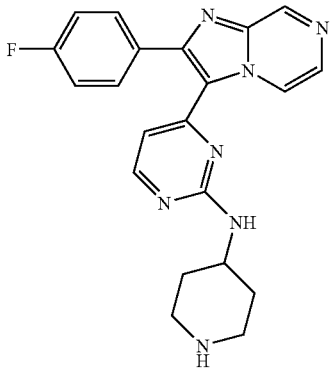

To a solution of 44-[2-(4-fluorophenyl)-imidazo[1,2-a]pyrazin-3-yl]-pyrimidin-2-ylaminopiperidine-1-carboxylic acid tert-butyl ester (Example #A.1, 0.148 g, 0.302 mmol) in DCM (5.0 mL) at about 0° C. was added TFA (0.75 mL). After about 3 h, the mixture was concentrated under reduced pressure and diluted with EtOAc, 1N NaOH, and water. The layers were separated and the aqueous layer was washed with EtOAc and DCM. The combined organic layers were dried over MgSO$_4$, filtered, and concentrated under reduced pressure to yield the title compound (0.070 g, 59%): LC/MS (Table 1, Method b) R$_t$=1.4 min; MS m/z: 390.5 (M+H)$^+$.

Example #F.1

1-(4-4-[2-(4-Fluorophenyl)-imidazo[1,2-a]pyrazin-3-yl]-pyrimidin-2-ylaminopiperidin-1-yl)-ethanone

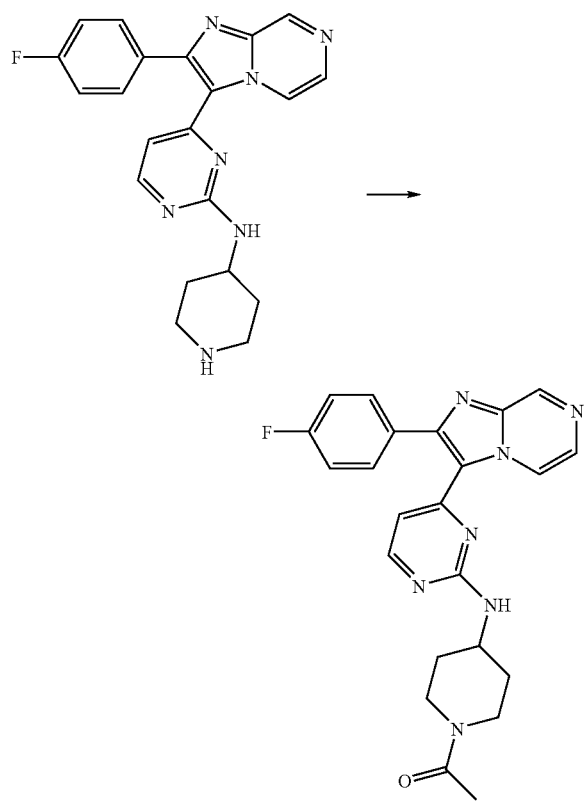

To a suspension of a 4-[2-(4-fluorophenyl)-imidazo[1,2-a]pyrazin-3-yl]-pyrimidin-2-ylpiperidin-4-ylamine (Example # H.1, 0.040 g, 0.10 mmol) in 1,4-dioxane (3.0 mL) at ambient temperature was added acetic anhydride (10.0 µL, 0.10 mmol), 4-dimethylaminopyridine (0.0025 g, 0.020 mmol), and triethylamine (29 µL, 0.205 mmol). The resulting solution was concentrated under reduced pressure after about 2 h. The crude material was purified by flash silica gel chromatography using DCM/2.5% NH$_4$OH in MeOH (95:5) to give the title compound (0.006 g, 30%): LC/MS (Table 1, Method b) R$_t$=1.6 min; MS m/z: 432.6 (M+H)$^+$.

Example #1

4-[2-(4-Fluorophenyl)-imidazo[1,2-a]pyrazin-3-yl]-pyrimidin-2-ol

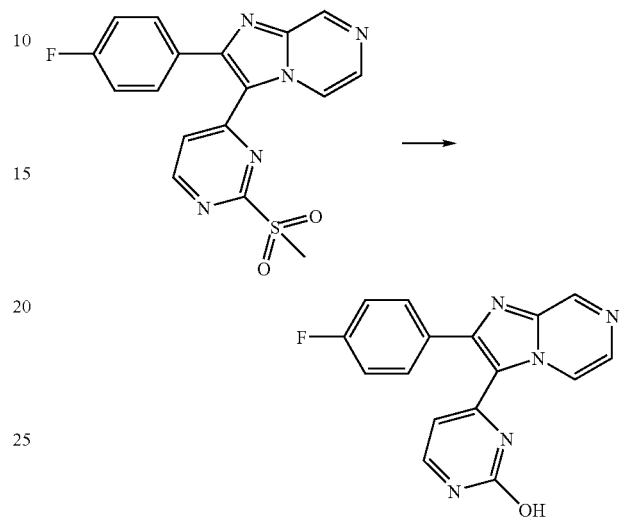

A solution of 2-(4-fluorophenyl)-3-(2-methanesulfonylpyrimidin-4-yl)-imidazo[1,2-a]pyrazine (Preparation #4, 0.050 g, 0.14 mmol), 3-aminoquinuclidine dihydrochloride (0.054 g, 0.27 mmol), DIEA (0.047 mL, 0.27 mmol), and DMSO (1 mL) were shaken at about 80° C. for about 24 h. Additional DIEA (0.100 mL) was added to the mixture. The mixture was concentrated in vacuo to remove DMSO. The material was treated with saturated solution of NaHCO$_3$ (30 mL) and EtOAc (50 mL). The layers were separated, and the aqueous layer was washed sequentially with EtOAc (3×50 mL) and DCM (50 mL). The combined organic layers were dried over MgSO$_4$ and concentrated. The mixture was triturated in EtOAc and filtered to yield the title compound (0.007 g, 20%): LC/MS (Table 1, Method b) R$_t$=1.3 min; MS m/z: 308.2 (M+H)$^+$.

Example #2

N-4-[2-(4-Fluorophenyl)-imidazo[1,2-a]pyrazin-3-yl]-pyrimidin-2-yl-benzamide

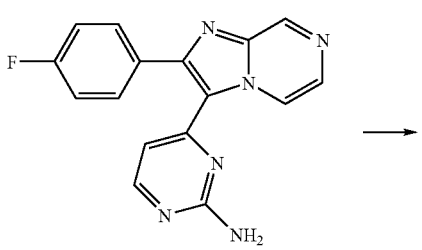

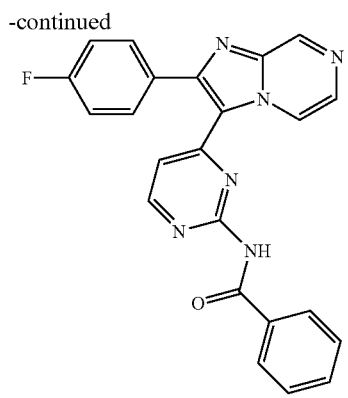

A mixture of 4-[2-(4-fluorophenyl)-imidazo[1,2-a]pyrazin-3-yl]-pyrimidin-2-ylamine (Example #D.1, 0.100 g, 0.326 mmol) and benzoic anhydride (2.2 g, 9.7 mmol) was warmed at about 100° C. for about 5 days. The mixture was cooled, diluted in DCM (10 mL), treated with concentrated HCl (20 mL, 37% aq), and warmed to about 100° C. After about 4 h, the mixture was cooled to ambient temperature, filtered, and quenched with aqueous NaOH (8 N). The mixture was treated with EtOAc, and the layers were separated. The aqueous layer was washed with EtOAc (3×100 mL), and the combined organic layers were dried over MgSO$_4$, filtered, and concentrated to yield the title compound as a white solid after drying (0.005 g, 4%): LC/MS (Table 1, Method b) R$_f$=2.1 min; MS m/z: 411.2 (M+H)$^+$.

Example #3

1-4-[2-(4-Fluorophenyl)-imidazo[1,2-a]pyrazin-3-yl]-pyrimidin-2-yl-3-phenyl-urea

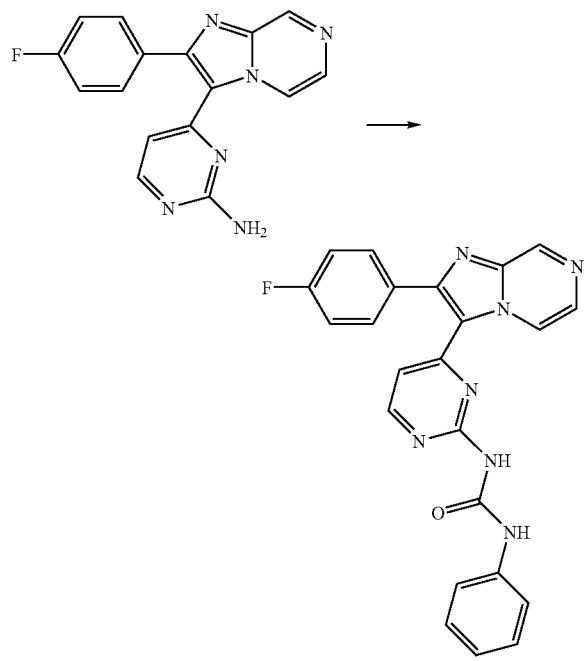

To a mixture of 4-[2-(4-fluorophenyl)-imidazo[1,2-a]pyrazin-3-yl]-pyrimidin-2-ylamine (Example #D.1, 0.200 g, 0.653 mmol) and phenyl isocyanate (0.31 g, 2.6 mmol) in THF (5 mL) was added 1.0 M LiHMDS in THF (2.6 mL, 2.6 mmol) over ice. The mixture was allowed to warm to ambient temperature after about 10 min. After about an additional 16 h, the mixture was treated with phenyl isocyanate (0.16 g, 1.3 mmol) and additional 1.0 M LiHMDS in THF (1.3 mL, 1.3 mmol) at ambient temperature. After about 3 h, the mixture was quenched with water and concentrated in vacuo. The material was treated with DCM (50 ml), and the layers were separated. The aqueous layer was washed with DCM (3×40 mL), and the combined organic layers were dried over MgSO$_4$, filtered, and concentrated. The resulting material was purified via RP-HPLC (Method c) followed by recrystallization in hot ACN to yield the title compound (0.019 g, 7%): LC/MS (Table 1, Method b) R$_f$=2.2 min; MS m/z: 426.1 (M+H)$^+$.

Example #4

2-(4-Fluorophenyl)-3-(2-methanesulfonylpyrimidin-4-yl)-imidazo[1,2-a]pyrazine 7-oxide

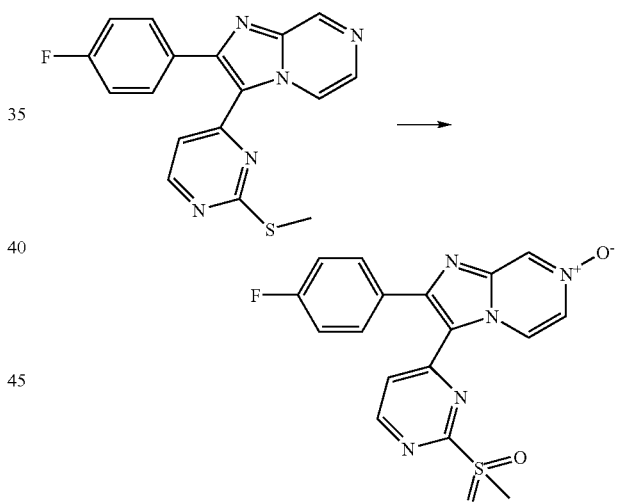

To a solution of 2-(4-fluorophenyl)-3-(2-methylsulfanylpyrimidin-4-yl)-imidazo[1,2-a]pyrazine (Preparation #3, 3.0 g, 8.9 mmol) in MeOH (130 mL) and DCM (60 mL) was added Oxone® (16 g, 27.0 mmol) in water (60 mL) to form a suspension. After about 18 h, the organic solvents were removed under vacuum, and the mixture was diluted with water. The product was partitioned between the aqueous layer and EtOAc. EtOAc extracts were combined, washed with water and saturated brine, dried over MgSO$_4$, filtered, and concentrated under reduced pressure. The material was purified via FCC using DCM/ACN (1:1) as an eluent to yield the title compound after concentration (0.20 g, 6%): LC/MS (Table 1, Method b) R$_f$=1.5 min; MS m/z: 386.1 (M+H)$^+$.

Example #5

Cyclopropyl-{6-[2-(4-fluorophenyl)-imidazo[1,2-a]pyrazin-3-yl]-1-oxypyrimidin-2-yl}-amine

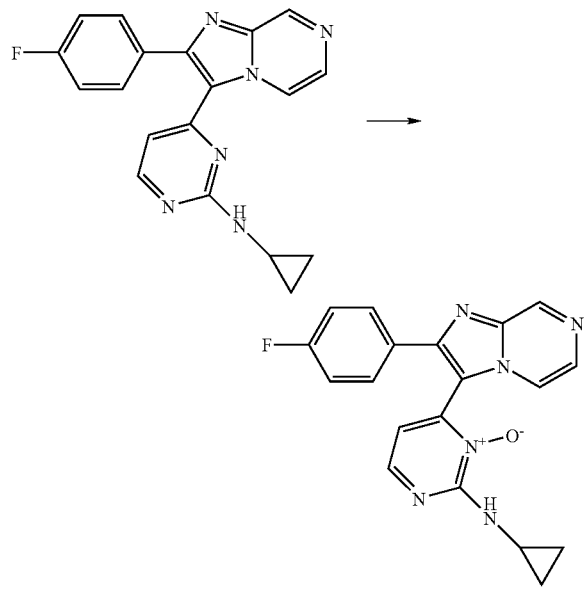

A mixture of cyclopropyl-4-[2-(4-fluorophenyl)-imidazo[1,2-a]pyrazin-3-yl]-pyrimidin-2-ylamine (Example #A.2, 0.075 g, 0.22 mmol) in DCM (1.0 mL) was cooled to about 0° C. and treated with m-CPBA (0.053 g, 0.24 mmol). The reaction was allowed to warm slowly to ambient temperature. After about 18 h, saturated aqueous NaHCO₃ (10 mL) was added and the mixture was extracted with DCM (3×10 mL). The combined organic layers were washed with brine, dried over Na₂SO₄, decanted, and concentrated. The crude material was purified by silica gel chromatography with DCM/MeOH/NH₄OH (stepwise gradient, 990:9:1 to 980:18:2) to give 0.042 g (54%) of title compound as a yellow solid: LC/MS (Table 1, Method b) $R_t$=1.66 min; MS m/z: 363.2 (M+H)⁺.

Example #6

3-{4-[2-(4-Fluorophenyl)-8-methylimidazo[1,2-a]pyrazin-3-yl]-pyrimidin-2-ylamino}-2,2-dimethyl-propan-1-ol

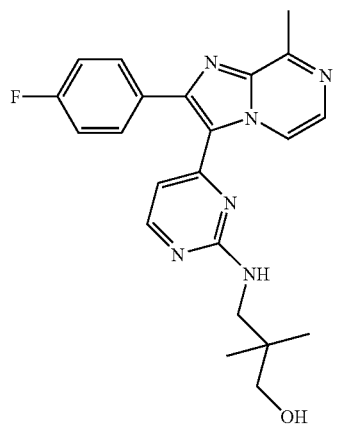

Step A:
8-Chloro-2-(4-fluorophenyl)-imidazo[1,2-a]pyrazine

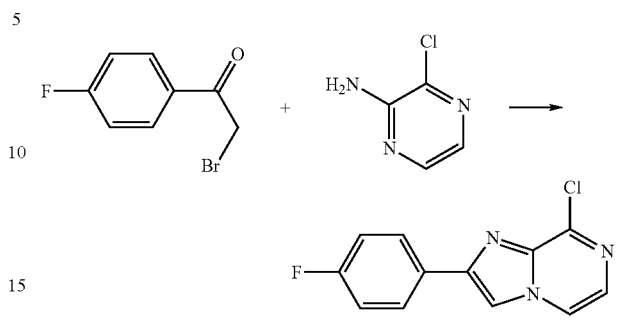

Into a 1-Neck round-bottom flask was added 2-bromo-1-(4-fluorophenyl)ethanone (125 g, 564 mmol) and 3-chloropyrazin-2-amine (128.9 g, 965.2 mmol) followed by ACN (750 mL). The mixture was stirred at reflux for about 24 h. The reaction mixture was cooled to about 45° C. before the solvent was removed in vacuo to yield a brown solid. The brown solid was suspended in water (500 mL) and basified, whilst stirring, with 2.5N NaOH (500 mL). The mixture was then stirred for about 30 min then re-acidified with 5N HCl (300 mL) and extracted with DCM (5×1000 mL). The combined organic layers were filtered from the insoluble material, washed with water (750 mL), followed by washing with 2.5N HCl (4×750 mL), 2.5N NaOH (500 mL) and water (2×500 mL), then dried over MgSO₄ and filtered. The filtrate was eluted through a Florisil® pad (3 inch diameter×3 inch depth), washing with repeated amounts of DCM until no product detected by TLC. The organic solvent was removed in vacuo to yield a yellow solid, which was suspended in 2-propanol (500 mL) at about 80° C. for about 15 min and then cooled to about 30° C. The solid was filtered, washing with petroleum ether [bp 30-60° C.] (2×100 mL) and heptane (2×100 mL) to remove impurities, dried in vacuo at 45° C. to yield the title compound (78.2 g, 55.4%): LC/MS (Table 1, Method g) $R_t$=2.48 min; MS m/z: 248.2 (M+H)⁺.

Step B:
2-(4-Fluorophenyl)-8-methylimidazo[1,2-a]pyrazine

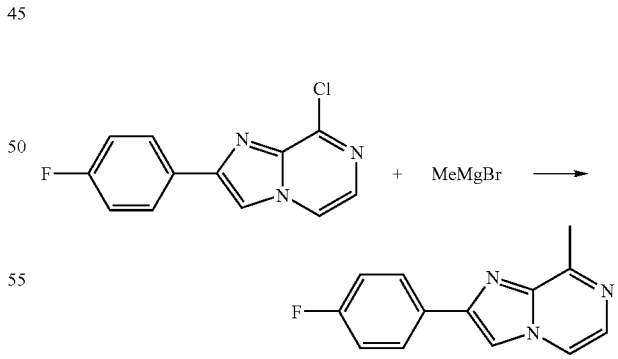

A solution of 3M MeMgBr in Et₂O (16.1 mL, 48.3 mmol) was added drop-wise to a mixture of 8-chloro-2-(4-fluorophenyl)-imidazo[1,2-a]pyrazine (10.0 g, 40.6 mmol), ferric acetylacetonate (0.71 g, 2.0 mmol), THF (240 mL), and NMP (23 mL) at about 0° C. The mixture was warmed to ambient temperature over about 1 hour. After about 1 hour, the reaction was cooled to about 0° C. and treated with additional 3M MeMgBr in Et₂O (4 mL, 12 mmol). The mixture was allowed to warm to ambient temperature over about 1 h. After about an additional 1 h, the mixture was quenched with water and extracted with EtOAc. The organic layers were combined and dried with Na$_2$SO$_4$. After concentration, the crude material was purified by FCC on silica gel using EtOAc as an eluent to afford the expected product as an off-white solid (9.6 g, 100%): LC/MS (Table 1, Method b) R$_t$=1.8 min; MS m/z: 228.2 (M+H)$^+$.

Step C: 2-(4-Fluorophenyl)-8-methyl-3-(2-methylsulfanylpyrimidin-4-yl)-imidazo[1,2-a]pyrazine

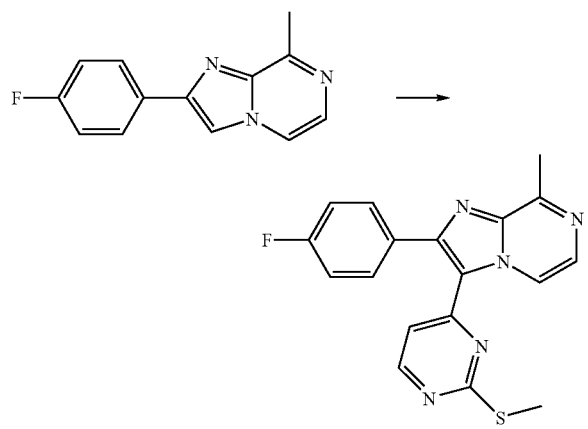

Into a flask was added 2-(4-fluorophenyl)-8-methylimidazo[1,2-a]pyrazine (4.8 g, 21.0 mmol), 4-iodo-2-(methylthio)pyrimidine (Frontier, 9.4 g, 31.7 mmol), Cs$_2$CO$_3$ (10.3 g, 31.7 mmol), PPh$_3$ (2.2 g, 8.4 mmol), and DMF (50 mL). The mixture was degassed under vacuum and back-filled with N$_2$. The mixture was charged with Pd(OAc)$_2$ (0.95 g, 4.2 mmol) and heated at about 100° C. for about 16 h. The mixture was cooled to ambient temperature, diluted with water (200 mL), and extracted with DCM (3×200 mL). The combined organic layers were washed with brine (200 mL), dried over Na$_2$SO$_4$, filtered, and concentrated under reduced pressure. Purification by flash column chromatography (0-5% MeOH:DCM) followed by trituration in EtOAc yielded the title compound (4.30 g, 58% yield): LC/MS (Table 1, Method b) R$_t$=2.2 min; MS m/z: 352.3 (M+H)$^+$.

Step D: 2-(4-Fluorophenyl)-3-(2-methanesulfonylpyrimidin-4-yl)-8-methylimidazo[1,2-a]pyrazine

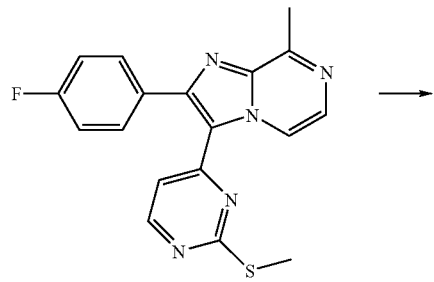

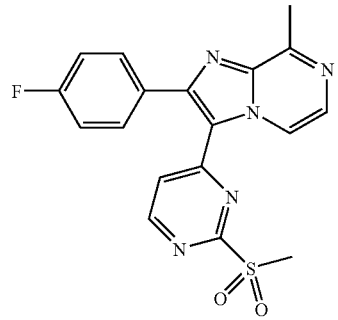

In a round bottom flask charged with 2-(4-fluorophenyl)-3-(2-methylsulfanylpyrimidin-4-yl)-imidazo[1,2-a]pyrazine (2.5 g, 7.1 mmol) dissolved in DCM (5 mL) and MeOH (500 mL) was added a suspension of Oxone® (13.2 g, 21.3 mmol) in water (50 mL) at ambient temperature. The reaction was allowed to stir at this temperature for about 1.5 h upon which time water (1 L) was added and the solution was allowed to stir for about 30 min upon which time an orange precipitate had formed. The precipitate was filtered and purified by silica gel chromatography (100% EtOAc) to yield the title compound (1.25 g, 48% yield): LC/MS (Table 1, Method b) R$_t$=1.7 min; MS m/z: 384.1 (M+H)$^+$.

Step E: 3-{4-[2-(4-Fluorophenyl)-8-methylimidazo[1,2-a]pyrazin-3-yl]-pyrimidin-2-ylamino}-2,2-dimethylpropan-1-ol

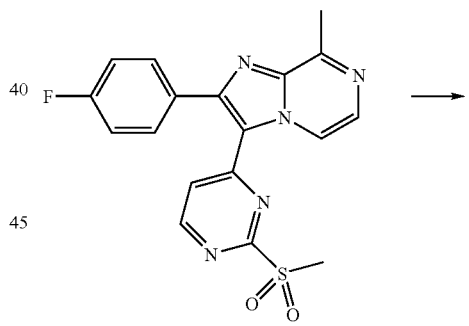

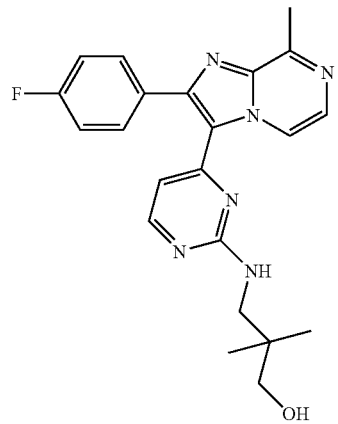

To a mixture of 2-(4-fluorophenyl)-3-(2-methanesulfonylpyrimidin-4-yl)-8-methylimidazo[1,2-a]pyrazine (1.50 g, 391 mmol) in ACN (30 mL) was added 3-amino-2,2-dimethyl-1-propanol (Lancaster, 2.0 g, 20 mmol). The reaction mixture was heated to about 80° C. After about 1.5 h, the reaction was cooled to ambient temperature and concentrated under reduced pressure. The resulting crude material was purified by silica gel chromatography with DCM/MeOH/NH$_4$OH (step-wise gradient, 990:9:1 then 980:18:2) to give an oil after concentration. The oil was dissolved in a minimum amount of DCM and heptane was added until a white precipitate formed. The suspension was concentrated under reduced pressure. The resulting solid was triturated with heptane and filtered to give the title compound (1.36 g, 86%): LC/MS (Table 1, Method g) R$_t$=2.41 min; MS m/z: 407.2 (M+H)$^+$.

Example #7

8-Chloro-2-(4-fluorophenyl)-3-(2-methylsulfanylpyrimidin-4-yl)imidazo[1,2-a]pyrazine

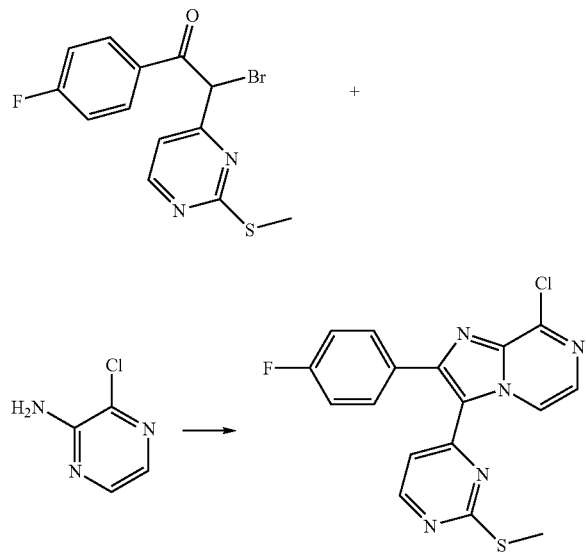

To a solution of 3-chloropyrazin-2-ylamine (1.3 g, 10 mmol) in 1-methyl-2-pyrrolidinone (1 mL) heated to about 150° C. was added dropwise over about 15 min a solution of 2-bromo-1-(4-fluorophenyl)-2-(2-methylsulfanylpyrimidin-4-yl)ethanone (prepared according to WO2003000682; 0.34 g, 1 mmol) in 1-methyl-2-pyrrolidinone (1 mL). After about 30 min of stirring at about 150° C., the mixture was cooled to ambient temperature, diluted with DCM, extracted three times with 1N HCl and six times with 2N NaOH. The organic layer was dried over Na$_2$SO$_4$ and concentrated. The crude material was purified by silica gel chromatography with heptane/EtOAc (stepwise gradient, 5:1, 3:1) to give 0.019 g (5%) of the title compound: LC/MS (Table 1, Method b) R$_t$=2.28 min; MS m/z: 372.2 (M+H)$^+$.

Example #8

3-{4-[8-Cyclopropylmethyl-2-(4-fluorophenyl)imidazo[1,2-a]pyrazin-3-yl]pyrimidin-2-ylamino}-2,2-dimethylpropan-1-ol

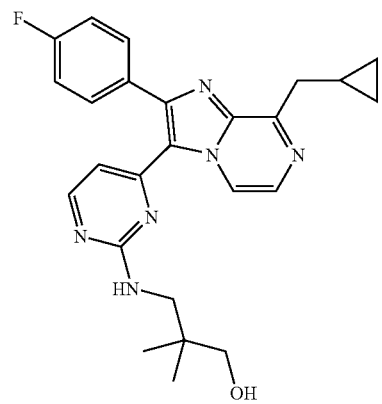

Step A:
8-Chloro-2-(4-fluorophenyl)imidazo[1,2-a]pyrazine

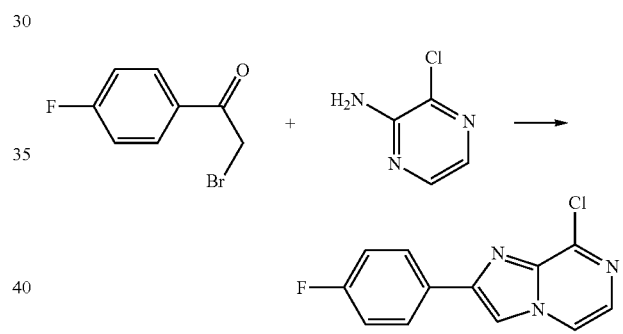

Into a 1-Neck round-bottom flask was added 2-bromo-1-(4-fluorophenyl)ethanone (125 g, 564 mmol) and 3-chloropyrazin-2-amine (128.9 g, 965.2 mmol) followed by ACN (750 mL). The mixture was stirred at reflux for about 24 h. The reaction mixture was cooled to about 45° C. before the solvent was removed in vacuo to yield a brown solid. The brown solid was suspended in water (500 mL) and basified, whilst stirring, with 2.5N NaOH (500 mL). The mixture was then stirred for about 30 min then re-acidified with 5N HCl (300 mL) and extracted with DCM (5×1000 mL). The combined organic layers were filtered from the insoluble material, washed with water (750 mL), followed by washing with 2.5N HCl (4×750 mL), 2.5N NaOH (500 mL) and water (2×500 mL), then dried over MgSO$_4$ and filtered. The filtrate was eluted through a Florisil® pad (3 inch diameter×3 inch depth), washing with repeated amounts of DCM until no product detected by TLC. The organic solvent was removed in vacuo to yield a yellow solid, which was suspended in 2-propanol (500 mL) at about 80° C. for about 15 min and then cooled to about 30° C. The solid was filtered, washing with petroleum ether [bp 30-60° C.] (2×100 mL) and heptane (2×100 mL) to remove impurities, dried in vacuo at 45° C. to yield the title compound (78.2 g, 55.4%): LC/MS (Table 1, Method g) R$_t$=2.48 min; MS m/z: 248.2 (M+H)$^+$.

Step B: 8-Cyclopropylmethyl-2-(4-fluorophenyl)imidazo[1,2-a]pyrazine

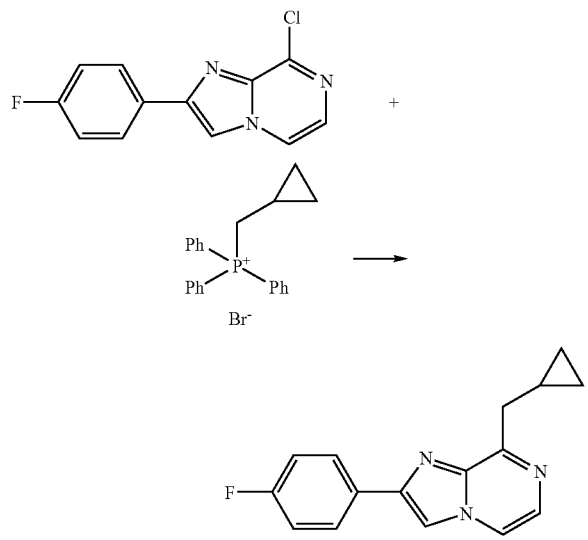

To a suspension of (cyclopropylmethyl)triphenylphosphonium bromide (Alfa Aesar, 20.3 g, 51 mmol) in dry DME (100 mL) kept between about −30° C. and −40° C. was added a 2.5M solution of n-butyllithium in hexanes (20.4 mL, 51 mmol) over 10 min. After stirring between about −30° C. and −40° C. for about 1 h, 8-chloro-2-(4-fluorophenyl)imidazo[1,2-a]pyrazine (5.74 g, 23.2 mmol) was added. The mixture was warmed to ambient temperature, then stirred at about 85° C. for about 2 h, at which point a solution of Na$_2$CO$_3$ (2.70 g, 25.5 mmol) in water (50 mL) was added and heating was continued for about 15 h. After cooling to ambient temperature, the mixture was partitioned between 0.5 N HCl and CHCl$_3$ and the aqueous phase washed two more times with CHCl$_3$. The combined organic phase was extracted six times with 0.5 N HCl. The combined aqueous phase was rendered alkaline with NaOH and extracted with Et$_2$O. After drying over Na$_2$SO$_4$ and concentration, the crude material was purified by silica gel chromatography with heptane/EtOAc (gradient 30-100% EtOAc) to give 3.77 g (61%) of the title compound as an orange solid: LC/MS (Table 1, Method g) R$_t$=2.78 min; MS m/z: 268.2 (M+H)$^+$.

Step C: 8-Cyclopropylmethyl-2-(4-fluorophenyl)-3-(2-methylsulfanylpyrimidin-4-yl)imidazo[1,2-a]pyrazine

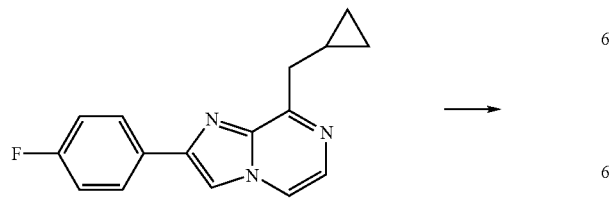

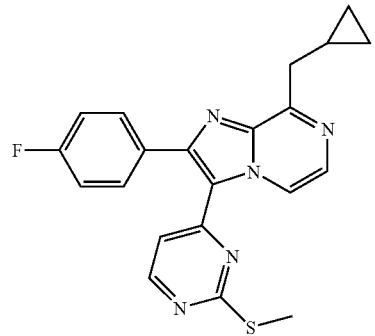

Into a flask were added 8-cyclopropylmethyl-2-(4-fluorophenyl)imidazo[1,2-a]pyrazine (5.84 g, 21.8 mmol), 4-iodo-2-(methylthio)pyrimidine (Frontier, 8.27 g, 32.8 mmol), Cs$_2$CO$_3$ (10.7 g, 32.8 mmol), PPh$_3$ (2.29 g, 8.73 mmol), and DMF (50 mL). The mixture was degassed by bubbling Ar through it for about 5 min, before being charged with Pd(OAc)$_2$ (0.981 g, 4.37 mmol) and heated at about 100° C. for about 18 h. The reaction was cooled to ambient temperature, the solvent was removed in vacuo, and the residue taken up in DCM and water. After filtration through a pad of Celite®, the organic layer was separated and the aqueous layer extracted about five more times with DCM, filtering through Celite® in every extraction step to break emulsions. The combined organic phase was dried over Na$_2$SO$_4$ and concentrated. The crude material was purified by silica gel chromatography with heptane/EtOAc (gradient 20-80% EtOAc). After concentration, the residue was twice re-dissolved in DCM and re-concentrated to give 5.16 g (60%) of the title compound as a greenish solid: LC/MS (Table 1, Method g) R$_t$=3.43 min; MS m/z: 392.2 (M+H)$^+$.

Step D: 8-Cyclopropylmethyl-2-(4-fluorophenyl)-3-(2-methanesulfonylpyrimidin-4-yl)imidazo[1,2-a]pyrazine

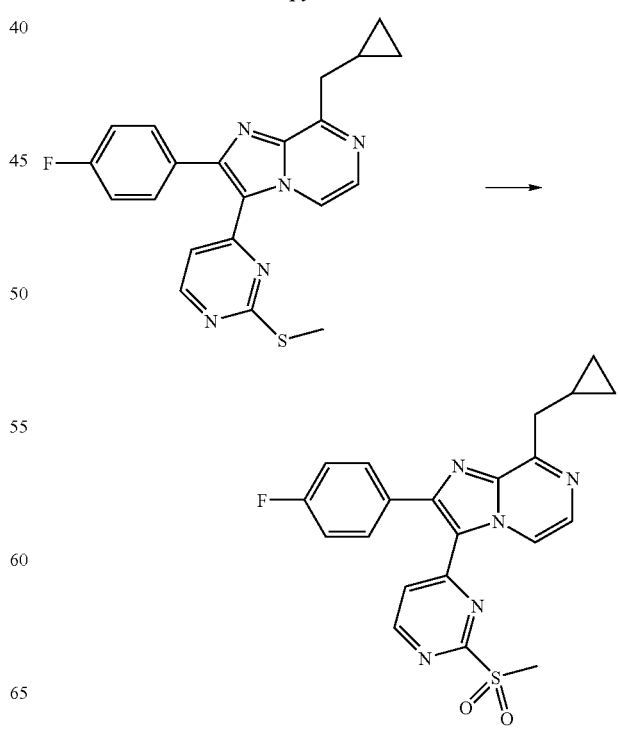

To a solution of 8-cyclopropylmethyl-2-(4-fluorophenyl)-3-(2-methylsulfanylpyrimidin-4-yl)imidazo[1,2-a]pyrazine (5.16 g, 13.2 mmol) in DCM (50 mL) and MeOH (50 mL) was added a solution of Oxone® (16.2 g, 26.4 mmol) in water (50 mL). After about 4 h of rapid stirring, the mixture was neutralized with saturated Na₂CO₃ solution and extracted with DCM. The combined organic phase was dried over Na₂SO₄ and concentrated. The crude material was purified by silica gel chromatography with heptane/EtOAc (gradient 50-100% EtOAc). After concentration, the residue was three times re-dissolved in DCM and re-concentrated to give 4.77 g (85%) of the title compound as a yellowish solid: LC/MS (Table 1, Method g) R_t=2.68 min; MS m/z: 424.1 (M+H)⁺.

Step E: 3-{4-[8-Cyclopropylmethyl-2-(4-fluorophenyl)imidazo[1,2-a]pyrazin-3-yl]pyrimidin-2-ylamino}-2,2-dimethylpropan-1-ol

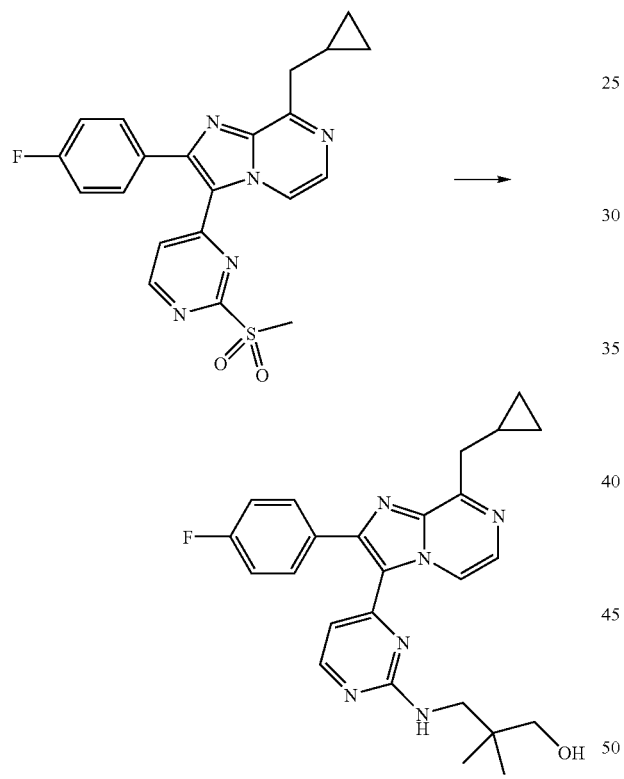

A solution of 8-cyclopropylmethyl-2-(4-fluorophenyl)-3-(2-methanesulfonylpyrimidin-4-yl)imidazo[1,2-a]pyrazine (3.00 g, 7.08 mmol) and 3-amino-2,2-dimethylpropan-1-ol (TCI-US, 3.65 g, 35.4 mmol) in ACN (100 mL) was heated at about 85° C. for about 2 d. After cooling to ambient temperature, a precipitate formed, which was filtered off, washed with ACN, dried in vacuo and purified by silica gel chromatography with heptane/EtOAc (gradient 50-100% EtOAc, then isocratic 100% EtOAc). After concentration, the residue was three times re-dissolved in DCM and re-concentrated, resulting in a colorless foam, which was dried in a vacuum oven for about 16 h at about 55° C. and about 21 Torr to give 1.809 g (56%) of the title compound as a colorless solid: LC/MS (Table 1, Method g) R_t=3.01 min; MS m/z: 447.2 (M+H)⁺.

Example #9

3-(2-Methanesulfonylpyrimidin-4-yl)-2-(3-trifluoromethylphenyl)-imidazo[1,2-a]pyrazine 7-oxide

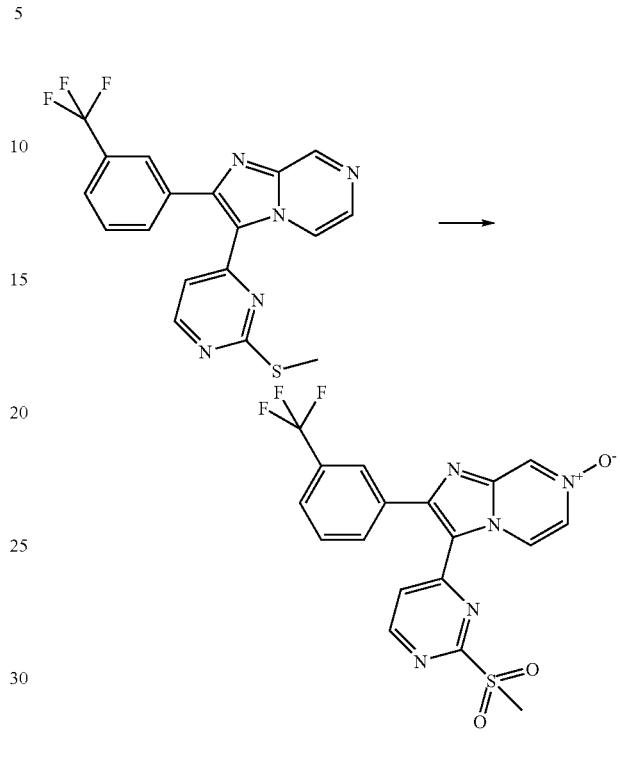

3-(2-Methylsulfanylpyrimidin-4-yl)-2-(3-trifluoromethylphenyl)-imidazo[1,2-a]pyrazine (Example #F.1.32, 1.1 g, 2.84 mmol) was dissolved in DCM (42 ml) and MeOH (42.0 ml). Oxone (5.2 g, 8.46 mmol) was dissolved in water (25 ml) and added to the reaction. The reaction was stirred rapidly for about 15 h. Water and DCM were added and the layers separated. The aqueous was extracted with DCM (2×). The combined extracts were washed with brine, dried over sodium sulfate, filtered and concentrated. The residue was chromatographed over silica gel in EtOAc and then 5% MeOH in DCM to provide the title compound (0.125 g, 10%) on concentration and trituration with Et₂O: LC/MS (Table 1, Method b) R_t=1.46 min; MS m/z: 436.1 (M+H)⁺.

Example #10

Cyclopropyl-{4-[7-oxy-2-(3-trifluoromethylphenyl)-imidazo[1,2-a]pyrazin-3-yl]-pyrimidin-2-yl}-amine

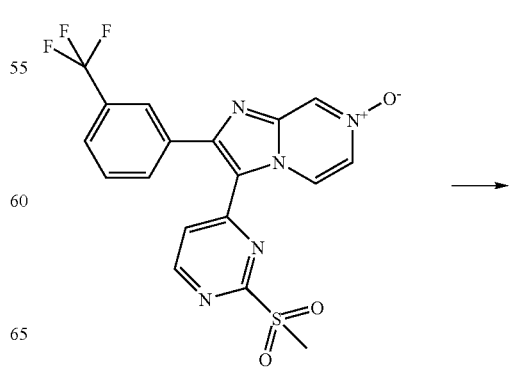

-continued

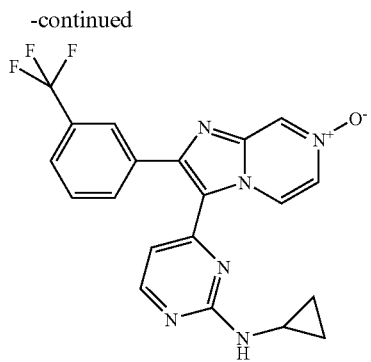

3-(2-Methanesulfonylpyrimidin-4-yl)-2-(3-trifluoromethylphenyl)-imidazo[1,2-a]pyrazine 7-oxide (Example #9, 0.10 g, 0.23 mmol) was stirred in ACN (2 mL). Cyclopropylamine (0.10 mL, 1.4 mmol) was added and the mixture heated in sealed vial at about 80° C. overnight. The reaction was cooled and filtered. The solid was washed with ACN and Et$_2$O. The solid was heated in EtOH and filtered to provide the title compound (0.075 g, 79%) on drying: LC/MS (Table 1, Method b) R$_t$=1.76 min; MS m/z: 413.19 (M+H)$^+$.

Example #11

Cyclopropyl-{4-[2-(4-fluorophenyl)-7-oxyimidazo[1,2-a]pyrazin-3-yl]-pyrimidin-2-yl}-amine

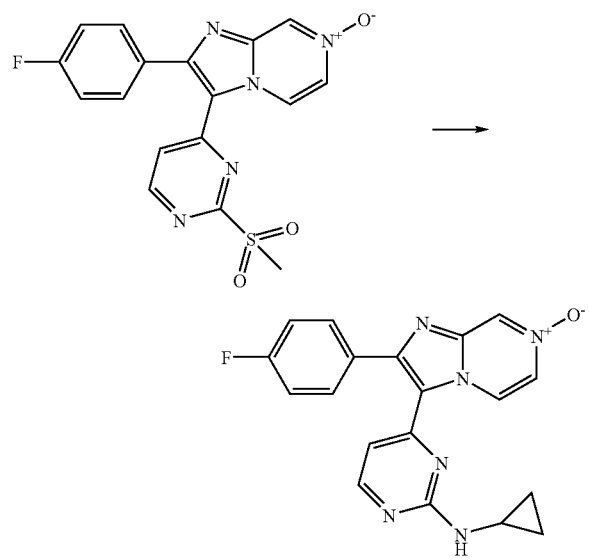

Cyclopropyl-{4-[2-(4-fluorophenyl)-7-oxyimidazo[1,2-a]pyrazin-3-yl]-pyrimidin-2-yl}-amine (Example #4, 0.10 g, 0.26 mmol) was stirred in ACN (2 mL). Cyclopropylamine (0.10 mL) was added and the mixture heated in sealed vial at about 80° C. overnight. The reaction was cooled and filtered. The solid was washed with ACN and Et$_2$O. The solid was heated in EtOH and filtered to provide the title compound (0.082 g, 87%) on drying: LC/MS (Table 1, Method g) R$_t$=1.96 min; MS m/z: 363.28 (M+H)$^+$.

Example #12

6-Ethyl-2-(4-fluorophenyl)-3-(2-methylsulfanylpyrimidin-4-yl)-imidazo[1,2-a]pyrazine

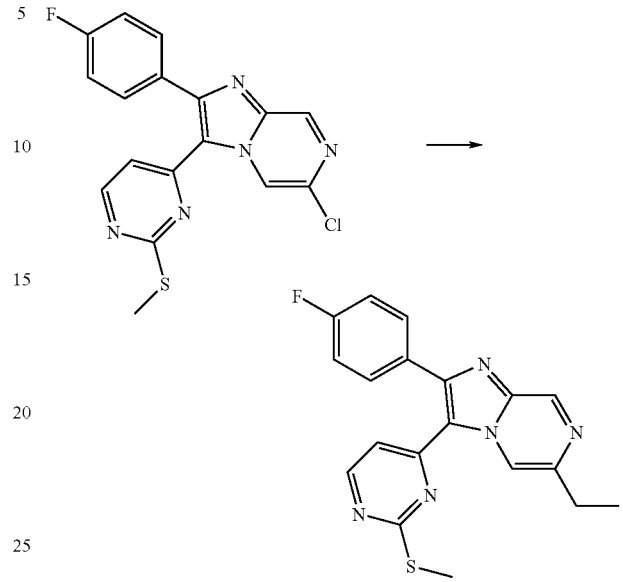

6-Chloro-2-(4-fluorophenyl)-3-(2-methylsulfanylpyrimidin-4-yl)-imidazo[1,2-a]pyrazine, (Example #F.1.34, 0.25 g, 0.27 mmol), tris(dibenylideneacetone)dipalladium(0) (0.0306 g, 0.034 mmol), sodium carbonate (0.213 g, 2.0 mmol), and tri-t-butylphosphine tetrafluoroborate (Strem, 0.0194 g, 0.07 mmol) were combined in water (0.645 mL) and dioxane (3.35 mL). The reaction was degassed with nitrogen and vinylboronic acid pinacol ester (0.227 mL, 1.34 mmol) was added and the reaction heated at about 95° C. overnight. The reaction was poured onto a pad of silica gel and eluted with EtOAc. The EtOAc solution was washed with brine, dried over sodium sulfate, and concentrated. Ethanol (7.5 mL), EtOAc (7.5 mL), and 10% palladium on carbon (0.050 g) were added. The reaction was purged with hydrogen and stirred under a balloon of hydrogen for about 4 h. The reaction was filtered and concentrated. The residue was purified by FCC using 1:1 EtOAc/heptane and then triturated with heptane to provide the title compound (0.16 g, 65%) on drying: LC/MS (Table 1, Method b) R$_t$=2.52 min; MS m/z: 366.3 (M+H)$^+$.

Example #13

3-{4-[2-(2,4-Difluorophenyl)-8-methylimidazo[1,2-a]pyrazin-3-yl]-pyrimidin-2-ylamino}-2,2-dimethyl-propan-1-ol

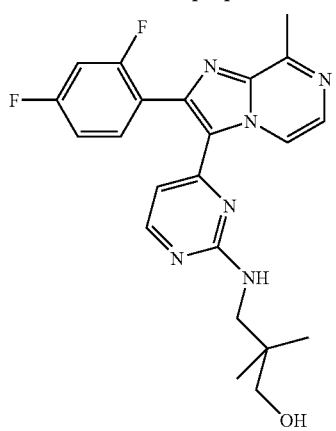

Step A: 8-Chloro-2-(2,4-difluorophenyl)-imidazo[1,2-a]pyrazine

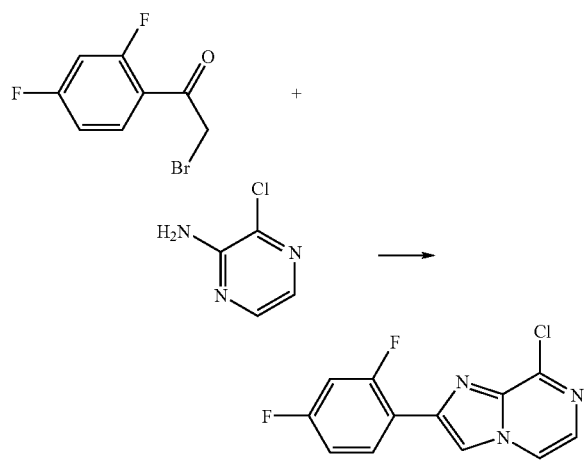

A mixture of 2-bromo-1-(2,4-difluorophenyl)ethanone (107.31 g, 442.89 mmol) and 3-chloropyrazin-2-amine (98.00 g, 756.5 mmol) in ACN (800 mL) was stirred at reflux for about 20 h. The reaction mixture was cooled to about 25° C. before the resultant solid was collected. The filtrate solvent was removed in vacuo to yield a brown solid. This filtration was done to negate the bumping associated with the removal of the ACN. The combined solids were then suspended in water (750 mL) and basified, whilst stirring, with 2N NaOH (750 mL). After about 30 min, the product was partitioned between DCM (9×1000 mL) and filtered from the insoluble material to aid extraction process. The organic extracts were combined and stirred with 2.5N HCl (4×750 mL). The organic layer was finally washed with 2.0N NaOH (500 mL) and water (2×500 mL), dried over MgSO$_4$, and filtered through a Florisil® pad (3 inch diameter×3 inch depth) to remove origin material. The Florisil® pad was washed with repeated amounts of solvent until no product was detected by TLC. The organic solvent was removed in vacuo to yield a yellow solid. The solid was suspended in IPA (200 mL) at about 80° C. for about 15 min and then cooled to about 20° C. The solid was collected and washed with ice-cold IPA (2×40 mL), followed by petroleum ether [bp 30-60° C.] (3×80 mL) to remove impurities. The solid was dried in vacuo at about 70° C. overnight to yield the title compound as a yellow powdery solid (69.75 g, 57%): LC/MS (Table 1, Method g) R$_t$=2.70 min; MS m/z: 266.1 (M+H)$^+$.

Step B: 2-(2,4-Difluorophenyl)-8-methylimidazo[1,2-a]pyrazine

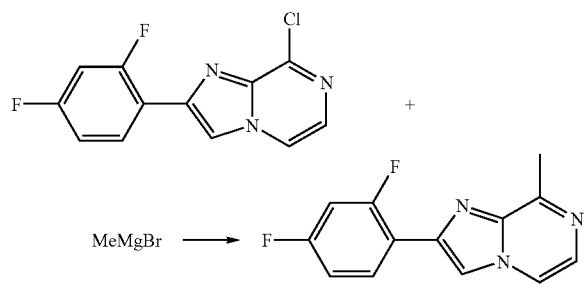

Into a 3-neck reaction flask equipped with a mechanical stirrer, was added 8-chloro-2-(2,4-difluorophenyl)imidazo[1,2-a]pyrazine (40.00 g, 150.6 mmol), ferric acetylacetonate (2.66 g, 7.53 mmol), tetrahydrofuran (970 mL) and N-methylpyrrolidinone (86 mL). The flask was charged with nitrogen and cooled to about −5-0° C. (acetone/DriKold cooling bath) before the drop-wise addition of 3M MeMgBr in Et$_2$O (150 mL) over about 20 min. After the addition was complete, the reaction was stirred at this temperature for about 15 min before the cooling bath was removed. The reaction mixture was allowed to warm to ambient temperature over about 1 hour and then stirred overnight. The reaction was concentrated and the residue was stirred with water (1000 mL) and EtOAc (1000 mL) for about 15 min. The mixture was filtered through a Celite® pad to remove salts. The Celite® pad was scraped and stirred with EtOAc (3×250 mL). The basic aqueous phase was separated and extracted with EtOAc (3×250 mL). The organic layers were combined, washed with water (3×350 mL), dried over MgSO$_4$, and filtered through a Florisil® pad to remove origin material. The solvent was removed to yield a yellow solid that was treated with boiling MeOH (125 mL), cooled to about 15° C. and petroleum ether [bp 30-60° C.] (250 mL) was added with stirring. The solid was filtered, washed with petroleum ether [bp 30-60° C.] (3×50 mL), and dried in vacuo at 70° C. to yield the title compound as a pale yellow powdery solid (23.25 g, 64%): LC/MS (Table 1, Method g) R$_t$=2.42 min; MS m/z: 246.1 (M+H)$^+$.

Step C: 2-(2,4-Difluorophenyl)-8-methyl-3-(2-methylsulfanylpyrimidin-4-yl)-imidazo[1,2-a]pyrazine

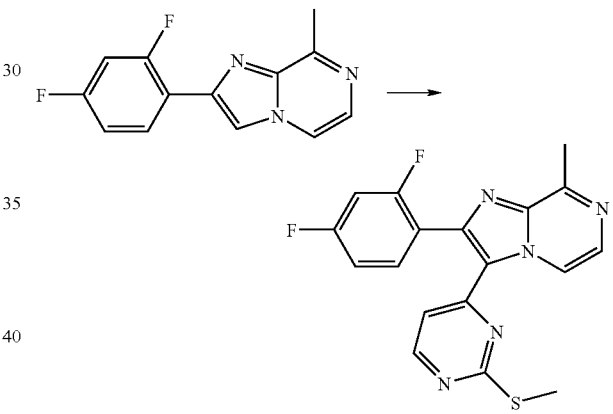

A mixture of triphenylphosphine (4.28 g, 16.3 mmol), palladium acetate (1.83 g, 8.16 mmol) and DMF (90.0 mL) was heated at about 100° C. for about 20 min then 2-(2,4-difluorophenyl)-8-methylimidazo[1,2-a]pyrazine (10.0 g, 40.8 mmol), 4-iodo-2-(methylthio)pyrimidine (12.3 g, 48.9 mmol), and cesium acetate (15.6 g, 81.6 mmol) were added. The reaction was heated at about 100° C. for about 17 h then the mixture was diluted with water (500 mL) and EtOAc (500 mL). The layers were stirred for about 20 min then filtered through a pad of Celite® (10 cm in diameter×4 cm in height) to remove the insoluble material. The Celite® pad was washed with EtOAc (2×150 mL). The aqueous layer was separated and washed with EtOAc (2×250 mL). The combined organic layers were washed with brine (2×200 mL), dried over MgSO$_4$, filtered through a pad of Florisil® (10 cm in diameter×4.5 cm in height), and concentrated under reduced pressure. The resulting solid was stirred with Et$_2$O (300 mL), filtered, washing with additional Et$_2$O (150 mL), to give a solid that was further triturated with MeOH (50 ml), filtered, washed with additional MeOH (50 mL), and dried under vacuum at about 55-65° C. to give 7.87 g of crude product. This material was further purified by silica gel chromatography using a step-wise gradient of DCM:EtOAc (4:1 to 7:3 to 3:2) to give 5.26 g (26%) of a ~3:1 mixture of 2-(2,4-difluorophenyl)-8-methyl-3-(2-methylsulfanylpyrimidin-4-yl)-imidazo[1,2-a]pyrazine/2-(2,4-difluorophenyl)-8-methylimidazo[1,2-a]pyrazine that can be used in the next step without additional purification. Additional product can be obtained from recovering the unreacted starting material and re-subjecting it to the reaction conditions: LC/MS (Table 1, Method b) $R_t$=2.14 min; MS m/z: 370.1 (M+H)$^+$.

Step D: 2-(2,4-Difluorophenyl)-3-(2-methanesulfonylpyrimidin-4-yl)-8-methylimidazo[1,2-a]pyrazine

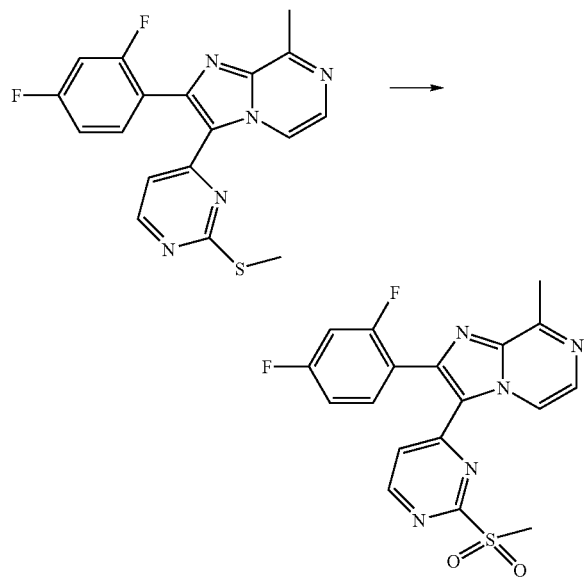

To a solution of 2-(2,4-difluorophenyl)-8-methyl-3-(2-methylsulfanylpyrimidin-4-yl)-imidazo[1,2-a]pyrazine (5.26 g, ~75% pure, 10.7 mmol) in DCM (90 mL) and MeOH (90 mL) was added a solution of Oxone® (13.1 g, 21.4 mmol) in water (45 mL). After about 16 h, the mixture was diluted with water (250 mL) and extracted with DCM (3×200 mL). The combine organic layers were washed with brine (100 mL), dried over MgSO$_4$, filtered, and concentrated. The crude material was purified by silica gel chromatography using a step-wise gradient of DCM:EtOAc (3:1 to 3:2 to 1:1). Fractions enriched in product were crystallized from hot ACN. The resulting solid was filtered, washing with additional ACN, and dried in a vacuum oven at about 70° C. for about 2 h to give 1.19 g (28%) of the title compound. Additional product can be obtained from further purification of column fractions and filtrate: LC/MS (Table 1, Method b) $R_t$=1.77 min; MS m/z: 402.1 (M+H)$^+$.

Step E: 3-{4-[2-(2,4-difluorophenyl)-8-methylimidazo[1,2-a]pyrazin-3-yl]-pyrimidin-2-ylamino}-2,2-dimethylpropan-1-ol

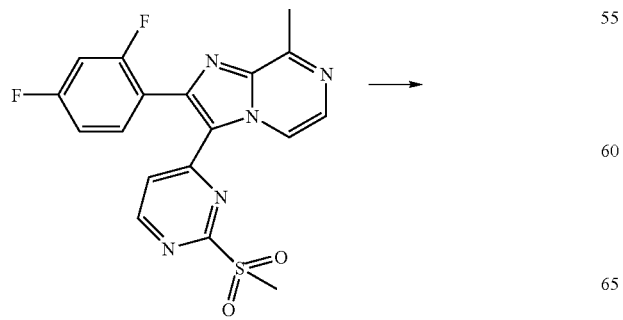

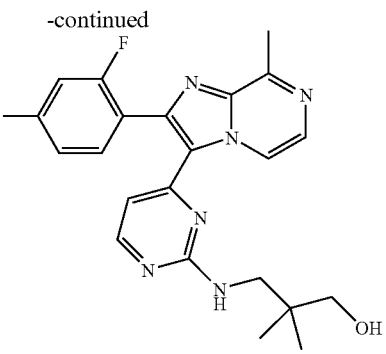

To a mixture of 2-(2,4-difluorophenyl)-3-(2-methanesulfonylpyrimidin-4-yl)-8-methyl-imidazo[1,2-a]pyrazine (1.4 g, 3.5 mmol) in ACN (30 mL) was added 3-amino-2,2-dimethyl-propan-1-ol (Lancaster, 0.79 g, 7.7 mmol). The mixture was heated to about 80° C. After about 16 h, the mixture was treated with additional 3-amino-2,2-dimethyl-propan-1-ol (Lancaster, 0.20 g, 1.9 mmol) and heated at about 80° C. for about another 4 h. The mixture was filtered through a pad of silica gel and eluted with EtOAc. The solution was evaporated, triturated with ether, and then filtered. The solid was dissolved in hot methanol (~10 mL). The solution was cooled and the solvent evaporated. The resulting solid was dried at 100° C. under vacuum to yield the title compound as a white solid (0.88 g, 59%): LC/MS (Table 1, Method g) $R_t$=2.38 min; MS m/z: 425.2 (M+H)$^+$, mp 173.8-174.5° C.

Example #14

3-{4-[2-(4-Fluorophenyl)-8-isopropoxyimidazo[1,2-a]pyrazin-3-yl]-pyrimidin-2-ylamino}-2,2-dimethyl-propan-1-ol

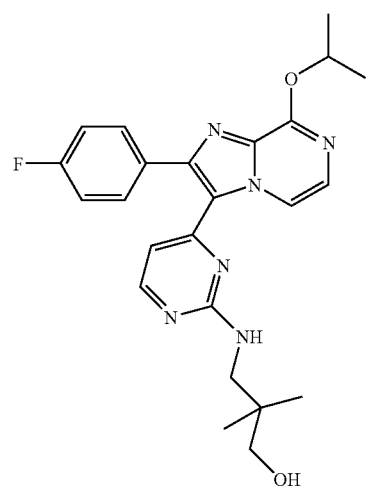

Step A:
8-Chloro-2-(4-fluorophenyl)-imidazo[1,2-a]pyrazine

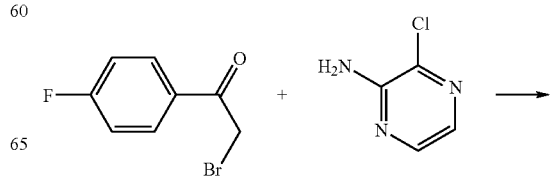

-continued

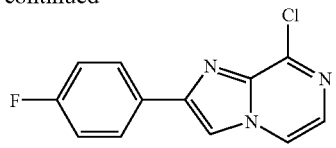

Into a 1-Neck round-bottom flask was added 2-bromo-1-(4-fluorophenyl)ethanone (125 g, 564 mmol) and 3-chloropyrazin-2-amine (128.9 g, 965.2 mmol) followed by ACN (750 mL). The mixture was stirred at reflux for about 24 h. The reaction mixture was cooled to about 45° C. before the solvent was removed in vacuo to yield a brown solid. The brown solid was suspended in water (500 mL) and basified, whilst stirring, with 2.5N NaOH (500 mL). The mixture was then stirred for about 30 min then re-acidified with 5N HCl (300 mL) and extracted with DCM (5×1000 mL). The combined organic layers were filtered from the insoluble material, washed with water (750 mL), followed by washing with 2.5N HCl (4×750 mL), 2.5N NaOH (500 mL) and water (2×500 mL), then dried over MgSO₄ and filtered. The filtrate was eluted through a Florisil® pad (3 inch diameter×3 inch depth), washing with repeated amounts of DCM until no product detected by TLC. The organic solvent was removed in vacuo to yield a yellow solid, which was suspended in 2-propanol (500 mL) at about 80° C. for about 15 min and then cooled to about 30° C. The solid was filtered, washing with petroleum ether [bp 30-60° C.] (2×100 mL) and heptane (2×100 mL) to remove impurities, dried in vacuo at 45° C. to yield the title compound (78.2 g, 55.4%): LC/MS (Table 1, Method g) $R_t$=2.48 min; MS m/z: 248.2 $(M+H)^+$.

Step B: 2-(4-Fluorophenyl)-8-isopropoxyimidazo[1,2-a]pyrazine

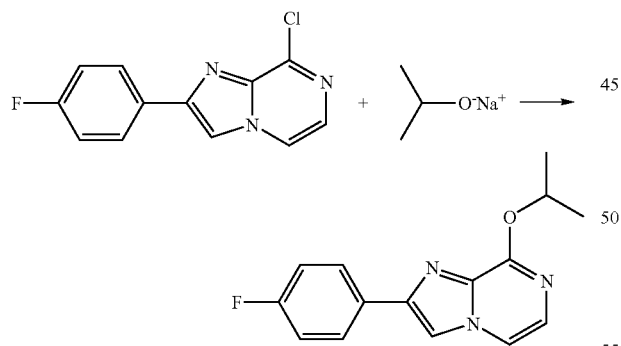

A mixture of anhydrous IPA (25 mL) and sodium (0.4 g, 17.4 mmol) was heated at reflux until the sodium was consumed. The reaction mixture was cooled to ambient temperature and the 8-chloro-2-(4-fluorophenyl)-imidazo[1,2-a]pyrazine (prepared from general procedure B using 3-chloropyrazin-2-ylamine and 2-bromo-1-(4-fluorophenyl)-ethanone; 2.0 g, 8 mmol) was added. The reaction mixture was heated at reflux for about 2 h, cooled to ambient temperature, and partitioned between EtOAc and water. The layers were separated and the organic phase was dried over MgSO₄, filtered, and evaporated. The resulting solid was triturated with heptane to afford 1.52 g (70%) of the title compound: LC/MS (Table 1, Method g) $R_t$=2.78 min; MS m/z: 272.2 $(M+H)^+$.

Step C: 2-(4-Fluorophenyl)-8-isopropoxy-3-(2-methylsulfanylpyrimidin-4-yl)-imidazo[1,2-a]pyrazine

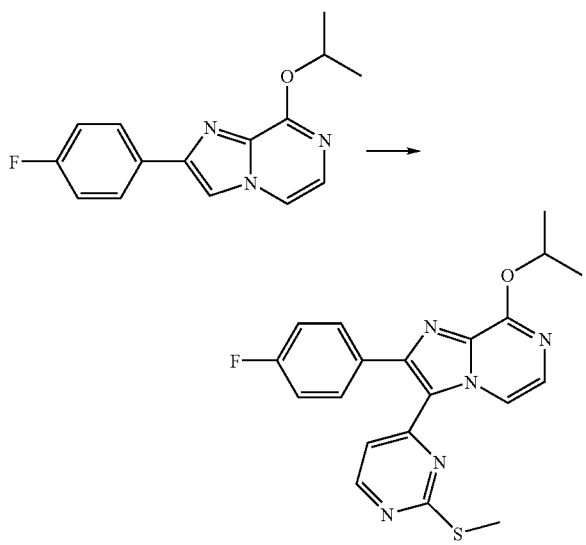

Pd(OAc)₂ (0.233 g, 1 mmol) was added to a degassed mixture of 2-(4-fluorophenyl)-8-isopropoxyimidazo[1,2-a]pyrazine (1.43 g, 5.2 mmol), 4-iodo-2-(methylthio)pyrimidine (Frontier, 1.96 g, 7.8 mmol), Cs₂CO₃ (2.57 g, 7.8 mmol) and PPh₃ (0.54 g, 2 mmol) in DMF (6 mL). The resulting reaction mixture was heated at about 100° C. for about 4 h, cooled to ambient temperature, and partitioned between EtOAc and brine. The organic layer was separated, dried over MgSO₄, filtered, and evaporated. The crude material was purified by silica gel chromatography using heptane/EtOAc (gradient, 100%/0% to 50%/50%) to afford 1.05 g (51%) of the title compound: LC/MS (Table 1, Method g) $R_t$=3.45 min; MS m/z: 396.2 $(M+H)^+$.

Step D: 2-(4-Fluorophenyl)-8-isopropoxy-3-(2-methanesulfonylpyrimidin-4-yl)-imidazo[1,2-a]pyrazine

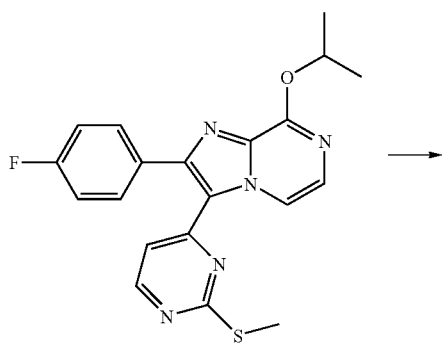

-continued

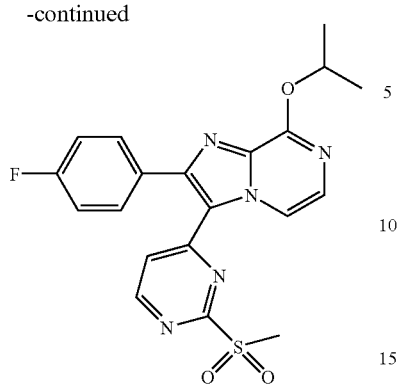

A solution of Oxone® (3.17 g, 5.15 mmol) in water (9 mL) was added to a solution of 2-(4-fluoro-phenyl)-8-isopropoxy-3-(2-methylsulfanylpyrimidin-4-yl)-imidazo[1,2-a]pyrazine (1.02 g, 2.57 mmol) in 41 mL of DCM/MeOH (1:1). The resulting reaction mixture was stirred overnight at ambient temperature, neutralized with a saturated aqueous solution of $Na_2CO_3$, and extracted with DCM. The organic phase was dried over $MgSO_4$, filtered, and concentrated. The crude material was sequentially triturated with MeOH and ACN to give 0.387 g (35%) of the title compound: LC/MS (Table 1, Method g) $R_t$=2.69 min; MS m/z: 428.2 $(M+H)^+$.

Step E: 3-{4-[2-(4-Fluorophenyl)-8-isopropoxyimidazo[1,2-a]pyrazin-3-yl]-pyrimidin-2-ylamino}-2,2-dimethylpropan-1-ol

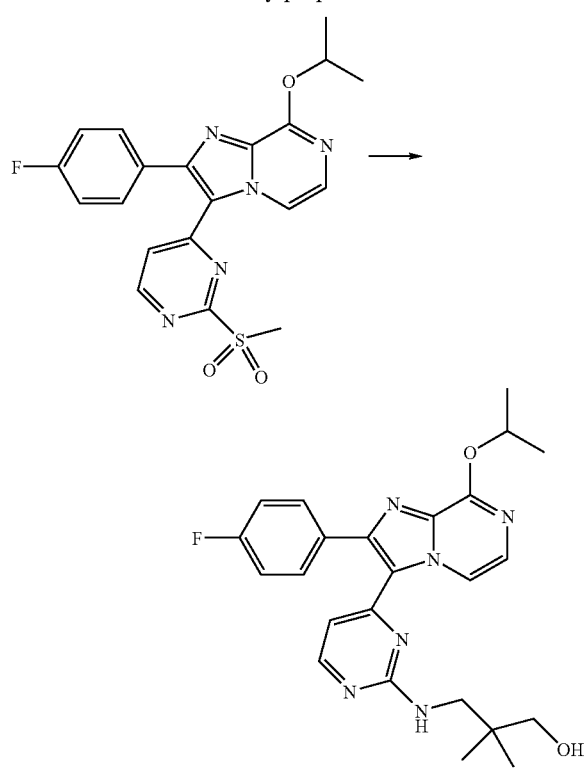

A suspension of 2-(4-fluorophenyl)-8-isopropoxy-3-(2-methanesulfonylpyrimidin-4-yl)-imidazo[1,2-a]pyrazine (0.16 g, 0.37 mmol) and 3-amino-2,2-dimethylpropan-1-ol (TCI-US, 0.208 g, 0.74 mmol) in ACN (5 mL) was heated at about 80° C. overnight to give a clear solution. The reaction mixture was cooled to ambient temperature, the volatiles were evaporated, and the resulting residue was dissolved in DCM and washed with water. The organic phase was dried over $MgSO_4$, filtered, and evaporated to give a white solid that was triturated with heptane to afford 0.109 g (64.7%) the title compound as a white solid: LC/MS (Table 1, Method g) $R_t$=3.01 min; MS m/z: 494.2 $(M+H)^+$.

Example #15

{5-Chloro-4-[2-(4-fluorophenyl)-8-methylimidazo[1,2-a]pyrazin-3-yl]-pyrimidin-2-yl}-cyclopropylamine

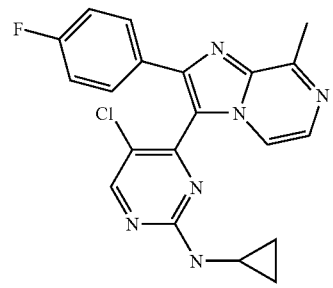

Trichloroisocyanuric acid (0.001 g, 0.04 mmol) was added portion-wise to a refluxing mixture of cyclopropyl-4-[2-(4-fluorophenyl)-8-methylimidazo[1,2-a]pyrazin-3-yl]-pyrimidin-2-ylamine (Example #A.2.1, 0.050 g, 0.14 mmol) in $CHCl_3$ (2.5 mL). The reaction mixture was refluxed for 3 h, cooled to room temperature, diluted with DCM and washed with a saturated aqueous solution of $Na_2CO_3$. The organic phase was dried over $MgSO_4$, filtered, and evaporated. The resulting residue was purified by silica gel chromatography using a gradient of heptane/EtOAc (50:50 to 0:100) to afford 0.015 g (27%) of the title compound. LC/MS (Table 1, Method g) $R_t$=2.71 min; MS m/z: 393.2 $(M+H)^+$.

Example #16

2-(4-Fluorophenyl)-3-(2-methanesulfonylpyrimidin-4-yl)-8-methyl-imidazo[1,2-a]pyrazine-7-oxide

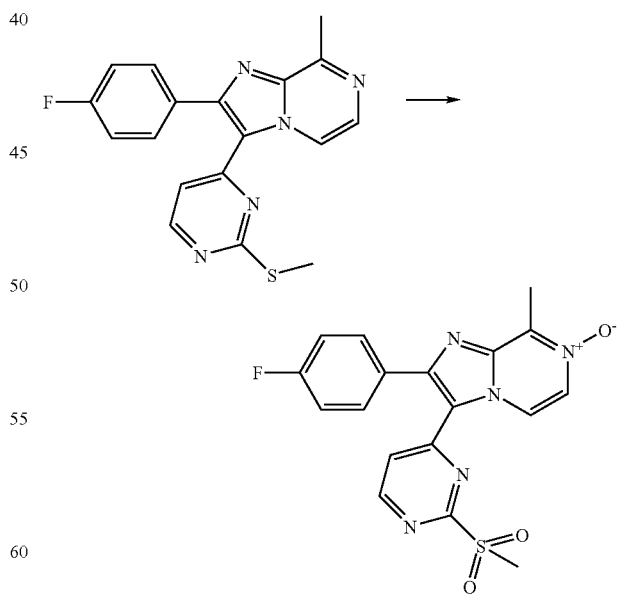

2-(4-Fluorophenyl)-8-methyl-3-(2-methylsulfanylpyrimidin-4-yl)imidazo[1,2-a]pyrazine (Example #F.1A, 0.55 g, 1.6 mmol) was dissolved in DCM (5 ml) and cooled to about 0° C. The mixture was treated with m-CPBA (0.77 g, 3.1 mmol)

in DCM (3 mL) over about 5 min. The mixture was allowed to warm slowly to ambient temperature and after about 4 h was treated with Na$_2$CO$_3$ and water. The layers were separated and the aqueous layer was extracted with DCM. The combined organic layers were dried over Na$_2$SO$_4$, decanted, and concentrated. The residue was purified by FCC using DCM/ 2.5% NH$_4$OH in MeOH (96:4) to provide the title compound (0.050 g, 8%) after concentration: LC/MS (Table 1, Method b) R$_t$=1.6 min; MS m/z: 400.1 (M+H)$^+$.

Example #17

3-{4-[2-(4-Fluorophenyl)-8-methylimidazo[1,2-a] pyrazin-3-yl]pyrimidin-2-ylamino}-2,2-dimethylpropionic acid

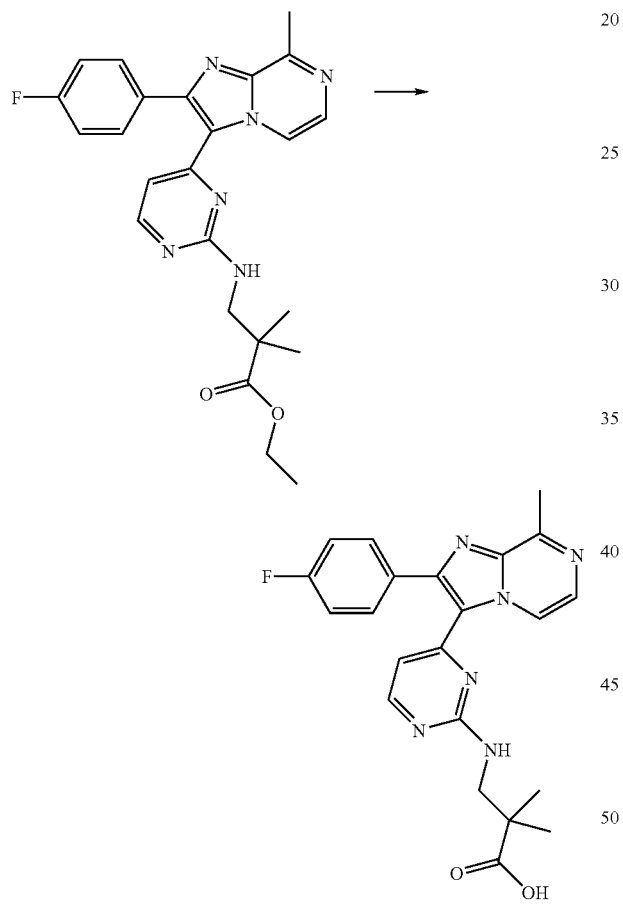

3-{4-[2-(4-Fluorophenyl)-8-methylimidazo[1,2-a] pyrazin-3-yl]pyrimidin-2-ylamino}-2,2-dimethyl-propionic acid ethyl ester (Example #A.9.19, 0.085 g, 0.19 mmol) was diluted in MeOH (3 mL) and treated with 2.5 M NaOH (0.36 mL, 0.9 mmol) at ambient temperature. After about 4 days, the mixture was neutralized with 1.0 M HCl (0.90 mL, 0.9 mmol) and diluted with DCM and water. The layers were separated and the aqueous layer was extracted with DCM. The combined organic layers were dried over Na$_2$SO$_4$, decanted, and concentrated to yield the title compound (0.036 g, 45%): LC/MS (Table 1, Method b) R$_t$=1.9 min; MS m/z: 421.3 (M+H)$^+$.

Example #18

8-Chloro-2-(4-fluorophenyl)-3-(2-methanesulfonylpyrimidin-4-yl)imidazo[1,2-a]pyrazine

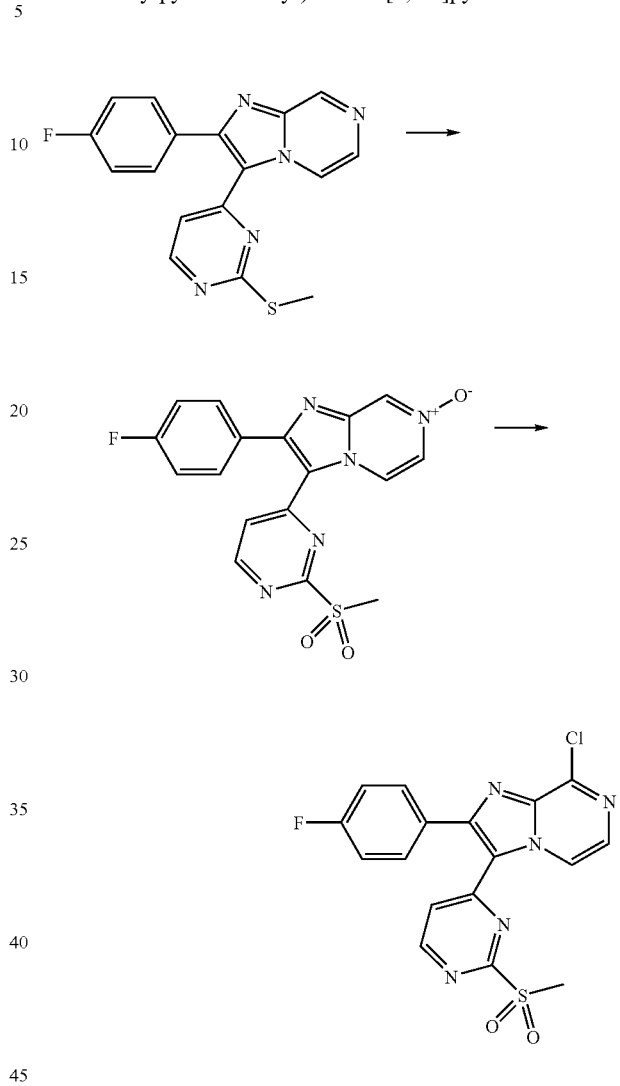

To a solution of 2-(4-fluorophenyl)-3-(2-methylsulfanylpyrimidin-4-yl)imidazo[1,2-a]pyrazine (Preparation #3, 1.012 g, 3 mmol) in DCM (30 mL) and MeOH (30 mL) was added a solution of Oxone® (18.4 g, 30.0 mmol) in water (100 mL) to form a suspension. After about 5 days, the mixture was diluted with saturated sodium bicarbonate solution and extracted with DCM. The organic phase was dried over Na$_2$SO$_4$, filtered, and concentrated under reduced pressure. The crude 2-(4-fluorophenyl)-3-(2-methanesulfonylpyrimidin-4-yl)imidazo[1,2-a]pyrazine-7-oxide was dissolved in DCM (20 mL), and phosphorous(III)oxychloride (0.46 g, 3 mmol) was added. After stirring overnight, the mixture was partitioned between DCM and saturated sodium bicarbonate solution. The organic layer was dried over Na$_2$SO$_4$ and concentrated. The crude material was purified by silica gel chromatography with heptane/EtOAc (gradient 50-100% EtOAc). After concentration, the residue was twice re-dissolved in DCM and re-concentrated to give 0.0529 g (4%, over 2 steps) of the title compound as a white foam: LC/MS (Table 1, Method g) R$_t$=2.42 min; MS m/z: 404.1 (M+H)$^+$.

Example #19

3-{4-[2-(4-Fluorophenyl)-8-methoxymethylimidazo[1,2-a]pyrazin-3-yl]-pyrimidin-2-ylamino}-2,2-dimethylpropan-1-ol

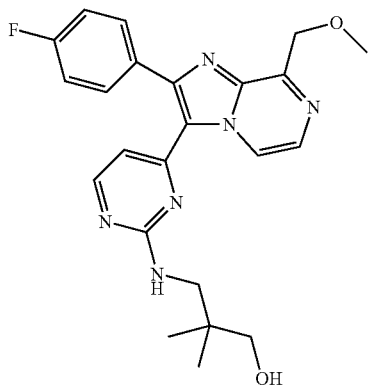

Step A: 2-(4-Fluorophenyl)-3-(2-methanesulfonylpyrimidin-4-yl)-8-methoxymethyl-imidazo[1,2-a]pyrazine

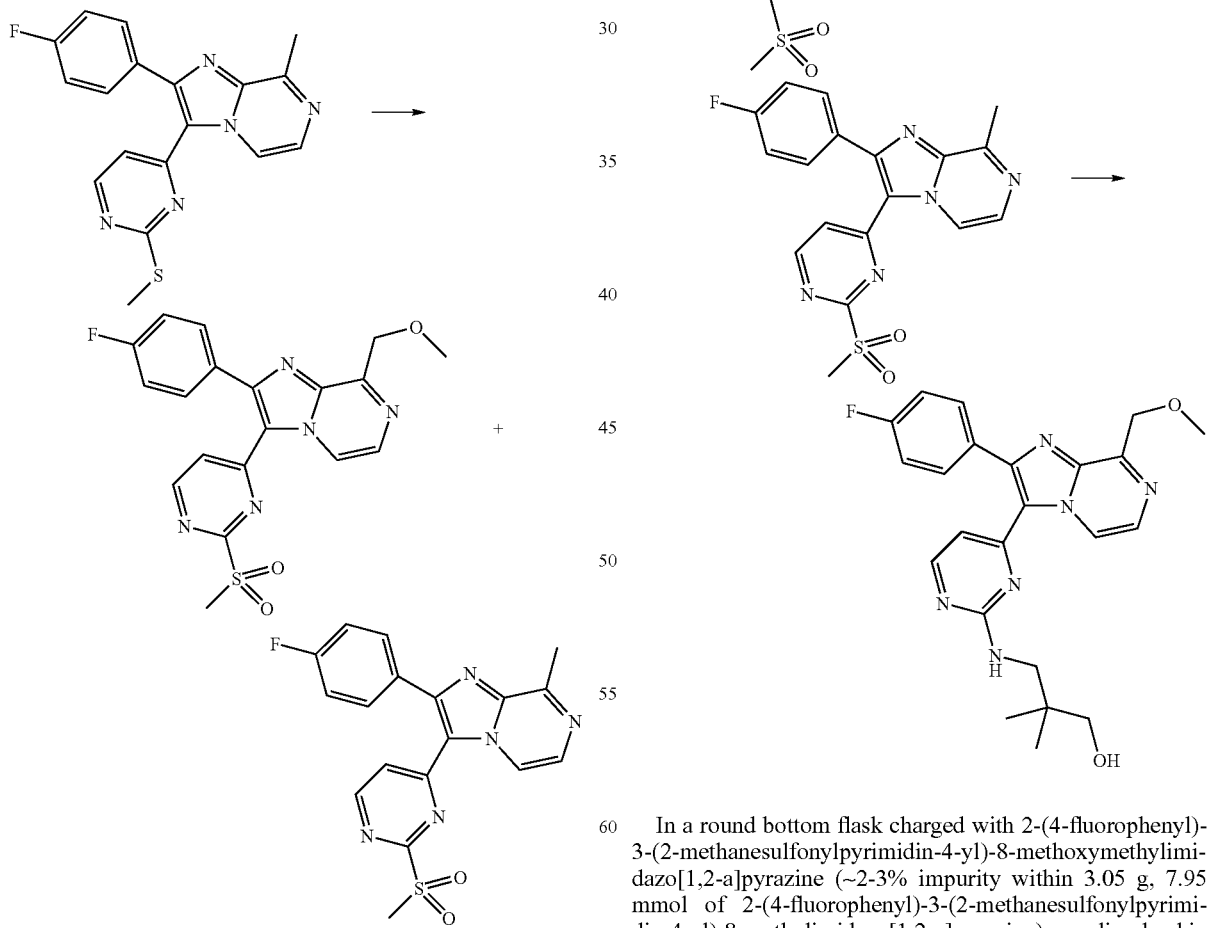

In a round bottom flask charged with 2-(4-fluorophenyl)-3-(2-methylsulfanylpyrimidin-4-yl)-imidazo[1,2-a]pyrazine (Example #F.1A, 4 g, 11.4 mmol) dissolved in DCM (15 mL) and MeOH (500 mL) was added a suspension of Oxone® (21 g, 34.2 mmol) in water (30 mL) at ambient temperature. The reaction was allowed to stir at this temperature for about 1.5 h upon which time DCM (300 mL) was added and the solution was allowed to stir for about another 10 min upon which the organic layer was separated and the aqueous layer was washed with DCM (3×100 mL). The combined organic layers were dried over MgSO$_4$ and concentrated. The resulting yellow solid was recrystallized from hot ACN to yield the title compound as a 3-10% impurity within 2-(4-fluorophenyl)-3-(2-methanesulfonylpyrimidin-4-yl)-8-methylimidazo[1,2-a]pyrazine (2.05 g, ~47% yield).

Step B: 3-{4-[2-(4-Fluorophenyl)-8-methylimidazo[1,2-a]pyrazin-3-yl]-pyrimidin-2-ylamino}-2,2-dimethylpropan-1-ol

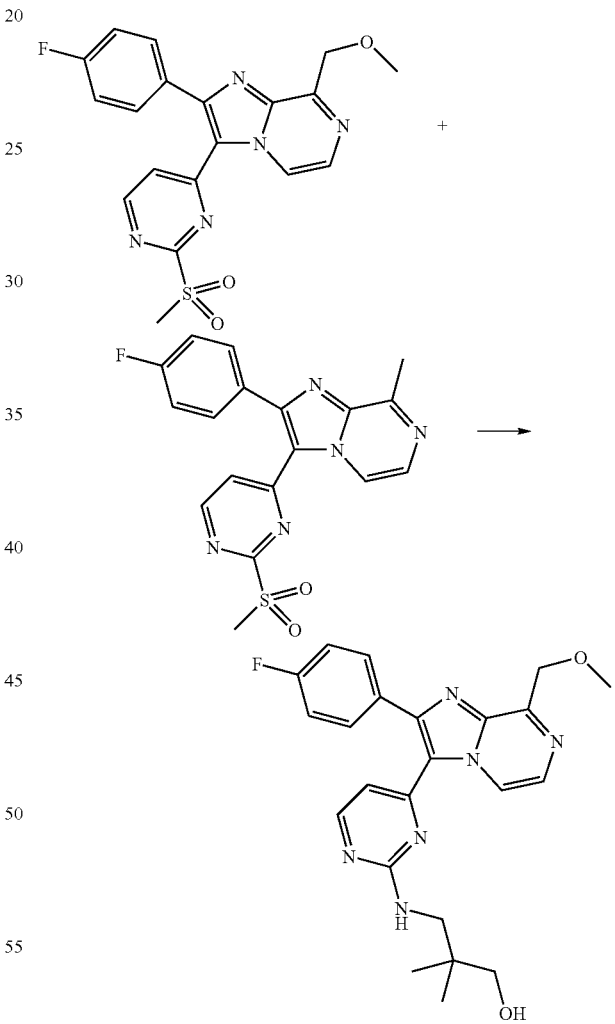

In a round bottom flask charged with 2-(4-fluorophenyl)-3-(2-methanesulfonylpyrimidin-4-yl)-8-methoxymethylimidazo[1,2-a]pyrazine (~2-3% impurity within 3.05 g, 7.95 mmol of 2-(4-fluorophenyl)-3-(2-methanesulfonylpyrimidin-4-yl)-8-methylimidazo[1,2-a]pyrazine) was dissolved in ACN (70 mL) to which was added 3-amino-2,2-dimethylpropan-1-ol (Lancaster, 4.1 g, 96.8 mmol) at ambient temperature followed by heating to about 80° C. for about 3 h.

After this time the reaction was cooled to ambient temperature and purified in 200-300 mg batches using RP-HPLC (Table 1, Method i). The pure fractions were combined and concentrated to remove the organic solvent. The resulting precipitate was filtered from the aqueous layer and dried in a vacuum overnight to give the title compound as a white solid (0.054 g, 1.5% yield). LC/MS (Table 1, Method b) $R_t$=1.77 min; MS m/z: 414.0 (M+H)$^+$.

What is claimed is:

1. A compound of formula (I),

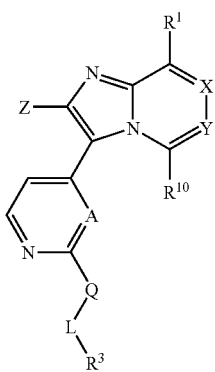

(I)

or pharmaceutically acceptable salts thereof wherein

Z is an optionally substituted aryl or heteroaryl;

X and Y are each independently N, $CR^4$ or N-oxide, provided that X and Y cannot both be $CR^4$ or X and Y cannot both be N-oxide;

A is N, $CR^4$ or N-oxide;

$R^1$ and $R^{10}$ is each independently H, OH, F, Cl, Br, I, $CF_3$, CN, $OCF_3$, nitro or amino; or $R^1$ and $R^{10}$ is each independently selected from the optionally substituted group consisting of aryloxy, $(C_1-C_6)$alkyl, $(C_1-C_6)$alkoxy, $(C_1-C_6)$alkyl-O—$(C_1-C_6)$alkyl, $(C_2-C_8)$alkenyl, $(C_2-C_8)$alkynyl, $(C_3-C_8)$cycloalkyl, $(C_3-C_8)$cycloalkyl$(C_1-C_6)$alkyl, heterocyclyl, aryl, —$CO_2(C_1-C_6)$alkyl, —$CONR^5R^6$, —$SO_2NR^5R^6$, $SO_{(n)}$alkyl, —$NHCOR^5$, —$NHSO_2R^5$, —$N((C_1-C_4)$alkyl)$COR^5$, —$N((C_1-C_4)$alkyl)$SO_2R^5$, $NR^5R^6$, $O(C_1-C_6)$alkyl-$R^7$ and $(C_1-C_6)$alkyl$R^7$;

Q is $N(R^2)$, O, S or is a bond;

L is a bond, $(C_1-C_6)$alkyl, C(O), —C(O)—O—, —C(O)—N(H)—, SO or $SO_2$;

$R^3$ selected from the group consisting of H, —C(O)$NR^5R^6$, —$NR^2C(O)R^5$, —$NR^2C(O)_2R^5$, C(O)$OR^2$,

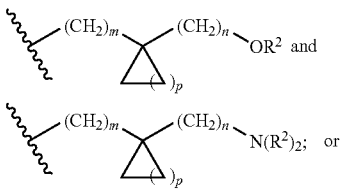

$R^3$ is selected from the optionally substituted group consisting of aryl, heterocyclyl, heterocyclylalkylaryl, 1,4-dioxaspiro[4.5]decane, azabicyclo[3.2.1]octane and azabicyclo[2.2.2]octane; or $R^3$ is selected from the optionally substituted group consisting of $(C_1-C_9)$alkyl and $(C_3-C_8)$cycloalkyl;

wherein the $(C_1-C_9)$alkyl and $(C_3-C_8)$cycloalkyl are optionally substituted with one or more $(C_1-C_6)$alkyl, $(C_1-C_6)$alkyl-$OR^2$, $OR^2$ or $N(R^2)_2$;

$R^2$ for each occurrence is independently H or $(C_1-C_4)$alkyl;

$R^4$ is H, OH, F, Cl, Br, I, $CF_3$, CN, $OCF_3$, nitro or amino; or $R^4$ is selected from optionally substituted group consisting of $(C_1-C_6)$alkyl, $(C_1-C_6)$alkoxy, aryloxy, $(C_2-C_8)$alkenyl, $(C_2-C_8)$alkynyl, heterocyclyl, aryl, —$CONR^5R^6$, —$SO_2NR^5R^6$, —$SO_{(n)}$alkyl, —$NR^2COR^5$, —$NR^2SO_2R^5$, —$NR^5R^6$, —$CO_2(C_1-C_6)$alkyl, —$N((C_1-C_4)$alkyl)CO—$R^5$, or —$N((C_1-C_4)$alkyl)$SO_2$—$R^5$;

$R^5$ and $R^6$ are each independently H, or are independently selected from the optionally substituted group consisting of $(C_1-C_6)$alkyl, $(C_1-C_6)$alkoxy, $(C_2-C_6)$hydroxyalkyl, $(C_2-C_6)$aminoalkyl, $(C_3-C_8)$cycloalkyl, aryl and heterocyclyl; or $R^5$ and $R^6$ are taken together with the N atom to which they are attached to form an optionally substituted heteroaryl or heterocyclyl ring;

$R^7$ is $CF_3$, $NR^5R^6$, OH, $(C_1-C_6)$alkoxy or optionally substituted $(C_3-C_8)$cycloalkyl;

m is 0, 1 or 2;

n is 0, 1, 2; and p is 1, 2, 3 or 4.

2. The compound according to claim 1, or pharmaceutically acceptable salts thereof wherein Z is optionally substituted aryl.

3. The compound according to claim 2, or pharmaceutically acceptable salts thereof, wherein $R^1$ is H, Cl, methoxy, methyl, ethyl, isopropyl, $OCH(CH_3)_2$, $OCH_2CF_3$, $OCF_3$, $OCH_2$-cyclopropyl, $CH_2$-cyclopropyl, $NHCH_3$, $N(CH_3)_2$, $NH_2$, $OCH_2CH_2OCH_3$, $OCH_2CH(CH_3)_2$ or cyclopropyl;

$R^{10}$ is H;

X is N or N-oxide;

Y is $CR^4$;

Z is optionally substituted naphthyl or optionally substituted phenyl wherein one or more substituents are selected from the group consisting of F, Cl, $CF_3$ and $CH_3$;

A is N;

Q is $N(R^2)$;

L is a bond, $CH(CH_3)$, $(C_1-C_4)$alkyl or $R^3$ is selected from the optionally substituted group consisting of $(C_2-C_5)$alkyl, cyclopropyl, cyclopentyl and cyclohexyl wherein the alkyl, cyclopropyl, cyclopentyl and cyclohexyl are optionally substituted with one or more alkyl, $OR^2$ or $N(R^2)_2$; or $R^3$ is selected from $NHC(O)R^5$ or the optionally substituted group consisting of azepanyl, phenyl, piperidinyl, pyrimidinyl, pyrrolidinyl, tetrahydrofuranyl, tetrahydrothiopyranyl, thienyl, $C(O)OR^2$, tetrahydropyranyl, 1,4-dioxaspiro[4.5]decane, azabicyclo[2.2.2]octane, azabicyclo[3.2.1]octane, wherein

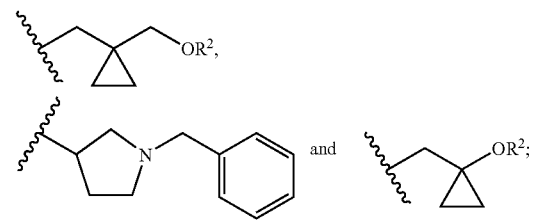

one or more substituents are selected from the group consisting of alkyl, alkyl-OR$^2$, OR$^2$, NR$^2$, S(O)$_2$—CH$_3$, C(O)CH$_3$, C(O)OC(CH$_3$)$_3$, C(O)CH$_2$OH, methyl, oxo and COOH; R$^2$ is H, methyl or t-butyl;

R$^4$ is H, methyl, ethyl, OCH$_3$ or Cl; and

R$^5$ is methyl or OC(CH$_3$)$_3$.

4. The compound according to claim 3, or pharmaceutically acceptable salts thereof wherein R$^1$ is H, methoxy, methyl, ethyl, isopropyl, OCH(CH$_3$)$_2$, OCH$_2$CF$_3$, OCH$_2$-cyclopropyl, CH$_2$-cyclopropyl, NHCH$_3$, N(CH$_3$)$_2$, NH$_2$, OCH$_2$CH$_2$OCH$_3$ or OCH$_2$CH(CH$_3$)$_2$;

X is N;

Z is unsubstituted naphthyl or phenyl optionally substituted with one or more F, Cl, CF$_3$ or methyl;

L is a bond, CH(CH$_3$), or CH$_2$;

R$^3$ is selected from the optionally substituted group consisting of cyclopropyl, cyclopentyl, cyclohexyl and (C$_3$-C$_5$)alkyl wherein one or more substituents are selected from the group consisting of alkyl, alkyl-OR$^2$, OR$^2$ and N(R$^2$)$_2$; or R$^3$ is selected from the optionally substituted group consisting of phenyl, piperidinyl, tetrahydropyranyl, tetrahydrothiopyranyl, thienyl, 1,4-dioxaspiro[4.5]decane, azabicyclo[3.2.1]octane,

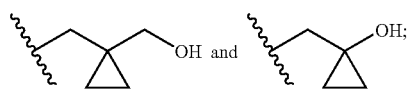

wherein one or more substituents are selected from the group consisting of alkyl, alkylOR$^2$, OR$^2$, S(O)$_2$—CH$_3$, C(O)CH$_3$, C(O)OC(CH$_3$)$_3$, C(O)CH$_2$OH, methyl and COOH;

R$^2$ is H or t-butyl; and

R$^4$ is H, methyl or ethyl.

5. The compound according to claim 4, or pharmaceutically acceptable salts thereof, wherein R$^1$ is H, methoxy, methyl, ethyl, OCH(CH$_3$)$_2$ or CH$_2$-cyclopropyl;

Y is CH;

Z is phenyl optionally substituted with one or more F, Cl, CF$_3$ or methyl;

wherein the substituents can be meta, para or disubstituted ortho, para;

R$^3$ is selected from the group consisting of unsubstituted cyclopropyl, unsubstituted phenyl, unsubstituted cyclopentyl, unsubstituted cyclohexyl, unsubstituted thienyl,

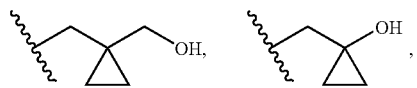

(C$_3$-C$_5$)alkyl substituted with one or more alkyl, alkyl-OR$^2$ or OR$^2$, and piperidinyl substituted with S(O)$_2$—CH$_3$, C(O)CH$_3$, C(O)OC(CH$_3$)$_3$, C(O)CH$_2$OH or COOH; and R$^2$ is H or t-butyl.

6. The compound according to claim 5, or pharmaceutically acceptable salts thereof, wherein R$^1$ is H, methoxy, methyl, OCH(CH$_3$)$_2$ or CH$_2$-cyclopropyl;

Q is N(H);

L is a bond or CH(CH$_3$); and

R$^3$ is selected from the group consisting of unsubstituted cyclopropyl, unsubstituted cyclopentyl, unsubstituted cyclohexyl, unsubstituted phenyl,

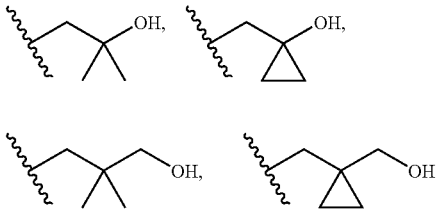

and piperidinyl wherein the piperidinyl is substituted with S(O)$_2$—CH$_3$ or C(O)CH$_3$.

7. The compound according to claim 6 or pharmaceutically acceptable salts thereof, wherein the compound is

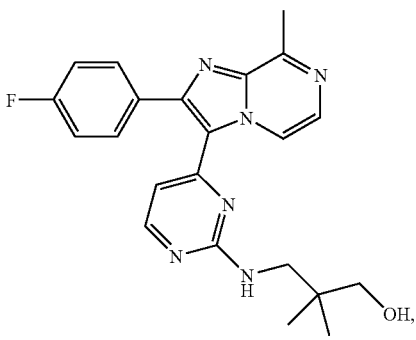

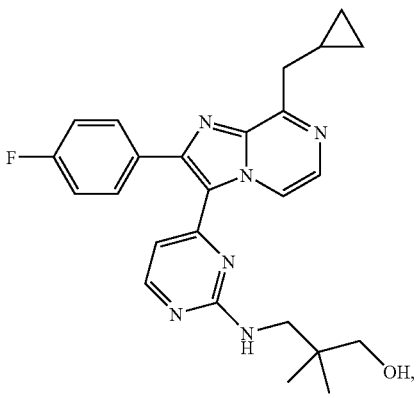

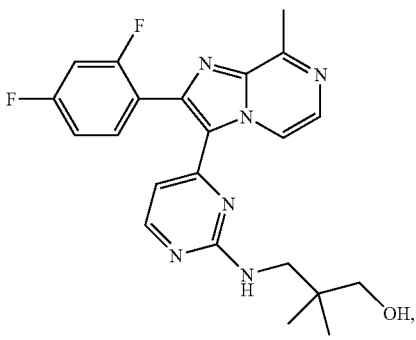

-continued

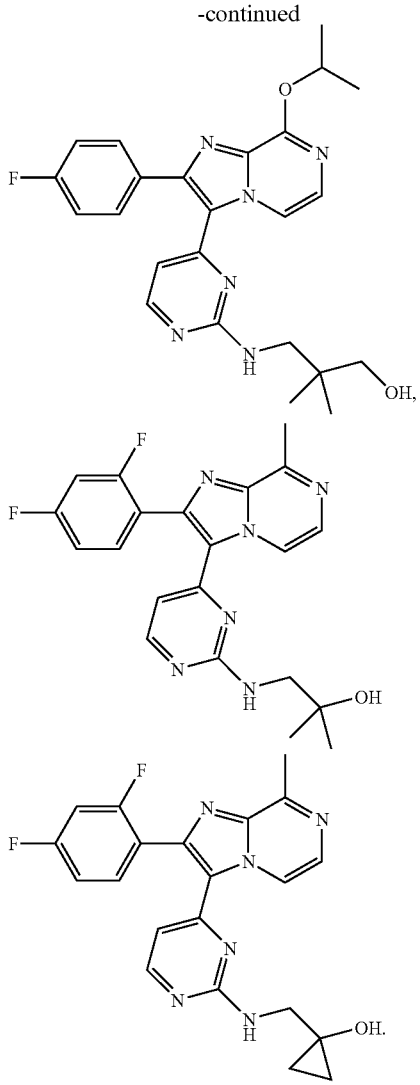

8. A compound of formula (I),

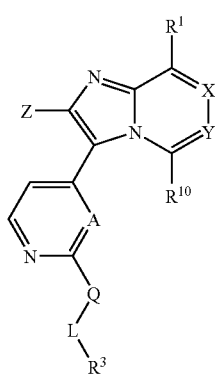

or pharmaceutically acceptable salts thereof wherein

Z is an optionally substituted aryl or heteroaryl;

X and Y are each independently N, $CR^4$ or N-oxide, provided that X and Y cannot both be $CR^4$ or X and Y cannot both be N-oxide;

A is N, $CR^4$ or N-oxide;

$R^1$ and $R^{10}$ is each independently H, OH, F, Cl, Br, I, $CF_3$, CN, $OCF_3$, nitro or amino; or $R^1$ and $R^{10}$ is each independently selected from the optionally substituted group consisting of aryloxy, $(C_1\text{-}C_6)$alkyl, $(C_1\text{-}C_6)$alkoxy, $(C_1\text{-}C_6)$alkyl-O—$(C_1\text{-}C_6)$alkyl, $(C_2\text{-}C_8)$alkenyl, $(C_2\text{-}C_8)$alkynyl, $(C_3\text{-}C_8)$cycloalkyl, $(C_3\text{-}C_8)$cycloalkyl$(C_1\text{-}C_6)$alkyl, heterocyclyl, aryl, —$CO_2(C_1\text{-}C_6)$alkyl, —$CONR^5R^6$, —$SO_2NR^5R^6$, $SO_{(n)}$alkyl, —$NHCOR^5$, —$NHSO_2R^5$, —$N((C_1\text{-}C_4)$alkyl)$COR^5$, —$N((C_1\text{-}C_4)$alkyl)$SO_2R^5$, $NR^5R^6$, $O(C_1\text{-}C_6)$alkyl-$R^7$ and $(C_1\text{-}C_6)$alkyl$R^7$;

Q is $N(R^2)$, O, S or is a bond;

L is a bond, $(C_1\text{-}C_6)$alkyl, C(O), —C(O)—O—, —C(O)—N(H)—, SO or $SO_2$;

$R^3$ is selected from the group consisting of H, —C(O)$NR^5R^6$, —$NR^2C(O)R^5$, —$NR^2C(O)_2R^5$,

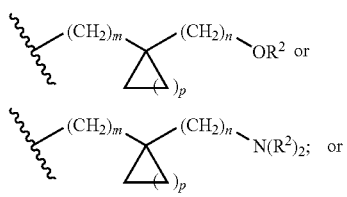

$R^3$ is selected from the optionally substituted group consisting of aryl, heterocyclyl, heterocyclylalkylaryl, 1,4-dioxaspiro[4.5]decane, azabicyclo[3.2.1]octane, azabicyclo[2.2.2]octane, $(C_1\text{-}C_9)$alkyl and $(C_3\text{-}C_8)$cycloalkyl;

wherein the $(C_1\text{-}C_9)$alkyl and $(C_3\text{-}C_8)$cycloalkyl are optionally substituted with one or more $(C_1\text{-}C_6)$alkyl, $(C_1\text{-}C_6)$alkyl-$OR^2$, $OR^2$ or $R^2$ for each occurrence is independently H or $(C_1\text{-}C_4)$alkyl;

$R^4$ is H, OH, F, Cl, Br, I, $CF_3$, CN, $OCF_3$, nitro or amino; or $R^4$ is selected from optionally substituted group consisting of $(C_1\text{-}C_6)$alkyl, $(C_1\text{-}C_6)$alkoxy, aryloxy, $(C_2\text{-}C_8)$alkenyl, $(C_2\text{-}C_8)$alkynyl, heterocyclyl, aryl, —$CONR^5R^6$, —$SO_2NR^5R^6$, —$SO_{(n)}$alkyl, —$NR^2COR^5$, —$NR^2SO_2R^5$, —$NR^5R^6$, —$CO_2(C_1\text{-}C_6)$alkyl, —$N((C_1\text{-}C_4)$alkyl)CO—$R^5$, or —$N((C_1\text{-}C_4)$alkyl)$SO_2$—$R^1$;

$R^5$ and $R^6$ are each independently H, or are independently selected from the optionally substituted group consisting of $(C_1\text{-}C_6)$alkyl, $(C_1\text{-}C_6)$alkoxy, $(C_2\text{-}C_6)$hydroxyalkyl, $(C_2\text{-}C_6)$aminoalkyl, $(C_3\text{-}C_8)$cycloalkyl, aryl and heterocyclyl; or $R^5$ AND $R^6$ are taken together with the N atom to which they are attached to form an optionally substituted heteroaryl or heterocyclyl ring;

$R^7$ is $CF_3$, $NR^5R^6$, OH, $(C_1\text{-}C_6)$alkoxy or optionally substituted $(C_3\text{-}C_8)$cycloalkyl;

m is 0, 1 or 2;

n is 0, 1, 2; and p is 1, 2, 3 or 4.

9. The compound according to claim 8, or pharmaceutically acceptable salts thereof, wherein Z is optionally substituted aryl.

10. The compound according to claim 9, or pharmaceutically acceptable salts thereof, wherein R¹ is H, methoxy, methyl, ethyl, isopropyl, OCH(CH₃)₂, OCH₂CF₃, OCH₂-cyclopropyl, CH₂-cyclopropyl, NHCH₃, N(CH₃)₂, NH₂, OCH₂CH₂OCH₃, OCH₂CH(CH₃)₂ or cyclopropyl;

R¹⁰ is H;

X is N or N-oxide;

Y is CR⁴;

Z is optionally substituted naphthyl or optionally substituted phenyl wherein one or more substituents are selected from the group consisting of F, Cl, CF₃ and CH₃;

A is N;

Q is N(R²);

L is a bond, CH(CH₃), (C₁-C₄)alkyl or

R³ is selected from the optionally substituted group consisting of (C₂-C₅)alkyl, cyclopropyl, cyclopentyl and cyclohexyl wherein the alkyl, cyclopropyl, cyclopentyl and cyclohexyl are optionally substituted with one or more alkyl, OR² or N(R²)₂; or R³ is selected from NHC(O)R⁵ or the optionally substituted group consisting of azepanyl, phenyl, piperidinyl, pyrimidinyl, pyrrolidinyl, tetrahydrofuranyl, tetrahydrothiopyranyl, thienyl, tetrahydropyranyl, 1,4-dioxaspiro[4.5]decane, azabicyclo[2.2.2]octane, azabicyclo[3.2.1]octane,

 OR² and

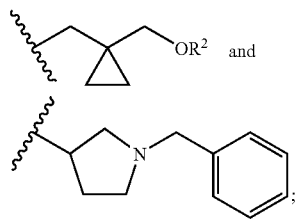

wherein one or more substituents are selected from the group consisting of alkyl, alkyl-OR², OR², NR², S(O)₂—CH₃, C(O)CH₃, C(O)OC(CH₃)₃, C(O)CH₂OH, methyl, oxo and COOH;

R² is H, methyl or t-butyl;

R⁴ is H, ethyl, OCH₃ or Cl; and

R⁵ is methyl or OC(CH₃)₃.

11. The compound according to claim 10, or pharmaceutically acceptable salts thereof, wherein R¹ is H, methoxy, methyl, ethyl, isopropyl, OCH(CH₃)₂, OCH₂CF₃, OCH₂-cyclopropyl, CH₂-cyclopropyl, NHCH₃, N(CH₃)₂, NH₂, OCH₂CH₂OCH₃ or OCH₂CH(CH₃)₂;

X is N;

Z is unsubstituted naphthyl or phenyl optionally substituted with one or more F, Cl, CF₃ or methyl;

L is a bond, CH(CH₃), or CH₂;

R³ is selected from the optionally substituted group consisting of cyclopropyl, cyclopentyl, cyclohexyl and (C₃-C₅)alkyl wherein one or more substituents are selected from the group consisting of alkyl, alkyl-OR², OR² and N(R²)₂; or R³ is selected from the optionally substituted group consisting of phenyl, piperidinyl, tetrahydropyranyl, tetrahydrothiopyranyl, thienyl, 1,4-dioxaspiro[4.5]decane and azabicyclo[3.2.1]octane or

 OH;

wherein one or more substituents are selected from the group consisting of alkyl, alkylOR², OR², S(O)₂—CH₃, C(O)CH₃, C(O)OC(CH₃)₃, C(O)CH₂OH, COOH and methyl;

R² is H or t-butyl; and

R⁴ is H or ethyl.

12. The compound according to claim 11, or pharmaceutically acceptable salts thereof, wherein R¹ is H, methoxy, methyl, ethyl, OCH(CH₃)₂ or CH₂-cyclopropyl;

Y is CH;

Z is phenyl optionally substituted with one or more F, Cl, CF₃ or methyl;

wherein the substituents can be meta, para or disubstituted ortho, para;

R³ is selected from the group consisting of unsubstituted cyclopropyl, (C₃-C₅)alkyl substituted with one or more alkyl, alkyl-OR² or OR², unsubstituted phenyl, unsubstituted cyclopentyl, unsubstituted cyclohexyl, unsubstituted thienyl and piperidinyl substituted with S(O)₂—CH₃, C(O)CH₃, C(O)OC(CH₃)₃, C(O)CH₂OH or COOH,; and R² is H or t-butyl.

13. The compound according to claim 12, or pharmaceutically acceptable salts thereof, wherein R¹ is H, methoxy, methyl, OCH(CH₃)₂ or CH₂-cyclopropyl;

Q is N(H);

L is a bond or CH(CH₃); and

R³ is selected from the group consisting of unsubstituted cyclopropyl, unsubstituted cyclopentyl, unsubstituted cyclohexyl, unsubstituted phenyl,

 OH and piperidinyl wherein the piperidinyl is substituted with S(O)₂—CH₃ or C(O)CH₃.

14. The compound according to claim 13 or pharmaceutically acceptable salts thereof, wherein the compound is

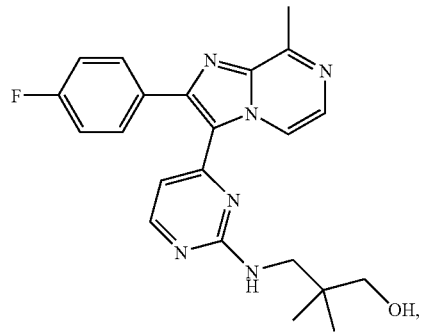

-continued

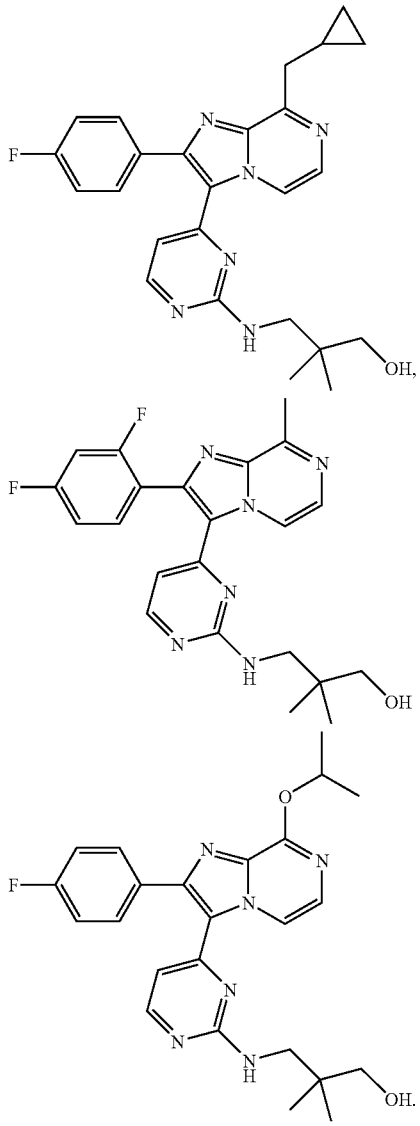

15. A compound of formula (I),

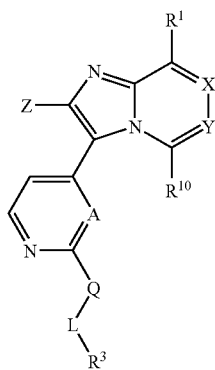

(I)

or pharmaceutically acceptable salts thereof, wherein

Z is an optionally substituted aryl or heteroaryl;

X and Y are each independently N, $CR^4$ or N-oxide, provided that X and Y cannot both be $CR^4$ or X and Y cannot both be N-oxide;

A is N or $CR^4$;

$R^4$ is H, F, Cl, Br, I, $CF_3$, CN, $OCF_3$, $(C_1-C_6)$alkyl, $(C_1-C_6)$alkoxy, nitro, amino, aryloxy, $(C_2-C_8)$alkenyl, $(C_2-C_8)$alkynyl, heterocyclyl, aryl, —$CONR^5R^6$, —$SO_2NR^5R^6$, —SO(O)alkyl, —$NR^2COR^5$, —$NR^2SO_2R^5$, or —$NR^5R^6$;

$R^1$ and $R^{10}$ is each independently H, F, Cl, Br, I, $CF_3$, CN, $OCF_3$, nitro, amino, aryloxy, $(C_1-C_6)$alkyl, $(C_1-C_6)$alkoxy, $(C_2-C_8)$alkenyl, $(C_2-C_8)$alkynyl, heterocyclyl, aryl, —$CO_2(C_1-C_6)$alkyl, —$CONR^5R^6$, —$SO_2NR^5R^6$, $SO_{(n)}$alkyl, —$NHCOR^5$, —$NHSO_2R^5$, —$N((C_1-C_4)$alkyl)$COR^5$, —$N((C_1-C_4)$alkyl)$SO_2R^5$, or $NR^5R^6$;

$R^5$ and $R^6$ are each independently H, $(C_1-C_6)$alkyl, $(C_2-C_6)$hydroxyalkyl, $(C_2-C_6)$aminoalkyl, $(C_3-C_8)$cycloalkyl, aryl or heterocyclyl;

or $R^5$ and $R^6$ are taken together with the N atom to which they are attached to form a heteroaryl or heterocyclyl ring;

Q is $N(R^2)$, O, S or is a bond;

$R^2$ is H or $(C_1-C_4)$alkyl;

L is a bond, $(C_1-C_4)$alkyl, C(O), —C(O)—O—, —C(O)—N(H)— or $SO_2$;

$R^3$ is H, $(C_1-C_6)$alkyl optionally substituted with one or more $OR^2$ or $N(R^2)_2$, $(C_3-C_8)$cycloalkyl optionally substituted with one or more $OR^2$ or $N(R^2)_2$, optionally substituted aryl, or optionally substituted heterocyclyl; and n is 0, 1, 2.

16. A compound according to claim 15, or pharmaceutically acceptable salts thereof, wherein Z is selected from the optionally substituted group consisting of phenyl, naphthyl, azaindolyl, benzo(b)thienyl, benzimidazolyl, benzofuranyl, benzoxazolyl, benzothiazolyl, benzothiadiazolyl, benzothiophenyl, benzoxadiazolyl, furanyl, imidazolyl, imidazopyridinyl, indolyl, indolinyl, indazolyl, isoindolinyl, isoxazolyl, isothiazolyl, oxadiazolyl, oxazolyl, purinyl, pyranyl pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, tetrahydroindolyl, tetrazolyl, thiadiazolyl, thienyl, thiomorpholinyl, thiophenyl, triazolyl and tropanyl.

17. A compound according to claim 16, or pharmaceutically acceptable salts thereof, wherein Z is optionally substituted with one or more substituents, each independently selected from the group consisting of F, Cl, Br, I, $CF_3$, CN, $OCF_3$, nitro, amino, aryloxy, $(C_1-C_6)$alkyl, $(C_1-C_6)$alkoxy, $(C_2-C_8)$alkenyl, $(C_2-C_8)$alkynyl, heterocyclyl, aryl, —$CONR^5R^6$, —$SO_2NR^5R^6$, —$SO_{(n)}$alkyl, —$NHCOR^5$, —$NHSO_2R^5$, —$N((C_1-C_4)$alkyl)$COR^5$, —$N((C_1-C_4)$alkyl)$SO_2R^5$, or —$NR^5R^6$.

18. A compound according to claim 17, or pharmaceutically acceptable salts thereof, wherein Z is optionally substituted phenyl, naphthyl, furanyl or thiophenyl.

19. A compound according to claim 18, or pharmaceutically acceptable salts thereof, wherein Z is phenyl or naphthyl optionally substituted with one or more substituents each independently selected from the group consisting of F, Cl, methyl, $CF_3$, and $OCF_3$.

20. A compound according to claim 19, or pharmaceutically acceptable salts thereof, wherein Z is optionally substituted phenyl, substituted at either the meta- or para- position by F, Cl, methyl, $CF_3$, and $OCF_3$.

21. A compound according to claim 18, or pharmaceutically acceptable salts thereof, wherein $R^1$ is H or halo.

22. A compound according to claim 19, or pharmaceutically acceptable salts thereof, wherein $R^{10}$ is H, halo or $-NR^5R^6$.

23. A compound according to claim 22, or pharmaceutically acceptable salts thereof, wherein $R^{10}$ is H.

24. A compound according to claim 18, or pharmaceutically acceptable salts thereof, wherein A is N.

25. A compound according to claim 18, or pharmaceutically acceptable salts thereof, wherein $R^2$ is H.

26. A compound according to claim 18, or pharmaceutically acceptable salts thereof, wherein L is a bond or CO.

27. A compound according to claim 18, or pharmaceutically acceptable salts thereof, wherein $R^3$ is selected from the optionally substituted group consisting of methyl, ethyl, propyl, isopropyl, butyl, iso-butyl, sec-butyl, tert-butyl, pentyl, isopentyl, hexyl, isohexyl, cyclopropyl, cyclobutyl, cyclopentyl, cyclohexyl, —C(H)(CH$_3$)phenyl, —C(H)(CH$_2$CH$_3$)phenyl, piperidinyl, N-acylpiperidinyl, tetrahydropyranyl, (C$_2$-C$_5$) alkyl, azabicyclo[2.2.2]octane, azabicyclo[3.2.1]octane, azepanyl, 1,4-dioxaspiro[4.5]decane, pyridinyl, pyrrolidinyl, tetrahydrofuranyl, tetrahydrothiopyranyl, thienyl, and NHC(O)R$^5$.

* * * * *

UNITED STATES PATENT AND TRADEMARK OFFICE
CERTIFICATE OF CORRECTION

PATENT NO. : 7,709,468 B1 Page 1 of 1
APPLICATION NO. : 11/514626
DATED : May 4, 2010
INVENTOR(S) : David J. Calderwood et al.

It is certified that error appears in the above-identified patent and that said Letters Patent is hereby corrected as shown below:

Claim 3, Column 168 line 44 insert --C(O);-- following the phrase "L is a bond, CH(CH$_3$), (C$_1$-C$_4$)alkyl or"
Claim 3, Column 168 line 55 delete "wherein" following the phrase "azabicyclo[3.2.1]octane,"
Claim 3, Column 168 line 65 insert --wherein-- following the structures

"  "

Claim 8, Column 172 line 3 insert --N(R$^2$)$_2$;-- following the phrase "(C$_1$-C$_6$)alkyl-OR$^2$, OR$^2$ or"
Claim 8, Column 172 line 41 insert --the-- following the phrase "R$^4$ is selected from"
Claim 8, Column 172 line 47 delete "SO$_2$-R$^1$" and insert --SO$_2$-R$^5$--
Claim 8, Column 172 line 53 delete "AND" and insert --and--
Claim 10, Column 173 line 14 insert --C(O);-- following the phrase "L is a bond, CH(CH$_3$), (C$_1$-C$_4$)alkyl or"
Claim 10, Column 173 line 41 delete "NR$^2$" following the phrase "group consisting of alkyl, alkyl-OR$^2$, OR$^2$," and insert --N(R$^2$)$_2$--
Claim 12, Column 174 line 30 delete "," following the word "COOH"
Claim 15, Column 176 line 5 delete "SO(O)alkyl" following the phrase "-CONR$^5$R$^6$, -SO$_2$NR$^5$R$^6$, -SO(O)alkyl," and insert --SO$_{(n)}$alkyl,--
Claim 16, Column 176 line 38 insert --,-- following the word "pyranyl"

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

PATENT NO.        : 7,709,468 B2
APPLICATION NO.   : 11/514626
DATED             : May 4, 2010
INVENTOR(S)       : David J. Calderwood et al.

It is certified that error appears in the above-identified patent and that said Letters Patent is hereby corrected as shown below:

Face of the patent, Item 75
    Delete "Brieinlinger" and insert -- Breinlinger --

Signed and Sealed this
Third Day of April, 2012

David J. Kappos
*Director of the United States Patent and Trademark Office*